(12) United States Patent
 Ochiai

(10) Patent No.: US 9,289,007 B2
(45) Date of Patent: Mar. 22, 2016

(54) POLYNUCLEOTIDE ENCODING ACYL-COA SYNTHETASE HOMOLOG AND USE THEREOF

(75) Inventor: Misa Ochiai, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 570 days.

(21) Appl. No.: 13/574,026

(22) PCT Filed: Feb. 1, 2011

(86) PCT No.: PCT/JP2011/052035
§ 371 (c)(1),
(2), (4) Date: Jul. 19, 2012

(87) PCT Pub. No.: WO2011/093509
PCT Pub. Date: Aug. 4, 2011

(65) Prior Publication Data
US 2012/0322992 A1    Dec. 20, 2012

(30) Foreign Application Priority Data
Feb. 1, 2010    (JP) ................................. 2010-019967

(51) Int. Cl.
| C12N 15/52 | (2006.01) |
| C12N 9/00  | (2006.01) |
| C12P 7/64  | (2006.01) |
| A23L 1/30  | (2006.01) |
| A61K 8/36  | (2006.01) |
| A61K 8/60  | (2006.01) |
| A61Q 1/02  | (2006.01) |
| A61Q 1/06  | (2006.01) |
| A61Q 5/00  | (2006.01) |
| A61Q 5/12  | (2006.01) |
| A61Q 11/00 | (2006.01) |
| A61Q 19/00 | (2006.01) |
| A61Q 19/08 | (2006.01) |
| C12N 15/82 | (2006.01) |
| A61K 38/00 | (2006.01) |

(52) U.S. Cl.
CPC .............. *A23L 1/3006* (2013.01); *A61K 8/361* (2013.01); *A61K 8/606* (2013.01); *A61Q 1/02* (2013.01); *A61Q 1/06* (2013.01); *A61Q 5/006* (2013.01); *A61Q 5/12* (2013.01); *A61Q 11/00* (2013.01); *A61Q 19/00* (2013.01); *A61Q 19/08* (2013.01); *C12N 9/93* (2013.01); *C12N 15/8247* (2013.01); *C12P 7/6409* (2013.01); *C12P 7/6427* (2013.01); *C12P 7/6463* (2013.01); *C12P 7/6472* (2013.01); *A61K 38/00* (2013.01)

(58) Field of Classification Search
CPC ....................................................... C12N 9/93
See application file for complete search history.

(56) References Cited

U.S. PATENT DOCUMENTS

| 7,183,458 B1 | 2/2007 | Heinz et al. |
| 7,927,845 B2 | 4/2011 | Ochiai |
| 8,541,208 B1 | 9/2013 | Plesch et al. |
| 2003/0037357 A1 | 2/2003 | Shockey et al. |
| 2003/0097676 A1 | 5/2003 | Shockey et al. |
| 2004/0010817 A1 | 1/2004 | Shockey et al. |
| 2007/0220634 A1 | 9/2007 | Metz |
| 2007/0244192 A1 | 10/2007 | Metz |
| 2007/0245431 A1 | 10/2007 | Metz et al. |
| 2007/0270494 A1 | 11/2007 | Metz et al. |

FOREIGN PATENT DOCUMENTS

| EP | 2 096 177      | 9/2009 |
| EP | 2 199 304      | 6/2010 |
| JP | 2009-529890 A  | 8/2009 |
| WO | 02/09295 A2    | 1/2002 |
| WO | 2006/037947    | 4/2006 |
| WO | 2006/069610    | 7/2006 |
| WO | 2010/115156    | 10/2010 |

OTHER PUBLICATIONS

Office Action issued with respect to Russian Patent App. No. 2012137109/10(060205), issued Dec. 3, 2013.
Office Action issued with respect to Russian Patent App. No. 2012137109/10(060205), issued Apr. 28, 2014, along with an English language translation.
Seiki Takeno et al., Journal of Bioscience and Bioengineering, 100 (6), pp. 617-622 (2005).
Chinese Office Action of 201180007631.0 with mailing date Feb. 13, 2014 with English Translation.
Black et al., "Yeast Acyl-CoA Synthetases at the Crossroads of Fatty Acid Metabolism and Regulation" *Biochimica et Biophysica Acta*, vol. 1771, No. 3, p. 286-298, 2007.
Hortmann et al., "Inhibitory Effect of Undecanoic Acid on the Biosynthesis of Long-chain Fatty Acids in *Mortierella isabellina*" *Appl. Microbiol. Biotechnol.*, vol. 20, No. 2, p. 139-145, 1984.
Sakuradani et al., "Cloning and Elucidation of Properties of Fatty Acid Elongase Gene of an Arachidonic Acid-producing Filamentous Fungus, *Mortierella alpina* 1S-4" 2009 Nendo Japan Society for Bioscience, Biotechnology, and Agrochemistry Kansai Shibu Koenkai Koen Yoshishu, Oct. 30, 2009, p. 107 (E14p), along with an English language translation.
Pei et al., "Mouse Very Long-chain Acyl-CoA Synthetase 3/Fatty Acid Transport Protein 3 Catalyzes Fatty Acid Activation but Not Fatty Acid Transport in MA-10 Cells" *The Journal of Biological Chemistry*, vol. 279, No. 52, p. 54454-54462, 2004.
Pei et al., "The Second Member of the Human and Murine "Bubblegum" Family is a Testis- and Brainstem-specific Acyl-CoA Synthetase" *The Journal of Biological Chemistry*, vol. 281, No. 10, p. 6632-6641, 2006.

(Continued)

*Primary Examiner* — Rebecca Prouty
(74) *Attorney, Agent, or Firm* — Greenblum & Bernstein, P.L.C.

(57) ABSTRACT

The present invention relates to an acyl-CoA synthetase homolog protein from microorganisms of the genus *Mortierella*, a polynucleotide encoding the protein, and so on. The invention provides polynucleotides comprising an acyl-CoA synthetase homolog protein gene from, e.g., *Mortierella alpina*, expression vectors comprising these polynucleotides and transformants thereof, a method for producing lipids or fatty acids using the transformants, food products containing the lipids or fatty acids produced by the method, etc.

9 Claims, 55 Drawing Sheets

(56) References Cited

OTHER PUBLICATIONS

Watkins et al., "Evidence for 26 Distinct Acyl-coenzyme A Synthetase Genes in the Human Genome" *Journal of Lipid Research*, vol. 48, No. 12, p. 2736-2750, 2007.

DiRusso et al., "Functional Domains of the Fatty Acid Transport Proteins: Studies Using Protein Chimeras" *Biochimica et Biophysica Acta*, vol. 1781, No. 3, p. 135-143, 2008.

Shimizu et al., "Metabolic Engineering of Oleaginous Fungus, *Mortierella alpina*" *Bioscience & Industry*, Jul. 1, 2001, vol. 59, No. 7, p. 451-454, along with an English language translation.

Soupene et al., "Mammalian Long-Chain Acyl-CoA Synthetases" *Experimental Biology and Medicine*, vol. 233, No. 5, p. 507-521, 2008.

Database EMBL [Online]EBI; Sep. 26, 2005, XP002727427, accession No. EIE80757.

Database UniParc [Online], XP002741551, Database accession No. UPI00025EDD2A, time-stamped Jun. 30, 2015.

Extended European Search Report issued in EP Patent Application No. 15153586.1, dated Jul. 22, 2015.

Office Action issued in AU Patent Appl. No. 2014202244, issued Aug. 13, 2015.

Extended European Search Report issued in EP Patent Application No. 14157739.5, dated Aug. 1, 2014.

2001  GAGCGGCTGTACTGGTGGACCCCAAAGGGTGAATATGCCCCTTTTGGCGTGGCAGAGAACGAGCAGATCCTGGCAGGACGCGCTCGTCTTTGAGGGATGT
      E  R  L  Y  W  W  T  P  K  G  E  Y  A  P  F  G  V  A  E  N  E  Q  I  L  A  G  R  A  R  L

2101  TTGTGAATGAAGTCATCGGCATGATCATCATCAAAAAAAAAAAAAAAAAA

```
2001  GTTAACAACCAAAGCTGGCCAGGCTGTCCTCAAAGAGCTGATCAAGGCTGCGAAGATGCTGGATTGAAAGCTTTGAGATTCCAAAGCGATCCTCC
       V N N Q S W P G C P Q R A D Q G C E D A G L K A L R F Q S K R S S

2101  TGAATCTGAGGCATTCAGGTCAAAAGCACAAGATGGCCCGGGCTTCAAGATGAAAGACGCCCTGTCCTCAAGGCTTACCGCCAAGAACTGACAGG
       E S E A F R S K A Q D G P G F K M K D A L S S R L T A K N *

2201  GCTCTACAACGAAATCAATCAAAAGGAATCCAAGCTCTAAAAGCAAGCCTTACAACCTGCCGTCCTCCACGGAATTAAAAAAAAGAGAGATATTACT
       L Y N E I N Q K E S K L *

2301  CTGACAGCTAAAAAAAAAAAAAAAAAAAAAAAAA
```

2301 TTTGAGCCCAGCTTCAAGCTGAAGAGAGATGCTGCCAAGAGAAGTATAAGGCGGAAATCGACGGCATGTATGCAGAATGGCTTAATATAAATAATGG
      L  E  P  S  F  K  L  K  R  R  A  A  K  E  R  Y  A  E  I  D  R  M  Y  A  E  I  A

2395 TTGTACTCAATATAAAAAAAA

```
         601                                                                                           700
MaACS-1  MAAIVSKDTMNWDS------------------FAKFALKNLPKYSVRIFIRKVP---EMEITGTFKQRKVELVNEGMDPSKIKDEMLWLDG-HSYRPF
MaACS-2  MAALVLKNSIVQMAGGSQAKFHVDEAALNAFLRDLSKDVVKKLPAYAIRRFLRIAEQ--ELETTGTFKNKKVELKKEGFDLGKVKERLYWTPKGEYAPF
MaACS-9  MAAIVSKSTMDWEK------------------FAAYALKNLPRYSVRIFIRKMP---EMEITGTFKQRKVELVNEGIDPKTIANEMLWLDG-HHYKPF
MaACS-7  AWISTKDGKTVSLEAVQK--------------FCEGKIAH--YKVRRYVVVVESNEFPTTPSGKIQKNVMRELTKAKLQLP-----------
ScFAT1   FAVIKLTDNSLDITAKTKLLN-----------DSLSRLNLPSYAMFLFVKFVDE--IKMTDNHKILKKVYREQKLPKGLDGNDTIFWKNYKRYEVL
ScFAT2   AAIVLKKGEKMTYEELVN--------------FLKKHLAS--FKIRTKVYFVDK--LPKTATGKIQRRVIAETFAKSSRNKSKL-----------

701            726
MaACS-1  KEAEHTRVVSGKARL-----------
MaACS-2  GVAENEQILAGRARL-----------
MaACS-9  KAAEHQRVISGKAKL-----------
MaACS-7  -------------------------
ScFAT1   TAADWEAIDAQTIKL-----------
ScFAT2   -------------------------
```

POLYNUCLEOTIDE ENCODING ACYL-COA SYNTHETASE HOMOLOG AND USE THEREOF

SEQUENCE LISTING

The instant application contains a Sequence Listing which has been submitted electronically in ASCII format and is hereby incorporated by reference in its entirety. Said ASCII copy, created on Sep. 24, 2015, is named P42026_SL.txt and is 294,294 bytes in size.

TECHNICAL FIELD

The present invention relates to a polynucleotide encoding an acyl-CoA synthetase homolog and use thereof.

BACKGROUND ART

Fatty acids containing two or more unsaturated bonds are collectively referred to as polyunsaturated fatty acids (PUFAs) and known to specifically include arachidonic acid (ARA), dihomo-γ-linolenic acid (DGLA), eicosapentaenoic acid (EPA), docosahexaenoic acid (DHA), etc. Some of these polyunsaturated fatty acids cannot be synthesized in the animal body. It is therefore necessary to compensate these polyunsaturated fatty acids as essential amino acids from food.

Polyunsaturated fatty acids are widely distributed; for instance, arachidonic acid can be separated from lipids extracted from the adrenal glands and livers of animals. However, polyunsaturated fatty acids contained in animal organs are only in a small quantity and cannot be obtained sufficiently for large supplies when simply extracted or separated from animal organs. For this reason, microbial techniques have been developed for obtaining polyunsaturated fatty acids by cultivation of various microorganisms. Above all, microorganisms of the genus *Mortierella* are known to produce lipids containing polyunsaturated fatty acids such as arachidonic acid and the like.

Other attempts have also been made to produce polyunsaturated fatty acids in plants. Polyunsaturated fatty acids constitute storage lipids such as triacylglycerols and are known to be accumulated within microorganism mycelia or plant seeds.

Acyl-CoA synthetase (ACS) is an enzyme catalyzing the thioesterification of fatty acids and coenzyme A (CoA) and catalyzes the following reaction.

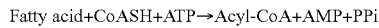

Fatty acid+CoASH+ATP→Acyl-CoA+AMP+PPi

Acyl-CoA produced by ACS is involved in various life phenomena including the biosynthesis and remodeling of lipids, energy production by β-oxidation, acylation of proteins, expression regulation by fatty acids, etc. Furthermore, ACS is reportedly associated with extracellular uptake of fatty acids, intracellular transport of fatty acids, etc. (Non-Patent Documents 1 and 2). In view of the foregoing, it is considered to control the activity of ACS when polyunsaturated fatty acids or the like are produced by utilizing microorganisms or plants.

In the yeast *Saccharomyces cerevisiae* used as a model eukaryote, six (6) acyl-CoA synthetase genes (ScFAA1, ScFAA2, ScFAA3, ScFAA4, ScFAT1 and ScFAT2) are known (Non-Patent Document 1). The proteins encoded by these genes are different in substrate specificity, timing of expression, intracellular localization and function.

Patent Document 1 discloses nine (9) genes as the acyl-CoA synthetase gene (ScACS) derived from *Schizochytrium* sp. Patent Document 1 also discloses an increased production of DPA (n-6) (docosapentanoic acid (n-6)) or DHA when the gene encoding the *Schizochytrium* sp. PUFA synthase system is co-expressed with ScACS, as compared to the case where the co-expression with ScACS is not involved.

In addition, acyl-CoA synthetase genes derived from animals and plants are also reported (Non-Patent Document 2 and Patent Document 2).

[Patent Document 1] Japanese Unexamined Patent Application Publication (Translation of PCT Application) No. 2009-529890
[Patent Document 2] PCT International Publication Pamphlet WO 0209295
[Non-Patent Document 1] B. B. A. 1771, 286-298, 2007
[Non-Patent Document 2] Exp. Biol. Med., 233 (5), 507-521, 2008

DISCLOSURE OF THE INVENTION

Under the foregoing circumstances, it has been desired to isolate a novel gene that increases the amount of the fatty acids produced in a host cell or changes the composition of fatty acids produced, when the gene is expressed in the host cell.

As a result of extensive investigations, the present inventors have succeeded in cloning a gene encoding an ACS homolog of lipid-producing fungus *Mortierella* alpina (hereinafter "*M. alpina*") (MaACS), and accomplished the present invention. That is, the present invention provides the following polynucleotides, proteins, expression vectors, transformants, and a method for producing lipids or lipid compositions and foods, etc. using the transformants, as well as foods produced by the method, etc.

That is, the present invention is characterized as follows.

[1] A polynucleotide according to any one selected from the group consisting of (a) to (e) below:

(a) a polynucleotide comprising any one nucleotide sequence selected from the group consisting of the nucleotide sequences shown by SEQ ID NOs: 1, 6, 11, 16, 21, 26, 31, 36, 41, 46, 51 and 56;

(b) a polynucleotide encoding a protein consisting of any one amino acid sequence selected from the group consisting of the amino acid sequences shown by SEQ ID NOs: 2, 7, 12, 17, 22, 27, 32, 37, 42, 47, 52 and 57;

(c) a polynucleotide encoding a protein consisting of an amino acid sequence wherein 1 to 100 amino acids are deleted, substituted, inserted and/or added in any one amino acid sequence selected from the group consisting of the amino acid sequences shown by SEQ ID NOs: 2, 7, 12, 17, 22, 27, 32, 37, 42, 47, 52 and 57, and having an acyl-CoA synthetase activity or an activity of increasing the amount or changing the composition, of the fatty acids produced in a host cell when expressed in the host cell;

(d) a polynucleotide encoding a protein having an amino acid sequence having at least 60% identity to any one amino acid sequence selected from the group consisting of the amino acid sequences shown by SEQ ID NOs: 2, 7, 12, 17, 22, 27, 32, 37, 42, 47, 52 and 57, and having an acyl-CoA synthetase activity or an activity of increasing the amount or changing the composition, of the fatty acids produced in a host cell when expressed in the host cell; and, (e) a polynucleotide which hybridizes to a polynucleotide consisting of a nucleotide sequence complementary to any one nucleotide sequence selected from the group consisting of the nucleotide sequences shown by SEQ ID NOs: 1, 6, 11, 16, 21, 26, 31, 36, 41, 46, 51 and 56 under stringent conditions, and which encodes a protein having an acyl-CoA synthetase activity or an activity of increasing the amount or changing the composition, of the fatty acids produced in a host cell when expressed in the host cell.

[2] The polynucleotide according to claim 1, which is either one defined in (f) or (g) below:

(f) a polynucleotide encoding a protein consisting of an amino acid sequence wherein 1 to 10 amino acids are deleted, substituted, inserted and/or added in any one amino acid sequence selected from the group consisting of the amino acid sequences shown by SEQ ID NOs: 2, 7, 12, 17, 22, 27, 32, 37, 42, 47, 52 and 57, and having an acyl-CoA synthetase activity or an activity of increasing the amount or changing the composition, of the fatty acids produced in a host cell when expressed in the host cell; and, (g) a polynucleotide encoding a protein having an amino acid sequence having at least 90% identity to any one amino acid sequence selected from the group consisting of the amino acid sequences shown by SEQ ID NOs: 2, 7, 12, 17, 22, 27, 32, 37, 42, 47, 52 and 57, and an acyl-CoA synthetase activity or an activity of increasing the amount or changing the composition, of the fatty acids produced in a host cell when expressed in the host cell.

[3] The polynucleotide according to [1] above, comprising any one nucleotide sequence selected from the group consisting of the nucleotide sequences shown by SEQ ID NOs: 1, 6, 11, 16, 21, 26, 31, 36, 41, 46, 51 and 56.

[4] The polynucleotide according to [1] above, encoding a protein consisting of any one amino acid sequence selected from the group consisting of the amino acid sequences shown by SEQ ID NOs: 2, 7, 12, 17, 22, 27, 32, 37, 42, 47, 52 and 57.

[5] The polynucleotide according to any one of [1] to [4] above, which is a DNA.

[6] A protein encoded by the polynucleotide according to any one of [1] to [5] above.

[7] A vector comprising the polynucleotide according to any one of [1] to [5] above.

[8] A non-human transformant, into which the polynucleotide according to any one of [1] to [5] above, or the vector according to [7] above is introduced.

[9] A method for producing a lipid or fatty acid composition, which comprises collecting the lipid or fatty acid composition from the culture of the transformant according to [8] above.

[10] The method according to [9] above, wherein the lipid is a triacylglycerol.

[11] The method according to [9] above, wherein the fatty acid is a polyunsaturated fatty acid having at least 18 carbon atoms.

[12] A food product, pharmaceutical, cosmetic or soap comprising the lipid or fatty acid composition obtained by the production method according to [9] above.

The polynucleotide of the present invention can be used for transformation of an appropriate host cell. The transformant thus produced can be used to produce fatty acid compositions, food products, cosmetics, pharmaceuticals, soaps, etc.

More specifically, the transformant of the present invention provides an extremely high production efficiency of lipids and fatty acids. Accordingly, the present invention can be effectively used to manufacture pharmaceuticals or health foods which require a large quantity of lipids or fatty acids.

BRIEF DESCRIPTION OF DRAWINGS

Figure 1:
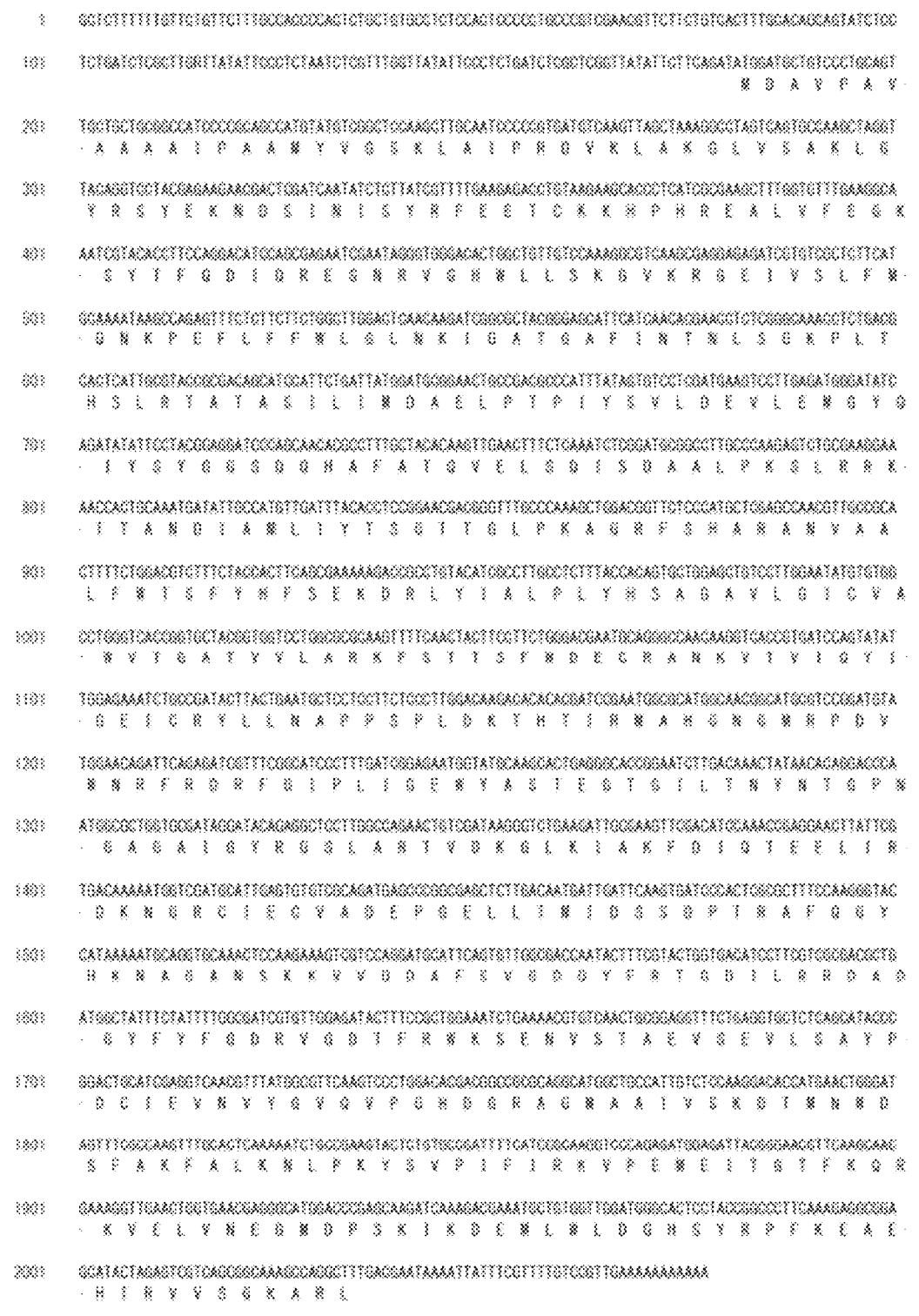

FIG. 1 shows the correspondence between the cDNA sequence of MaACS-1 (SEQ ID NO: 4) and putative amino acid sequence of MaACS-1 (SEQ ID NO: 2).

Figure 2A:
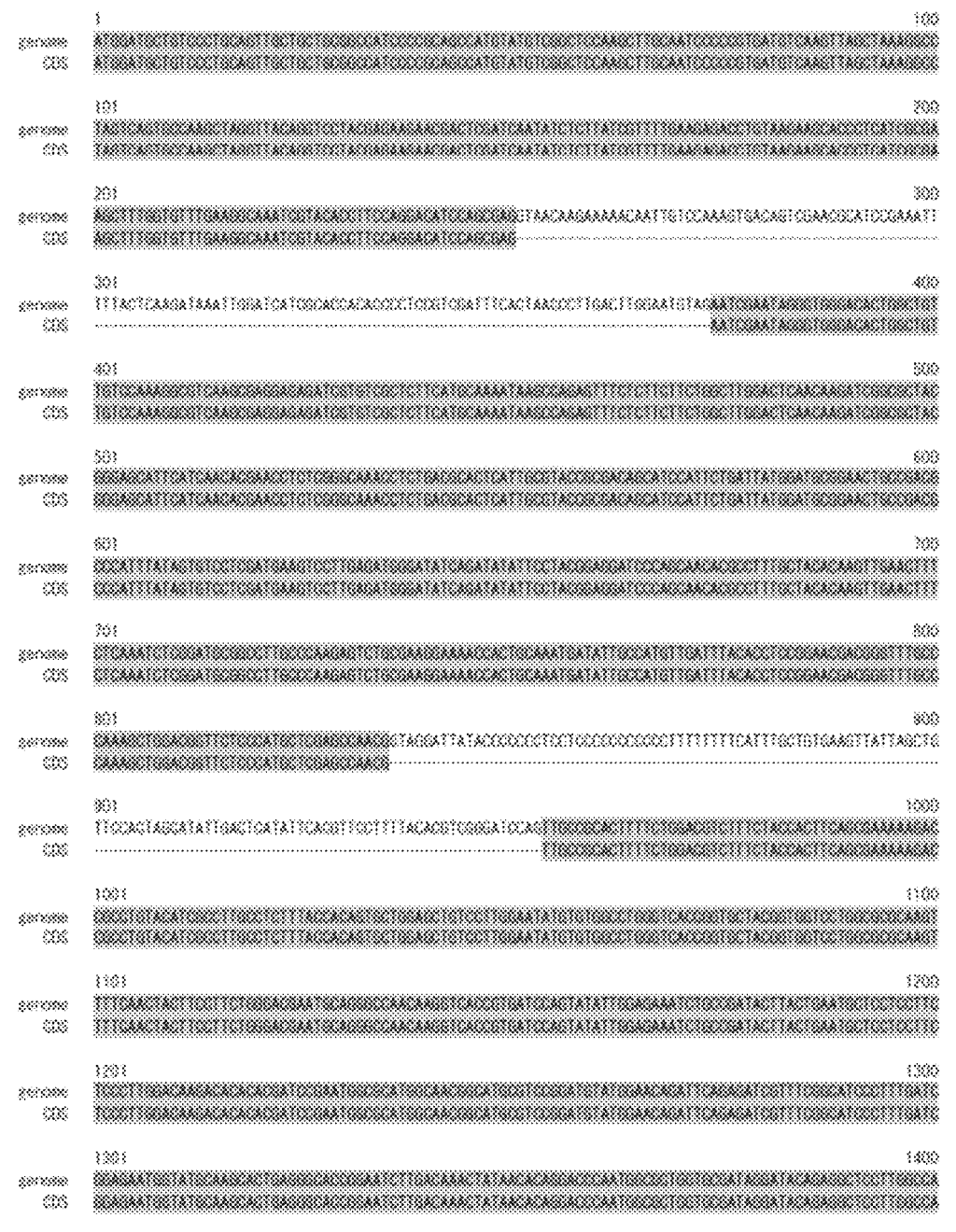

FIG. 2A shows the alignment between the genome sequence of MaACS-1 (SEQ ID NO: 5) and CDS sequence of MaACS-1 (SEQ ID NO: 3).

FIG. 2B is a continuation from FIG. 2A.

Figure 3A:
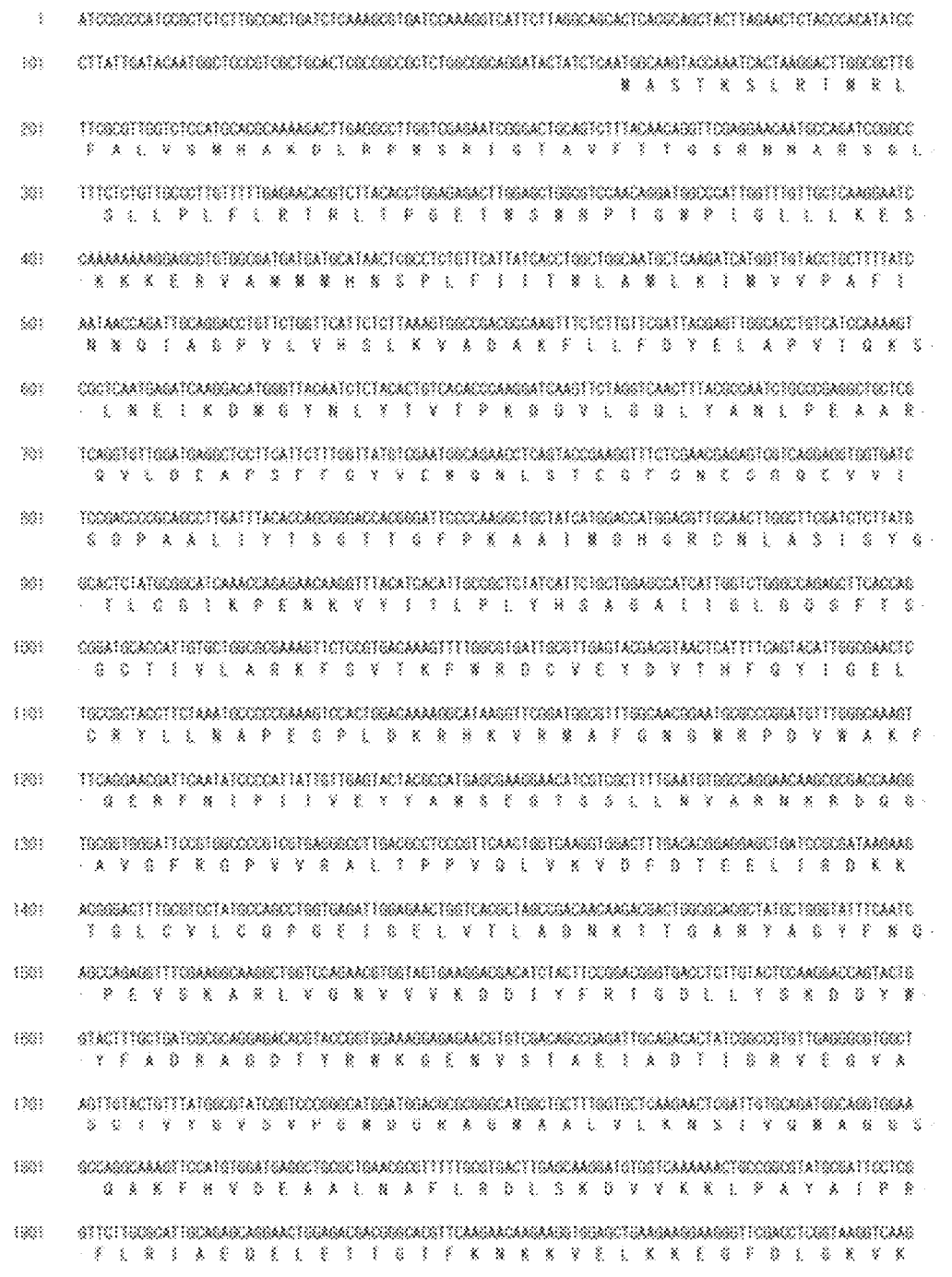

FIG. 3A shows the correspondence between the cDNA sequence of MaACS-2 (SEQ ID NO: 9) and putative amino acid sequence of MaACS-2 (SEQ ID NO: 7).

FIG. 3B is a continuation from FIG. 3A.

Figure 4A:
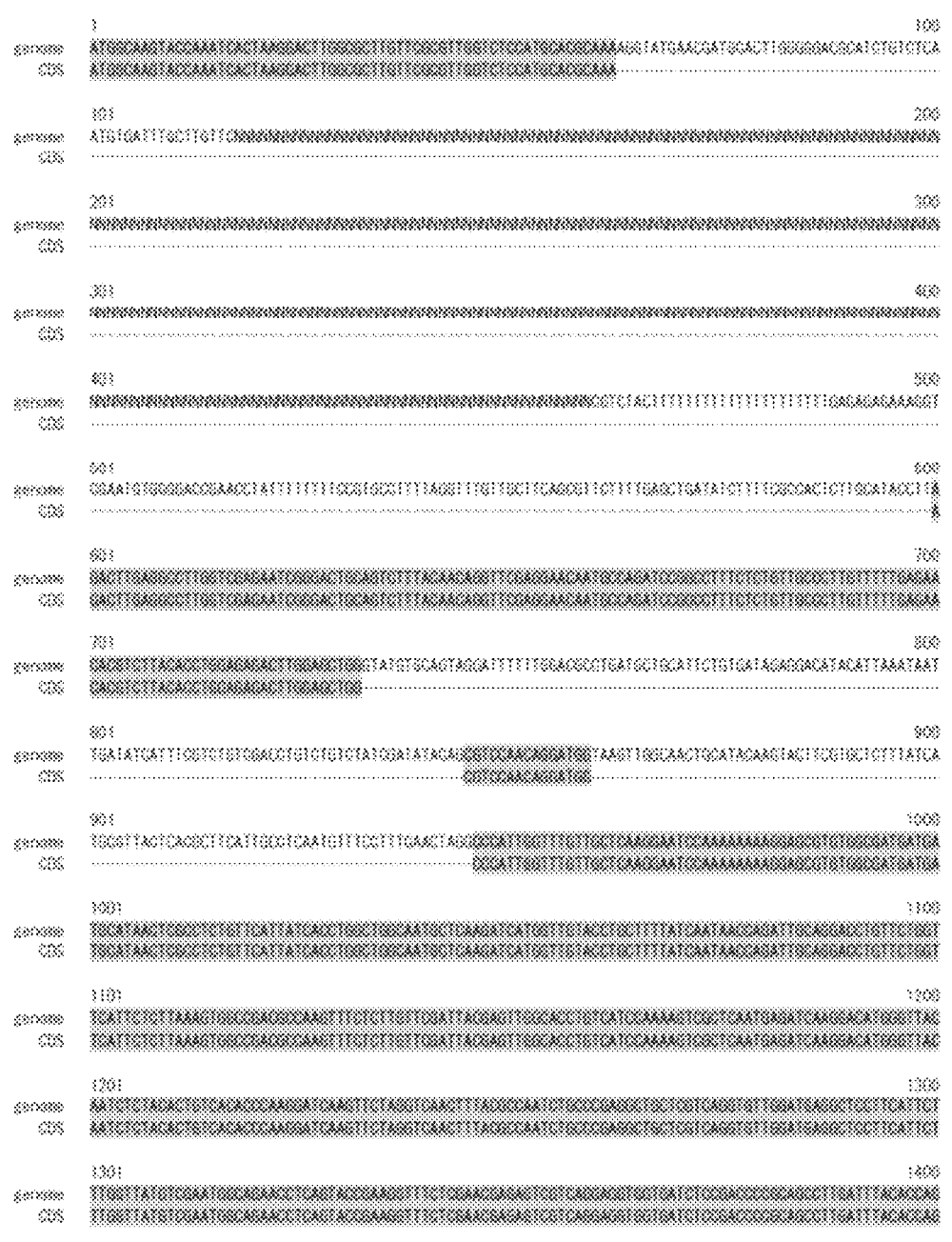
Figure 4B:
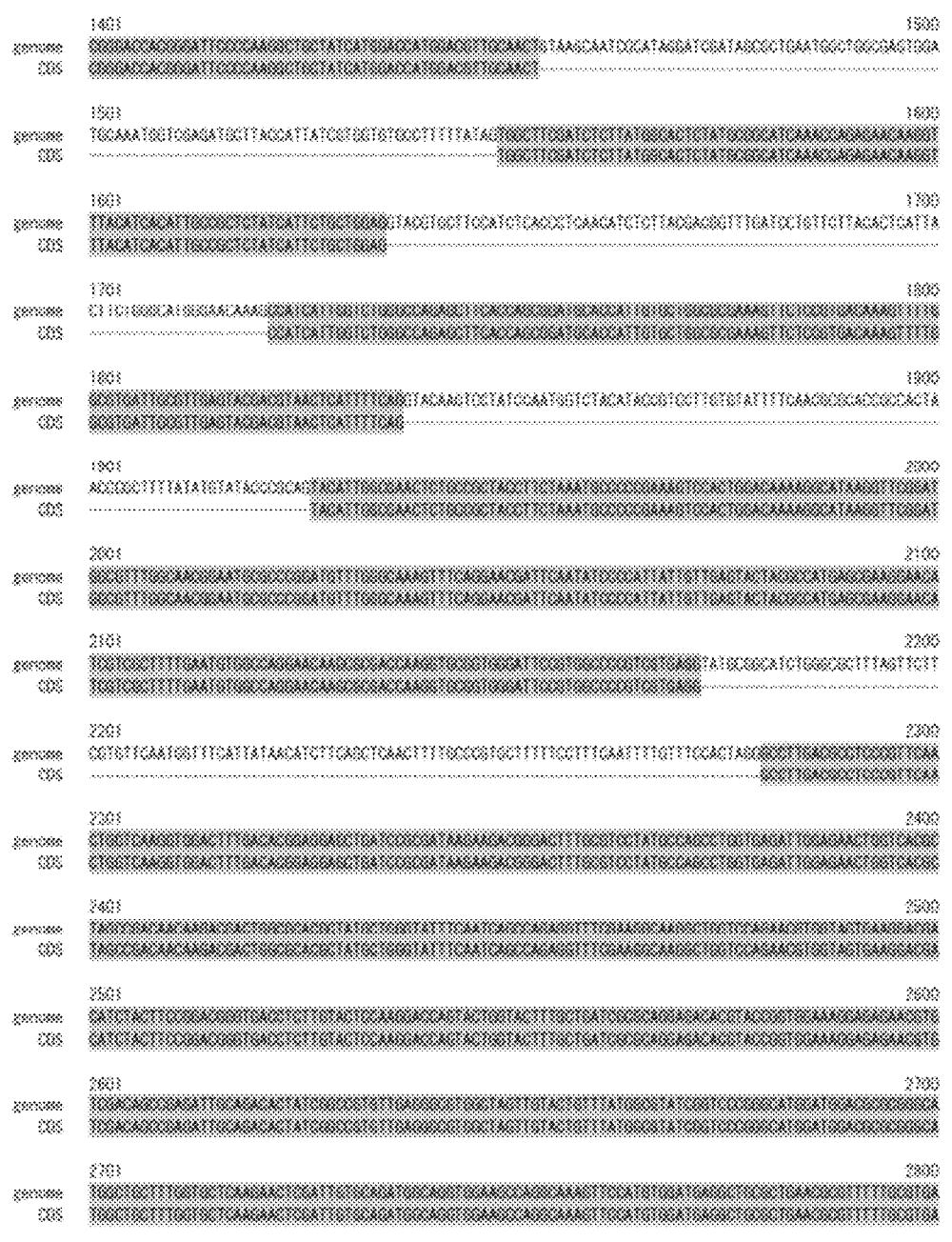

FIG. 4A shows the alignment between the genome sequence of MaACS-2 (SEQ ID NO: 10) and CDS sequence of MaACS-2 (SEQ ID NO: 8).

FIG. 4B is a continuation from FIG. 4A.

Figure 5:
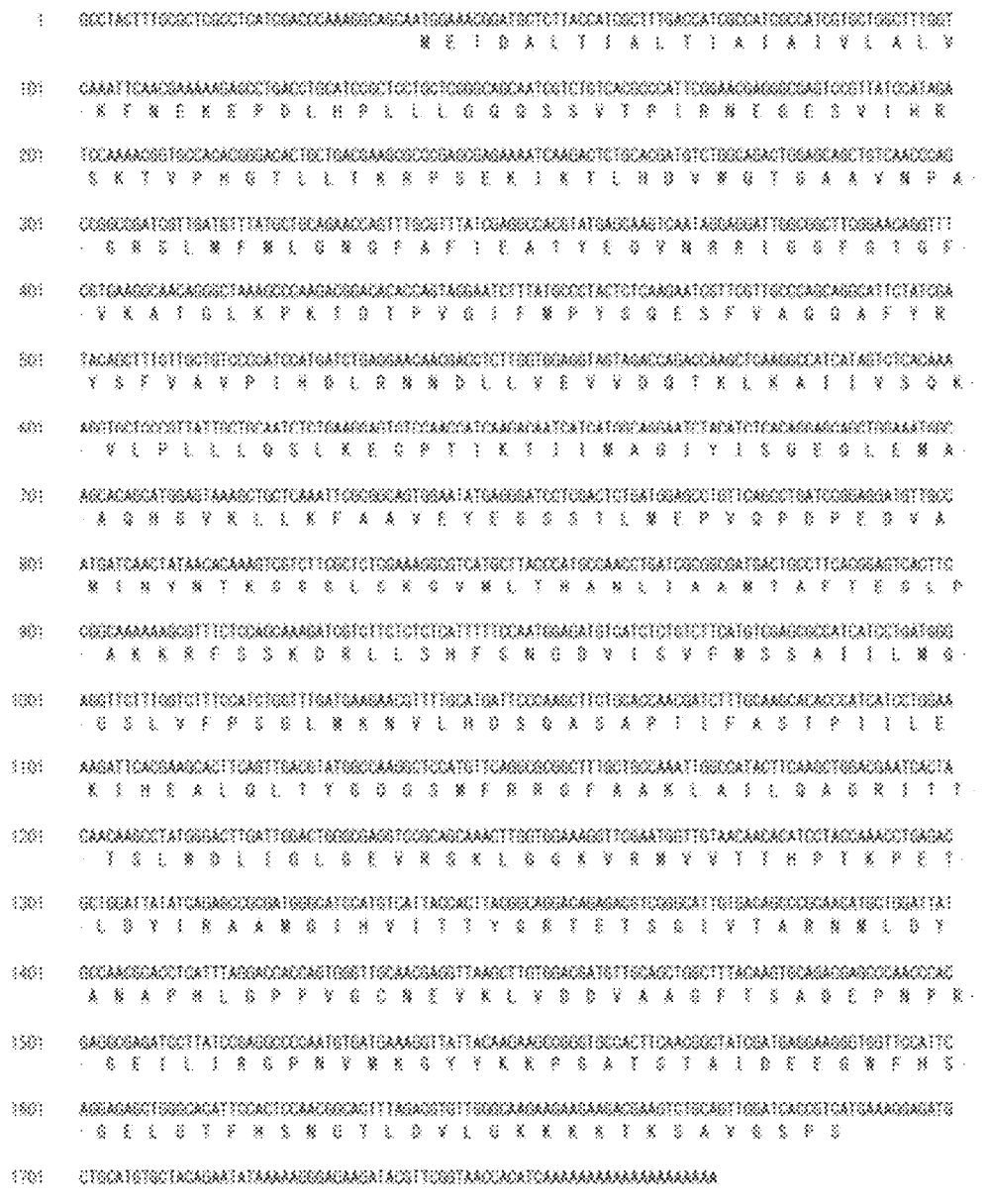

FIG. 5 shows the correspondence between the cDNA sequence of MaACS-3 (SEQ ID NO: 14) and putative amino acid sequence of MaACS-3 (SEQ ID NO: 12).

FIG. 6B is a continuation from FIG. 6A.

Figure 7A:
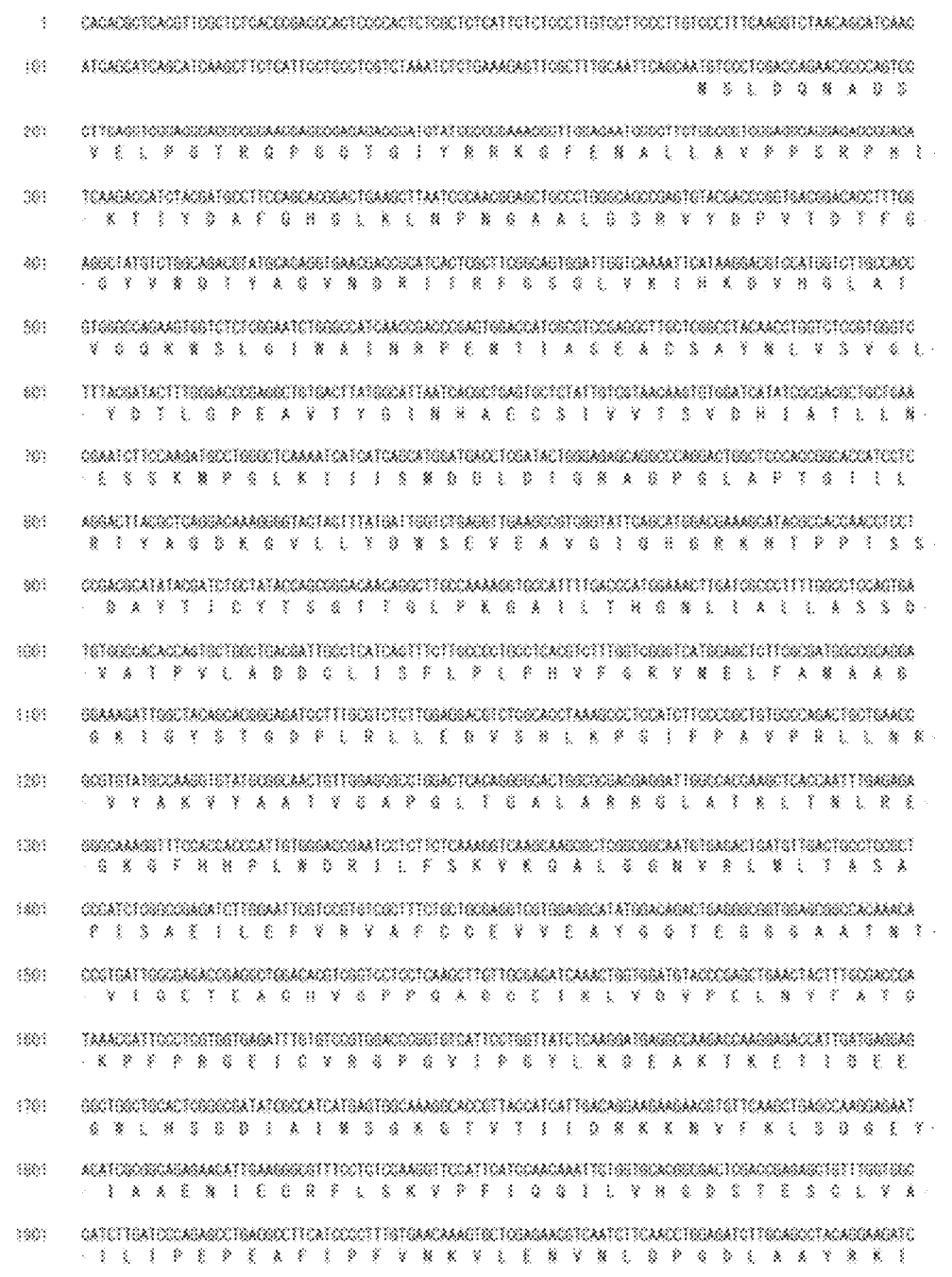

FIG. 7A shows the correspondence between the cDNA sequence of MaACS-4 (SEQ ID NO: 19) and putative amino acid sequence of MaACS-4 (SEQ ID NO: 17).

FIG. 7B is a continuation from FIG. 7A.

Figure 8A:
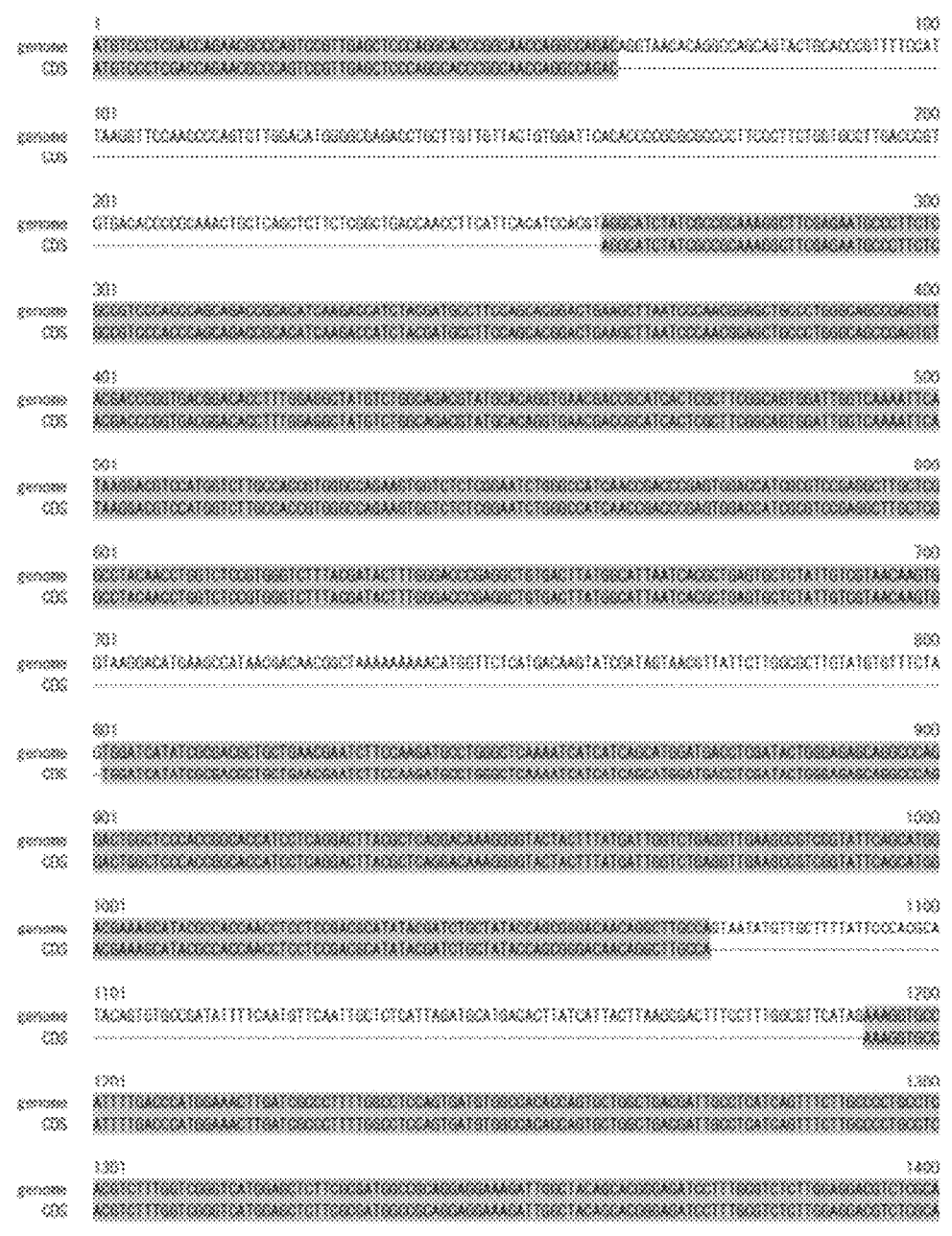
Figure 8B:
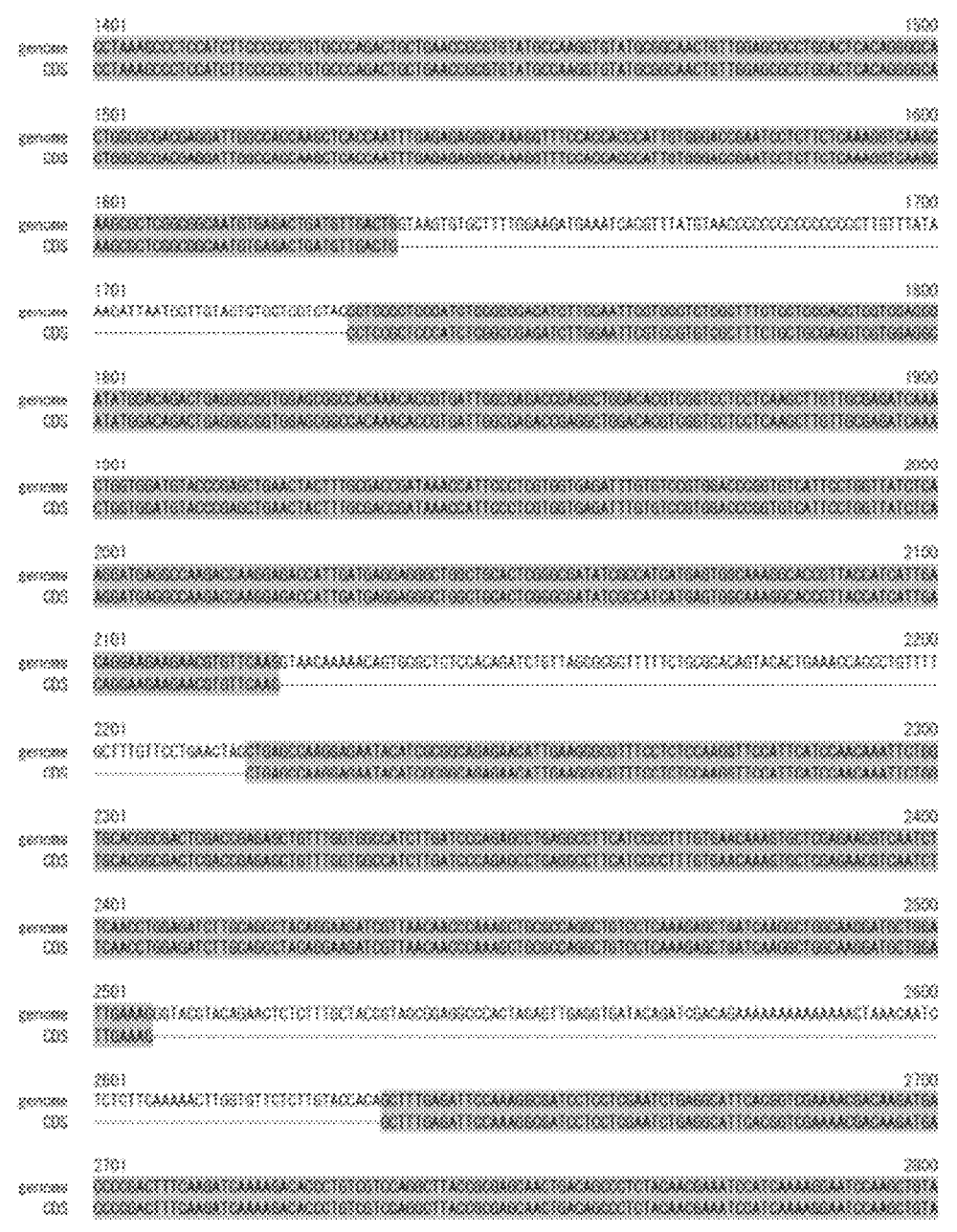

FIG. 8A shows the alignment between the genome sequence of MaACS-4 (SEQ ID NO: 20) and CDS sequence of MaACS-4 (SEQ ID NO: 18).

FIG. 8B is a continuation from FIG. 8A

Figure 9A:
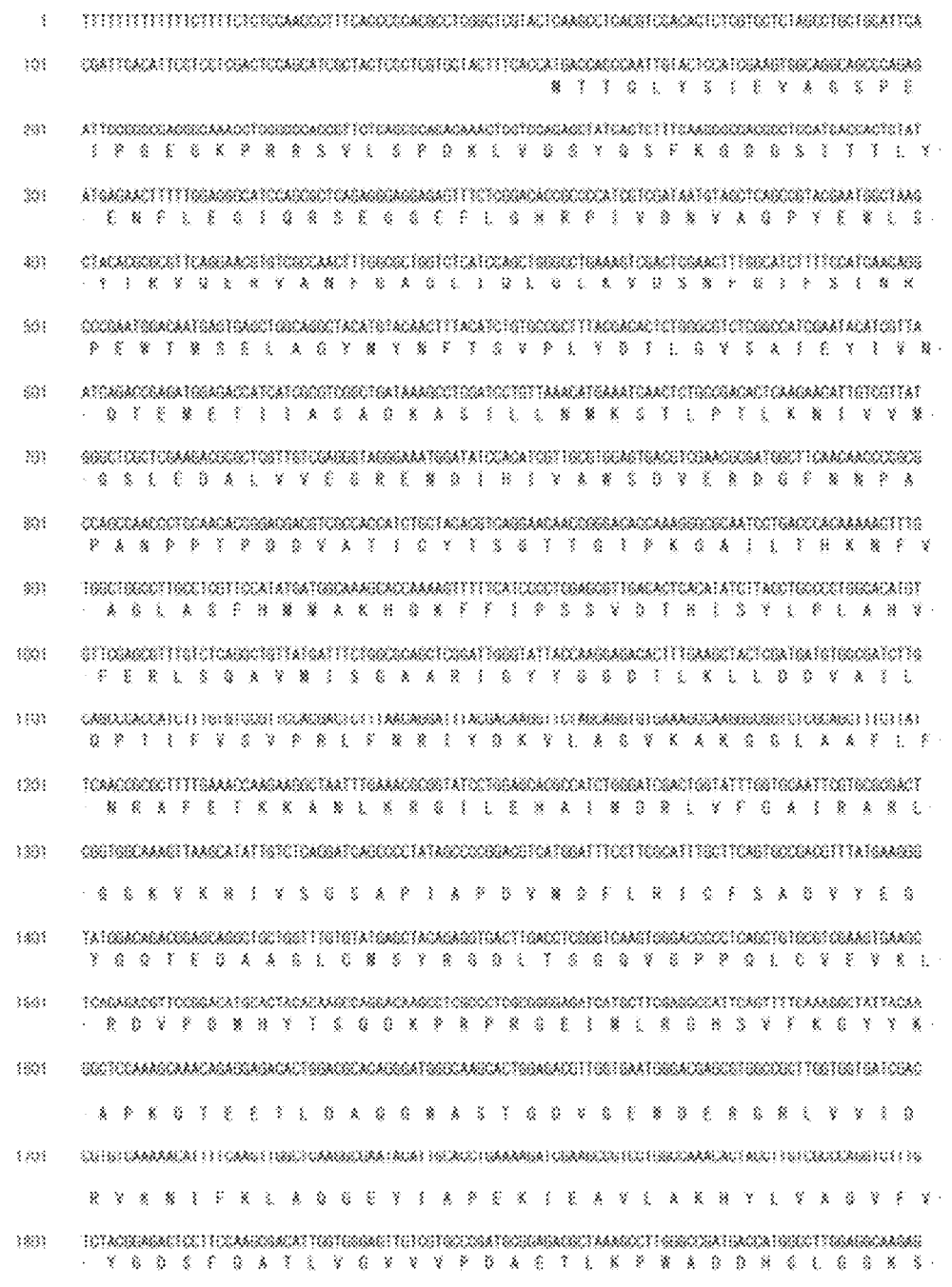
Figure 9B:
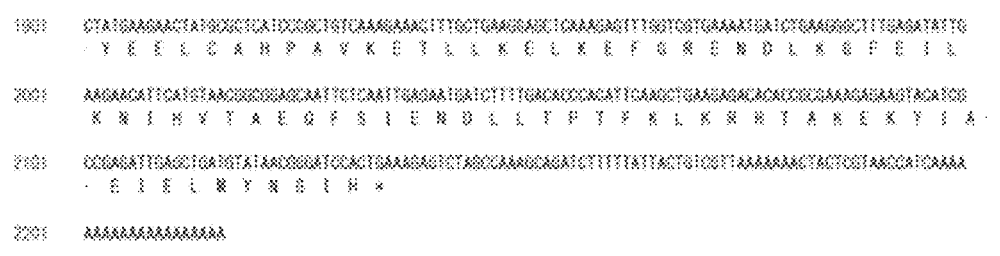

FIG. 9A shows the correspondence between the cDNA sequence of MaACS-5 (SEQ ID NO: 24) and putative amino acid sequence of MaACS-5 (SEQ ID NO: 22).

FIG. 9B is a continuation from FIG. 9A.

Figure 10A:
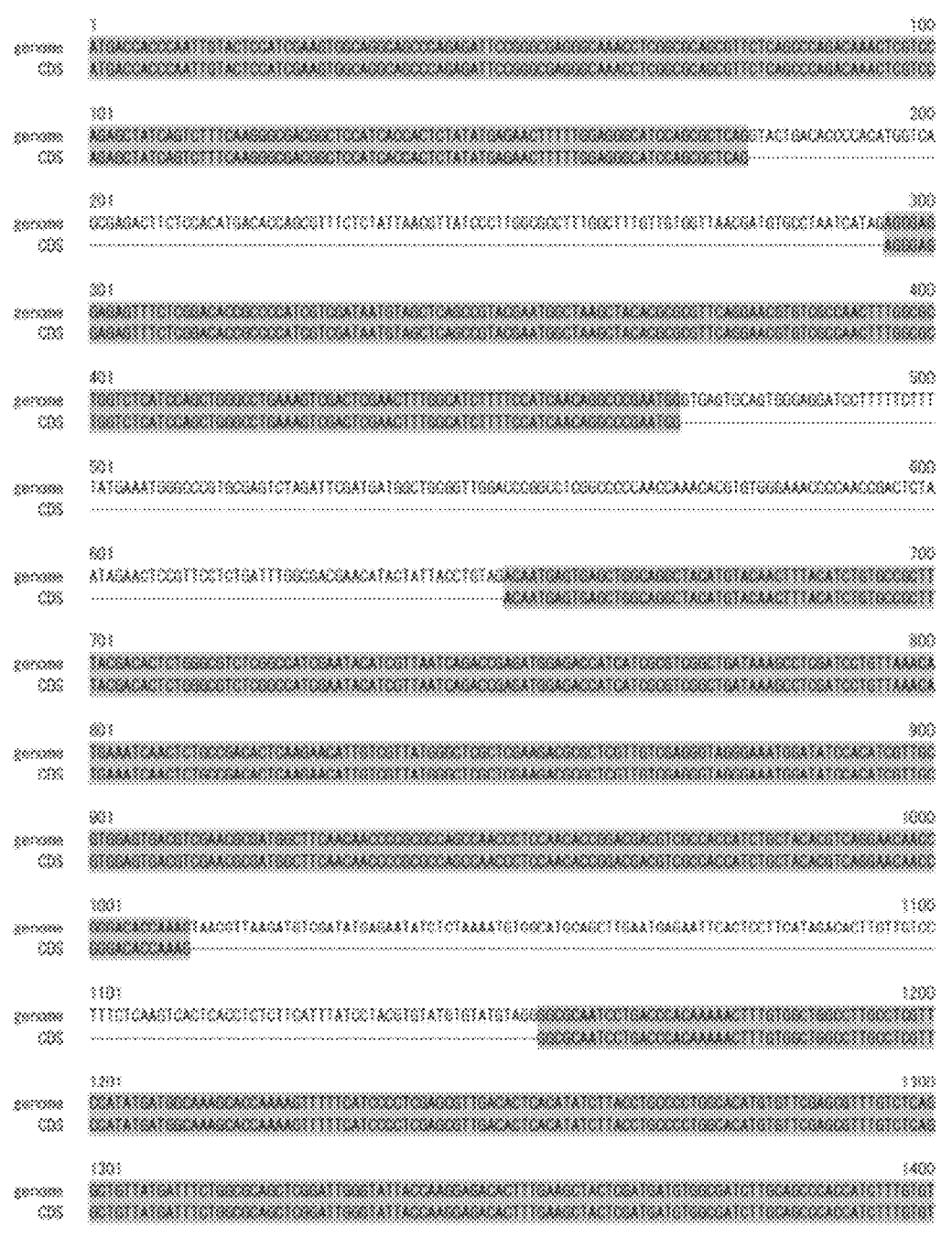
Figure 10B:
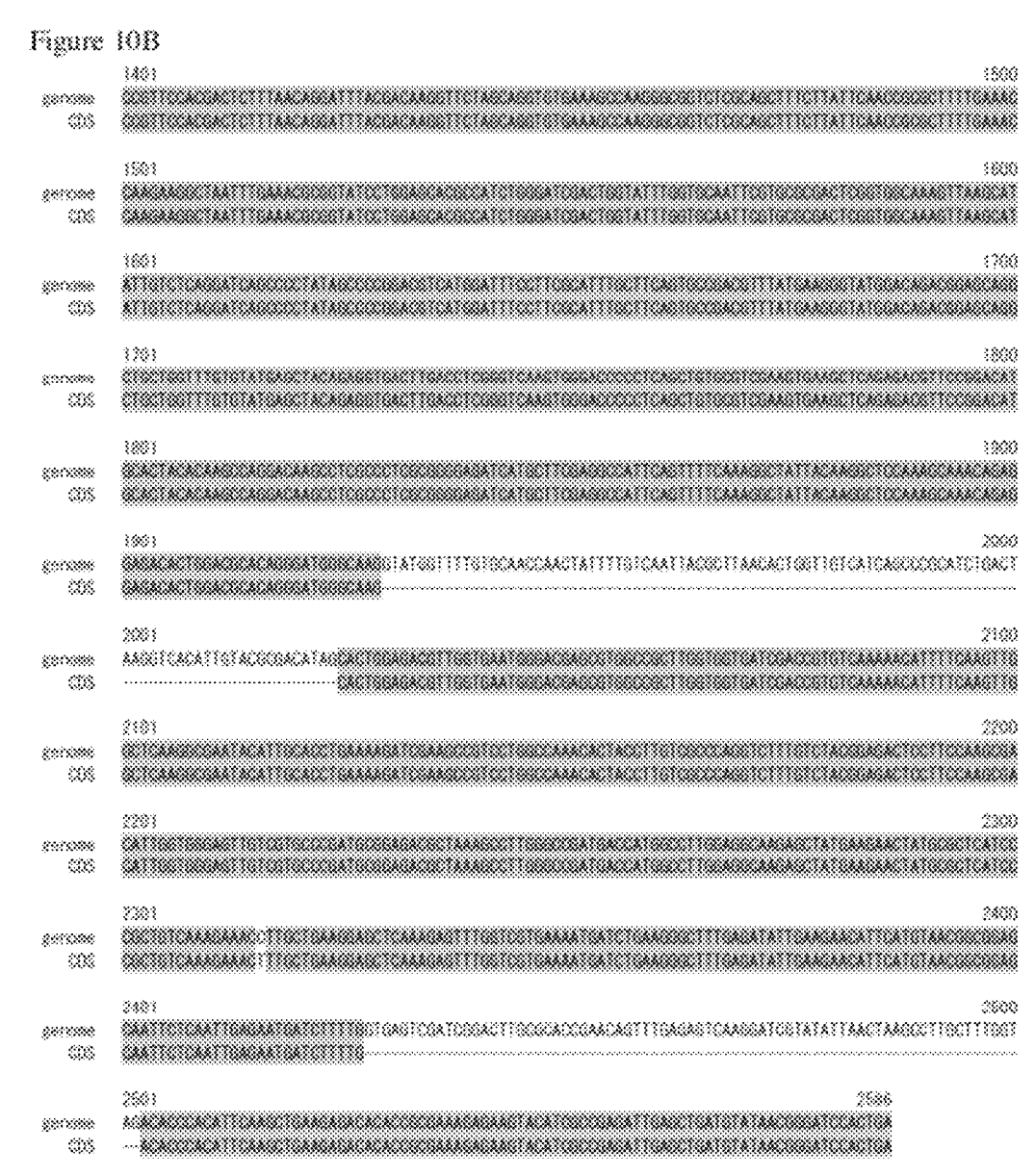

FIG. 10A shows the alignment between the genome sequence of MaACS-5 (SEQ ID NO: 25) and CDS sequence of MaACS-5 (SEQ ID NO: 23).

FIG. 10B is a continuation from FIG. 10A.

Figure 11A:
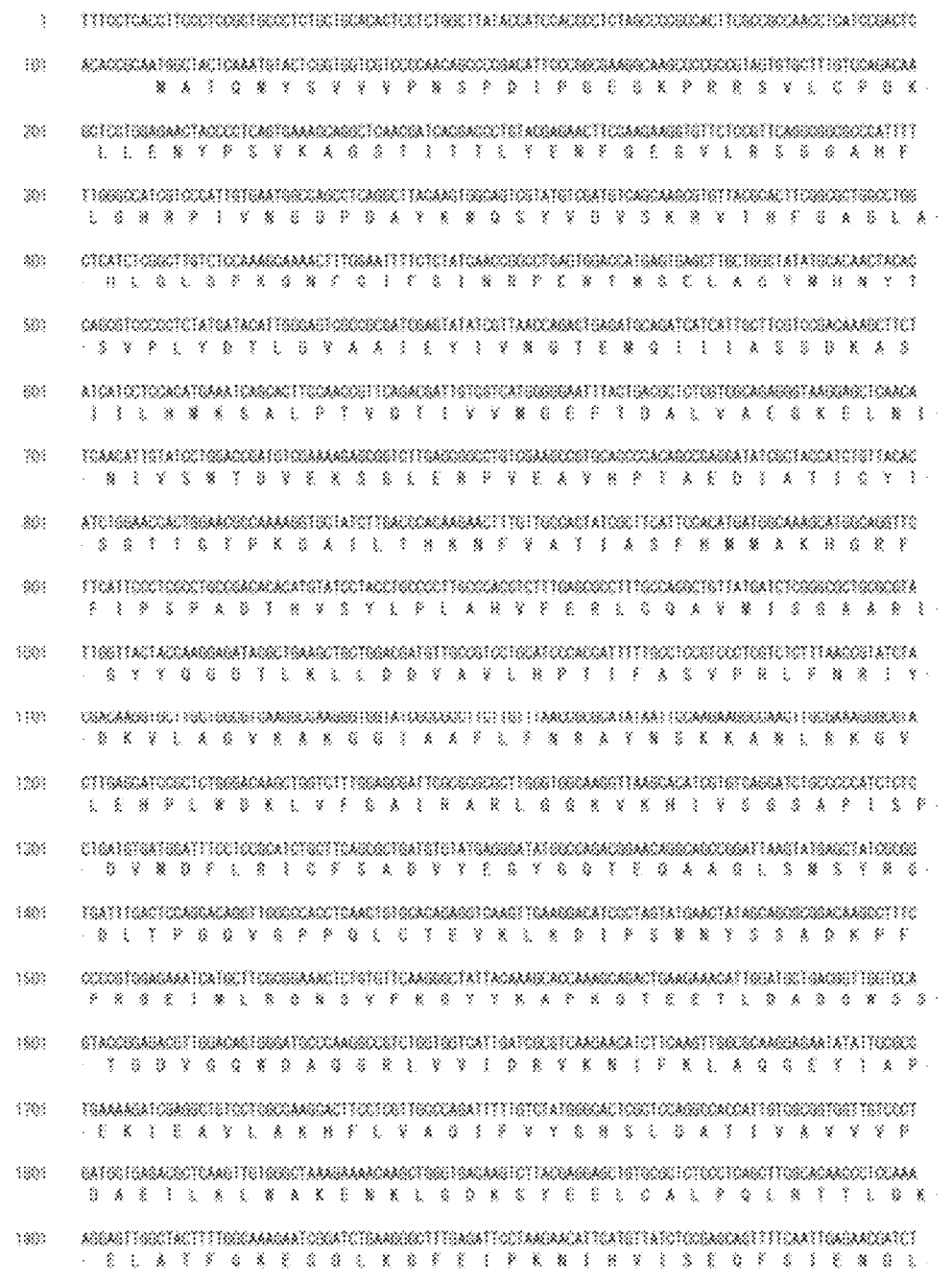

FIG. 11A shows the correspondence between the cDNA sequence of MaACS-6 (SEQ ID NO: 29) and putative amino acid sequence of MaACS-6 (SEQ ID NO: 27).

FIG. 11B is a continuation from FIG. 11A.

Figure 12A:
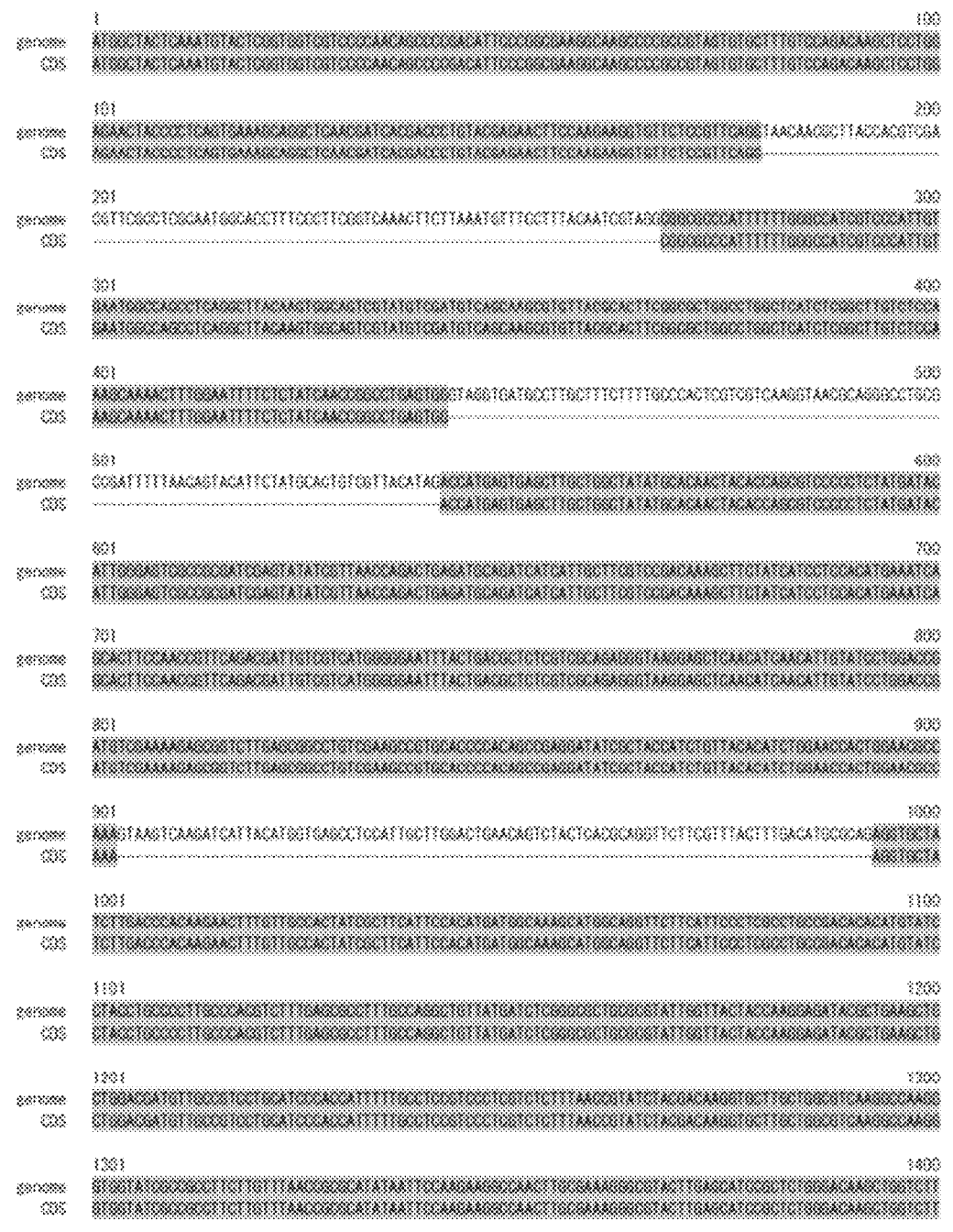
Figure 12B:
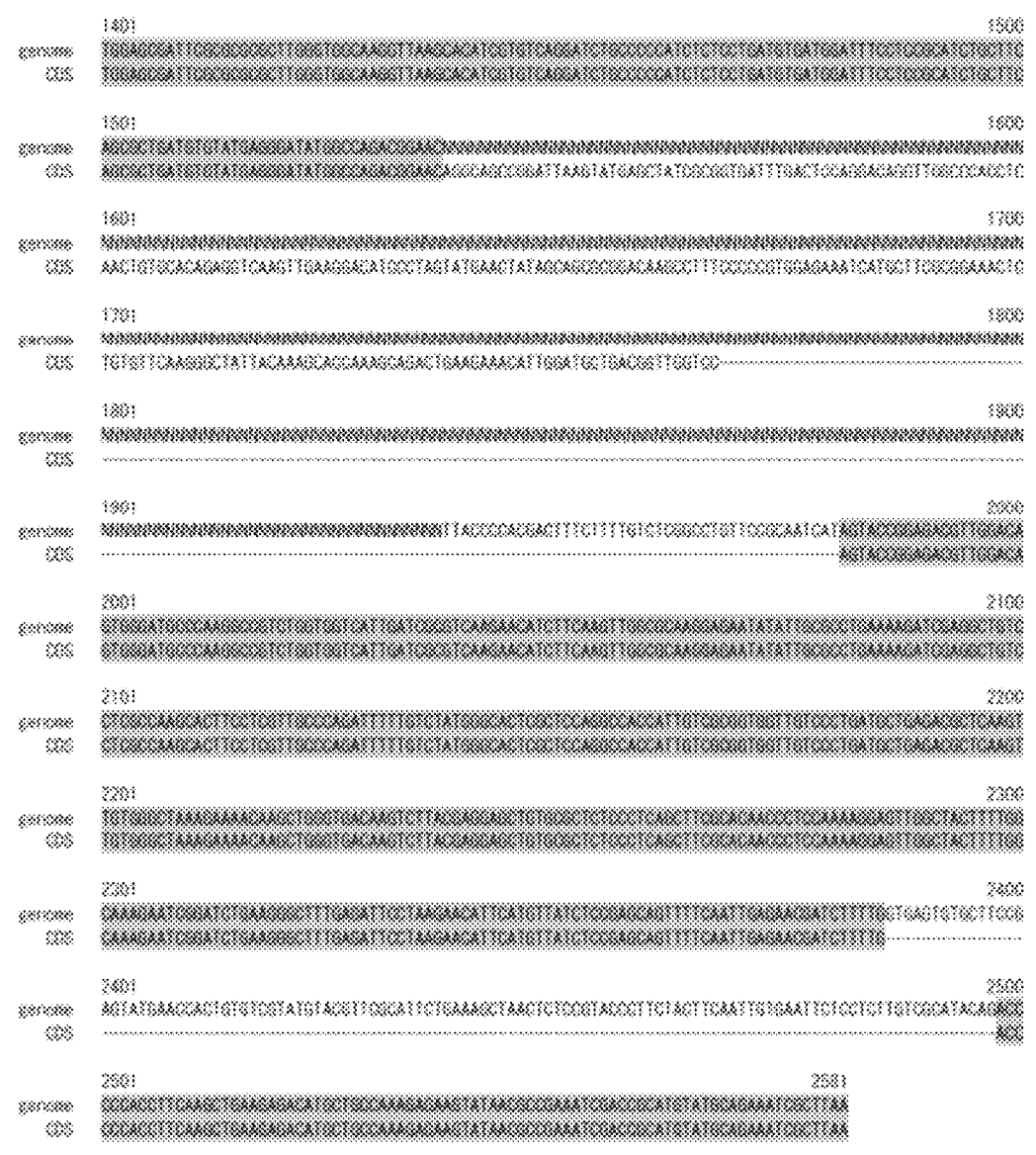

FIG. 12A shows the alignment between the genome sequence of MaACS-6 (SEQ ID NO: 30) and CDS sequence of MaACS-6 (SEQ ID NO: 28).

FIG. 12B is a continuation from FIG. 12A.

Figure 13:
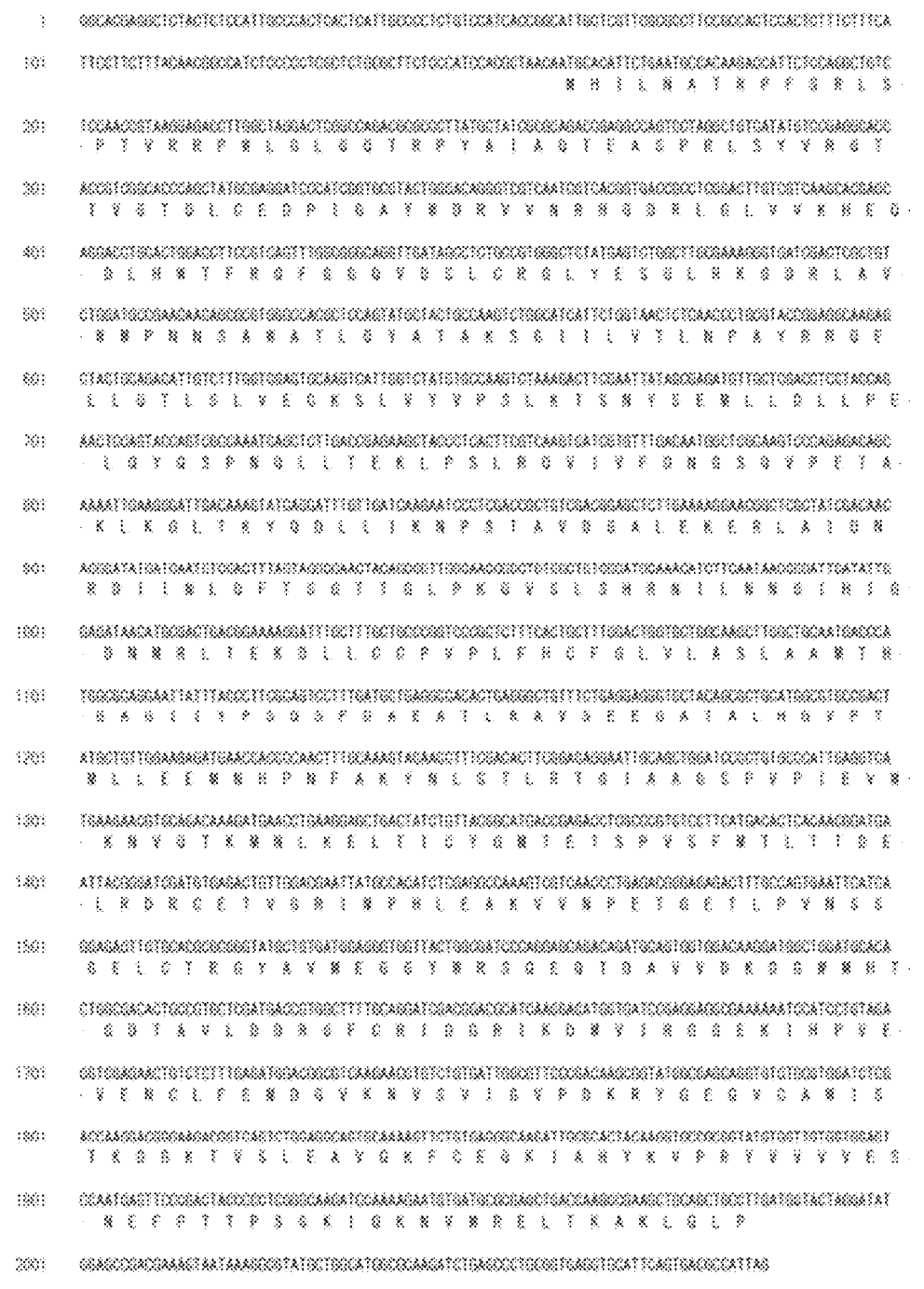

FIG. 13 shows the correspondence between the cDNA sequence of MaACS-7 (SEQ ID NO: 34) and putative amino acid sequence of MaACS-7 (SEQ ID NO: 32).

Figure 14A:
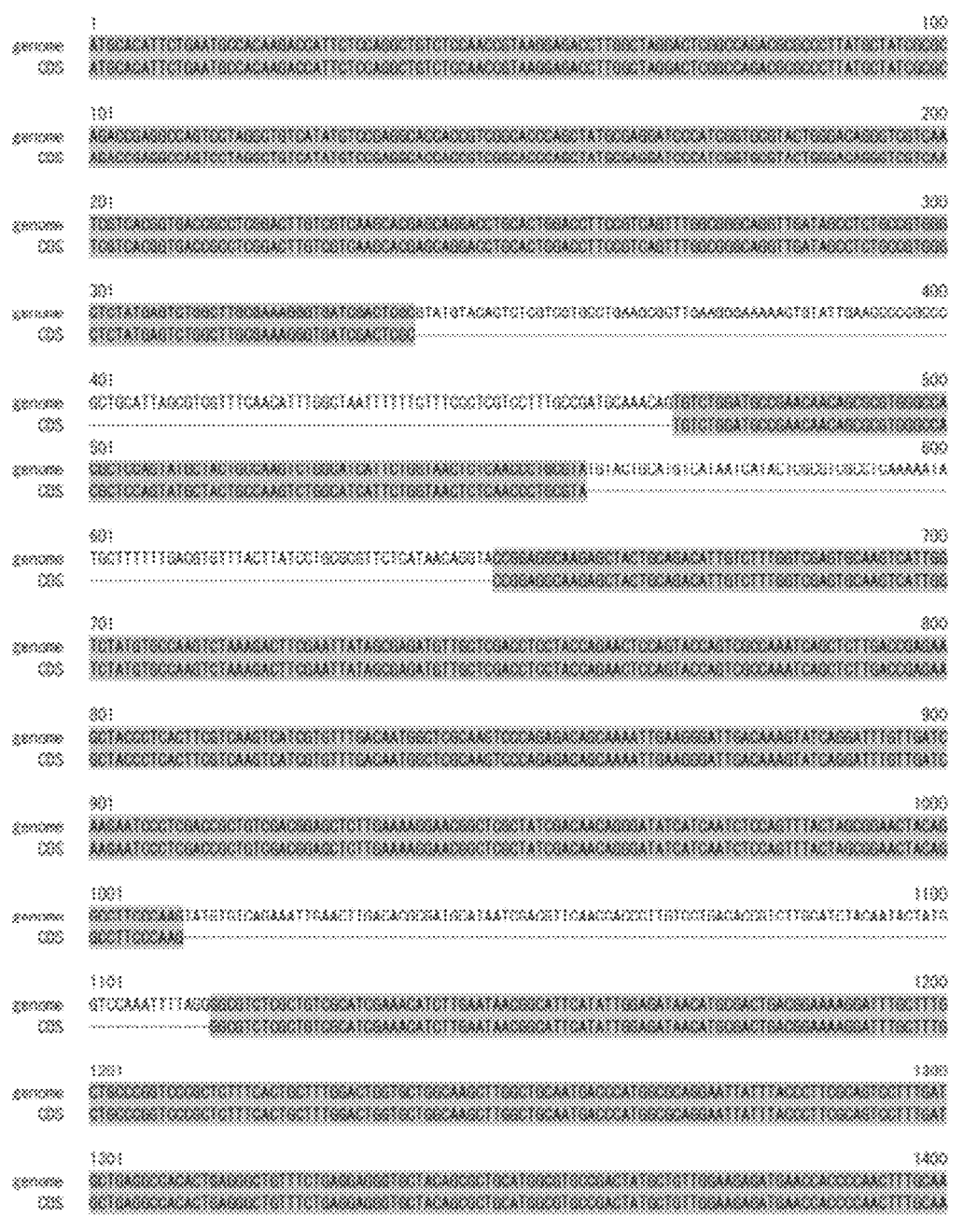

FIG. 14A shows the alignment between the genome sequence of MaACS-7 (SEQ ID NO: 35) and CDS sequence of MaACS-7 (SEQ ID NO: 33).

Figure 15A:
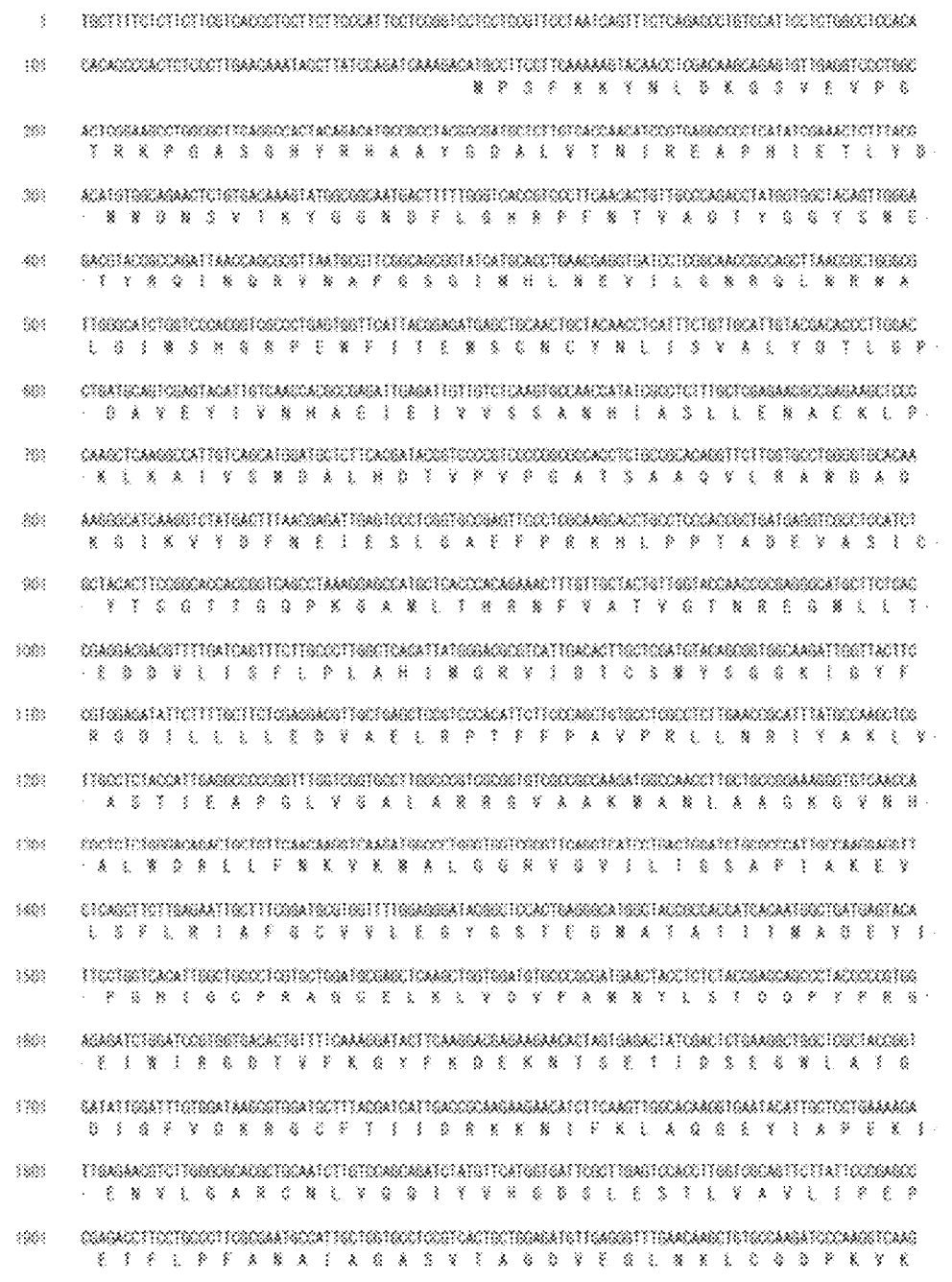
Figure 15B:
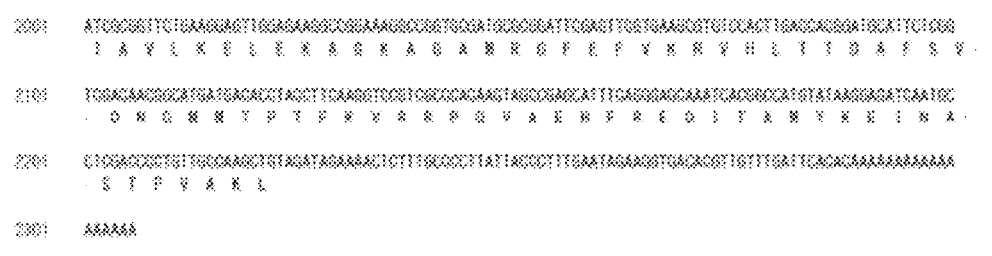

FIG. 15A shows the correspondence between the cDNA sequence of MaACS-8 (SEQ ID NO: 39) and putative amino acid sequence of MaACS-8 (SEQ ID NO: 37).

FIG. 15B is a continuation from FIG. 15A.

Figure 16A:
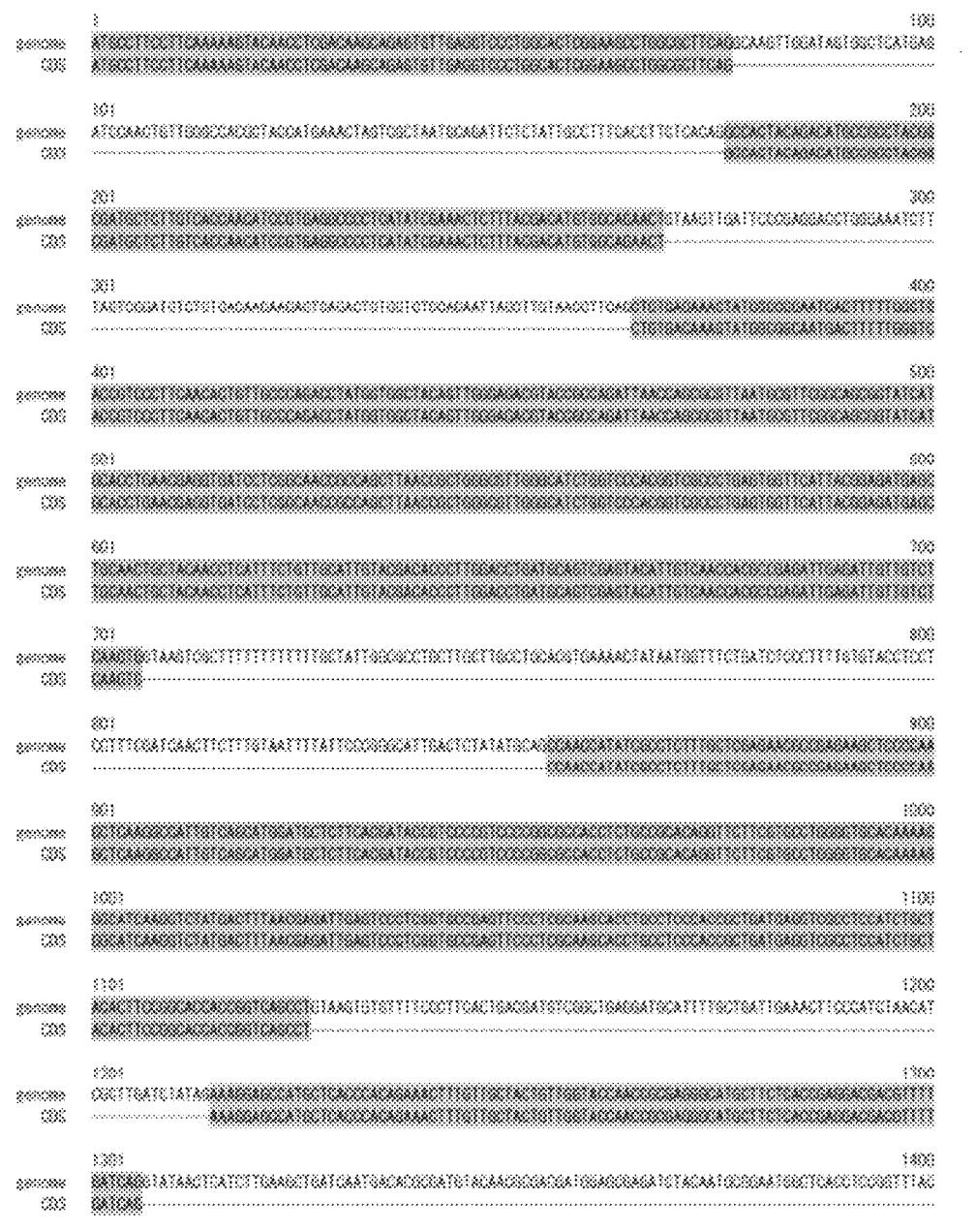
Figure 16B:
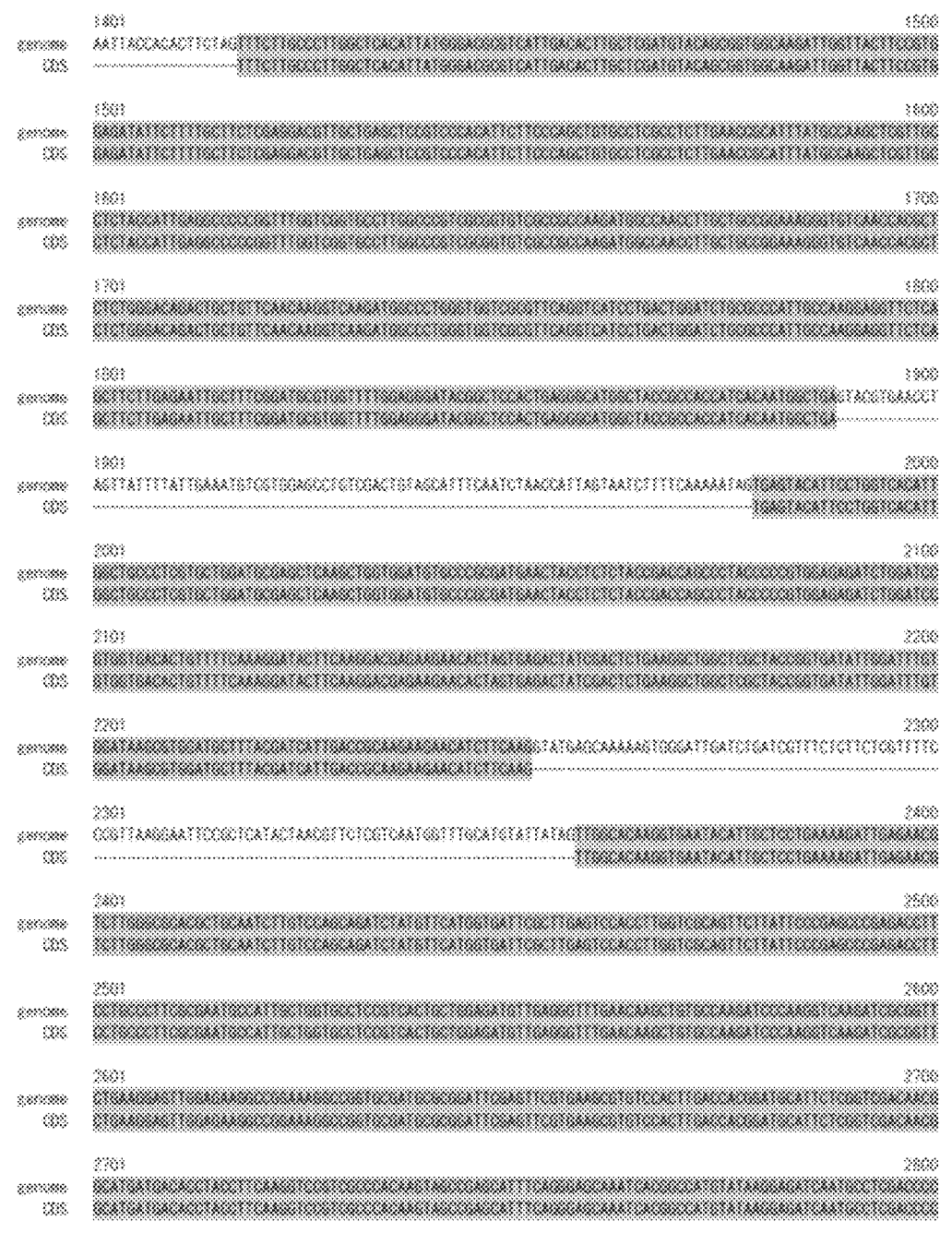

FIG. 16A shows the alignment between the genome sequence of MaACS-8 (SEQ ID NO: 40) and CDS sequence of MaACS-8 (SEQ ID NO: 38).

FIG. 16B is a continuation from FIG. 16A.

FIG. 17 shows the correspondence between the cDNA sequence of MaACS-9 (SEQ ID NO: 44) and putative amino acid sequence of MaACS-9 (SEQ ID NO: 42).

FIG. 18A shows the alignment between the genome sequence of MaACS-9 (SEQ ID NO: 45) and CDS sequence of MaACS-9 (SEQ ID NO: 43).

FIG. 18B is a continuation from FIG. 18A.

FIG. 19A shows the correspondence between the cDNA sequence of MaACS-10 (SEQ ID NO: 49) and putative amino acid sequence of MaACS-10 (SEQ ID NO: 47).

FIG. 19B is a continuation from FIG. 19A.

FIG. 20A shows the alignment between the genome sequence of MaACS-10 (SEQ ID NO: 50) and CDS sequence of MaACS-10 (SEQ ID NO: 48).

FIG. 20B is a continuation from FIG. 20A.

FIG. 21A shows the correspondence between the cDNA sequence of MaACS-11 (SEQ ID NO: 54) and putative amino acid sequence of MaACS-11 (SEQ ID NO: 52).

FIG. 21B is a continuation from FIG. 21A

FIG. 22A shows the alignment between the genome sequence of MaACS-11 (SEQ ID NO: 55) and CDS sequence of MaACS-11 (SEQ ID NO: 53).

FIG. 23A shows the correspondence between the cDNA sequence of MaACS-12 (SEQ ID NO: 59) and putative amino acid sequence of MaACS-12 (SEQ ID NO: 57).

FIG. 23B is a continuation from FIG. 23A

FIG. 24A shows the alignment between the genome sequence of MaACS-12 (SEQ ID NO: 60) and CDS sequence of MaACS-12 (SEQ ID NO: 58).

FIG. 25A shows the alignment between MaACS having relatively high amino acid sequence homology to S. cerevisiae-derived FAA protein (FAA: fatty acid activation) and the FAA protein (SEQ ID NOS: 12, 17, 22, 27, 37, 47, 52, 57, and 124-127, in order of appearance). The single underlined and double underlined sequences denote the ATP-AMP motif and the FACS/VLACS-FATP motif, respectively.

FIG. 25B is a continuation from FIG. 25A.

FIG. 25C is a continuation from FIG. 25B.

FIG. 26A shows the alignment between MaACS having relatively high amino acid sequence homology to S. cerevisiae-derived FAT protein (FAT: fatty acid transferase) and the FAT protein (SEQ ID NOS: 2, 7, 42, 32, and 128-129, in order of appearance). The single underlined and double underlined sequences denote the ATP-AMP motif and the FACS/VLACS-FATP motif, respectively.

FIG. 26B is a continuation from FIG. 26A.

BEST MODE FOR CARRYING OUT THE INVENTION

Figure 4C:
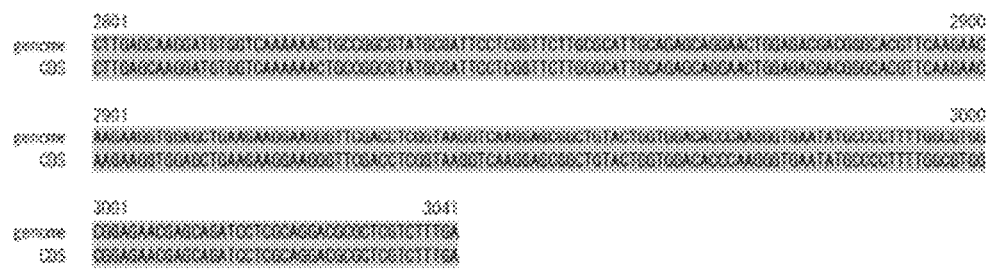
FIG. 4C is a continuation from FIG. 4B.

Hereinafter, the present invention is described in detail. The embodiments described below are intended to be presented by way of example merely to describe the invention but not limited only to the following embodiments. The present invention may be implemented in various ways without departing from the gist of the invention.

All of the publications, published patent applications, patents and other patent documents cited in this application are herein incorporated by reference in their entirety. This application hereby incorporates by reference the contents of the specification and drawings in the Japanese Patent Application (No. 2010-19967) filed Feb. 1, 2010, from which the priority was claimed.

As will be later described in detail in EXAMPLES below, the present inventors have succeeded for the first time in cloning the full-length cDNA of lipid-producing fungus M. alpina -derived ACS homolog genes (MaACS-1~12). The present inventors have also identified the nucleotide sequences of genomic DNAs of MaACS-1~12 from M. alpina and putative amino acid sequences thereof. The ORF sequences, putative amino acid sequences, CDS sequences, cDNA sequences and genome sequences of MaACS-1, 2, 3, 4, 5, 6, 7, 8, 9, 10, 11 and 12 are SEQ ID NOs: 1, 6, 11, 16, 21, 26, 31, 36, 41, 46, 51 and 56 (hereinafter these sequences are collectively referred to as "ORF sequences of MaACS-1~12"), SEQ ID NOs: 2, 7, 12, 17, 22, 27, 32, 37, 42, 47, 52 and 57 (hereinafter these sequences are collectively referred to as "amino acid sequences of MaACS-1~12"), SEQ ID NOs: 3, 8, 13, 18, 23, 28, 33, 38, 43, 48, 53 and 58 (hereinafter these sequences are collectively referred to as "CDS sequences of MaACS-1~12"), SEQ ID NOs: 4, 9, 14, 19, 24, 29, 34, 39, 44, 49, 54 and 59 (hereinafter these sequences are collectively referred to as "cDNA sequences of MaACS-1~12") and SEQ ID NOs: 5, 10, 15, 20, 25, 30, 35, 40, 45, 50, 55 and 60 (hereinafter these sequences are collectively referred to as "genome sequences of MaACS-1~12"), respectively. These polynucleotides and proteins may be obtained by the methods described in EXAMPLES below, known genetic engineering techniques, known methods for synthesis, and so on.

1. Polynucleotide of the Invention

First, the present invention provides the polynucleotide described in any one selected from the group consisting of (a) to (g) below:

(a) a polynucleotide comprising any one nucleotide sequence selected from the group consisting of the ORF sequences of MaACS-1~12;

(b) a polynucleotide comprising any one nucleotide sequence selected from the group consisting of the cDNA sequences of MaACS-1~12;

(c) a polynucleotide encoding a protein consisting of any one amino acid sequence selected from the group consisting of the amino acid sequences of MaACS-1~12;

(d) a polynucleotide encoding a protein consisting of an amino acid sequence wherein 1 to 100 amino acids are deleted, substituted, inserted and/or added in any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell;

(e) a polynucleotide encoding a protein having an amino acid sequence having at least 60% identity to any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell; and, (f) a polynucleotide which hybridizes to a polynucleotide consisting of a nucleotide sequence complementary to any one nucleotide sequence selected from the group consisting of the ORF sequences of MaACS-1~12 under stringent conditions, and which encodes a protein having an acyl-CoA synthetase activity or an activity of increasing the amount and/or changing the composition, of the fatty acids produced in a host cell when expressed in the host cell; and, (g) a polynucleotide which hybridizes to a polynucleotide consisting of a nucleotide sequence complementary to any one nucleotide sequence selected from the group consisting of the cDNA sequences of MaACS-1~12 under stringent conditions, and which encodes a protein having an acyl-CoA synthetase activity or an activity of increasing the amount and/or changing the composition, of the fatty acids produced in a host cell when expressed in the host cell.

As used herein, the term "polynucleotide" means a DNA or RNA.

As used herein, the term "polynucleotide which hybridizes under stringent conditions" refers to a polynucleotide obtained by the colony hybridization method, plaque hybridization method, Southern hybridization method or the like, using as a probe, for example, a polynucleotide consisting of a nucleotide sequence complementary to any one nucleotide sequence selected from the group consisting of the ORF sequences of MaACS-1~12 or any one nucleotide sequence selected from the group consisting of the cDNA sequences of MaACS-1~12, or the whole or part of a polynucleotide consisting of the nucleotide sequence encoding any one amino acid sequence selected from the group consisting of the amino acid sequences of MaACS-1~12. For the methods of hybridization, there are used the methods described in, e.g., "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "stringent conditions" may be any of low stringent conditions, moderate stringent conditions and high stringent conditions. The term "low stringent conditions" are, for example, 5×SSC, 5×Denhardt's solution, 0.5% SDS, 50% formamide at 32° C. The term "moderate stringent conditions" are, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent conditions" are, for example, 5×SSC, 5×Denhardt's solution, 0.5% SDS, 50% formamide at 50° C. or 0.2×SSC, 0.1% SDS at 65° C. Under these conditions, a DNA with higher identity is expected to be obtained efficiently at higher temperatures, though multiple factors are involved in hybridization stringency including temperature, probe concentration, probe length, ionic strength, time, salt concentration and others, and a person skilled in the art may appropriately select these factors to achieve similar stringency.

When commercially available kits are used for hybridization, for example, an Alkphos Direct Labeling and Detection System (GE Healthcare) may be used. In this case, according to the attached protocol, after cultivation with a labeled probe overnight, the membrane is washed with a primary wash buffer containing 0.1% (w/v) SDS at 55° C. to detect the hybridized DNA. Alternatively, in producing a probe based on the nucleotide sequence complementary to any one nucleotide sequence selected from the group consisting of the ORF sequences of MaACS-1~12 or any one nucleotide sequence selected from the group consisting of the cDNA sequences of MaACS-1~12, or based on the entire or part of the nucleotide sequence encoding any one amino acid sequence selected from the group consisting of the amino acid sequences of MaACS-1~12, hybridization can be detected with a DIG Nucleic Acid Detection Kit (Roche Diagnostics) when the probe is labeled with digoxigenin (DIG) using a commercially available reagent (e.g., a PCR Labeling Mix (Roche Diagnostics), etc.).

In addition to those described above, other polynucleotides that can be hybridized include DNAs having 50% or higher, 51% or higher, 52% or higher, 53% or higher, 54% or higher, 55% or higher, 56% or higher, 57% or higher, 58% or higher, 59% or higher, 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the DNA for any one nucleotide sequence selected from the group consisting of the ORF sequences of MaACS-1~12 or for any one nucleotide sequence selected from the group consisting of the cDNA sequences of MaACS-1~12, or with the DNA encoding any one amino acid sequence selected from the group consisting of the amino acid sequences of MaACS-1~12, as calculated by a homology search software, such as FASTA, BLAST, etc. using default parameters.

Identity between amino acid sequences or nucleotide sequences may be determined using FASTA (Science 227 (4693): 1435-1441, (1985)), algorithm BLAST (Basic Local Alignment Search Tool) by Karlin and Altschul (Proc. Natl. Acad. Sci. USA, 87: 2264-2268, 1990; Proc. Natl. Acad. Sci. USA, 90: 5873, 1993). Programs called blastn, blastx, blastp, tblastn and tblastx based on the BLAST algorithm have been developed (Altschul S. F. et al., J. Mol. Biol. 215: 403, 1990). When a nucleotide sequence is sequenced using blastn, the parameters are, for example, score=100 and wordlength=12. When an amino acid sequence is sequenced using blastp, the parameters are, for example, score=50 and wordlength=3. When BLAST and Gapped BLAST programs are used, default parameters for each of the programs are employed.

The polynucleotides of the present invention described above can be obtained by known genetic engineering techniques or known methods for synthesis.

2. Protein of the Invention

The present invention provides the proteins shown below.

(i) A protein encoded by the polynucleotide of any one of (a) to (g) above.

(ii) A protein comprising any one amino acid sequence selected from the group consisting of the amino acid sequences of MaACS-1~12.

(iii) A protein consisting of an amino acid sequence wherein one or more amino acids are deleted, substituted, inserted and/or added in any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell.

(iv) A protein having an amino acid sequence having at least 90% identity to any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell.

The proteins described in (iii) or (iv) above are typically naturally occurring mutants of the protein consisting of any one amino acid sequence selected from the group consisting of the amino acid sequences of MaACS-1~12 and include those proteins which may be artificially obtained using site-directed mutagenesis described in, e.g., "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-

1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the "protein consisting of an amino acid sequence wherein one or several acids are deleted, substituted, inserted and/or added in any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell" includes proteins consisting of an amino acid sequence wherein, e.g., 1 to 100, 1 to 90, 1 to 80, 1 to 70, 1 to 60, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid is/are deleted, substituted, inserted and/or added in any one amino acid sequence selected from the group consisting of the amino acid sequences of MaACS-1~12, and having the acyl-CoA synthetase activity or the activity of increasing the amount and/or changing the composition, of the fatty acids produced in a host cell when expressed in the host cell. In general, the number of deletions, substitutions, insertions, and/or additions is preferably smaller.

Such proteins include a protein having an amino acid sequence having the identity of approximately 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, to any one amino acid sequence selected from the group consisting of the amino acid sequences of MaACS-1~12, and having the diacylglycerol acyltransferase activity. As the identity percentage described above is higher, the protein is preferable in general.

The term deletion, substitution, insertion and/or addition of one or more amino acid residues in the amino acid sequence of the protein of the invention is intended to mean that one or more amino acid residues are deleted, substituted, inserted and/or added at optional and one or more positions in the same sequence. Two or more types of deletions, substitutions, insertions and additions may occur at the same time.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, α-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may also be produced by chemical synthesis methods such as the Fmoc method (fluorenylmethyloxycarbonyl method), the tBoc method (t-butyloxycarbonyl method), etc. In addition, peptide synthesizers available from Advanced Automation Peptide Protein Technologies, Perkin Elmer, Protein Technologies, Perseptive, Applied Biosystems, SHIMADZU Corp., etc. may also be used for the chemical synthesis.

Figure 25A:
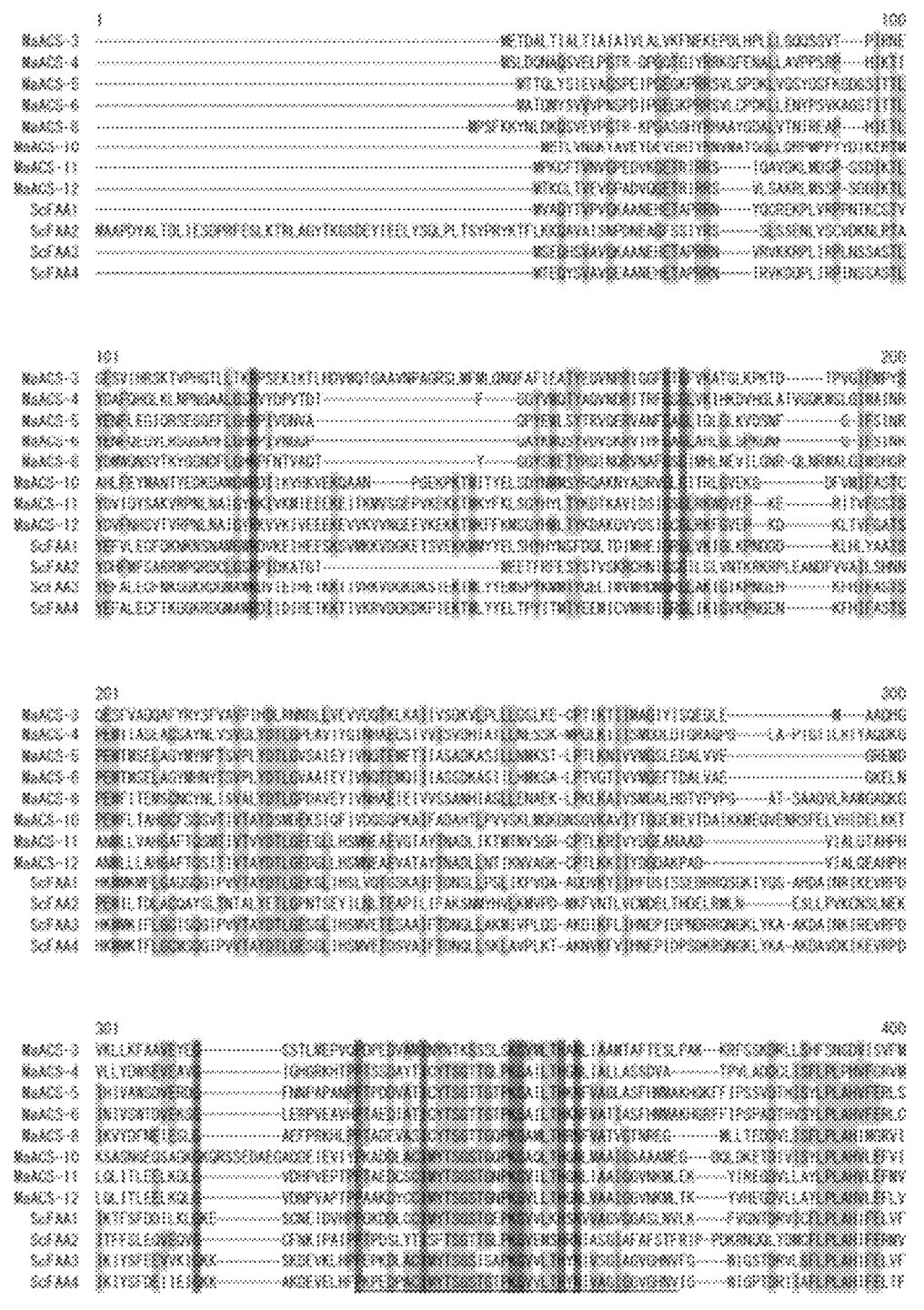
Figure 25B:
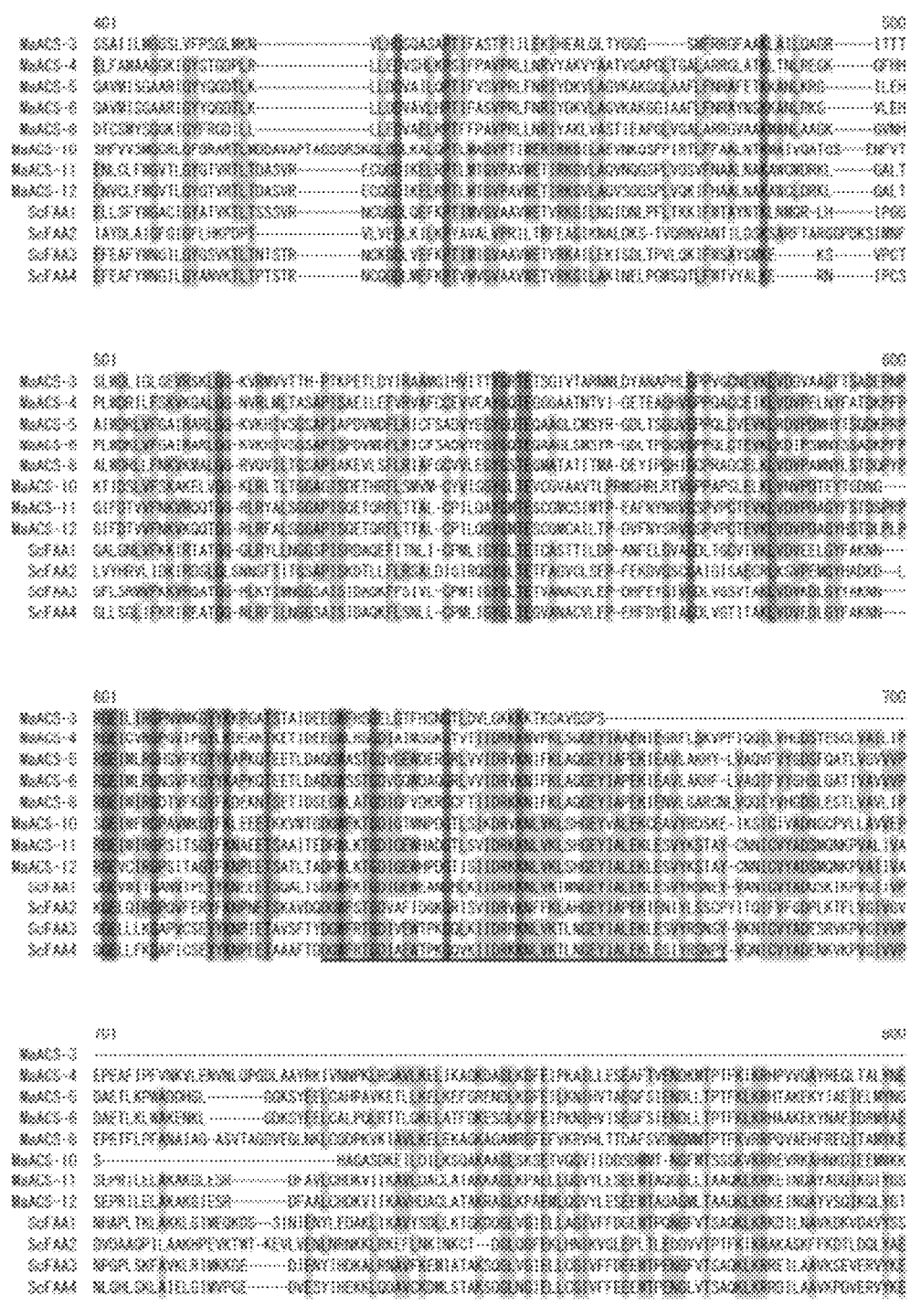
Figure 25C:
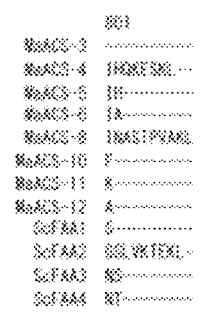
Figure 26A:
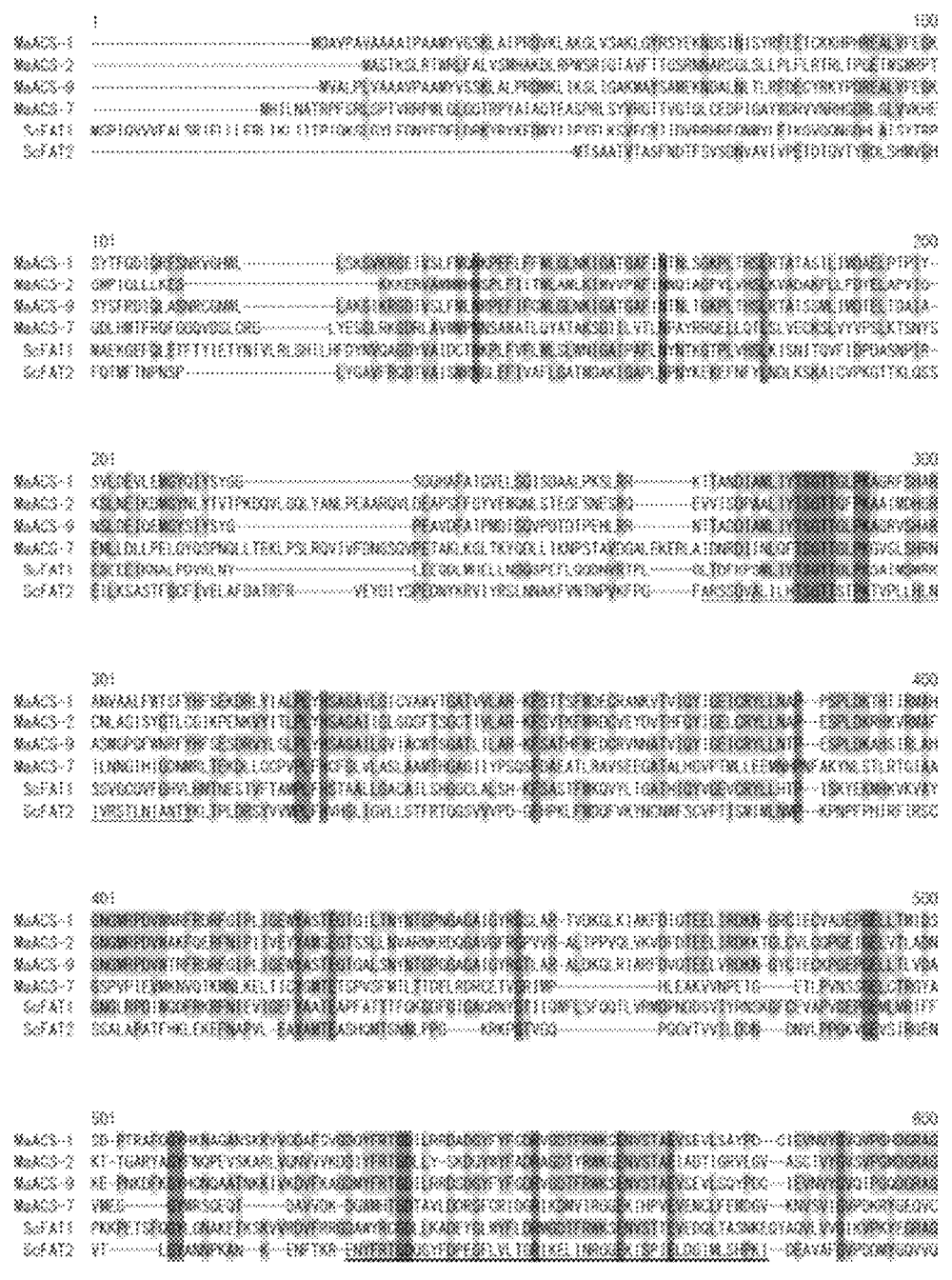

The protein encoded by the polynucleotide of the invention and the protein of the invention are both ACS homolog proteins and considered to have the acyl-CoA synthetase activity since the ATP-AMP motif and FACSNLACS-FATP motif, which are important for the acyl-CoA synthetase activity, are conserved. As used herein, ATP, AMP, FACS, VLACS and FATP are intended to mean adenosine triphosphate, adenosine monophosphate, fatty acyl-CoA synthetase, very long chain acyl-CoA synthetase and fatty acid transport protein, respectively. Specific amino acid sequences of the ATP-AMP motif and FACSNLACS-FATP motif contained in the protein of the present invention are shown in FIGS. 25 and 26 at the single underlined and double underlined sequences, respectively. With regard to representative amino acid sequences of the ATP-AMP motif and FACSNLACS-FATP motif, reference may be made to databases including pfam (http://pfam.sanger.ac.uk/), etc.

As used herein, the term "acyl-CoA synthetase activity (ACS activity)" is intended to mean the activity of promoting the acyl-CoA-forming reaction through formation of a thioester bond between a fatty acid and coenzyme A (chemical reaction equation below).

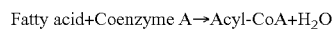

Fatty acid+Coenzyme A→Acyl-CoA+H$_2$O

The acyl-CoA synthetase activity can be quantitatively confirmed, for example, by cultivating for a certain period of time host cells, into which the polypeptide of the present invention is introduced, preparing the lysate of the host cells, mixing the cell lysate with a labeled fatty acid (e.g., polyunsaturated fatty acid labeled with a radioactive isotope, etc.) and coenzyme A, reacting them for a certain period of time, then extracting free fatty acids with n-heptane, and quantifying the fatty acyl-CoA which is formed during the above reaction and remained in the aqueous fraction, using a scintillation counter. For details of the method for confirming the acyl-CoA synthetase activity, reference may be made to Black P. N., et al. (J. B. C., 272 (8), 4896-4903, 1997). Alternatively, the acyl-CoA synthetase activity may also be assayed by the method described in "Evaluation of ACS Activity" of EXAMPLE 2, which involves no radioactive label.

The "activity of increasing the amount of the fatty acids produced in a host cell when expressed in the host cell" is intended to mean the activity that, when the polynucleotide of the present invention or the polynucleotide encoding the protein of the present invention is introduced (transformed) into a host cell and expressed in the host cell, increases the total fatty acid production, as compared to a reference cell (control) derived from the same strain as the host cell in which the polynucleotide described above is not introduced.

The "activity of changing the composition of the fatty acids produced in a host cell when expressed in the host cell" is intended to mean the activity that, when the polynucleotide of the present invention or the polynucleotide encoding the protein of the present invention is introduced (transformed) into a host cell and expressed in the host cell, changes the amount or ratio of various fatty acids produced, as compared to a reference cell (control) derived from the same strain as the host cell in which the polynucleotide described above is not introduced.

As used herein, the term "fatty acid" is intended to mean an aliphatic monocarboxylic acid (a carboxylic acid having one carboxylic residue and carbon atoms connected to each other in a chain) represented by general formula RCOOH (wherein R is an alkyl). The fatty acid includes a saturated fatty acid having no double bond and an unsaturated fatty acid containing a double bond(s) in the hydrocarbon chain. The fatty acid is preferably an unsaturated fatty acid, and more preferably, a polyunsaturated fatty acid containing a plurality of double bonds in the hydrocarbon chain. The polyunsaturated fatty acid includes preferably an unsaturated fatty acid having carbon atoms of 18 or more, e.g., an unsaturated fatty acid having carbon atoms of 18 or 20, and examples include, but not limited to, oleic acid, linoleic acid, linolenic acid (γ-linolenic acid, dihomo-γ-linolenic acid, etc.), arachidonic acid, and the like. The polyunsaturated fatty acids are particularly preferably linoleic acid, γ-linolenic acid, dihomo-γ-linolenic acid and arachidonic acid, more preferably, linoleic acid, dihomo-γ-linolenic acid and arachidonic acid, and most preferably, dihomo-γ-linolenic acid and arachidonic acid.

In the present invention, the "host cell" is not particularly limited so long as the cell is capable of expressing the polynucleotide of the invention when the polynucleotide is introduced. The cells include cells derived from mammals (excluding human), insects, plants, fungi, bacteria, etc., preferably cells from plants and fungi, more preferably, cells from fungi, and most preferably, lipid-producing fungi or yeast.

The lipid-producing fungi which can be used are the lipid-producing fungi described in, e.g., MYCOTAXON, Vol. XLIV, No. 2, pp. 257-265 (1992). Specific examples include, but not limited to, microorganisms belonging to the genus *Mortierella* including microorganisms belonging to the subgenus *Mortierella*, e.g., *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70 and CBS754.68, etc., or microorganisms belonging to the subgenus Micromucor, e.g., *Mortierella isabellina* CBS194.28, IFO6336, IFO7824, IFO7873, IFO7874, IFO8286, IFO8308 and IFO7884, *Mortierella nana* IFO8190, *Mortierella ramanniana* IFO5426, IFO8186, CBS112.08, CBS212.72, IFO7825, IFO8184, IFO8185 and IFO8287, *Mortierella vinacea* CBS236.82, etc. Among others, *Mortierella* alpina is preferable.

Specific examples of the yeast include the genus *Saccharomyces*, the genus *Candida*, the genus *Zygosaccharomyces*, the genus *Pichia* and the genus *Hansenula*, and preferably, *Saccharomyces cerevisiae* in the genus *Saccharomyces*. In wild strains of yeast such as *Saccharomyces cerevisiae*, etc., saturated fatty acids or monovalent fatty acids having mainly 18 or less carbon atoms can be synthesized within the cells, but polyunsaturated fatty acids cannot be synthesized therein. For this reason, when yeast such as *Saccharomyces cerevisiae*, etc. is used as a host cell, it is preferred to impart the ability to synthesize polyunsaturated fatty acids to the yeast cells by genetic engineering, etc. The ability to synthesize polyunsaturated fatty acids can be imparted by introducing a gene encoding a protein derived from an organism that already possesses the ability to synthesize polyunsaturated fatty acids and takes part in fatty acid synthesis.

The "organism that already possesses the ability to synthesize polyunsaturated fatty acids" includes, for example, lipid-producing fungi. Specific examples of the lipid-producing fungi are the same as those given hereinabove.

Examples of the gene encoding a protein derived from an organism that already possesses the ability to synthesize polyunsaturated fatty acids and "gene encoding the protein that takes part in fatty acid synthesis" include, but not limited to, Δ12 fatty acid desaturase gene, Δ6 fatty acid desaturase gene, GLELO fatty acid elongase gene and Δ5 fatty acid desaturase gene, etc. The nucleotide sequences of Δ12 fatty acid desaturase gene, Δ6 fatty acid desaturase gene, GLELO fatty acid elongase gene and Δ5 fatty acid desaturase gene are available by having access to databases including GenBank, etc. For example, in GenBank, Accession No. AB020033, No. AB020032, No. AB193123 and No. AB188307 are entered to access the respective sequences.

The genes for fatty acid synthesis-related proteins described above are inserted into appropriate vectors (e.g., pESC (Stratagene), pYES (Invitrogen), etc.), which are then introduced into yeast by the electroporation method, the spheroplast method (Proc. Natl. Acad. Sci. USA, 75 p1929 (1978)), the lithium acetate method (J. Bacteriology, 153, p163 (1983)), and the methods described in Proc. Natl. Acad. Sci. USA, 75 p1929 (1978), Methods in Yeast Genetics, 2000 Edition: A Cold Spring Harbor Laboratory Course Manual, etc.

Fatty acids can be extracted from the host cells transformed by the polynucleotide of the present invention or the polynucleotide encoding the protein of the present invention in the following manner. A host cell is cultured and then treated in a conventional manner, e.g., by centrifugation, filtration, etc. to obtain cultured cells. The cells are thoroughly washed with water and preferably dried. Drying may be accomplished by lyophilization, air-drying, etc. Depending upon necessity, the dried cells are disrupted using a Dynomil or by ultrasonication, and then extracted with an organic solvent preferably in a nitrogen flow. Examples of the organic solvent include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. Removal of the organic solvent from the extract by distillation under reduced pressure may give fatty acid-containing lipids. The fatty acids extracted may be converted into the methyl esters by the hydrochloric acid methanol method, etc.

The quantity or ratio of various fatty acids may be determined by analyzing the fatty acids extracted as described above using various chromatography techniques. Examples of the chromatography techniques include, but not limited to, high performance liquid chromatography and gas chromatography, and particularly preferably, gas chromatography.

3. Vector of the Invention and Vector-Introduced Transformants

In another embodiment, the present invention further provides the expression vector comprising the polynucleotide of the invention.

The vector of the invention is generally constructed to contain an expression cassette comprising:

(i) a promoter that can be transcribed in a host cell;

(ii) any of the polynucleotides defined in (a) to (g) above that is linked to the promoter; and, (iii) an expression cassette comprising as a component a signal that functions in the host cell with respect to the transcription termination and polyadenylation of RNA molecule.

The vector thus constructed is introduced into a host cell. Examples of host cells which may be appropriately used in the present invention are the same as described above.

In these host cells transformed by the vector of the present invention, the ACS activity is more increased, fatty acids are more produced or the quantity or ratio of various fatty acids contained in the cells are changed, when compared to the host cells which are not transformed by the vector of the present invention.

Examples of the vectors available for introducing into lipid-producing fungi include, but not limited to, pDura5 (Appl. Microbiol. Biotechnol., 65, 419-425, (2004)).

Any vector is available as the vector used to introduce into the yeast and not particularly limited so long as it is a vector capable of expressing the insert in the yeast cells. The vector includes, e.g., pYE22m (Biosci. Biotech. Biochem., 59, 1221-1228, 1995).

Promoters/terminators for regulating gene expression in host cells may be used in an optional combination as far as they function in the host cells. For example, a promoter of the histone H4.1 gene, a promoter of the glyceraldehyde-3-phosphate dehydrogenase, etc. may be used.

As selection markers used for the transformation, there may be utilized auxotrophic markers (ura5, niaD), hygromycin-resistant gene, zeocin-resistant gene, genecitin-resistant gene (G418r), copper-resistant gene (CUP1) (Marin et al., Proc. Natl. Acad. Sci. USA, 81, 337 1984), cerulenin-resistant gene (fas2m, PDR4) (Junji Inokoshi, et al., Biochemistry, 64, 660, 1992; and Hussain et al., Gene, 101: 149, 1991, respectively), and the like.

For the transformation of host cells, generally known methods may be used. In lipid-producing fungi, the transformation may be performed, e.g., by the electroporation method (Mackenzie, D. A. et al., Appl. Environ. Microbiol., 66, 4655-4661, 2000) and the particle delivery method (the method described in JPA 2005-287403 "Method of Breeding Lipid-Producing Fungus"). On the other hand, the electroporation method, the spheroplast method (Proc. Natl. Acad. Sci. USA, 75 p1929 (1978)) and the lithium acetate method (J. Bacteriology, 153 p163 (1983)) as well as the methods described in Proc. Natl. Acad. Sci. USA, 75 p1929 (1978), Methods in yeast genetics, 2000 Edition: A Cold Spring Harbor Laboratory Course Manual, etc) may be used for the transformation of yeast. However, the method for transformation is not limited to those described above.

For general cloning techniques, reference may be made to "Sambrook & Russell, Molecular Cloning: A Laboratory Manual Vol. 3, Cold Spring Harbor Laboratory Press 2001", "Methods in Yeast Genetics, A laboratory manual (Cold Spring Harbor Laboratory Press, Cold Spring Harbor, N.Y.)," etc.

4. Method for Producing the Lipid or Fatty Acid Composition of the Invention

In another embodiment, the present invention further provides a method for preparing a lipid or fatty acid composition which comprises using the transformant described above.

As used herein, the term "lipid" is intended to mean a simple lipid including a compound (e.g., a glyceride) which is composed of a fatty acid and an alcohol attached via an ester linkage, or its analog (e.g., a cholesterol ester), etc.; a complex lipid in which phosphoric acid, amino acid(s), saccharide(s) or the like are bound to a part of the simple lipid; or a derived lipid which is a hydrolysate of the lipid and is insoluble in water.

As used herein, the term "oil and fat" is intended to mean an ester of glycerol and a fatty acid (glyceride).

The term "fatty acid" is the same as defined above.

The method for extracting the lipid or fatty acid composition of the present invention is the same as the method for extracting fatty acids described above.

Fatty acids can be separated from the above fatty acid-containing lipids in a state of mixed fatty acids or mixed fatty acid esters by concentration and separation in a conventional manner (e.g., urea addition, separation under cooling, column chromatography, etc.).

The lipids produced by the method of the present invention include preferably unsaturated fatty acids, and more preferably, polyunsaturated fatty acids. Preferred examples of the polyunsaturated fatty acids are unsaturated fatty acids having 18 or more carbon atoms, e.g., unsaturated fatty acids having 18 to 20 carbon atoms, and include, but not limited to, oleic acid, linoleic acid, linolenic acid (γ-linolenic acid and dihomo-γ-linolenic acid, etc.), arachidonic acid, etc. Particularly preferred polyunsaturated fatty acids are linoleic acid, γ-linoleic acid, dihomo-γ-linoleic acid and arachidonic acid, more preferably, linoleic acid, dihomo-γ-linoleic acid and arachidonic acid, and most preferably, dihomo-γ-linolenic acid and arachidonic acid.

The lipids produced by the method of the present invention and the composition of the fatty acids contained in the lipids may be confirmed by the lipid extraction method or fatty acid separation method described above, or a combination thereof.

The lipid or fatty acid composition obtained by the production method of the present invention can be provided for use in producing, e.g., food products, pharmaceuticals, industrial materials (raw materials for cosmetics, soaps, etc.), which contain oils and fats, in a conventional manner.

In a still other embodiment, the present invention provides a method for preparing food products, cosmetics, pharmaceuticals, soaps, etc. using the transformant of the present invention. The method involves the step of forming lipids or fatty acids using the transformant of the present invention.

Food products, cosmetics, pharmaceuticals, soaps, etc. containing the lipids or fatty acids produced are prepared in a conventional manner. As such, the food products, cosmetics, pharmaceuticals, soaps, etc. produced by the method of the present invention contain the lipids or fatty acids produced using the transformant of the present invention. The present invention further provides the food products, cosmetics, pharmaceuticals, soaps, etc. produced by such a method.

The form of the cosmetic (composition) or pharmaceutical (composition) of the present invention is not particularly limited and may be any form including the state of a solution, paste, gel, solid or powder. The cosmetic composition or pharmaceutical composition of the present invention may also be used as cosmetics or topical agents for the skin, including an oil, lotion, cream, emulsion, gel, shampoo, hair rinse, hair conditioner, enamel, foundation, lipstick, face powder, facial pack, ointment, perfume, powder, eau de cologne, tooth paste, soap, aerosol, cleansing foam, etc., an anti-aging skin care agent, anti-inflammatory agent for the skin, bath agent, medicated tonic, skin beauty essence, sun protectant, or protective and improving agent for skin troubles caused by injury, chapped or cracked skin, etc.

The cosmetic composition of the present invention may further be formulated appropriately with other oils and fats and/or dyes, fragrances, preservatives, surfactants, pigments, antioxidants, etc., if necessary. The formulation ratio of these materials may be appropriately determined by those skilled in the art, depending upon purpose (for example, oils and fats may be contained in the composition in 1 to 99.99 wt %, preferably, 5 to 99.99 wt %, and more preferably, 10 to 99.95 wt %). If necessary, the pharmaceutical composition of the present invention may also contain other pharmaceutically active components (e.g., anti-inflammatory components) or aid components (e.g., lubricants or vehicle components). Examples of the other components commonly used in a cosmetic or a skin preparation for external use include an agent for acne, an agent for preventing dandruff or itching, an antiperspirant and deodorant agent, an agent for burn injury, an anti-mite and lice agent, an agent for softening keratin, an agent for xeroderma, an antiviral agent, a percutaneous absorption promoting agent, and the like.

The food product of the present invention includes a dietary supplement, health food, functional food, food product for young children, baby food, infant modified milk, premature infant modified milk, geriatric food, etc. As used herein, the food or food product is intended to mean a solid, fluid and liquid food as well as a mixture thereof, and collectively means an edible stuff.

The term dietary supplement refers to food products enriched with specific nutritional ingredients. The term health food refers to food products which are healthful or beneficial to health, and encompasses dietary supplements, natural foods, diet foods, etc. The term functional food refers to a food product for replenishing nutritional ingredients which assist body control functions and is synonymous with a food for specified health use. The term food for young children refers to a food product given to children up to about 6 years old. The term geriatric food refers to a food product treated to facilitate digestion and absorption when compared to untreated foods. The term infant modified milk refers to modified milk given to children up to about one year old. The term premature infant modified milk refers to modified milk given to premature infants until about 6 months after birth.

The form of these food products includes natural foods (treated with fats and oils) such as meat, fish and nuts; foods supplemented with fats and oils during cooking, e.g., Chinese foods, Chinese noodles, soups, etc.; foods prepared using fats and oils as heating media, e.g., tempura or deep-fried fish and vegetables, deep-fried foods, fried bean curd, Chinese fried rice, doughnuts, Japanese fried dough cookies or karinto; fat- and oil-based foods or processed foods supplemented with fats and oils during processing, e.g., butter, margarine, mayonnaise, dressing, chocolate, instant noodles, caramel, biscuits, cookies, cakes, ice cream; and foods sprayed or coated with fats and oils upon finishing, e.g., rice crackers, hard biscuits, sweet bean paste bread, etc. However, the food product is not limited to foods containing fats and oils, and other examples include agricultural foods such as bakery products, noodles, cooked rice, sweets (e.g., candies, chewing gums, gummies, sweet tablets, Japanese sweets), bean curd or tofu and processed products thereof; fermented foods such as Japanese rice wine or sake, medicinal liquor, sweet cooking sherry or mirin, vinegar, soy sauce and bean paste or miso, etc.; livestock food products such as yoghurt, ham, bacon, sausage, etc.; seafood products such as minced and steamed fish cake or kamaboko, deep-fried fish cake or ageten and puffy fish cake or hanpen, etc.; as well as fruit drinks, soft drinks, sports drinks, alcoholic beverages, tea, etc.

The food product of the present invention may also be in the form of pharmaceutical preparations such as capsules, etc., or in the form of a processed food such as natural liquid diets, defined formula diets and elemental diets formulated with the oil and fat of the present invention together with proteins, sugars, trace elements, vitamins, emulsifiers, aroma chemicals, etc., health drinks, enteral nutrients, and the like.

As described above, fatty acids can be efficiently produced by expressing the ACS homolog gene of the present invention in host cells.

Furthermore, the expression level of the gene can be used as an indicator to study conditions for cultivation, cultivation control, etc. for efficient fatty acid production.

EXAMPLES

Hereinafter, the present invention is described in more detail with reference to EXAMPLES but it should be understood that the invention is not deemed to limit the scope of the invention to these EXAMPLES.

Example 1

Genome Analysis of *M. alpina*

The *M. alpina* 1S-4 strain was plated on 100 ml of GY2:1 medium (2% glucose and 1% yeast extract, pH 6.0) followed by shake culture at 28° C. for 2 days. The mycelial cells were collected by filtration, and genomic DNA was prepared using DNeasy (QIAGEN). The nucleotide sequence of the genomic DNA described above was determined using a Roche 454 GS FLX Standard. On this occasion, nucleotide sequencing of a fragment library was performed in two runs and nucleotide sequencing of a mate paired library in three runs. The resulting nucleotide sequences were assembled to give 300 supercontigs.

Synthesis of cDNA and Construction of cDNA Library

The M. alpina strain 1S-4 was plated on 100 ml of medium (1.8% glucose, 1% yeast extract, pH 6.0) and precultured for 3 days at 28° C. A 10 L culture vessel (Able Co., Tokyo) was charged with 5 L of medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$ and 0.05% $MgCl_2.6H_2O$, pH 6.0), and the whole amount of the precultured product was plated thereon, followed by aerobic spinner culture under conditions of 300 rpm, 1 vvm and 26° C. for 8 days. On Days 1, 2 and 3 of the cultivation, glucose was added in an amount corresponding to 2%, 2% and 1.5%, respectively. The mycelial cells were collected at each stage on Days 1, 2, 3, 6 and 8 of the cultivation to prepare total RNA by the guanidine hydrochloride/CsC1 method. Using an Oligotex-dT3O<Super>mRNA Purification Kit (Takara Bio Inc.)("dT30" disclosed as SEQ ID NO: 130), poly(A)+RNA was purified from the total RNA. A cDNA library was constructed for each stage using a ZAP-cDNA Gigapack III Gold Cloning Kit (STRATAGENE).

Search for ACS Homolog

Using as a query the amino acid sequences of ScFAA1 (YOR317W), ScFAA2 (YER015W), ScFAA3 (YIL009W), ScFAA4 (YMR246W), ScFAT1 (YBR041W) and ScFAT2 (YBR222C), which are ACS from yeast, a tblastn search was performed against the genome nucleotide sequence of the *M. alpina* strain 1S-4. As a result, hits were found in twelve (12) sequences. That is, hit was found on supercontigs containing the sequence shown by SEQ ID NO: 5, SEQ ID NO: 10, SEQ ID NO: 15, SEQ ID NO: 20, SEQ ID NO: 25, SEQ ID NO: 30, SEQ ID NO: 35, SEQ ID NO: 40, SEQ ID NO: 45, SEQ ID NO: 50, SEQ ID NO: 55 or SEQ ID NO: 60. The genes bearing SEQ ID NO: 5, SEQ ID NO: 10, SEQ ID NO: 15, SEQ ID NO: 20, SEQ ID NO: 25, SEQ ID NO: 30, SEQ ID NO: 35, SEQ ID NO: 40, SEQ ID NO: 45, SEQ ID NO: 50, SEQ ID NO: 55 and SEQ ID NO: 60 were designated respectively as MaACS-1, MaACS-2, MaACS-3, MaACS-4, MaACS-5, MaACS-6, MaACS-7, MaACS-8, MaACS-9, MaACS-10, MaACS-11 and MaACS-12.

Cloning of ACS Homolog

For cloning of the cDNAs corresponding to the MaACS-1~12 genes, screening of the cDNA library described above was performed. Probe labeling was performed by PCR using an ExTaq (Takara Bio Inc.). That is, digoxigenin (DIG)-labeled amplified DNA probes were prepared using a PCR Labeling Mix (Roche Diagnostics) instead of dNTP mix attached to ExTaq.

Conditions for hybridization were set as follows.
Buffer: 5×SSC, 1% SDS, 50 mM Tris-HCl (pH 7.5), 50% formaldehyde;
Temperature: 42° C. (overnight);
Wash conditions: 0.2×SSC, in 0.1% SDS solution (65° C.) for 20 mins.×3

Detection was performed using a DIG Nucleic Acid Detection Kit (Roche Diagnostics). Phage clones were obtained by screening and plasmids were excised from the phage clones by in vivo excision to give the respective plasmid DNAs.

Primers for preparing the probes used for screening of the respective genes, the number of nucleotides in CDS of the respective genes, the number of amino acids in the amino acid sequences deduced from the nucleotide sequences of CDS, and the number of exons and introns by comparison of genomic DNA sequences with CDS sequences are given below.

(1) MaACS-1

```
                              (SEQ ID NO: 61)
Primer ACS-1-1F:   5'-GTCGGCTCCAAGCTTGCAATCC-3'

(SEQ ID NO: 62)
Primer ACS-1-2R:   5'-GGACAGCTCCAGCACTGTGGTAAAG-3'
``` cDNA (SEQ ID NO: 4)
CDS (SEQ ID NO: 3): 1857 bp
ORF (SEQ ID NO: 1): 1854 bp
Amino acid sequence (SEQ ID NO: 2): 618 amino acids (see FIG. 1)
Number of exons: 5, number of introns: 4 (see FIG. 2)

(2) MaACS-2

```
                              (SEQ ID NO: 63)
Primer ACS-2-1F:   5'-GACCACGGGATTCCCCAAGGCTGC-3'

(SEQ ID NO: 64)
Primer ACS-2-2R:   5'-CTTGGTCGCGCTTGTTCCTGGCCAC-3'
``` cDNA (SEQ ID NO: 9)
CDS (SEQ ID NO: 8): 1929 bp
ORF (SEQ ID NO: 6): 1926 bp
Amino acid sequence (SEQ ID NO: 7): 642 amino acids (see FIG. 3)
Number of exons: 8, number of introns: 7 (see FIG. 4)

(3) MaACS-3

```
                              (SEQ ID NO: 65)
Primer ACS-3-1F:   5'-TACAGCTTTGTTGCTGTCCCCATC-3'

Figure 6A:
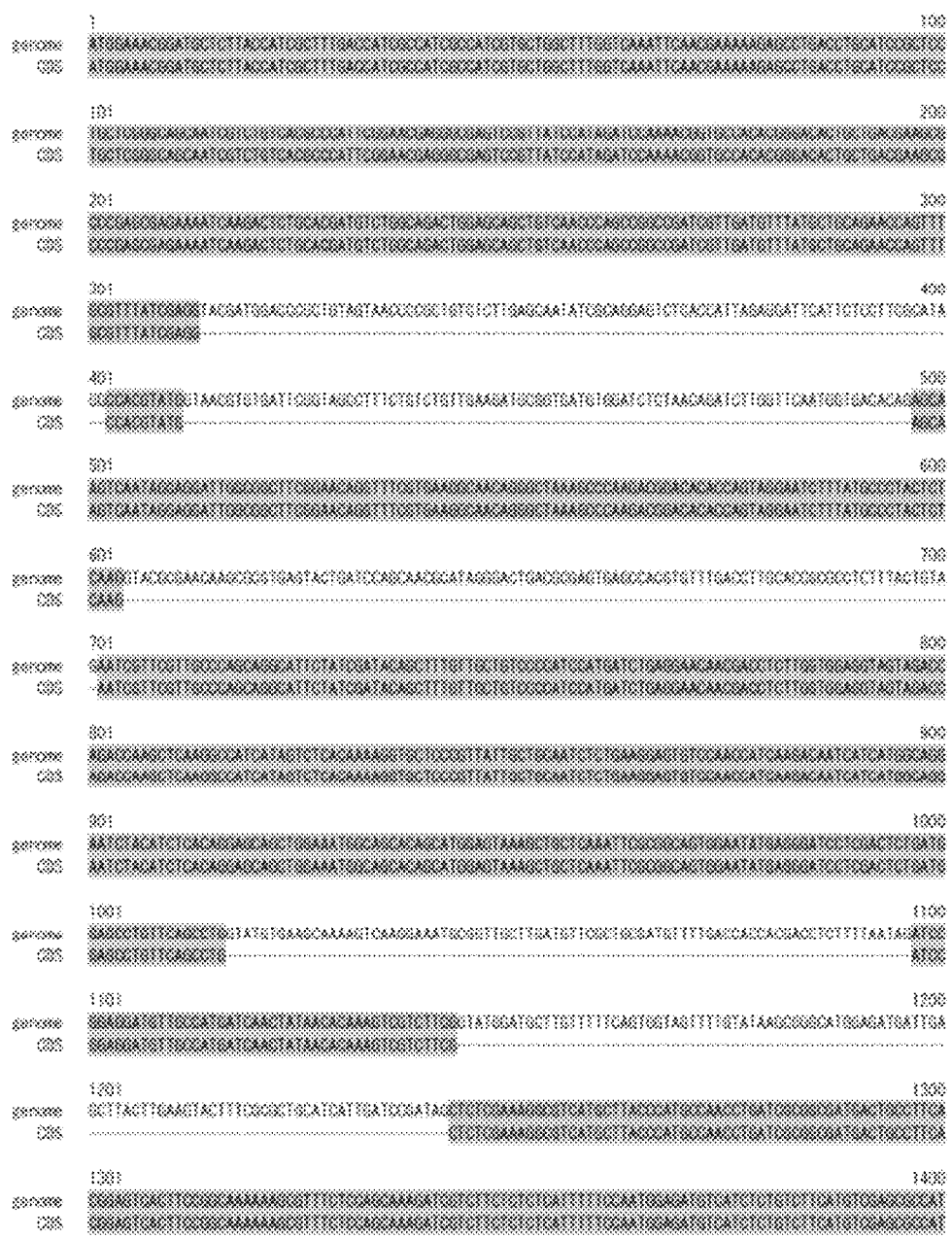
FIG. 6A shows the alignment between the genome sequence of MaACS-3 (SEQ ID NO: 15) and CDS sequence of MaACS-3 (SEQ ID NO: 13).

(SEQ ID NO: 66)
Primer ACS-3-2R:   5'-GATGATGGGTGTGCTTGCAAAGATC-3'
``` cDNA (SEQ ID NO: 14)
CDS (SEQ ID NO: 13): 1653 bp
ORF (SEQ ID NO: 11): 1650 bp
Amino acid sequence (SEQ ID NO: 12): 550 amino acids (see FIG. 5)
Number of exons: 9, number of introns: 8 (see FIG. 6)

(4) MaACS-4

```
                              (SEQ ID NO: 67)
Primer ACS-4-1F:   5'-AACCCAAAGCTGCGCCAGGCTGTCC-3'

Figure 8C:
FIG. 8C is a continuation from FIG. 8B.

(SEQ ID NO: 68)
Primer ACS-4-2R:   5'-TTACAGCTTGGATTCCTTTTGATGG-3'
``` cDNA (SEQ ID NO: 19)
CDS (SEQ ID NO: 18): 2067 bp
ORF (SEQ ID NO: 16): 2064 bp
Amino acid sequence (SEQ ID NO: 17): 688 amino acids (see FIG. 7)
Number of exons: 7, number of introns: 6 (see FIG. 8)

(5) MaACS-5

```
                              (SEQ ID NO: 69)
Primer ACS-5-1F:   5'-GTCGTGCCCGATGCGGAGACGC-3'

(SEQ ID NO: 70)
Primer ACS-5-2R:   5'-TCAGTGGATCCCGTTATACATCAG-3'
``` cDNA (SEQ ID NO: 24)
CDS (SEQ ID NO: 23): 1980 bp
ORF (SEQ ID NO: 21): 1977 bp
Amino acid sequence (SEQ ID NO: 22): 659 amino acids (see FIG. 9)
Number of exons: 6, number of introns: 5 (see FIG. 10)

(6) MaACS-6

```
                              (SEQ ID NO: 71)
Primer ACS-6-1F:   5'-GCGTCCCCCTCTATGATACATTG-3'

(SEQ ID NO: 72)
Primer ACS-6-2R:   5'-GTGGGATGCAGGACGGCAACATCG-3'
``` cDNA (SEQ ID NO: 29)
CDS (SEQ ID NO: 28): 1980 bp
ORF (SEQ ID NO: 26): 1977 bp
Amino acid sequence (SEQ ID NO: 27): 659 amino acids (see FIG. 11)
Number of introns: at least 5 (see FIG. 12)

(7) MaACS-7

```
                              (SEQ ID NO: 73)
Primer ACS-7-1F:   5'-GGATGCCGAACAACAGCGCGTGG-3'

Figure 14B:
FIG. 14B is a continuation from FIG. 14A.

(SEQ ID NO: 74)
Primer ACS-7-2R:   5'-GCACCCTCCTCAGAAACAGCCCTC-3'
``` cDNA (SEQ ID NO: 34)
CDS (SEQ ID NO: 33): 1827 bp
ORF (SEQ ID NO: 31): 1824 bp
Amino acid sequence (SEQ ID NO: 32): 608 amino acids (see FIG. 13)
Number of exons: 5, number of introns: 4 (see FIG. 14)

(8) MaACS-8

```
                              (SEQ ID NO: 75)
Primer ACS-8-1F:   5'-CAGTCGAGTACATTGTCAACCACG-3'

Figure 16C:
FIG. 16C is a continuation from FIG. 16B.

(SEQ ID NO: 76)
Primer ACS-8-2R:   5'-GCGGTTCAAGAGGCGAGGCACAGC-3'
``` cDNA (SEQ ID NO: 39)
CDS (SEQ ID NO: 38): 2079 bp
ORF (SEQ ID NO: 36): 2076 bp
Amino acid sequence (SEQ ID NO: 37): 692 amino acids (see FIG. 15)
Number of exons: 8, number of introns: 7 (see FIG. 16)

(9) MaACS-9

```
                              (SEQ ID NO: 77)
Primer ACS-9-1F:   5'-GTTCATCTTCTGCTGGCTGGGTCTC-3'
```

Figure 17:
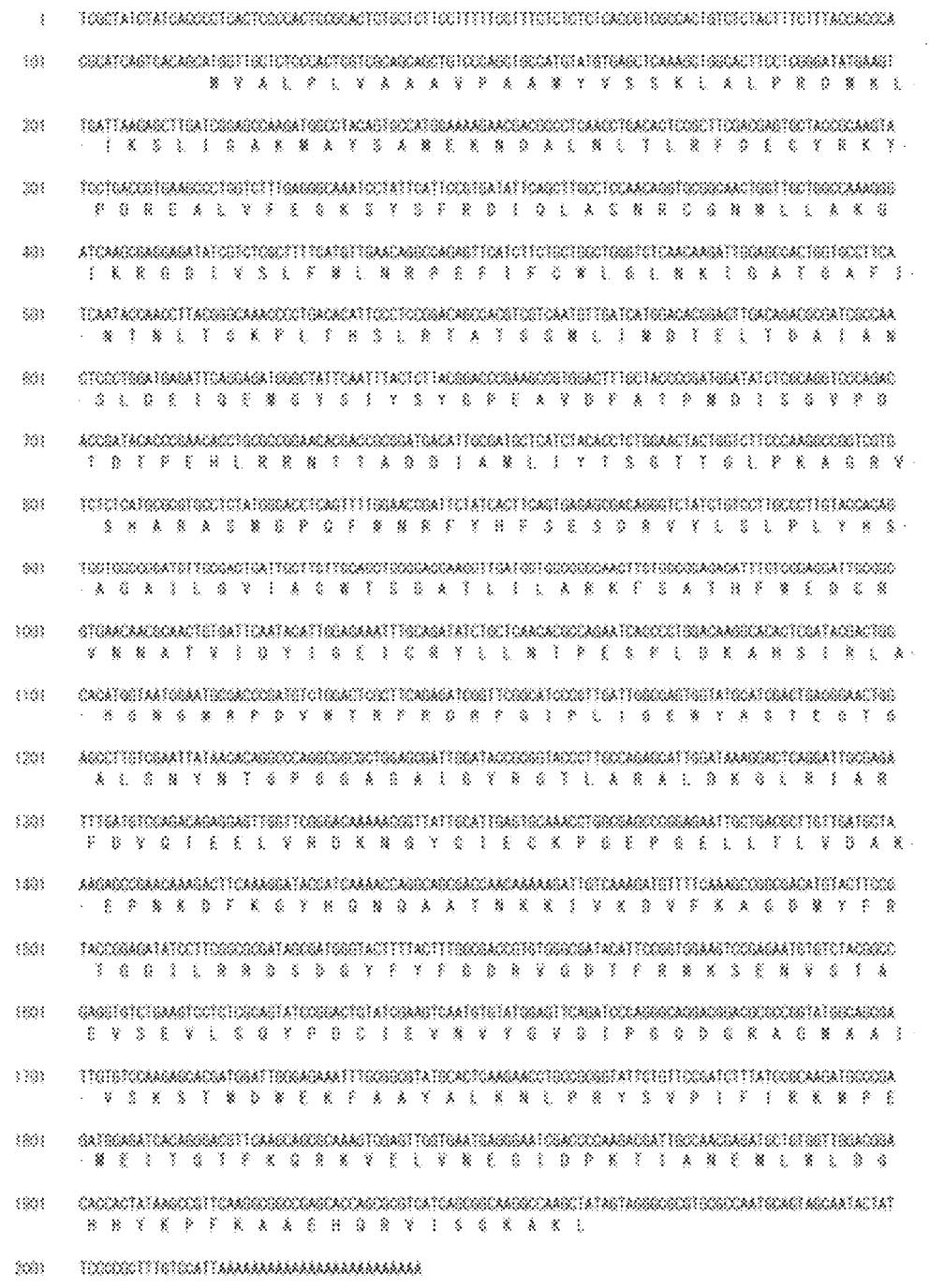
Figure 18A:
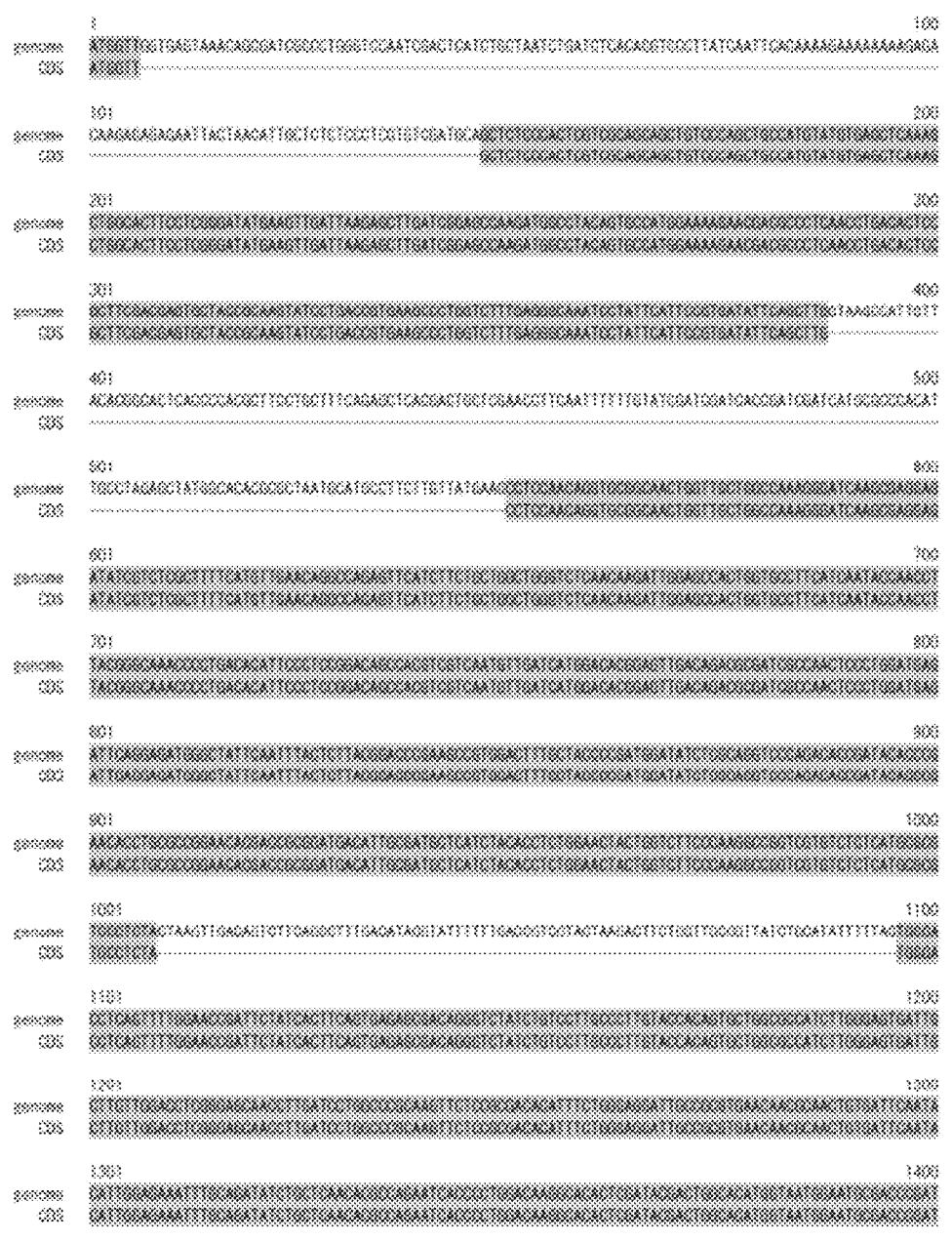
Figure 18B:
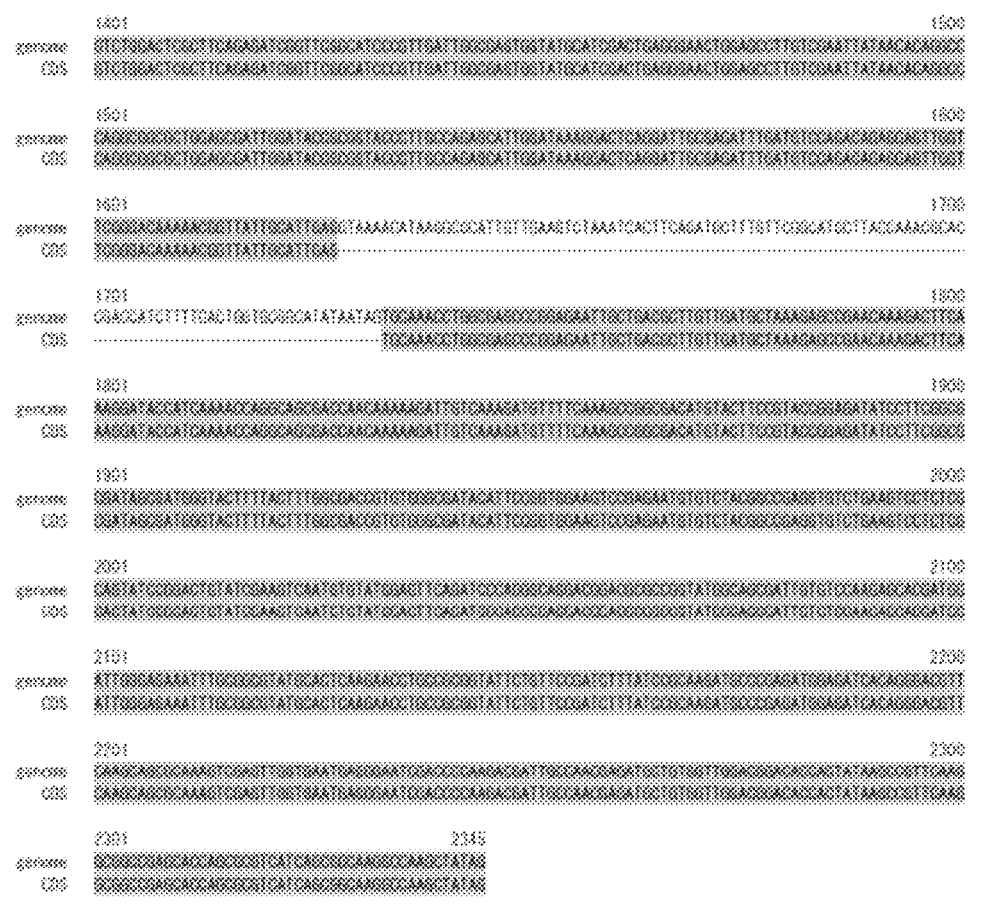

(SEQ ID NO: 78)
Primer ACS-9-2R:    5'-GTTGCGTTGTTCACGCGGCAATCC-3' cDNA (SEQ ID NO: 44)
CDS (SEQ ID NO: 43): 1851 bp
ORF (SEQ ID NO: 41): 1848 bp
Amino acid sequence (SEQ ID NO: 42): 616 amino acids (see FIG. 17)
Number of exons: 5, number of introns: 4 (see FIG. 18)
(10) MaACS-10

(SEQ ID NO: 79)
Primer ACS-10-1F:    5'-ATGGAAACCTTGGTTAACGGAAAG-3'

Figure 19A:
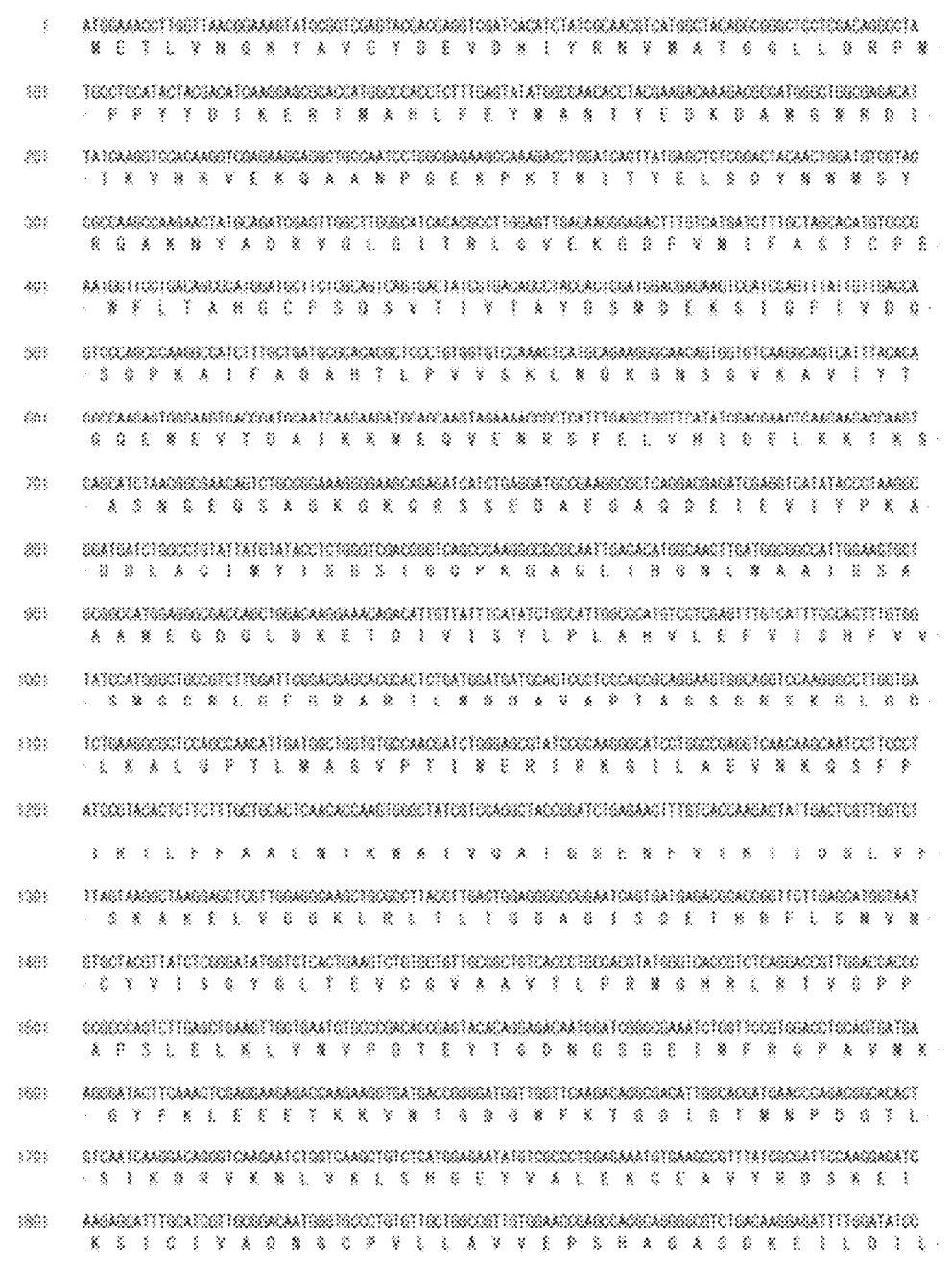
Figure 19B:
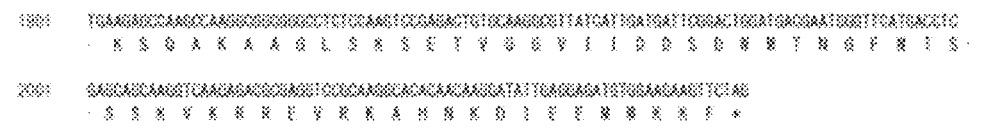
Figure 20A:
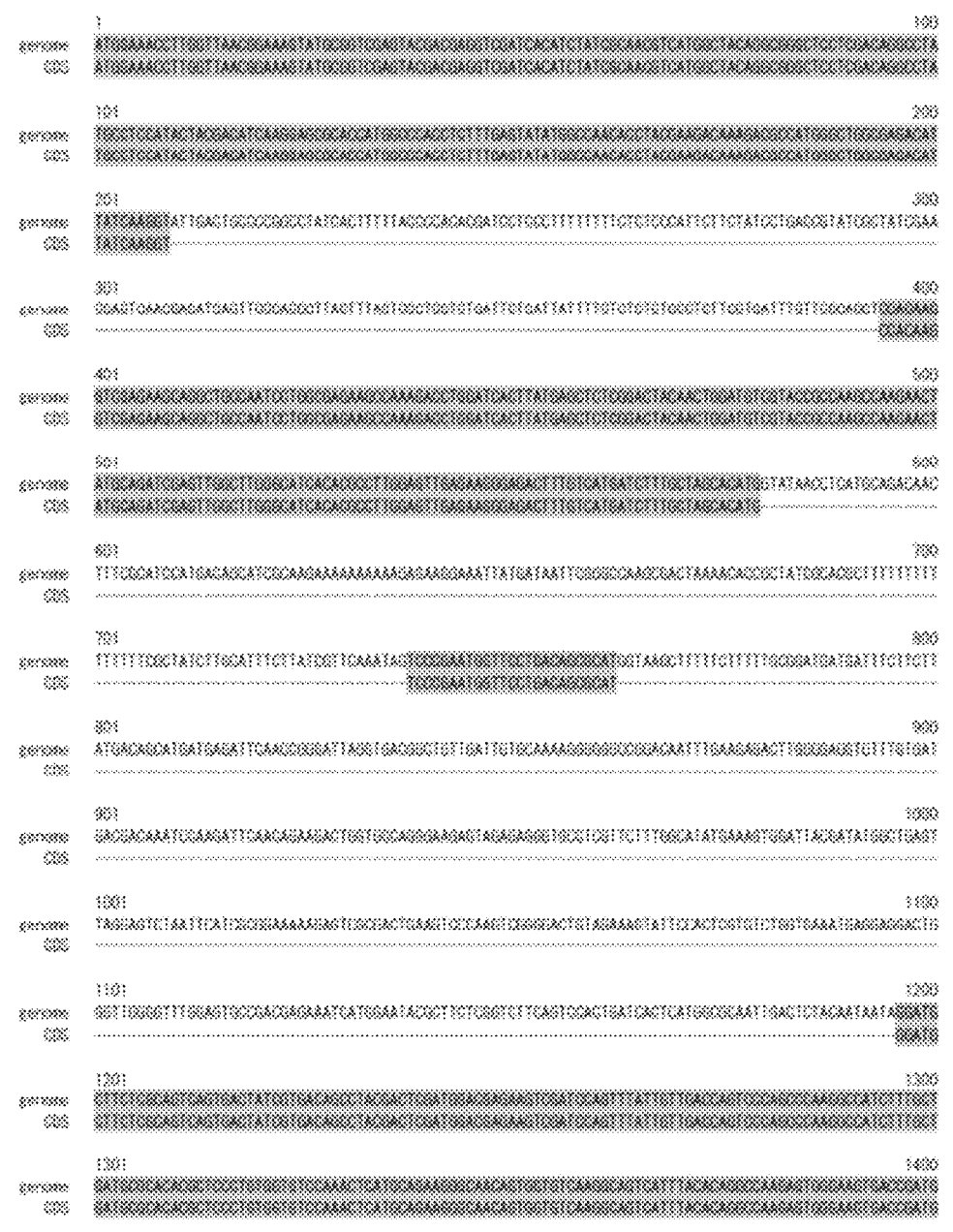
Figure 20B:
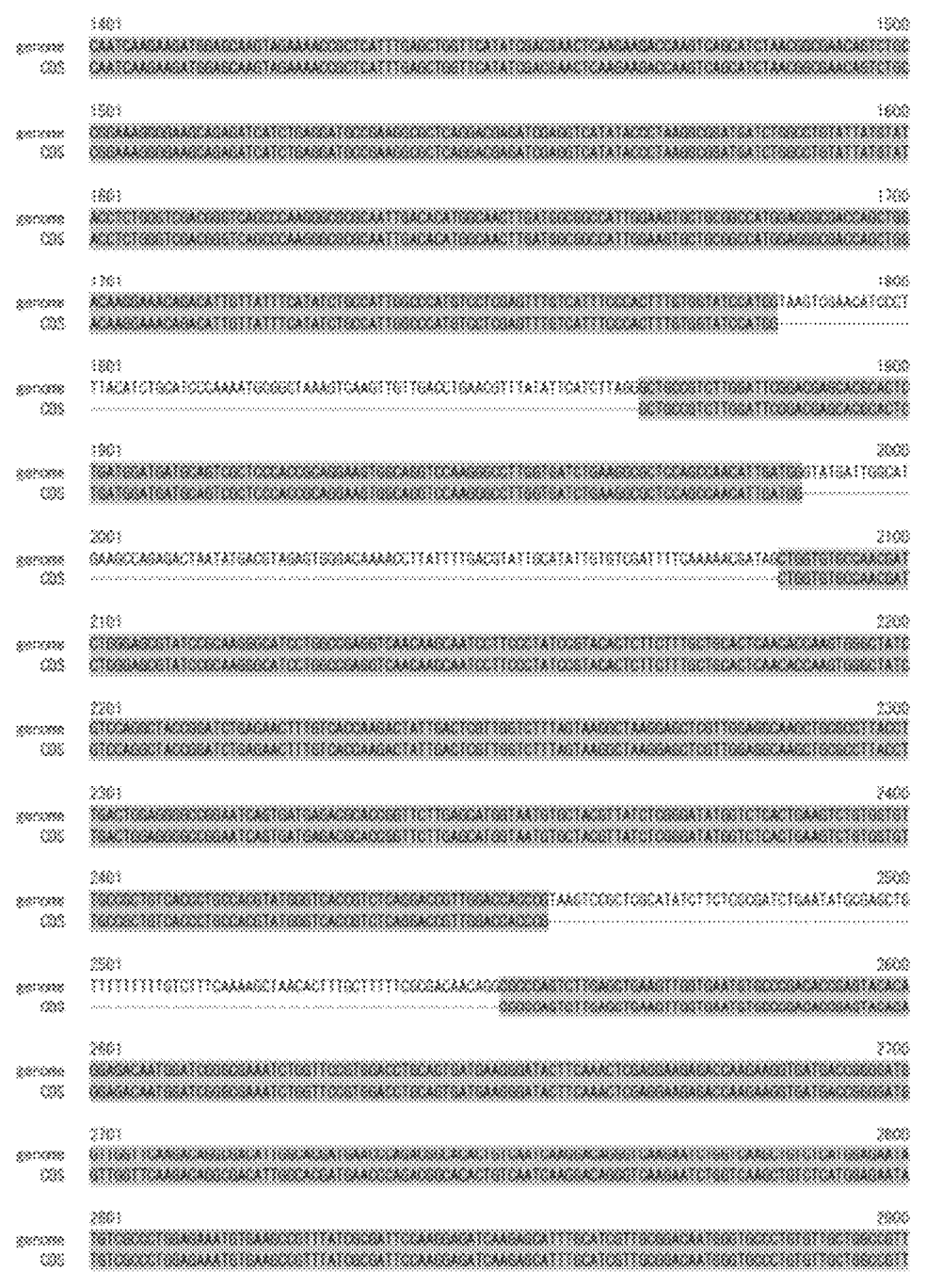
Figure 20C:
FIG. 20C is a continuation from FIG. 20B.

(SEQ ID NO: 80)
Primer ACS-10-2R:    5'-TCAGCAAAGATGGCCTTGGGCTGG-3' cDNA (SEQ ID NO: 49)
CDS (SEQ ID NO: 48): 2076 bp
ORF (SEQ ID NO: 46): 2073 bp
Amino acid sequence (SEQ ID NO: 47): 691 amino acids (see FIG. 19)
Number of exons: 8, number of introns: 7 (see FIG. 20)
(11) MaACS-11

(SEQ ID NO: 81)
Primer ACS-11-1F:    5'-GTCAAGGGCGAGACTCGCATCC-3'

Figure 21A:
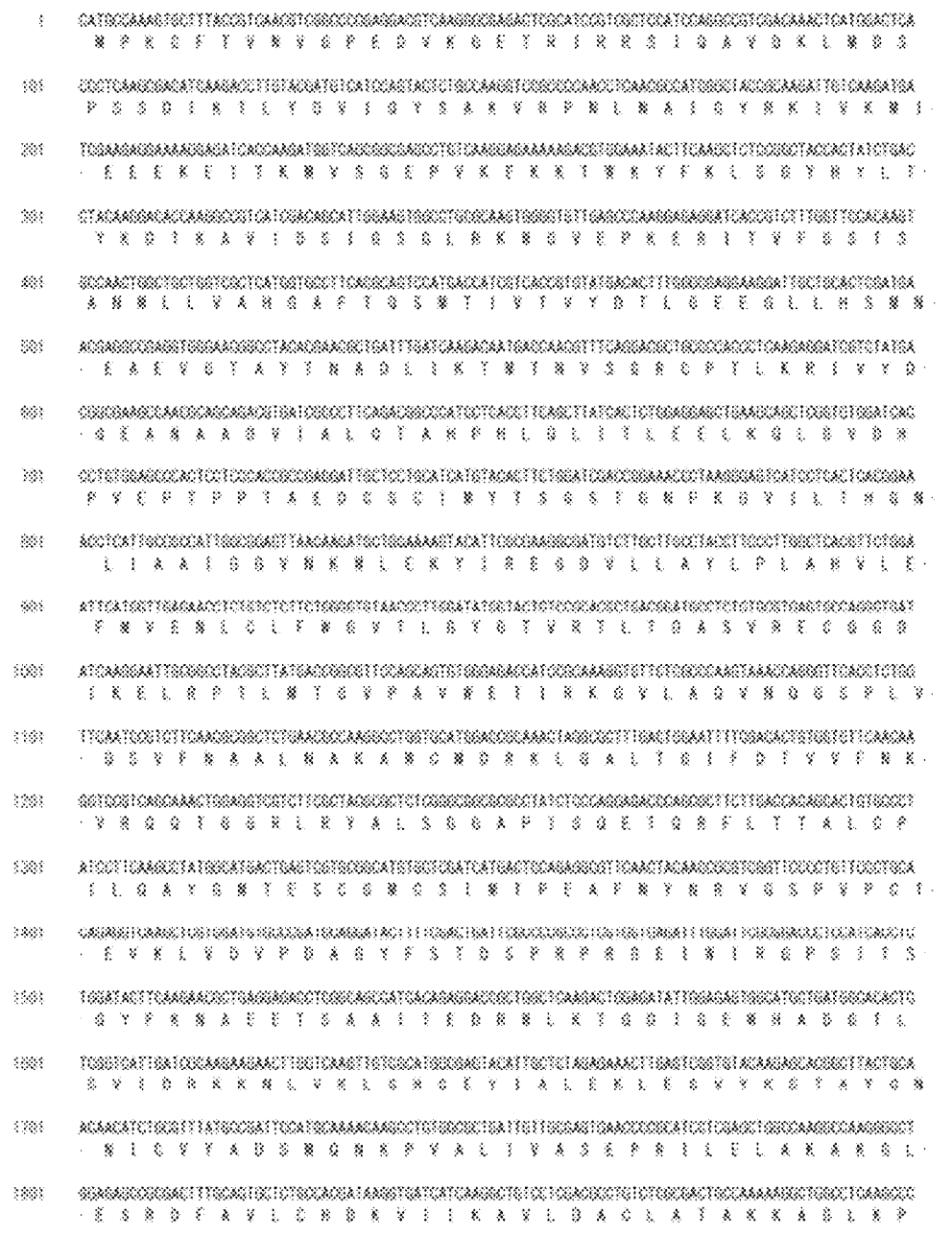
Figure 21B:
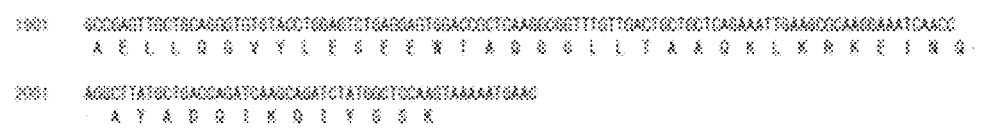
Figure 22A:
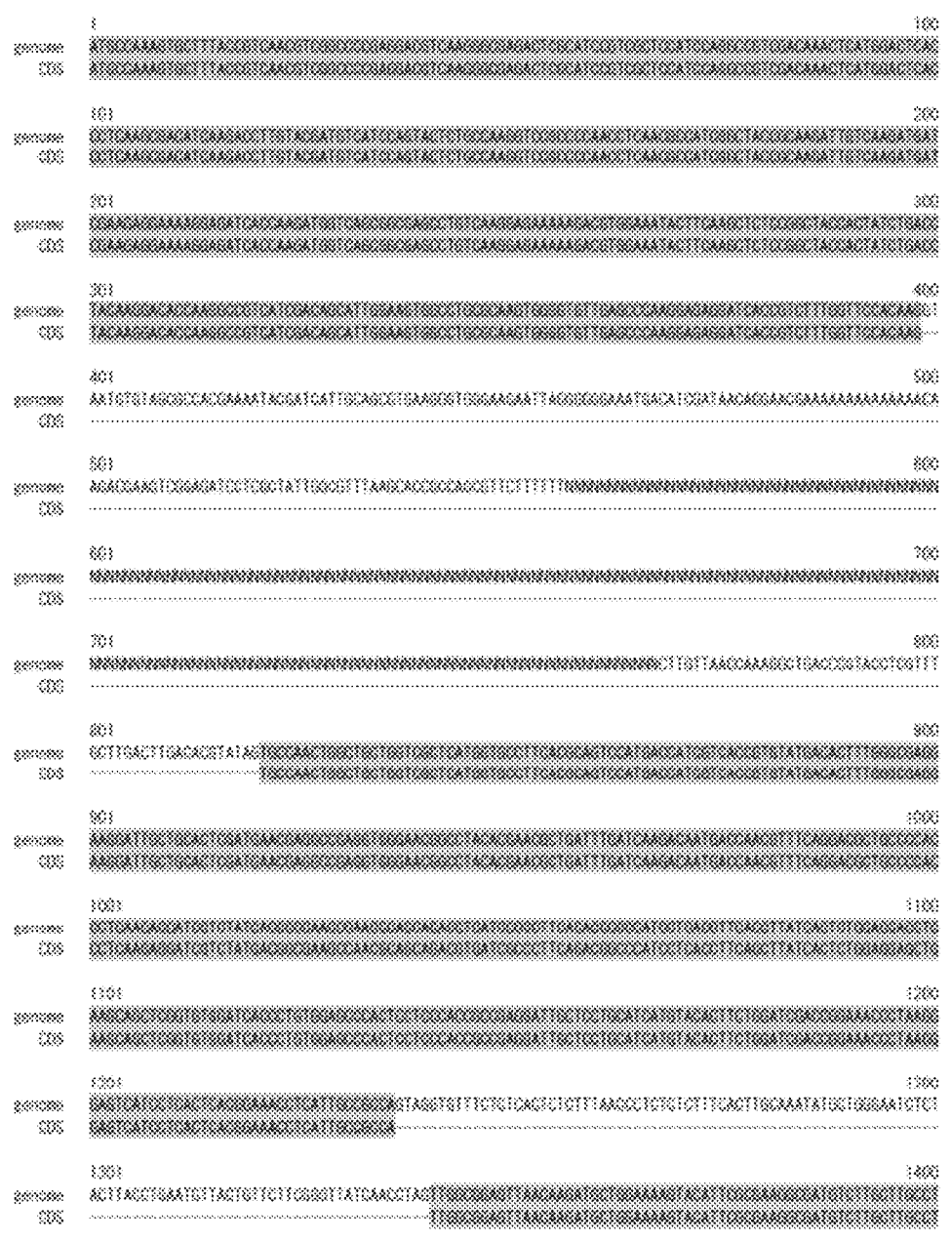
Figure 22B:
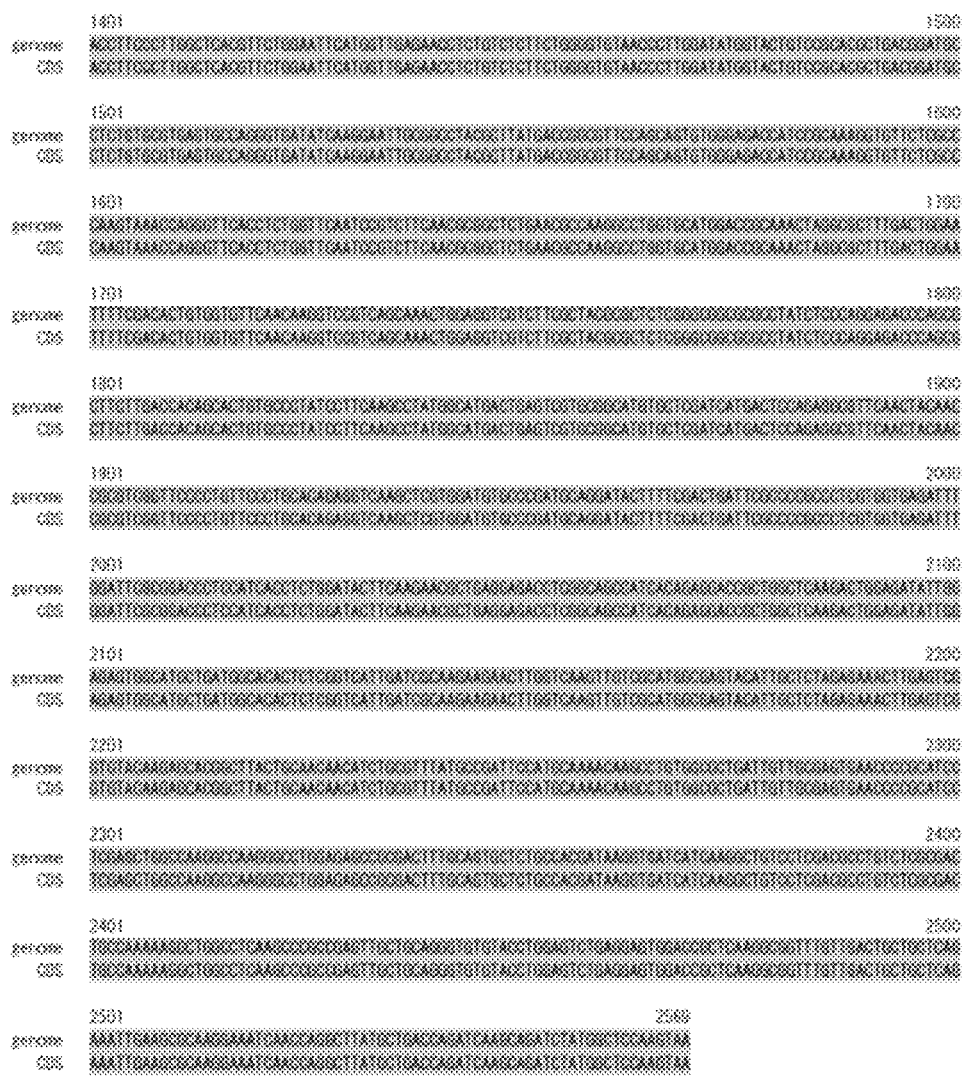
FIG. 22B is a continuation from FIG. 22A.

(SEQ ID NO: 82)
Primer ACS-11-2R:    5'-CGGTGACGATGGTCATGGACTGC-3' cDNA (SEQ ID NO: 54)
CDS (SEQ ID NO: 53): 2043 bp
ORF (SEQ ID NO: 51): 2040 bp
Amino acid sequence (SEQ ID NO: 52): 680 amino acids (see FIG. 21)
Number of exons: 3, number of introns: 2 (see FIG. 22)
(12) MaACS-12

(SEQ ID NO: 83)
Primer ACS-12-1F:    5'-GCGAGACCCGCATCCGCCGCTCC-3'

Figure 23A:
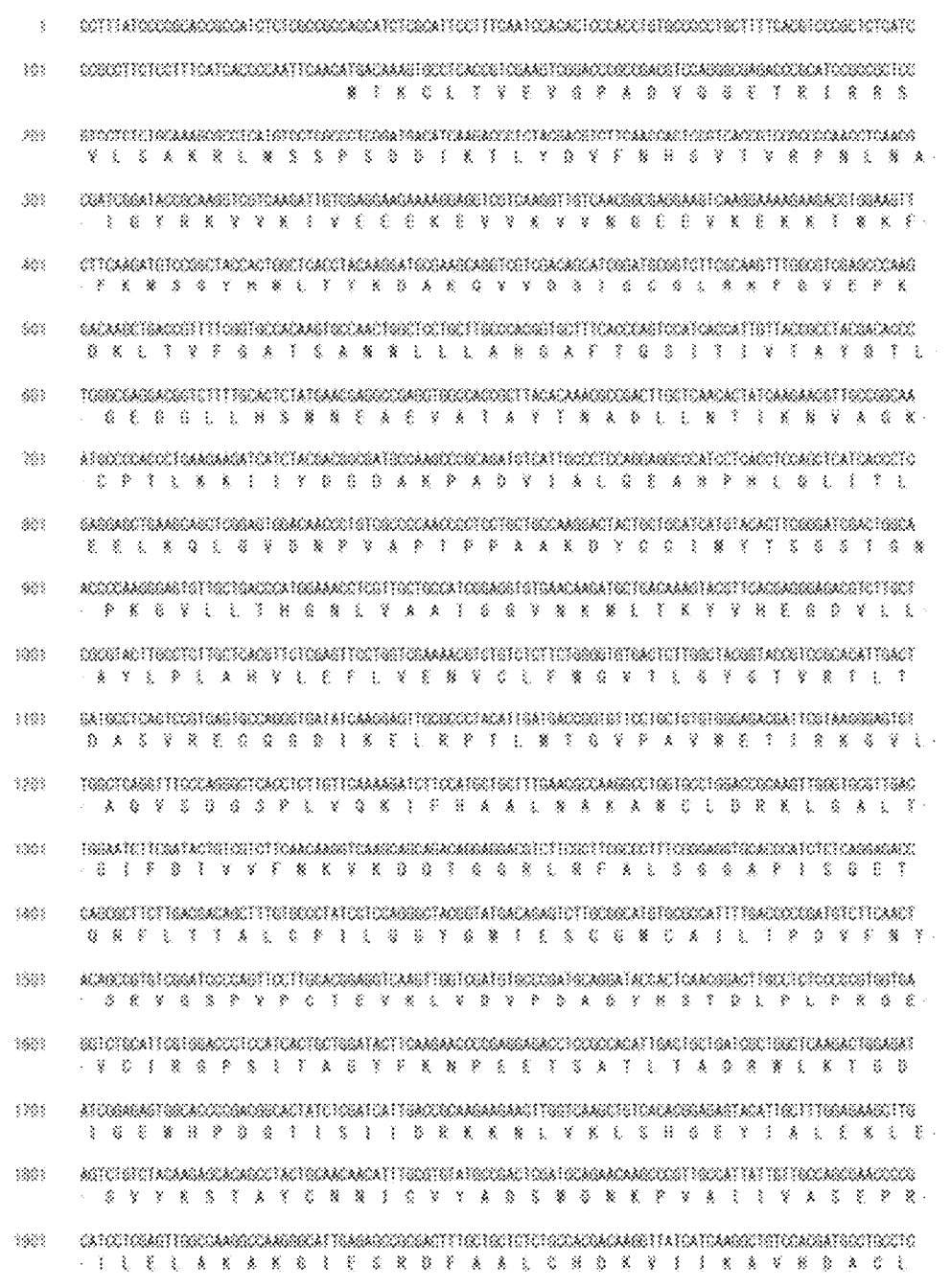
Figure 23B:
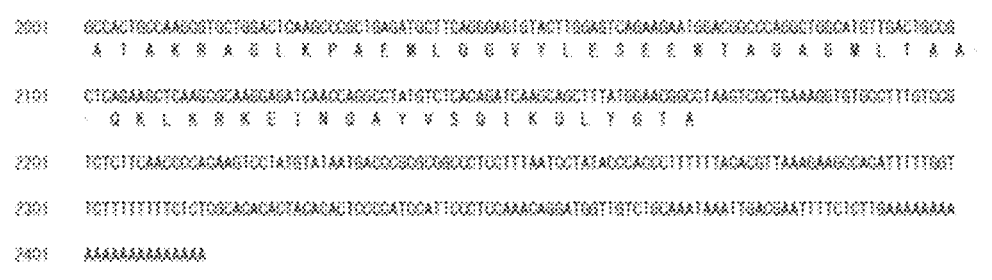
Figure 24A:
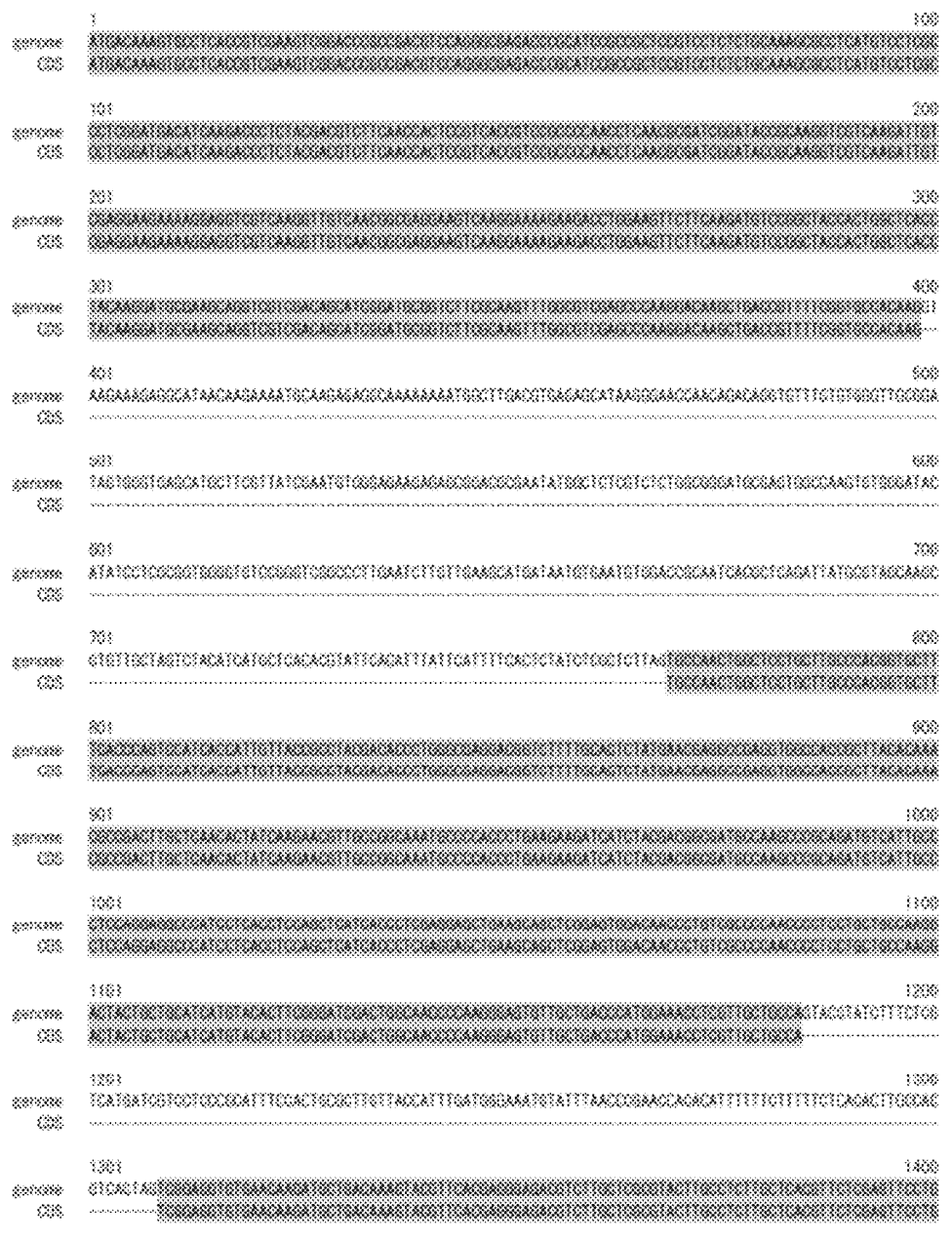
Figure 24B:
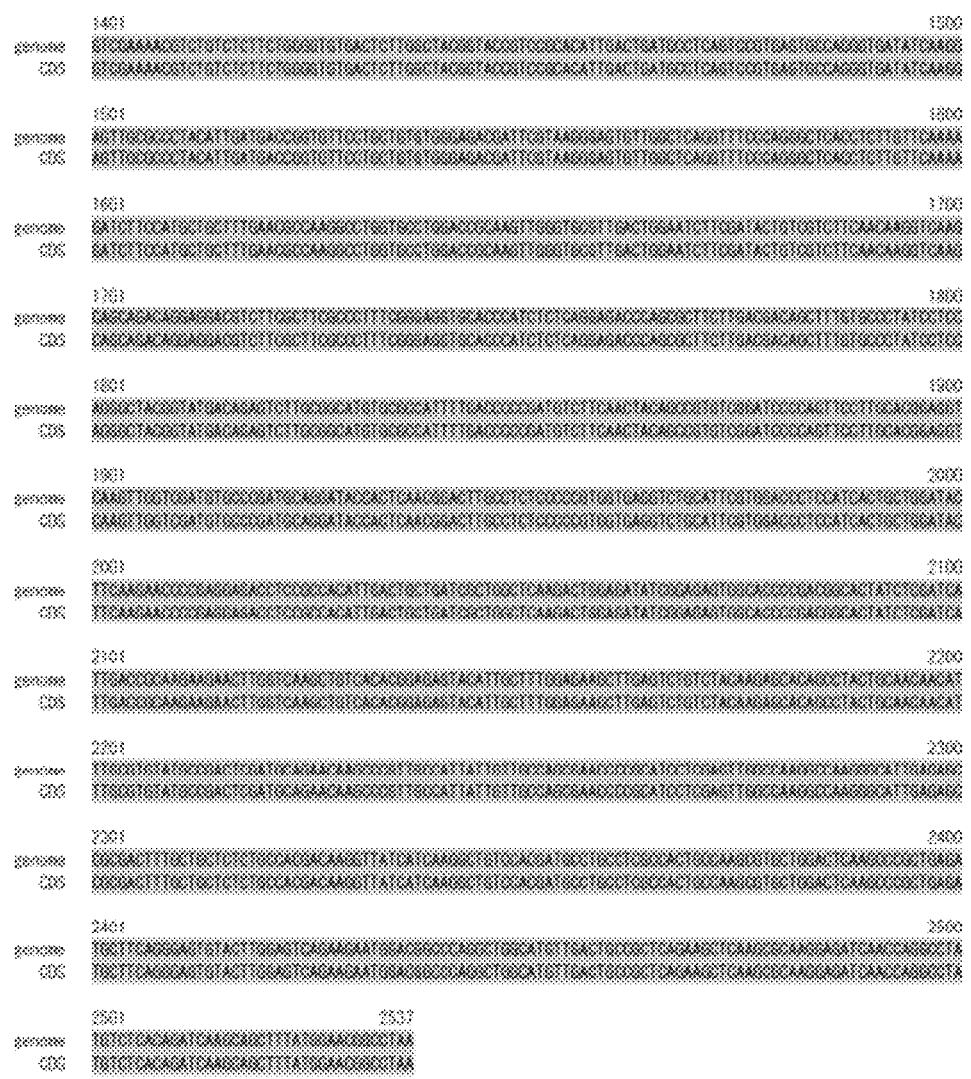
FIG. 24B is a continuation from FIG. 24A

(SEQ ID NO: 84)
Primer ACS-12-2R:    5'-GACCGTCCTCGCCCAGGGTGTCG-3' cDNA (SEQ ID NO: 59)
CDS (SEQ ID NO: 58): 2043 bp
ORF (SEQ ID NO: 56): 2040 bp
Amino acid sequence (SEQ ID NO: 57): 680 amino acids (see FIG. 23)
Number of exons: 3, number of introns: 2 (see FIG. 24)

Sequencing Analysis

The identity between the CDS nucleotide sequences of 12 ACS homologs from *M. alpina* is shown in TABLE 1 and the identity between the amino acid sequences is shown in TABLE 2. MaACS-11 and MaACS-12 showed high identity of 80.2% in the nucleotide sequence and 84.3% in the amino acid sequence.

TABLE 1

Sequence identity among CDS nucleotide sequences of ACS homologs from *M. alpina*

|  | MaACS-1 | MaACS-2 | MaACS-3 | MaACS-4 | MaACS-5 | MaACS-6 | MaACS-7 |
|---|---|---|---|---|---|---|---|
| MaACS-1 | — | 51.3 | 42.9 | 45.4 | 44.7 | 46.6 | 46.0 |
| MaACS-2 |  | — | 43.4 | 46.8 | 46.9 | 45.7 | 46.5 |
| MaACS-3 |  |  | — | 38.0 | 38.2 | 38.9 | 43.7 |
| MaACS-4 |  |  |  | — | 50.4 | 51.6 | 43.8 |
| MaACS-5 |  |  |  |  | — | 70.8 | 44.7 |
| MaACS-6 |  |  |  |  |  | — | 46.2 |
| MaACS-7 |  |  |  |  |  |  | — |
| MaACS-8 |  |  |  |  |  |  |  |
| MaACS-9 |  |  |  |  |  |  |  |
| MaACS-10 |  |  |  |  |  |  |  |
| MaACS-11 |  |  |  |  |  |  |  |
| MaACS-12 |  |  |  |  |  |  |  |

|  | MaACS-8 | MaACS-9 | MaACS-10 | MaACS-11 | MaACS-12 |
|---|---|---|---|---|---|
| MaACS-1 | 45.6 | 69.5 | 44.7 | 46.2 | 45.8 |
| MaACS-2 | 44.6 | 52.5 | 44.9 | 44.9 | 44.0 |
| MaACS-3 | 37.5 | 42.8 | 41.5 | 39.0 | 39.1 |
| MaACS-4 | 57.7 | 44.2 | 47.0 | 49.7 | 49.3 |
| MaACS-5 | 53.0 | 44.9 | 46.6 | 48.9 | 47.2 |
| MaACS-6 | 53.0 | 45.2 | 47.9 | 49.2 | 49.4 |
| MaACS-7 | 44.2 | 45.9 | 42.3 | 45.0 | 44.6 |
| MaACS-8 | — | 44.3 | 48.1 | 50.7 | 50.8 |
| MaACS-9 |  | — | 42.7 | 46.2 | 47.8 |
| MaACS-10 |  |  | — | 51.8 | 52.1 |
| MaACS-11 |  |  |  | — | 80.2 |
| MaACS-12 |  |  |  |  | — |

TABLE 2

Sequence identity among amino acid sequences of ACS homologs from *M. alpina*

|  | MaACS-1 | MaACS-2 | MaACS-3 | MaACS-4 | MaACS-5 | MaACS-6 | MaACS-7 |
|---|---|---|---|---|---|---|---|
| MaACS-1 | — | 36.6 | 11.8 | 13.9 | 15.1 | 15.8 | 18.0 |
| MaACS-2 |  | — | 11.0 | 14.0 | 15.4 | 15.0 | 17.2 |
| MaACS-3 |  |  | — | 21.7 | 21.5 | 20.8 | 13.1 |
| MaACS-4 |  |  |  | — | 37.5 | 37.5 | 17.0 |
| MaACS-5 |  |  |  |  | — | 77.9 | 17.0 |
| MaACS-6 |  |  |  |  |  | — | 16.6 |
| MaACS-7 |  |  |  |  |  |  | — |
| MaACS-8 |  |  |  |  |  |  |  |
| MaACS-9 |  |  |  |  |  |  |  |
| MaACS-10 |  |  |  |  |  |  |  |
| MaACS-11 |  |  |  |  |  |  |  |
| MaACS-12 |  |  |  |  |  |  |  |

|  | MaACS-8 | MaACS-9 | MaACS-10 | MaACS-11 | MaACS-12 |
|---|---|---|---|---|---|
| MaACS-1 | 14.8 | 71.9 | 13.5 | 14.6 | 15.0 |
| MaACS-2 | 13.2 | 37.0 | 12.3 | 12.7 | 13.8 |
| MaACS-3 | 21.1 | 10.5 | 17.7 | 18.5 | 17.9 |
| MaACS-4 | 50.9 | 15.4 | 22.8 | 29.8 | 29.5 |
| MaACS-5 | 41.2 | 16.4 | 25.2 | 29.1 | 29.8 |
| MaACS-6 | 39.8 | 16.6 | 25.3 | 29.9 | 29.4 |
| MaACS-7 | 15.5 | 17.0 | 15.3 | 16.2 | 16.7 |
| MaACS-8 | — | 15.2 | 24.9 | 27.8 | 28.6 |
| MaACS-9 |  | — | 14.1 | 14.5 | 14.7 |
| MaACS-10 |  |  | — | 32.8 | 32.6 |
| MaACS-11 |  |  |  | — | 84.3 |
| MaACS-12 |  |  |  |  | — |

Using as query sequences the putative amino acid sequences for the CDS sequences of MaACS-1~12, BLASTp search was performed against the amino acid sequences registered in GenBank. The proteins having the amino acid sequence which matched the putative amino acid sequences of MaACS-1~12 with highest score and the identity between these proteins and the putative amino acid sequences of MaACS-1~12 are shown in TABLE 3. The identity of the putative amino acid sequences of MaACS-1~12 with the amino acid sequences of *S. cerevisiae*-derived acyl-CoA synthetases are also shown in TABLE 4.

TABLE 3

Sequence identity between the amino acid sequences of *M. alpina*-derived ACS homologs and known amino acid sequences

|  | identity(%) | gi |  |
|---|---|---|---|
| MaACS-1 | 41.8 | 71014575 | Putative protein from *Ustilago maydis* |
| MaACS-2 | 35.4 | 71014575 | Putative protein from *Ustilago maydis* |
| MaACS-3 | 23.5 | 71895089 | Chick ACS long-chain family member 5 |
| MaACS-4 | 36.9 | 115487304 | Putative protein from *Oryza sativa* |
| MaACS-5 | 42.5 | 168065128 | Putative protein from *Physcomitrella patens* |
| MaACS-6 | 40.9 | 13516481 | Long-chain acyl-CoA synthetase from *Arabidopsis thaliana* |
| MaACS-7 | 45.7 | 120612991 | Putative protein from *Acidovorax avenae* subsp. *citrulli* |
| MaACS-8 | 40.0 | 13516481 | Long-chain acyl-CoA synthetase from *Arabidopsis thaliana* |
| MaACS-9 | 37.8 | 67538044 | Putative protein from *Aspergillus nidulans* |
| MaACS-10 | 33.2 | 171682488 | Putative protein from *Podospora Anserina* |
| MaACS-11 | 48.8 | 169854433 | Putative protein from *Coprinopsis atramentarius* |
| MaACS-12 | 45.1 | 156045509 | Putative protein from *Sclerotinia sclerotiorum* |

TABLE 4

Comparison of amino acid sequences of *M. alpina*-derived ACS homologs and amino acid sequences of *S. cerevisiae*-derived ACS

|  | ScFAA1 | ScFAA2 | ScFAA3 | ScFAA4 | ScFAT1 | ScFAT2 |
|---|---|---|---|---|---|---|
| MaACS-1 | 13.8 | 15.3 | 13.6 | 13.5 | 29.8 | 18.1 |
| MaACS-2 | 12.5 | 13.6 | 13.4 | 13.5 | 26.3 | 17.5 |
| MaACS-3 | 15.8 | 14.0 | 15.0 | 14.8 | 13.6 | 12.9 |
| MaACS-4 | 26.3 | 28.3 | 23.9 | 24.2 | 14.0 | 16.0 |
| MaACS-5 | 25.6 | 28.2 | 25.5 | 25.8 | 13.2 | 18.6 |
| MaACS-6 | 25.3 | 28.4 | 25.8 | 25.5 | 13.0 | 18.1 |
| MaACS-7 | 16.5 | 17.5 | 16.0 | 16.9 | 16.6 | 20.6 |

TABLE 4-continued

Comparison of amino acid sequences of *M. alpina*-derived ACS homologs and amino acid sequences of *S. cerevisiae*-derived ACS

|         | ScFAA1 | ScFAA2 | ScFAA3 | ScFAA4 | ScFAT1 | ScFAT2 |
|---------|--------|--------|--------|--------|--------|--------|
| MaACS-8 | 23.0   | 28.0   | 21.3   | 22.8   | 12.2   | 14.8   |
| MaACS-9 | 15.6   | 15.5   | 14.3   | 14.7   | 30.1   | 18.3   |
| MaACS-10| 30.8   | 20.6   | 30.6   | 30.6   | 14.0   | 14.2   |
| MaACS-11| 39.6   | 22.6   | 37.3   | 38.7   | 12.9   | 15.8   |
| MaACS-12| 41.3   | 22.3   | 39.8   | 39.0   | 14.4   | 16.2   |

FIG. 25 shows the alignment between MaACS from MaACS-1~12, which have relatively high amino acid sequence homology to the *S. cerevisiae*-derived FAA proteins, and the FAA proteins. FIG. 26 shows the alignment of the ACS homologs having relatively high amino acid sequence homology to *S. cerevisiae*-derived FAT proteins. The regions of the ATP-AMP motif and FACS/VLACS-FATP motif, which are important motifs for the ACS activity, are highly conserved in both groups shown in FIGS. 25 and 26.

Construction of Expression Vector

Vectors for expressing MaACS-1, MaACS-10, MaACS-11, MaACS-6, MaACS-8 and MaACS-9, respectively, in yeast were constructed as follows, using the expression vector pYE22m (Biosci. Biotech. Biochem., 59, 1221-1228, 1995).

The plasmid containing SEQ ID NO: 29, which was obtained by screening MaACS-6, was digested with restriction enzymes BamHI and XhoI. The resulting DNA fragment of approximately 2.1 kbp was ligated to the DNA fragment obtained by digestion of vector pYE22m with restriction enzymes BamHI and SalI using a Ligation High (TOYOBO) to give plasmid pYE-ACS-6.

Using the plasmid containing cDNA of MaACS-8 as a template, PCR was performed with the primers below using ExTaq (Takara Bio Inc.). The thus amplified DNA fragment was cloned by a TOPO-TA Cloning Kit (Invitrogen).

```
Primer EcoRI-ACS-8-F:
                                      (SEQ ID NO: 85)
5'-GGATCCATGCCTTCCTTCAAAAAGTACAACC-3'

Primer SmaI-ACS-8-R:
                                      (SEQ ID NO: 86)
5'-CCCGGGCAAAGAGTTTTCTATCTACAGCTT-3'
```

The nucleotide sequence of the insert was verified and the plasmid containing the correct nucleotide sequence was digested with restriction enzymes EcoRI and SmaI. Using a Ligation High (TOYOBO), the resulting DNA fragment of approximately 2.1 kbp was ligated to the DNA fragment obtained by digesting vector pYE22m with restriction enzymes EcoRII and SmaI to give plasmid pYE-ACS-8.

Using the plasmid containing cDNA of MaACS-9 as a template, PCR was performed with the primers below using ExTaq (Takara Bio Inc.). The thus amplified DNA fragment was cloned by a TOPO-TA Cloning Kit (Invitrogen).

```
Primer EcoRI-ACS-9-F:
                                      (SEQ ID NO: 87)
5'-GAATTCATGGTTGCTCTCCCACTCG-3'

Primer BamHI-ACS-9-R:
                                      (SEQ ID NO: 88)
5'-GGATCCCTACTATAGCTTGGCCTTGCC-3'
```

The nucleotide sequence of the insert was verified and the plasmid containing the correct nucleotide sequence was digested with restriction enzymes EcoRI and BamHI. Using a Ligation High (TOYOBO), the resulting DNA fragment of approximately 2.0 kbp was ligated to the DNA fragment obtained by digesting vector pYE22m with restriction enzymes EcoRII and BamHI to give plasmid pYE-ACS-9.

Using the plasmid containing cDNA of MaACS-1 as a template, PCR was performed with the primers below using ExTaq (Takara Bio Inc.). The thus amplified DNA fragment was cloned by a TOPO-TA Cloning Kit (Invitrogen).

```
Primer EcoRI-ACS-1-F:
                                      (SEQ ID NO: 89)
5'-GGATCCATGTATGTCGGCTCCAAGCTTGC-3'

Primer SalI-ACS-1-R:
                                      (SEQ ID NO: 90)
5'-GTCGACTCAAAGCCTGGCTTTGCCGCTGACG-3'
```

The nucleotide sequence of the insert was verified and the plasmid containing the correct nucleotide sequence was digested with restriction enzymes EcoRI and SalI. Using a Ligation High (TOYOBO), the resulting DNA fragment of approximately 1.9 kbp was ligated to the DNA fragment obtained by digesting vector pYE22m with restriction enzymes EcoRI and SalI to give plasmid pYE-ACS-1.

Using the plasmid containing cDNA of MaACS-10 as a template, PCR was performed with the primers below using ExTaq (Takara Bio Inc.). The thus amplified DNA fragment was cloned by a TOPO-TA Cloning Kit (Invitrogen).

```
Primer ACS-10-1F:
                                      (SEQ ID NO: 91)
5'-GGATCCATGGAAACCTTGGTTAACGGAAAG-3'

Primer KpnI-ACS-10-R:
                                      (SEQ ID NO: 92)
5'-GGTACCTAGAACTTCTTCCACATCTCCTC-3'
```

The nucleotide sequence of the insert was verified and the plasmid containing the correct nucleotide sequence was digested with restriction enzymes EcoRI and KpnI. Using a Ligation High (TOYOBO), the resulting DNA fragment of approximately 2.1 kbp was ligated to the DNA fragment obtained by digesting vector pYE22m with restriction enzymes EcoRI and KpnI. Plasmid pYE-ACS-10 was obtained by screening for the orientation that the GAPDH promoter of vector pYE22m was located at its 5' end of CDS of MaACS-10.

Using the plasmid containing cDNA of MaACS-11 as a template, PCR was performed with the primers below using ExTaq (Takara Bio Inc.). The thus amplified DNA fragment was cloned by a TOPO-TA Cloning Kit (Invitrogen).

```
Primer SacI-ACS-11-F:
                                           (SEQ ID NO: 93)
5'-GAGCTCATGCCAAAGTGCTTTACCGTCAACG-3'

Primer BamHI-ACS-11-R:
                                           (SEQ ID NO: 94)
5'-GGATCCTTACTTGGAGCCATAGATCTGCTTG-3'
```

The nucleotide sequence of the insert was verified and the plasmid containing the correct nucleotide sequence was digested with restriction enzymes SacI and BamHI. Using a Ligation High (TOYOBO), the resulting DNA fragment of approximately 2.0 kbp was ligated to the DNA fragment obtained by digesting vector pYE22m with restriction enzymes SacI and BamHI to give plasmid pYE-ACS-11.

Expression in Yeast
Acquisition of Transformants

The yeast *S. cerevisiae* EH13-15 strain (trp1,MATα) (Appl. Microbiol. Biotechnol., 30, 515-520, 1989) was transformed with plasmids pYE22m, pYE-MaACS-6, pYE-MaACS-8 and pYE-MaACS-9, respectively, by the lithium acetate method. The transformants were screened for the ability to grow on SC-Trp agar medium (2% agar) (per liter, 6.7 g Yeast Nitrogen Base w/o Amino Acids (DIFCO), 20 g glucose, 1.3 g amino acid powders (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Cultivation of Yeast

One each from the transformants obtained using the respective plasmids was provided for the following cultivation experiment.

One platinum loop of the yeast was plated on 10 ml of SC-Trp and cultured with shaking for preincubation at 30° C. for a day. After 1 ml of the preincubation was added to the SC-Trp medium, main cultivation was performed by shake culturing at 30° C. for a day.

Analysis of Fatty Acids in Mycelia

The yeast culture broth was centrifuged to recover the mycelial cells. After washing with 10 ml of sterile water, the mycelial cells were again centrifuged, recovered and lyophilized. The fatty acids in the mycelial cells were converted into the methyl esters by the hydrochloric acid-methanol method followed by extraction with hexane. After hexane was removed by distillation, the fatty acids were analyzed by gas chromatography.

The fatty acid production per medium is shown in TABLE 5. In the strains transformed by ppYE-MaACS-6, pYE-MaACS-8 or pYE-MaACS-9, the fatty acid production per medium was increased as compared to the control which was transformed by pYE22m.

TABLE 5

Fatty Acid Production by Transformant per Medium

|  | Control | MaACS-6 | MaACS-8 | MaACS-9 |
|---|---|---|---|---|
| Fatty acid production (mg/L) | 135 | 159 | 196 | 187 |

Expression in Arachidonic Acid-Producing Yeast
(1) Breeding of Arachidonic Acid-Producing Yeast Strains To breed arachidonic acid-producing yeast strain (*S. cerevisiae*), the following plasmids were constructed.

First, using the cDNA prepared from *M. alpina* strain 1S-4 as a template, PCR was performed with ExTaq using the primer pair of Δ12-f and Δ12-r, Δ6-f and Δ6-r, GLELO-f and GLELO-r, or Δ5-f and Δ5-r to amplify the Δ12 fatty acid desaturase gene (GenBank Accession No. AB020033) (hereinafter "Δ12 gene"), the Δ6 fatty acid desaturase gene (GenBank Accession No. AB020032) (hereinafter "Δ6 gene"), the GLELO fatty acid elongase gene (GenBank Accession No. AB193123) (hereinafter "GLELO gene") and the Δ5 fatty acid desaturase gene (GenBank Accession No. AB188307) (hereinafter "Δ5 gene") in the *M. alpina* strain 1S-4.

```
                                           (SEQ ID NO: 95)
Δ12-f:      5'-TCTAGAATGGCACCTCCCAACACTATTG-3'

(SEQ ID NO: 96)
Δ12-r:      5'-AAGCTTTTACTTCTTGAAAAAGACCACGTC-3'

(SEQ ID NO: 97)
Δ6-f:       5'-TCTAGAATGGCTGCTGCTCCCAGTGTGAG-3'

(SEQ ID NO: 98)
Δ6-r:       5'-AAGCTTTTACTGTGCCTTGCCCATCTTGG-3'

(SEQ ID NO: 99)
GLELO-f:    5'-TCTAGAATGGAGTCGATTGCGCAATTCC-3'

(SEQ ID NO: 100)
GLELO-r:    5'-GAGCTCTTACTGCAACTTCCTTGCCTTCTC-3'

(SEQ ID NO: 101)
Δ5-f:       5'-TCTAGAATGGGTGCGGACACAGGAAAAACC-3'

(SEQ ID NO: 102)
Δ5-r:       5'-AAGCTTTTACTCTTCCTTGGGACGAAGACC-3'
```

These genes were cloned with the TOPO-TA-Cloning Kit. The clones were confirmed by their nucleotide sequences. The clones containing the nucleotide sequences of the Δ12 gene, Δ6 gene, GLELO gene and Δ5 gene were designated as plasmids pCR-MAΔ12DS (containing the nucleotide sequence of the Δ12 gene), pCR-MAΔ6DS (containing the nucleotide sequence of the Δ6 gene), pCR-MAGLELO (containing the nucleotide sequence of the GLELO gene) and pCR-MAΔ5DS (containing the nucleotide sequence of the Δ5 gene), respectively.

On the other hand, the plasmid pURA34 (JPA 2001-120276) was digested with restriction enzyme HindIII. The resulting DNA fragment of approximately 1.2 kb was inserted into the HindIII site of the vector, which was obtained by digesting pUC18 vector (Takara Bio Inc.) with restriction enzymes EcoRI and SphI, then blunt ending and self ligating said vector. The clone in which the EcoRI site of the vector was located at its 5' end of URA3 was designated as pUC-URA3. Also, the DNA fragment of approximately 2.2 kb, which was obtained by digesting YEp13 with restriction enzymes SalI and XhoI, was inserted into the SalI site of vector pUC18. The clone in which the EcoRI site of the vector was located at its 5' end of LUE2 was designated as pUC-LEU2.

Next, the plasmid pCR-MAΔ12DS was digested with restriction enzyme HindIII, followed by blunt ending and further digestion with restriction enzyme XbaI. The resulting DNA fragment of approximately 1.2 kbp was ligated to the DNA fragment of approximately 6.6 kbp, which was obtained by digesting vector pESC-URA (STRATAGENE) with restriction enzyme SacI, blunt ending and further digesting with restriction enzyme SpeI. Thus, the plasmid pESC-U-Δ12 was obtained. The plasmid pCR-MAΔ6DS was digested with restriction enzyme XbaI, followed by blunt ending and further digestion with restriction enzyme HindIII. The resulting DNA fragment of approximately 1.6 kbp was ligated to the DNA fragment of approximately 8 kbp, which was obtained by digesting the plasmid pESC-U-Δ12 with restriction enzyme SalI, blunt ending and further digesting with restriction enzyme HindIII, thereby to give the plasmid pESC-U-Δ12:Δ6. This plasmid was partially digested with restriction enzyme PvuII. The resulting fragment of approximately 4.2 kb was inserted into the SmaI site of pUC-URA3 to give the plasmid pUC-URA-Δ12:Δ6.

Also, the plasmid pCR-MAGLELO was digested with restriction enzymes XbaI and SacI. The resulting DNA fragment of approximately 0.95 kbp was ligated to the DNA fragment of approximately 7.7 kbp, which was obtained by digesting vector pESC-LEU (STRATAGENE) with restriction enzymes XbaI and SacI. Thus, the plasmid pESC-L-GLELO was obtained. The plasmid pCR-MAΔ5DS was digested with restriction enzyme XbaI, followed by blunt ending and further digestion with restriction enzyme HindIII. The resulting DNA fragment of approximately 1.3 kbp was ligated to the DNA fragment of approximately 8.7 kbp, which was obtained by digesting the plasmid pESC-L-GLELO with restriction enzyme ApaI, blunt ending and further digesting with restriction enzyme HindIII, thereby to give the plasmid pESC-L-GLELO:Δ5. This plasmid was digested with restriction enzyme PvuII and the resulting fragment of approximately 3.2 kbp was inserted into the SmaI site of pUC-LEU2 to give plasmid pUC-LEU-GLELO:Δ5. The *Saccharomyces cerevisiae* strain YPH499 (STRATAGENE) was co-transformed by the plasmid pUC-URA-Δ12:Δ6 and plasmid pUC-LEU-GLELO:Δ5. The transformants were screened for the ability to grow on SC-Leu, Ura agar medium Among the transformants thus obtained, random one strain was designated as the strain ARA3-1. By cultivating the strain in a galactose-supplemented medium, the strain became capable of expressing from the GAL1/10 promoter the Δ12 fatty acid desaturase gene, the Δ6 fatty acid desaturase gene, the GLELO gene and the Δ5 fatty acid desaturase gene.

(2) Transformation into Arachidonic Acid-Producing Yeast and Analysis

The ARA3-1 strain was transformed by plasmids pYE22m, pYE-ACS-1, pYE-ACS-10 and pYE-ACS-11, respectively. Transformants were screened for the ability to grow on SC-Trp,Leu,Ura agar medium (2% agar) (per liter, 6.7 g Yeast Nitrogen Base w/o Amino Acids (DIFCO), 20 g glucose and 1.3 g amino acid powders (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g of threonine). Random four strains from the respective plasmid-transfected strains were used for the subsequent cultivation.

These strains were cultivated at 30° C. for a day in 10 ml of the SC-Trp,Leu,Ura liquid medium described above. One milliliter of the culture was plated on 10 ml of SG-Trp,Leu,Ura liquid medium (per liter, 6.7 g Yeast Nitrogen Base w/o Amino Acids (DIFCO), 20 g galactose and 1.3 g amino acid powders (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine) and then cultivated at 15° C. for 6 days. The mycelial cells were collected, washed with water and then lyophilized. After the fatty acids in the dried mycelial cells were converted to the methyl esters by the hydrochloric acid-methanol method, the analysis of fatty acids was performed by gas chromatography. The ratio of each PUFA to the total fatty acids in the control strain transformed by plasmid pYE22m, and in the strains transformed by each ACS homolog from *Mortierella* is shown in TABLE 6.

TABLE 6

| % Ratio of PUFA in ACS homolog expression strains from *Mortierella* | | | | |
|---|---|---|---|---|
| | control | MaACS-1 | MaACS-10 | MaACS-11 |
| 18:2 | 7.23 ± 0.11 | 8.15 ± 0.29 | 14.87 ± 0.28 | 10.57 ± 0.30 |
| 18:3 (n − 6) | 0.38 ± 0.01 | 0.44 ± 0.04 | 1.67 ± 0.10 | 0.92 ± 0.07 |

TABLE 6-continued

| % Ratio of PUFA in ACS homolog expression strains from *Mortierella* | | | | |
|---|---|---|---|---|
| | control | MaACS-1 | MaACS-10 | MaACS-11 |
| DGLA | 0.41 ± 0.01 | 0.42 ± 0.02 | 0.30 ± 0.17 | 0.33 ± 0.03 |
| ARA | 0.42 ± 0.01 | 0.63 ± 0.04 | 0.47 ± 0.10 | 0.75 ± 0.10 |

Average ± Standard Deviation

As shown in TABLE 6, the ratio of fatty acids could be modified by expressing the ACS homolog from *Mortierella*. Particularly in the MaACS-11 expression strain, the ratios of arachidonic acid, linoleic acid and γ-linolenic acid were increased by about 1.8 times, about 1.5 times and about 2.4 times, respectively, as compared to the control strain. In the MaACS-1 expression strain, the ratio of arachidonic acid was increased by about 1.5 times, as compared to the control strain. Further in the MaACS-10 expression strain, the ratios of linoleic acid and γ-linolenic acid were increased by about 2 times and about 4 times, respectively, as compared to the control strain.

Example 2

Construction of Expression Vector

Expression Vector for Yeast

The vector pYE-ACS-12 for expressing MaACS-12 in yeast was constructed as follows. Using a plasmid containing the cDNA of MaACS-12 as a template, PCR was performed with the following primers using KOD-Plus-(TOYOBO).

```
Primer Eco-ACS-G-F:
                                (SEQ ID NO: 103)
5'-GAATTCATGACAAAGTGCCTCACCGTCG-3'

Primer Sma-ACS-G-R:
                                (SEQ ID NO: 104)
5'-CCCGGGACTTAGGCCGTTCCATAAAGCTG-3'
```

The amplified DNA fragment was cloned using a Zero Blunt TOPO PCR Cloning Kit (Invitrogen). The nucleotide sequence of the insert was verified and the plasmid containing the correct nucleotide sequence was digested with restriction enzymes EcoRI and SmaI. Using a Ligation High (TOYOBO), the resulting DNA fragment of approximately 2 kbp was ligated to the DNA fragment obtained by digesting vector pYE22m with restriction enzyme BamHI and then blunt ending with a Blunting Kit (TAKARA Bio) and further digesting with EcoRI, to give plasmid pYE-ACS-12.

Expression Vector for *M. alpina*

The vector for expressing MaACS-10 and MaACS-11 in *M. alpina* was constructed as follows.

First, pUC18 was digested with restriction enzymes EcoRI and HindIII and an adapter obtained by annealing oligo DNA MCS-for-pUC18-F2 with MCS-for-pUC18-R2 was inserted therein to construct plasmid pUC18-RF2.

```
MCS-for-pUC18-F2:
                                (SEQ ID NO: 105)
5'-AATTCATAAGAATGCGGCCGCTAAACTATTCTAGACTAGGTCG
ACGGCGCGCCA-3'

MCS-for-pUC18-R2:
                                (SEQ ID NO: 106)
5'-AGCTTGGCGCGCCGTCGACCTAGTCTAGAATAGTTTAGCGGCC
GCATTCTTATG-3'
```

Using the genome DNA of *M. alpina* as a template, PCR was performed with the primers NotI-GAPDHt-F and EcoRI- Asc1-GAPDHt-R using KOD-Plus-(Toyobo). The amplified DNA fragment of about 0.5 kbp was cloned using a Zero Blunt TOPO PCR Cloning Kit (Invitrogen). After the nucleotide sequence of the insert was verified, the DNA fragment of about 0.9 kbp obtained by digesting with restriction enzymes NotI and EcoRI was inserted into the NotI and EcoRI site of plasmid pUC18-RF2 to construct plasmid pDG-1.

```
Not1-GAPDHt-F:
                                    (SEQ ID NO: 107)
5'-AGCGGCCGCATAGGGGAGATCGAACC-3'

EcoR1-Asc1-GAPDHt-R:
                                    (SEQ ID NO: 108)
5'-AGAATTCGGCGCGCCATGCACGGGTCCTTCTCA-3'
```

Using the genome of *M. alpina* as a template, PCR was performed with the primers URA5g-F1 and URA5g-R1 using KOD-Plus- (Toyobo). The amplified DNA fragment was cloned using a Zero Blunt TOPO PCR Cloning Kit (Invitrogen). After the nucleotide sequence of the insert was verified, the DNA fragment of about 2 kbp obtained by digestion with SalI was inserted into the SalI site of plasmid pDG-1. The plasmid that the 5' end of URA5 gene inserted was oriented toward the EcoRI side of the vector was designated as the plasmid pDuraG.

```
                                    (SEQ ID NO: 109)
URA5g-F1:     5'-GTCGACCATGACAAGTTTGC-3'

(SEQ ID NO: 110)
URA5g-R1:     5'-GTCGACTGGAAGACGAGCACG-3'
```

Subsequently, PCR was performed with KOD-Plus- (TOYOBO) using the genome of *M. alpina* as a template and the primers hisHp+URA5-F and hisHp+MGt-F. Using an In-Fusion (registered trade name) Advantage PCR Cloning Kit (TAKARA Bio), the amplified DNA fragment of about 1.0 kbp was ligated to the DNA fragment of about 5.3 kbp amplified by PCR with KOD-Plus- (TOYOBO) using pDuraG as a template and the primers pDuraSC-GAPt-F and URA5gDNA-F, to give plasmid pDUra-RhG.

```
hisHp + URA5-F:
                                    (SEQ ID NO: 111)
5'-GGCAAACTTGTCATGAAGCGAAAGAGAGATTATGAAAACAAGC-3' hisHp + MGt-F:
                                    (SEQ ID NO: 112)
5'-CACTCCCTTTTCTTAATTGTTGAGAGAGTGTTGGGTGAGAGT-3' pDuraSC-GAPt-F:
                                    (SEQ ID NO: 113)
5'-TAAGAAAAGGGAGTGAATCGCATAGGG-3'

URA5gDNA-F:
                                    (SEQ ID NO: 114)
5'-CATGACAAGTTTGCCAAGATGCG-3'
```

Using the plasmid pDUra-RhG as a template, the DNA fragment of about 6.3 kbp was amplified by PCR with KOD-Plus- (TOYOBO) using the primers pDuraSC-GAPt-F and pDurahG-hisp-R.

```
pDurahG-hisp-R:
                                    (SEQ ID NO: 115)
5'-ATTGTTGAGAGAGTGTTGGGTGAGAGTG-3'
```

Using the plasmid containing cDNA of MaACS-10, the DNA fragment of about 2.1 kbp was amplified by PCR with KOD-Plus- (TOYOBO), using the primers below.

```
Primer ACS-10 + hisp-F:
                                    (SEQ ID NO: 116)
5'-CACTCTCTCAACAATATGGAAACCTTGGTTAACGGAAAGT-3'

Primer ACS-10 + MGt-R:
                                    (SEQ ID NO: 117)
5'-CACTCCCTTTTCTTACTAGAACTTCTTCCACATCTCCTCAATA
TC-3'
```

The resulting DNA fragment was ligated to the 6.3 kbp DNA fragment described above using an In-Fusion (registered trade name) Advantage PCR Cloning Kit (TAKARA BIO) to give plasmid pDUraRhG-ACS-10.

Using the plasmid containing cDNA of MaACS-11 as a template, the 2.1 kbp DNA fragment was amplified by PCR with KOD-Plus- (TOYOBO) using the primers below.

```
Primer ACS-11 + MGt-R:
                                    (SEQ ID NO: 118)
5'-CACTCCCTTTTCTTATTACTTGGAGCCATAGATCTGCTTGA-3'

Primer ACS-11 + hisp-F:
                                    (SEQ ID NO: 119)
5'-CACTCTCTCAACAATATGCCAAAGTGCTTTACCGTCAAC-3'
```

The resulting DNA fragment was ligated to the 6.3 kbp DNA fragment described above using an In-Fusion (registered trade name) Advantage PCR Cloning Kit (TAKARA BIO) to give the plasmid pDUraRhG-ACS-11.

Evaluation of ACS Activity

The yeast EH13-15 was transformed by plasmids pYE22m, pYE-ACS-5, pYE-ACS-8, pYE-ACS-10, pYE-ACS-11 and pYE-ACS-12, respectively, and random two transformants obtained were cultivated as follows. One platinum loop of the mycelial cells were plated on 10 ml of SC-Trp medium and cultivated with shaking for preincubation at 30° C. for a day. After 1% of the preincubation was added to 100 ml of the SD-Trp medium, main cultivation was performed by shake culturing at 28° C. for a day.

The crude enzyme solution was prepared as follows. The mycelial cells were collected by centrifugation, washed with water and temporarily stored at −80° C. The mycelial cells were suspended in 5 ml of Buffer B (50 mM sodium sulfate buffer (pH 6.0), 10% glycerol and 0.5 mM PMSF). The mycelial cells were then disrupted with a French press (16 kPa, 3 times). Centrifugation was carried out at 1,500×g at 4° C. for 10 minutes and centrifuged. The supernatant obtained was used as the crude enzyme solution.

The ACS activity was determined by the following procedures based on the description of a reference literature (J.B.C., 272 (8), 1896-4903, 1997). The reaction solution contained 200 mM Tris-HCl (pH7.5), 2.5 mM ATP, 8 mM $MgCl_2$, 2 mM EDTA, 20 mM NaF, 0.1% TritonX-100, 50 µg/ml fatty acids, 50 µM CoA and 100 µA of the crude enzyme solution (suitably diluted in Buffer B), and was made 500 p. 1 in total. The reaction was carried out at 28° C. for 30 minutes. After completion of the reaction, 2.5 ml of stop solution (isopropanol:n-heptane:1M sulfuric acid (40:20:1)) was added and the mixture was thoroughly agitated. Furthermore, 2 ml of n-heptane was added thereto. After thoroughly mixing them, the mixture was centrifuged to recover the upper layer. Further 2 ml of n-heptane was added to the lower layer and treated in the same manner to recover the upper layer. The upper layers recovered were combined and evaporated to dryness using a centrifugal concentrator. Then, 50 ml of 0.2 mg/ml tricosanoic acid (23:0) was added thereto as an internal standard. The fatty acids were converted into the methyl esters by the hydrochloric acid-methanol method, followed by fatty acid analysis using gas chromatography. The amount of the fatty acids, which were changed to acyl-CoA and thus distributed into the lower layer by the procedures above, was calculated from the amount of fatty acids detected. The results are shown in the table below. The ACS activity is expressed as the amount of fatty acids distributed into the lower layer by the procedures above, per weight of the protein in the crude enzyme solution. The control is the strain transformed by pYE22m and the others are the transformants in which the expression vectors of the respective genes were introduced.

TABLE 7

| | ACS Activity on Palmitic Acid | | | | | | | | | |
|---|---|---|---|---|---|---|---|---|---|---|
| | MaACS-5 | | MaACS-10 | | MaACS-11 | | MaACS-12 | | Control | |
| | #1 | #2 | #1 | #2 | #1 | #2 | #1 | #2 | #1 | #2 |
| mg/mg · protein | 0.26 | 0.20 | 0.41 | 0.34 | 0.49 | 0.43 | 0.31 | 0.40 | 0.11 | 0.12 |

When palmitic acid was used as substrate, MaACS-5, MaACS-10, MaACS-11 and MaACS-12 showed the ACS activity of approximately 2 to 4 times the control.

TABLE 8

| | ACS Activity on Oleic Acid | | | | | | | |
|---|---|---|---|---|---|---|---|---|
| | MaACS-10 | | MaACS-11 | | MaACS-12 | | Control | |
| | #1 | #2 | #1 | #2 | #1 | #2 | #1 | #2 |
| mg/mg · protein | 0.25 | 0.20 | 0.25 | 0.16 | 0.16 | 0.18 | 0.09 | 0.11 |

When oleic acid was used as substrate, MaACS-10, MaACS-11 and MaACS-12 showed the ACS activity of approximately twice the control.

TABLE 9

| | ACS Activity on Linoleic Acid | | | | | | | | | | | |
|---|---|---|---|---|---|---|---|---|---|---|---|---|
| | MaACS-5 | | MaACS-8 | | MaACS-10 | | MaACS-11 | | MaACS-12 | | Control | |
| | #1 | #2 | #1 | #2 | #1 | #2 | #1 | #2 | #1 | #2 | #1 | #2 |
| mg/mg · protein | 0.47 | 0.42 | 0.42 | 0.38 | 5.24 | 5.67 | 3.46 | 3.20 | 0.95 | 0.78 | 0.14 | 0.14 |

When linoleic acid was used as substrate, MaACS-5, MaACS-8 and MaACS-12 showed the ACS activity of several times (approximately 3, 3 and 6 times, respectively) the control, whereas MaACS-10 and MaACS-11 showed the ACS activity of several tens times (approximately 40 and 20 times, respectively) the control.

TABLE 10

| | ACS Activity on γ-Linoleic Acid | | | | | | | | | | | |
|---|---|---|---|---|---|---|---|---|---|---|---|---|
| | MaACS-5 | | MaACS-8 | | MaACS-10 | | MaACS-11 | | MaACS-12 | | Control | |
| | #1 | #2 | #1 | #2 | #1 | #2 | #1 | #2 | #1 | #2 | #1 | #2 |
| mg/mg · protein | 0.26 | 0.28 | 0.16 | 0.31 | 0.63 | 0.59 | 0.90 | 0.75 | 0.52 | 0.63 | 0.07 | 0.09 |

When γ-linoleic acid was used as substrate, all of MaACS-5, MaACS-8, MaACS-10, MaACS-11 and MaACS-12 showed the ACS activity of approximately 2 to 10 times the control.

TABLE 11

ACS Activity on Dihomo-γ-Linoleic Acid

| | MaACS-10 | | MaACS-11 | | MaACS-12 | | Control | |
|---|---|---|---|---|---|---|---|---|
| | #1 | #2 | #1 | #2 | #1 | #2 | #1 | #2 |
| mg/mg · protein | 4.98 | 4.21 | 2.75 | 2.98 | 2.04 | 1.86 | 0.09 | 0.05 |

When dihomo-γ-linoleic acid was used as substrate, all of MaACS-10, MaACS-11 and MaACS-12 showed the ACS activity of several tens times (approximately 60 times, 40 times and 30 times, respectively) the control.

TABLE 12

ACS Activity on Arachidonic Acid

| | MaACS-10 | | MaACS-11 | | MaACS-12 | | Control | |
|---|---|---|---|---|---|---|---|---|
| | #1 | #2 | #1 | #2 | #1 | #2 | #1 | #2 |
| mg/mg · protein | 8.12 | 7.19 | 2.73 | 2.87 | 1.08 | 0.87 | 0.13 | 0.03 |

When arachidonic acid was used as substrate, MaACS-10, MaACS-11 and MaACS-12 showed the ACS activity of several tens times (approximately 90 times, 30 times and 10 times, respectively) the control.

As above, MaACS-10, MaACS-11 and MaACS-12 in particular showed a higher activity on polyunsaturated fatty acids of 20 carbon atoms such as dihomo-γ-linoleic acid or arachidonic acid.

Arachidonic Acid Uptake Activity of ACS-Expressed Yeast

The yeast EH13-15 was transformed by plasmids pYE22m, pYE-ACS-10, pYE-ACS-11 and pYE-ACS-12, respectively, and random two transformants obtained were cultivated as follows. One platinum loop of the cells were plated on 10 ml of SC-Trp medium and cultivated with shaking for preincubation at 30° C. for a day. After 100 μl of the preincubation was added to 10 ml of the SC-Trp medium in which 50 μg/ml of arachidonic acid was supplemented, main cultivation was performed by shake culturing at 25° C. for a day. The mycelial cells were collected, lyophilized and subjected to fatty acid analysis. The ratio of arachidonic acid taken up into the mycelial cells to the added arachidonic acid was determined. The results are shown in TABLE 14. The control is the strain transformed by pYE22m and the others are the transformants in which the expression vectors of the respective genes were introduced.

TABLE 13

Dry Mycelial Weight

| | Control | | MaACS-10 | | MaACS-11 | | MaACS-12 | |
|---|---|---|---|---|---|---|---|---|
| | #1 | #2 | #1 | #2 | #1 | #2 | #1 | #2 |
| % | 36.63 | 37.81 | 65.86 | 66.64 | 61.53 | 61.35 | 63.64 | 67.06 |

TABLE 14

Ratio of Arachidonic Acid Taken Up into Mycelia

| | Control | | MaACS-10 | | MaACS-11 | | MaACS-12 | |
|---|---|---|---|---|---|---|---|---|
| | #1 | #2 | #1 | #2 | #1 | #2 | #1 | #2 |
| mg/10 ml | 15.30 | 15.80 | 19.60 | 18.10 | 16.70 | 17.40 | 16.80 | 16.20 |

Acquisition of M. Alpina Transformants

Using as a host the uracil-auxotrophic strain Aura-3 derived from M. alpina strain 1S-4 as described in PCT International Publication Pamphlet WO 2005/019437 entitled "Method of Breeding Lipid-Producing Fungus"), transformation was performed by the particle delivery method using the plasmids pDUraRhG-ACS-10 and pDUraRhG-ACS-11, respectively. For screening of the transformants, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

Evaluation of M. Alpina Transformants

The transformants obtained were plated on 4 ml of GY medium and cultured with shaking at 28° C. for 2 days. The mycelial cells were collected by filtration, and RNA was extracted with an RNeasy Plant Kit (QIAGEN). A SuperScript First Strand System for RT-PCR (Invitrogen) was used to synthesize cDNA. To confirm expression of the respective genes from the introduced constructs, RT-PCR was performed with the following primer pairs.

```
                                 (SEQ ID NO: 120)
ACS10-RT1:      5'-GTCCCGAATGGTTCCT-3'

(SEQ ID NO: 121)
ACS10-RT2:      5'-AGCGGTTTTCTACTTGC-3'

(SEQ ID NO: 122)
ACS11-RT1:      5'-AACTACAACCGCGTCG-3'

(SEQ ID NO: 123)
ACS11-RT2:      5'-CGGCATAAACGCAGAT-3'
```

In the transformants that overexpression was confirmed, one transformant each was plated on 10 ml of GY medium (2% glucose and 1% yeast extract) and cultured with shaking at 28° C. at 300 rpm for 3 days. The whole volume of the culture was transferred to 500 ml of GY medium (2 L Sakaguchi flask) and shake cultured at 28° C. and 120 rpm. Three, seven, ten and twelve days after this day, 5 ml each and 10 ml each were taken and filtered. After the mycelial cells were dried at 120° C., fatty acids were converted into the methyl esters by the hydrochloric acid-methanol method and analyzed by gas chromatography. The fatty acid production and the amount of arachidonic acid produced, per dried mycelial cells were monitored with the passage of time. The transformant host strain Aura-3 was used as control. The results are shown in FIG. 27 (MaACS-10) and FIG. 28 (MaACS-11).

Figure 27:
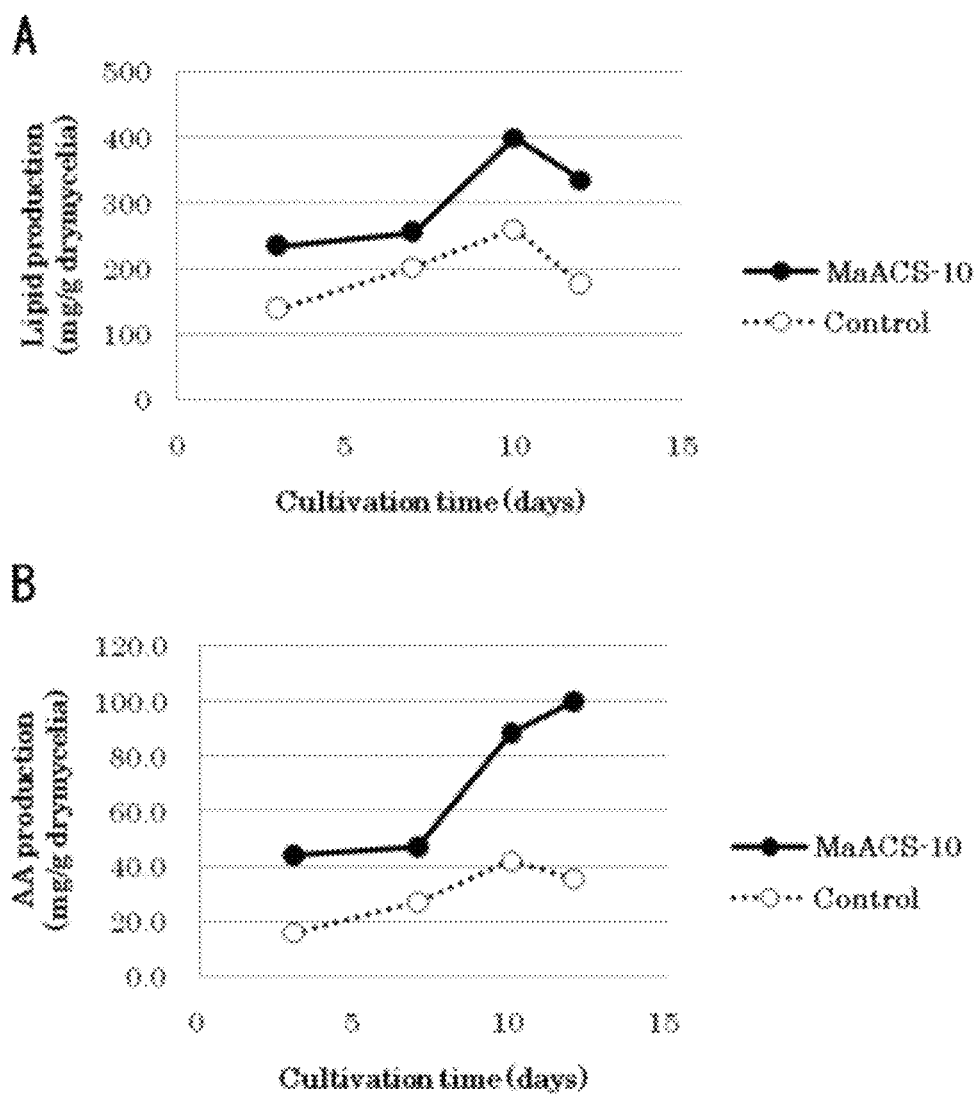
FIG. 27 shows changes with the passage of time in lipid production (FIG. 27A) and arachidonic acid production (FIG. 27B), per mycelia in MaACS-10-overexpressed M. alpina.
Figure 28:
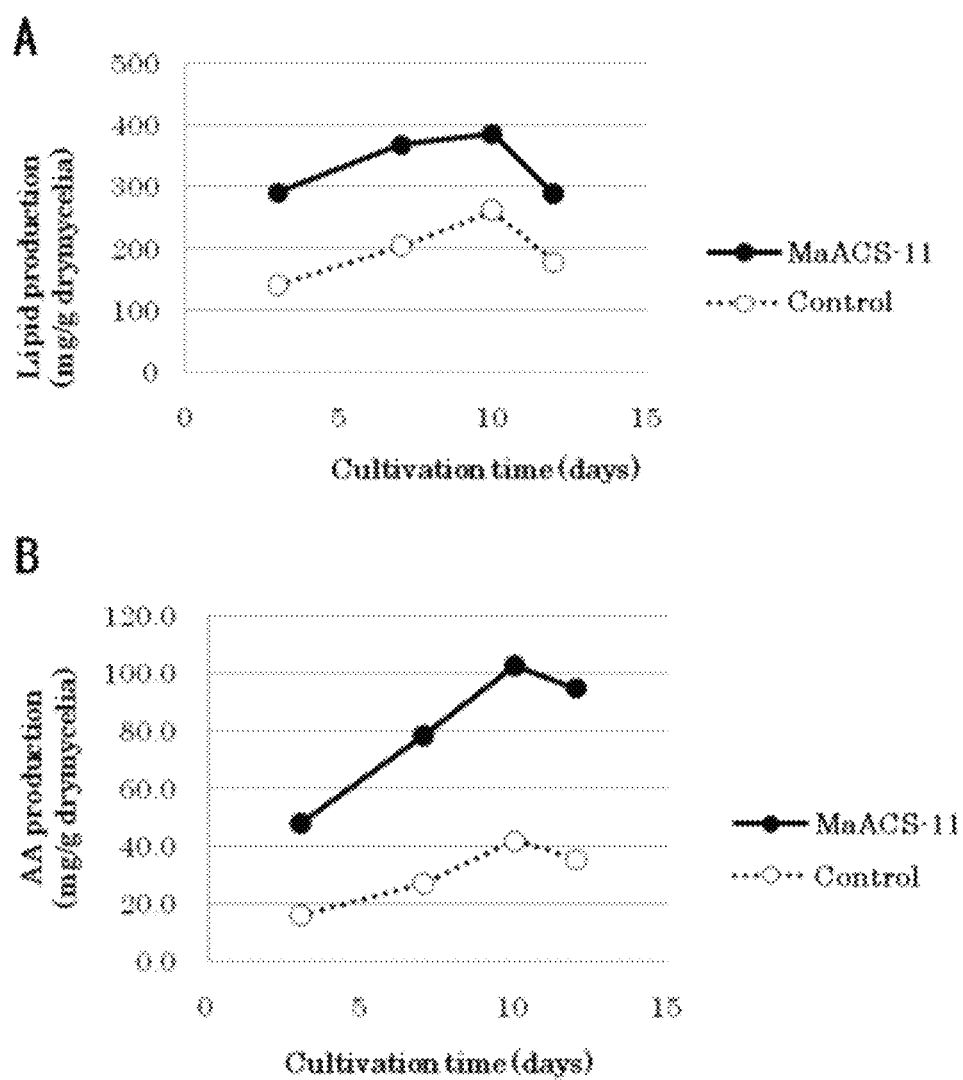
FIG. 28 shows changes with the passage of time in lipid production (FIG. 28A) and arachidonic acid production (FIG. 28B), per mycelia in MaACS-11-overexpressed M. alpina.

As shown in FIGS. 27 and 28, when MaACS-10 and MaACS-11 were overexpressed in M. alpina, both the amount of fatty acids and the amount of arachidonic acid per mycelia were increased as compared to the control.

Industrial Applicability

The polynucleotide of the present invention is expressed in an appropriate host cell to efficiently produce fatty acids, in particular, polyunsaturated fatty acids. The fatty acids produced in host cells according to the present invention can be used to produce fatty acid compositions, food products, cosmetics, pharmaceuticals, soaps, etc.

The invention claimed is:

1. A polynucleotide, which is a cDNA, according to any one selected from the group consisting of (a) to (d) below:
   (a) a polynucleotide comprising the nucleotide sequence shown by SEQ ID NO: 46;
   (b) a polynucleotide encoding a protein consisting of the amino acid sequence shown by SEQ ID NO: 47;
   (c) a polynucleotide encoding a protein consisting of an amino acid sequence wherein 1 to 10 amino acids are deleted, substituted, inserted and/or added in the amino acid sequence shown by SEQ ID NO: 47, and having an acyl-CoA synthetase activity; and
   (d) a polynucleotide encoding a protein having an amino acid sequence having at least 95% identity to the amino acid sequence shown by SEQ ID NO: 47, and having an acyl-CoA synthetase activity.

2. The polynucleotide according to claim 1, comprising the nucleotide sequence shown by SEQ ID NO: 46.

3. The polynucleotide according to claim 1, encoding a protein consisting of the amino acid sequence shown by SEQ ID NO: 47.

4. A vector comprising the polynucleotide according to claim 1.

5. A non-human transformant into which the polynucleotide according to claim 1 is introduced.

6. A non-human transformant into which the vector according to claim 4 is introduced.

7. A method for producing a lipid or fatty acid composition, which comprises culturing the transformant according to claim 5, and collecting the lipid or fatty acid composition from the culture.

8. The method according to claim 7, wherein the lipid is a triacylglycerol.

9. The method according to claim 7, wherein the fatty acid is a polyunsaturated fatty acid having at least 18 carbon atoms.

* * * * *

```
                           SEQUENCE LISTING

<160> NUMBER OF SEQ ID NOS: 142

<210> SEQ ID NO 1
<211> LENGTH: 1854
<212> TYPE: DNA
<213> ORGANISM: Mortierella alpina

<400> SEQUENCE: 1
atggatgctg tccctgcagt tgctgctgcg gccatccccg cagccatgta tgtcggctcc      60
aagcttgcaa tcccccgtga tgtcaagtta gctaaaggcc tagtcagtgc caagctaggt     120
tacaggtcct acgagaagaa cgactcgatc aatatctctt atcgttttga agagacctgt     180
aagaagcacc ctcatcgcga agctttggtg tttgaaggca aatcgtacac cttccaggac     240
atccagcgag aatcgaatag ggtgggacac tggctgttgt ccaaaggcgt caagcgagga     300
gagatcgtgt cgctcttcat gcaaaataag ccagagtttc tcttcttctg gcttggactc     360
aacaagatcg gcgctacggg agcattcatc aacacgaacc tctcgggcaa acctctgacg     420
cactcattgc gtaccgcgac agcatccatt ctgattatgg atgcggaact gccgacgccc     480
atttatagtg tcctcgatga agtccttgag atgggatatc agatatattc ctacggagga     540
tcccagcaac acgcctttgc tacacaagtt gaactttctc aaatctcgga tgcggccttg     600
cccaagagtc tgcgaaggaa aaccactgca atgatattg ccatgttgat ttacacctcc      660
ggaacgacgg gtttgcccaa agctggacgg ttctcccatg ctcgagccaa cgttgccgca     720
cttttctgga cgtctttcta ccacttcagc gaaaaagacc gcctgtacat cgccttgcct     780
ctttaccaca gtgctggagc tgtccttgga atatgtgtgg cctgggtcac cggtgctacg     840
gtggtcctgg cgcgcaagtt ttcaactact tccttctggg acgaatgcag ggccaacaag     900
gtcaccgtga tccagtatat tggagaaatc tgccgatact tactgaatgc ctctccttct     960
cccttggaca agacacacac gatccgaatg gcgcatggca acggcatgcg tccggatgta    1020
tggaacagat tcagagatcg tttcggcatc cctttgatcg gagaatggta tgcaagcact    1080
gagggcaccg gaatcttgac aaactataac acaggaccca atggcgctgg tgcgatagga    1140
tacagaggct ccttggccag aactgtcgat aagggtctga agattgcgaa gttcgacatc    1200
caaaccgagg aacttattcg tgacaaaaat ggtcgatgca ttgagtgtgt cgcagatgag    1260
cccggcgagc tcttgacaat gattgattca agtgatccca ctcgcgcttt ccaagggtac    1320
cataaaaatg caggtgcaaa ctccaagaaa gtcgtccagg atgcattcag tgttggcgac    1380
caatactttc gtactggtga catccttcgt cgcgacgctg atggctattt ctattttggc    1440
gatcgtgttg gagatacttt ccgctggaaa tctgaaaacg tgtcaactgc ggaggtttct    1500
gaggtgctct cagcataccc ggactgcatc gaggtcaacg tttatggcgt tcaagtccct    1560
ggacacgacg gccgcgcagg catggctgcc attgtctcca aggacaccat gaactgggat    1620
agtttcgcca gtttgcact caaaaatctg ccgaagtact ctgtgccgat tttcatccgc    1680
aaggtcccag agatggagat tacgggaacg ttcaagcaac gaaaggttga actggtgaac    1740
gagggcatgg acccgagcaa gatcaaagac gaaatgctgt ggttggatgg cactcctac    1800 cggcccttca aagaggcgga gcatactaga gtcgtcagcg gcaaagccag gctt         1854

<210> SEQ ID NO 2
<211> LENGTH: 618
<212> TYPE: PRT
```

-continued

<213> ORGANISM: Mortierella alpina

<400> SEQUENCE: 2

```
Met Asp Ala Val Pro Ala Val Ala Ala Ala Ile Pro Ala Ala Met
1               5                   10                  15

Tyr Val Gly Ser Lys Leu Ala Ile Pro Arg Asp Val Lys Leu Ala Lys
            20                  25                  30

Gly Leu Val Ser Ala Lys Leu Gly Tyr Arg Ser Tyr Glu Lys Asn Asp
            35                  40                  45

Ser Ile Asn Ile Ser Tyr Arg Phe Glu Glu Thr Cys Lys Lys His Pro
    50                  55                  60

His Arg Glu Ala Leu Val Phe Glu Gly Lys Ser Tyr Thr Phe Gln Asp
65                  70                  75                  80

Ile Gln Arg Glu Ser Asn Arg Val Gly His Trp Leu Leu Ser Lys Gly
                85                  90                  95

Val Lys Arg Gly Glu Ile Val Ser Leu Phe Met Gln Asn Lys Pro Glu
            100                 105                 110

Phe Leu Phe Phe Trp Leu Gly Leu Asn Lys Ile Gly Ala Thr Gly Ala
        115                 120                 125

Phe Ile Asn Thr Asn Leu Ser Gly Lys Pro Leu Thr His Ser Leu Arg
    130                 135                 140

Thr Ala Thr Ala Ser Ile Leu Ile Met Asp Ala Glu Leu Pro Thr Pro
145                 150                 155                 160

Ile Tyr Ser Val Leu Asp Glu Val Leu Glu Met Gly Tyr Gln Ile Tyr
                165                 170                 175

Ser Tyr Gly Gly Ser Gln His Ala Phe Ala Thr Gln Val Glu Leu
            180                 185                 190

Ser Gln Ile Ser Asp Ala Ala Leu Pro Lys Ser Leu Arg Arg Lys Thr
        195                 200                 205

Thr Ala Asn Asp Ile Ala Met Leu Ile Tyr Thr Ser Gly Thr Thr Gly
    210                 215                 220

Leu Pro Lys Ala Gly Arg Phe Ser His Ala Arg Ala Asn Val Ala Ala
225                 230                 235                 240

Leu Phe Trp Thr Ser Phe Tyr His Phe Ser Glu Lys Asp Arg Leu Tyr
                245                 250                 255

Ile Ala Leu Pro Leu Tyr His Ser Ala Gly Ala Val Leu Gly Ile Cys
            260                 265                 270

Val Ala Trp Val Thr Gly Ala Thr Val Val Leu Ala Arg Lys Phe Ser
        275                 280                 285

Thr Thr Ser Phe Trp Asp Glu Cys Arg Ala Asn Lys Val Thr Val Ile
    290                 295                 300

Gln Tyr Ile Gly Glu Ile Cys Arg Tyr Leu Leu Asn Ala Pro Pro Ser
305                 310                 315                 320

Pro Leu Asp Lys Thr His Thr Ile Arg Met Ala His Gly Asn Gly Met
                325                 330                 335

Arg Pro Asp Val Trp Asn Arg Phe Arg Asp Arg Phe Gly Ile Pro Leu
            340                 345                 350

Ile Gly Glu Trp Tyr Ala Ser Thr Glu Gly Thr Gly Ile Leu Thr Asn
        355                 360                 365

Tyr Asn Thr Gly Pro Asn Gly Ala Gly Ala Ile Gly Tyr Arg Gly Ser
    370                 375                 380

Leu Ala Arg Thr Val Asp Lys Gly Leu Lys Ile Ala Lys Phe Asp Ile
385                 390                 395                 400
```

```
Gln Thr Glu Glu Leu Ile Arg Asp Lys Asn Gly Arg Cys Ile Glu Cys
                405                 410                 415
Val Ala Asp Glu Pro Gly Glu Leu Leu Thr Met Ile Asp Ser Ser Asp
            420                 425                 430
Pro Thr Arg Ala Phe Gln Gly Tyr His Lys Asn Ala Gly Ala Asn Ser
        435                 440                 445
Lys Lys Val Val Gln Asp Ala Phe Ser Val Gly Asp Gln Tyr Phe Arg
    450                 455                 460
Thr Gly Asp Ile Leu Arg Arg Asp Ala Asp Gly Tyr Phe Tyr Phe Gly
465                 470                 475                 480
Asp Arg Val Gly Asp Thr Phe Arg Trp Lys Ser Glu Asn Val Ser Thr
                485                 490                 495
Ala Glu Val Ser Glu Val Leu Ser Ala Tyr Pro Asp Cys Ile Glu Val
            500                 505                 510
Asn Val Tyr Gly Val Gln Val Pro Gly His Asp Gly Arg Ala Gly Met
        515                 520                 525
Ala Ala Ile Val Ser Lys Asp Thr Met Asn Trp Asp Ser Phe Ala Lys
    530                 535                 540
Phe Ala Leu Lys Asn Leu Pro Lys Tyr Ser Val Pro Ile Phe Ile Arg
545                 550                 555                 560
Lys Val Pro Glu Met Glu Ile Thr Gly Thr Phe Lys Gln Arg Lys Val
                565                 570                 575
Glu Leu Val Asn Glu Gly Met Asp Pro Ser Lys Ile Lys Asp Glu Met
            580                 585                 590
Leu Trp Leu Asp Gly His Ser Tyr Arg Pro Phe Lys Glu Ala Glu His
        595                 600                 605
Thr Arg Val Val Ser Gly Lys Ala Arg Leu
    610                 615

<210> SEQ ID NO 3
<211> LENGTH: 1857
<212> TYPE: DNA
<213> ORGANISM: Mortierella alpina

<400> SEQUENCE: 3
atggatgctg tccctgcagt tgctgctgcg gccatccccg cagccatgta tgtcggctcc      60
aagcttgcaa tccccgtga tgtcaagtta gctaaaggcc tagtcagtgc aagctaggt     120 tacaggtcct acgagaagaa cgactcgatc aatatctctt atcgttttga agagacctgt     180
aagaagcacc ctcatcgcga agctttggtg tttgaaggca atcgtacac cttccaggac     240 atccagcgag aatcgaatag ggtgggacac tggctgttgt ccaaaggcgt caagcgagga     300
gagatcgtgt cgctcttcat gcaaaataag ccagagtttc tcttcttctg gcttggactc     360
aacaagatcg gcgctacggg agcattcatc aacacgaacc tctcgggcaa acctctgacg     420
cactcattgc gtaccgcgac agcatccatt ctgattatgg atgcggaact gccgacgccc     480
atttatagtg tcctcgatga agtccttgag atgggatatc agatatattc ctacggagga     540
tcccagcaac acgcctttgc tacacaagtt gaactttctc aaatctcgga tgcggccttg     600
cccaagagtc tgcgaaggaa aaccactgca atgatattg ccatgttgat ttacacctcc     660
ggaacgacgg gtttgcccaa agctggacgg ttctcccatg ctcgagccaa cgttgccgca     720
cttttctgga cgtctttcta ccacttcagc gaaaagacc gcctgtacat cgccttgcct     780
ctttaccaca gtgctggagc tgtccttgga atatgtgtgg cctgggtcac cggtgctacg     840
gtggtcctgg cgcgcaagtt ttcaactact tccttctggg acgaatgcag ggccaacaag     900
```

```
gtcaccgtga tccagtatat tggagaaatc tgccgatact tactgaatgc tcctccttct    960
cccttggaca agacacacac gatccgaatg gcgcatggca acggcatgcg tccggatgta   1020
tggaacagat tcagagatcg tttcggcatc cctttgatcg gagaatggta tgcaagcact   1080
gagggcaccg gaatcttgac aaactataac acaggaccca atggcgctgg tgcgatagga   1140
tacagaggct ccttggccag aactgtcgat aagggtctga agattgcgaa gttcgacatc   1200
caaaccgagg aacttattcg tgacaaaaat ggtcgatgca ttgagtgtgt cgcagatgag   1260
cccggcgagc tcttgacaat gattgattca agtgatccca ctcgcgcttt ccaagggtac   1320
cataaaaatg caggtgcaaa ctccaagaaa gtcgtccagg atgcattcag tgttggcgac   1380
caatactttc gtactggtga catccttcgt cgcgacgctg atggctattt ctattttggc   1440
gatcgtgttg agatactttt ccgctggaaa tctgaaaacg tgtcaactgc ggaggtttct   1500
gaggtgctct cagcataccc ggactgcatc gaggtcaacg tttatggcgt tcaagtccct   1560
ggacacgacg gccgcgcagg catggctgcc attgtctcca aggacaccat gaactgggat   1620
agtttcgcca gtttgcact caaaaatctg ccgaagtact ctgtgccgat tttcatccgc   1680
aaggtcccag agatggagat tacgggaacg ttcaagcaac gaaaggttga actggtgaac   1740
gagggcatgg acccgagcaa gatcaaagac gaaatgctgt ggttggatgg gcactcctac   1800
cggcccttca agaggcgga gcatactaga gtcgtcagcg gcaaagccag gctttga    1857

<210> SEQ ID NO 4
<211> LENGTH: 2077
<212> TYPE: DNA
<213> ORGANISM: Mortierella alpina

<400> SEQUENCE: 4 gctcttttt  gttctgttct ttgccacccc actctgctgt gcctctccac tcccctgcc     60 cgtcgaacgt tcttctgtca ctttgcacag cagtatctcc tctgatctcg cttgrttata    120
ttccctctaa tctcgtttgg ttatattccc tctgatctcg ctcggttata ttcttcagat    180
atggatgctg tccctgcagt tgctgctgcg gccatccccg cagccatgta tgtcggctcc    240
aagcttgcaa tcccccgtga tgtcaagtta gctaaaggcc tagtcagtgc caagctaggt    300
tacaggtcct acgagaagaa cgactcgatc aatatctctt atcgttttga agagacctgt    360
aagaagcacc ctcatcgcga agctttggtg tttgaaggca aatcgtacac cttccaggac    420
atccagcgag aatcgaatag ggtgggacac tggctgttgt ccaaaggcgt caagcgagga    480
gagatcgtgt cgctcttcat gcaaaataag ccagagtttc tcttcttctg gcttggactc    540
aacaagatcg gcgctacggg agcattcatc aacacgaacc tctcgggcaa acctctgacg    600
cactcattgc gtaccgcgac agcatccatt ctgattatgg atgcggaact gccgacgccc    660
atttatagtg tcctcgatga agtccttgag atgggatatc agatatattc ctacggagga    720
tcccagcaac acgcctttgc tacacaagtt gaactttctc aaatctcgga tgcggccttg    780
cccaagagtc tgcgaaggaa aaccactgca aatgatattg ccatgttgat ttacacctcc    840
ggaacgacgg gtttgcccaa agctggacgg ttctcccatg ctcgagccaa cgttgccgca    900
cttttctgga cgtcttctta ccacttcagc gaaaagacc gcctgtacat cgccttgcct    960
ctttaccaca gtgctggagc tgtccttgga atatgtgtgg cctgggtcac cggtgctacg   1020
gtggtcctgg cgcgcaagtt ttcaactact tccttctggg acgaatgcag ggccaacaag   1080
gtcaccgtga tccagtatat tggagaaatc tgccgatact tactgaatgc tcctccttct   1140
```

```
ccccttggaca agacacacac gatccgaatg gcgcatggca acggcatgcg tccggatgta      1200
tggaacagat tcagagatcg tttcggcatc cctttgatcg gagaatggta tgcaagcact      1260
gagggcaccg gaatcttgac aaactataac acaggaccca atggcgctgg tgcgatagga      1320
tacagaggct ccttggccag aactgtcgat aagggtctga agattgcgaa gttcgacatc      1380
caaaccgagg aacttattcg tgacaaaaat ggtcgatgca ttgagtgtgt cgcagatgag      1440
cccggcgagc tcttgacaat gattgattca agtgatccca ctcgcgcttt ccaagggtac      1500
cataaaaatg caggtgcaaa ctccaagaaa gtcgtccagg atgcattcag tgttggcgac      1560
caatactttc gtactggtga catccttcgt cgcgacgctg atggctattt ctattttggc      1620
gatcgtgttg agatactttt ccgctggaaa tctgaaaacg tgtcaactgc ggaggtttct      1680
gaggtgctct cagcataccc ggactgcatc gaggtcaacg tttatggcgt tcaagtccct      1740
ggacacgacg gccgcgcagg catggctgcc attgtctcca aggacaccat gaactgggat      1800
agtttcgcca gtttgcact caaaaatctg ccgaagtact ctgtgccgat tttcatccgc      1860
aaggtcccag agatggagat tacgggaacg ttcaagcaac gaaaggttga actggtgaac      1920
gagggcatgg acccgagcaa gatcaaagac gaaatgctgt ggttggatgg gcactcctac      1980
cggcccttca aagaggcgga gcatactaga gtcgtcagcg gcaaagccag gctttgacga      2040
ataaaattat ttcgttttgt ccgttgaaaa aaaaaaa                                2077

<210> SEQ ID NO 5
<211> LENGTH: 2278
<212> TYPE: DNA
<213> ORGANISM: Mortierella alpina

<400> SEQUENCE: 5
atggatgctg tccctgcagt tgctgctgcg gccatccccg cagccatgta tgtcggctcc        60
aagcttgcaa tcccccgtga tgtcaagtta gctaaaggcc tagtcagtgc caagctaggt       120
tacaggtcct acgagaagaa cgactcgatc aatatctctt atcgttttga agagacctgt       180
aagaagcacc ctcatcgcga agctttggtg tttgaaggca aatcgtacac cttccaggac       240
atccagcgag gtaacaagaa aaacaattgt ccaaagtgac agtcgaacgc atccgaaatt       300
tttactcaag ataaattgga tcatcgcacc acacccctcc gtcgatttca ctaacccttg       360
acttggaatg tagaatcgaa tagggtggga cactggctgt tgtccaaagg cgtcaagcga       420
ggagagatcg tgtcgctctt catgcaaaat aagccagagt ttctcttctt ctggcttgga       480
ctcaacaaga tcgcgctac gggagcattc atcaacacga acctctcggg caaacctctg       540
acgcactcat tgcgtaccgc gacagcatcc attctgatta tggatgcgga actgccgacg       600
cccatttata tgtcctcga tgaagtcctt gagatgggat atcagatata ttcctacgga       660
ggatcccagc aacacgcctt tgctacacaa gttgaacttt ctcaaatctc ggatgcggcc       720
ttgcccaaga gtctgcgaag gaaaaccact gcaaatgata ttgccatgtt gatttacacc       780
tccggaacga cgggtttgcc caaagctgga cggttctccc atgctcgagc aacggtagg       840 attatacccc cctcctccc ccccccctt tttttcatt tgctgtgaag ttattagctg        900
ttccactagc atattgactc atattcacgt tcctttaca cgtcgggatc cagttgccgc        960 actttctgg acgtctttct accacttcag cgaaaaagac cgcctgtaca tcgccttgcc      1020
tctttaccac agtgctggag ctgtccttgg aatatgtgtg gcctgggtca ccggtgctac      1080
ggtggtcctg gcgcgcaagt tttcaactac ttccttctgg gacgaatgca gggccaacaa      1140
ggtcaccgtg atccagtata ttggagaaat ctgccgatac ttactgaatg ctcctccttc      1200
```

| | |
|---|---|
| tcccttggac aagacacaca cgatccgaat ggcgcatggc aacggcatgc gtccggatgt | 1260 |
| atggaacaga ttcagagatc gtttcggcat ccctttgatc ggagaatggt atgcaagcac | 1320 |
| tgagggcacc ggaatcttga caaactataa cacaggaccc aatggcgctg gtgcgatagg | 1380 |
| atacagaggc tccttggcca gaactgtcga taagggtctg aagattgcga agttcgacat | 1440 |
| ccaaaccgag gaacttattc gtgacaaaaa tggtcgatgc attgaggtaa agttgacagt | 1500 |
| attaagttga acatattcca cagtacccttt tgtcttcggt gtccaaaata ctgactactt | 1560 |
| gcttgatgcc ccttcaagtg tgtcgcagat gagcccggcg agctcttgac aatgattgat | 1620 |
| tcaagtgatc ccactcgcgc tttccaaggg taccataaaa atgcaggtgc aaactccaag | 1680 |
| aaagtcgtcc aggatgcatt cagtgttggt aggtgtaatc ttcaccttgc gtgccttcaa | 1740 |
| cagcaaactt tgtgatccgc gctgactcga tgaccctgtc ctgcctacat ttctaggcga | 1800 |
| ccaatacttt cgtactggtg acatccttcg tcgcgacgct gatggctatt tctattttgg | 1860 |
| cgatcgtgtt ggagatactt tccgctggaa atctgaaaac gtgtcaactg cggaggtttc | 1920 |
| tgaggtgctc tcagcatacc cggactgcat cgaggtcaac gtttatggcg ttcaagtccc | 1980 |
| tggacacgac ggccgcgcag gcatggctgc cattgtctcc aaggacacca tgaactggga | 2040 |
| tagtttcgcc aagtttgcac tcaaaaatct gccgaagtac tctgtgccga ttttcatccg | 2100 |
| caaggtccca gagatggaga ttacgggaac gttcaagcaa cgaaaggttg aactggtgaa | 2160 |
| cgagggcatg gacccgagca agatcaaaga cgaaatgctg tggttggatg gcactcctta | 2220 |
| ccggcccttc aaagaggcgg agcatactag agtcgtcagc ggcaaagcca ggctttga | 2278 |

<210> SEQ ID NO 6
<211> LENGTH: 1926
<212> TYPE: DNA
<213> ORGANISM: Mortierella alpina

<400> SEQUENCE: 6

| | |
|---|---|
| atggcaagta ccaaatcact aaggacttgg cgcttgttcg cgttggtctc catgcacgca | 60 |
| aaagacttga ggccttggtc gagaatcggg actgcagtct ttacaacagg ttcgaggaac | 120 |
| aatgccagat ccggccttc tctgttgccc ttgttttga gaacacgtct tacacctgga | 180 |
| gagacttgga gctggcgtcc aacaggatgg cccattggtt tgttgctcaa ggaatccaaa | 240 |
| aaaaggagc gtgtggcgat gatgatgcat aactcgcctc tgttcattat cacctggctg | 300 |
| gcaatgctca agatcatggt tgtacctgct tttatcaata accagattgc aggacctgtt | 360 |
| ctggttcatt ctcttaaagt ggccgacgcc aagtttctct tgttcgatta cgagttggca | 420 |
| cctgtcatcc aaaagtcgct caatgagatc aaggacatgg ttacaatctc tacactgtc | 480 |
| acacccaagg atcaagttct aggtcaactt acgccaatc tgcccgaggc tgctcgtcag | 540 |
| gtgttggatg aggctccttc attctttggt tatgtcgaat ggcagaacct cagtaccgaa | 600 |
| ggtttctcga cgagagtcg tcaggaggtg gtgatctccg accccgcagc cttgatttac | 660 |
| accagcggga ccacgggatt ccccaaggct gctatcatgg accatggacg ttgcaacttg | 720 |
| gcttcgatct cttatggcac tctatgcggc atcaaaccag agaacaaggt ttacatcaca | 780 |
| ttgccgctct atcattctgc tggagccatc attggtctgg ccagagctt caccagcgga | 840 |
| tgcaccattg tgctggcgcg aaagttctcc gtgacaaagt tttggcgtga ttgcgttgag | 900 |
| tacgacgtaa ctcattttca gtacattggc gaactctgcc gctaccttct aaatgccccc | 960 |
| gaaagtccac tggacaaaag gcataaggtt cggatggcgt ttggcaacgg aatgcgcccg | 1020 |

```
gatgtttggg caaagtttca ggaacgattc aatatcccca ttattgttga gtactacgcc   1080
atgagcgaag gaacatcgtc gcttttgaat gtggccagga acaagcgcga ccaaggtgcg   1140
gtgggattcc gtggccccgt cgtgagggcc ttgacgcctc ccgttcaact ggtcaaggtg   1200
gactttgaca cggaggagct gatccgcgat aagaagacgg actttgcgt cctatgccag    1260
cctggtgaga ttggagaact ggtcacgcta gccgacaaca agacgactgg cgcacgctat   1320
gctgggtatt tcaatcagcc agaggtttcg aaggcaaggc tggtccagaa cgtggtagtg   1380
aaggacgaca tctacttccg gacgggtgac ctcttgtact ccaaggacca gtactggtac   1440
tttgctgatc gcgcaggaga cacgtaccgg tggaaaggag agaacgtgtc gacagccgag   1500
attgcagaca ctatcggccg tgttgagggc gtggctagtt gtactgttta tggcgtatcg   1560
gtcccgggca tggatggacg cgcgggcatg gctgctttgg tgctcaagaa ctcgattgtg   1620
cagatggcag gtggaagcca ggcaaagttc catgtggatg aggctgcgct gaacgcgttt   1680
ttgcgtgact tgagcaagga tgtggtcaaa aaactgccgg cgtatgcgat tcctcggttc   1740
ttgcgcattg cagagcagga actggagacg acgggcacgt tcaagaacaa gaaggtggag   1800
ctgaagaagg aagggttcga cctcggtaag gtcaaggagc ggctgtactg gtggacaccc   1860
aagggtgaat atgccccttt tggcgtggcg gagaacgagc agatcctcgc aggacgcgct   1920
cgtctt                                                             1926
```

<210> SEQ ID NO 7
<211> LENGTH: 642
<212> TYPE: PRT
<213> ORGANISM: Mortierella alpina

<400> SEQUENCE: 7

```
Met Ala Ser Thr Lys Ser Leu Arg Thr Trp Arg Leu Phe Ala Leu Val
1               5                   10                  15

Ser Met His Ala Lys Asp Leu Arg Pro Trp Ser Arg Ile Gly Thr Ala
            20                  25                  30

Val Phe Thr Thr Gly Ser Arg Asn Asn Ala Arg Ser Gly Leu Ser Leu
        35                  40                  45

Leu Pro Leu Phe Leu Arg Thr Arg Leu Thr Pro Gly Glu Thr Trp Ser
    50                  55                  60

Trp Arg Pro Thr Gly Trp Pro Ile Gly Leu Leu Leu Lys Glu Ser Lys
65                  70                  75                  80

Lys Lys Glu Arg Val Ala Met Met Met His Asn Ser Pro Leu Phe Ile
                85                  90                  95

Ile Thr Trp Leu Ala Met Leu Lys Ile Met Val Pro Ala Phe Ile
            100                 105                 110

Asn Asn Gln Ile Ala Gly Pro Val Leu Val His Ser Leu Lys Val Ala
        115                 120                 125

Asp Ala Lys Phe Leu Leu Phe Asp Tyr Glu Leu Ala Pro Val Ile Gln
    130                 135                 140

Lys Ser Leu Asn Glu Ile Lys Asp Met Gly Tyr Asn Leu Tyr Thr Val
145                 150                 155                 160

Thr Pro Lys Asp Gln Val Leu Gly Gln Leu Tyr Ala Asn Leu Pro Glu
                165                 170                 175

Ala Ala Arg Gln Val Leu Asp Glu Ala Pro Ser Phe Phe Gly Tyr Val
            180                 185                 190

Glu Trp Gln Asn Leu Ser Thr Glu Gly Phe Ser Asn Glu Ser Arg Gln
        195                 200                 205
```

-continued

```
Glu Val Val Ile Ser Asp Pro Ala Ala Leu Ile Tyr Thr Ser Gly Thr
210                 215                 220

Thr Gly Phe Pro Lys Ala Ala Ile Met Asp His Gly Arg Cys Asn Leu
225                 230                 235                 240

Ala Ser Ile Ser Tyr Gly Thr Leu Cys Gly Ile Lys Pro Glu Asn Lys
                245                 250                 255

Val Tyr Ile Thr Leu Pro Leu Tyr His Ser Ala Gly Ala Ile Ile Gly
                260                 265                 270

Leu Gly Gln Ser Phe Thr Ser Gly Cys Thr Ile Val Leu Ala Arg Lys
                275                 280                 285

Phe Ser Val Thr Lys Phe Trp Arg Asp Cys Val Glu Tyr Asp Val Thr
290                 295                 300

His Phe Gln Tyr Ile Gly Glu Leu Cys Arg Tyr Leu Leu Asn Ala Pro
305                 310                 315                 320

Glu Ser Pro Leu Asp Lys Arg His Lys Val Arg Met Ala Phe Gly Asn
                325                 330                 335

Gly Met Arg Pro Asp Val Trp Ala Lys Phe Gln Glu Arg Phe Asn Ile
                340                 345                 350

Pro Ile Ile Val Glu Tyr Tyr Ala Met Ser Glu Gly Thr Ser Ser Leu
                355                 360                 365

Leu Asn Val Ala Arg Asn Lys Arg Asp Gln Gly Ala Val Gly Phe Arg
370                 375                 380

Gly Pro Val Val Arg Ala Leu Thr Pro Pro Val Gln Leu Val Lys Val
385                 390                 395                 400

Asp Phe Asp Thr Glu Glu Leu Ile Arg Asp Lys Lys Thr Gly Leu Cys
                405                 410                 415

Val Leu Cys Gln Pro Gly Glu Ile Gly Glu Leu Val Thr Leu Ala Asp
                420                 425                 430

Asn Lys Thr Thr Gly Ala Arg Tyr Ala Gly Tyr Phe Asn Gln Pro Glu
435                 440                 445

Val Ser Lys Ala Arg Leu Val Gln Asn Val Val Lys Asp Asp Ile
450                 455                 460

Tyr Phe Arg Thr Gly Asp Leu Leu Tyr Ser Lys Asp Gln Tyr Trp Tyr
465                 470                 475                 480

Phe Ala Asp Arg Ala Gly Asp Thr Tyr Arg Trp Lys Gly Glu Asn Val
                485                 490                 495

Ser Thr Ala Glu Ile Ala Asp Thr Ile Gly Arg Val Glu Gly Val Ala
                500                 505                 510

Ser Cys Thr Val Tyr Gly Val Ser Val Pro Gly Met Asp Gly Arg Ala
                515                 520                 525

Gly Met Ala Ala Leu Val Leu Lys Asn Ser Ile Val Gln Met Ala Gly
530                 535                 540

Gly Ser Gln Ala Lys Phe His Val Asp Glu Ala Ala Leu Asn Ala Phe
545                 550                 555                 560

Leu Arg Asp Leu Ser Lys Asp Val Lys Lys Leu Pro Ala Tyr Ala
                565                 570                 575

Ile Pro Arg Phe Leu Arg Ile Ala Glu Gln Glu Leu Glu Thr Thr Gly
                580                 585                 590

Thr Phe Lys Asn Lys Lys Val Glu Leu Lys Lys Glu Gly Phe Asp Leu
                595                 600                 605

Gly Lys Val Lys Glu Arg Leu Tyr Trp Trp Thr Pro Lys Gly Glu Tyr
610                 615                 620

Ala Pro Phe Gly Val Ala Glu Asn Glu Gln Ile Leu Ala Gly Arg Ala
```

Arg Leu

<210> SEQ ID NO 8
<211> LENGTH: 1929
<212> TYPE: DNA
<213> ORGANISM: Mortierella alpina

<400> SEQUENCE: 8

```
atggcaagta ccaaatcact aaggacttgg cgcttgttcg cgttggtctc catgcacgca      60
aaagacttga ggccttggtc gagaatcggg actgcagtct ttacaacagg ttcgaggaac     120
aatgccagat ccggcctttc tctgttgccc ttgttttttga aacacgtctt acacctgga     180
gagacttgga gctggcgtcc aacaggatgg cccattggtt tgttgctcaa ggaatccaaa     240
aaaaaggagc gtgtggcgat gatgatgcat aactcgcctc tgttcattat cacctggctg     300
gcaatgctca agatcatggt tgtacctgct tttatcaata accagattgc aggacctgtt     360
ctggttcatt ctcttaaagt ggccgacgcc aagtttctct tgttcgatta cgagttggca     420
cctgtcatcc aaaagtcgct caatgagatc aaggacatgg ttacaatct ctacactgtc      480
acacccaagg atcaagttct aggtcaactt acgccaatc tgcccgaggc tgctcgtcag      540
gtgttggatg aggctccttc attctttggt tatgtcgaat ggagaacct cagtaccgaa      600
ggtttctcga cgagagtcg tcaggagtg gtgatctccg accccgcagc cttgatttac       660
accagcggga ccacgggatt ccccaaggct gctatcatgg accatggacg ttgcaacttg     720
gcttcgatct cttatggcac tctatgcggc atcaaaccag aaacaaggt ttacatcaca      780
ttgccgctct atcattctgc tggagccatc attggtctgg ccagagctt caccagcgga      840
tgcaccattg tgctggcgcg aaagttctcc gtgacaaagt tttggcgtga ttgcgttgag     900
tacgacgtaa ctcattttca gtacattggc gaactctgcc gctaccttct aaatgccccc     960
gaaagtccac tggacaaaag cataaggtt cggatggcgt ttggcaacgg aatgcgcccg    1020
gatgtttggg caagttttca ggaacgattc aatatcccca ttattgttga gtactacgcc    1080
atgagcgaag aacatcgtc gcttttgaat gtggccagga caagcgcga ccaaggtgcg     1140
gtgggattcc gtggccccgt cgtgagggcc ttgacgcctc ccgttcaact ggtcaaggtg    1200
gactttgaca cggaggagct gatccgcgat aagaagacgg actttgcgt cctatgccag    1260
cctggtgaga ttggagaact ggtcacgcta gccgacaaca agacgactgg cgcacgctat    1320
gctgggtatt tcaatcagcc agaggtttcg aaggcaaggc tggtccagaa cgtggtagtg    1380
aaggacgaca tctacttccg gacgggtgac ctcttgtact ccaaggacca gtactggtac    1440
tttgctgatc gcgcaggaga cacgtaccgg tggaaaggag agaacgtgtc gacagccgag    1500
attgcagaca ctatcggccg tgttgagggc gtggctagtt gtactgttta tggcgtatcg    1560
gtcccgggca tggatggacg cgcgggcatg gctgctttgg tgctcaagaa ctcgattgtg    1620
cagatggcag gtgaagcca ggcaaagttc catgtggatg aggctgcgct gaacgcgttt    1680
ttgcgtgact tgagcaagga tgtggtcaaa aaactgccgg cgtatgcgat tcctcggttc    1740
ttgcgcattg cagagcagga actggagacg acgggcacgt tcaagaacaa gaaggtggag    1800
ctgaagaagg aagggttcga cctcggtaag gtcaaggagc ggctgtactg gtggacaccc    1860
aagggtgaat atgccccttt tggcgtggcg gagaacgagc agatcctcgc aggacgcgct    1920
cgtctttga                                                            1929
```

<210> SEQ ID NO 9
<211> LENGTH: 2155
<212> TYPE: DNA
<213> ORGANISM: Mortierella alpina

<400> SEQUENCE: 9

| | | | | | |
|---|---|---|---|---|---|
| atccgcccat | ccgctctctt | gccactgatc | tcaaagcgtg | atccaaaggt | cattcttagg | 60 |
| cagcactcac | gcagctactt | agaactctac | ccacatatcc | cttattgata | caatggctcc | 120 |
| cgtcgctgca | ctcgccgccg | ctctggcggc | aggatactat | ctcaatggca | agtaccaaat | 180 |
| cactaaggac | ttggcgcttg | ttcgcgttgg | tctccatgca | cgcaaaagac | ttgaggcctt | 240 |
| ggtcgagaat | cgggactgca | gtcttt aca a | caggttcgag | gaacaatgcc | agatccggcc | 300 |
| tttctctgtt | gcccttgttt | ttgagaacac | gtcttacacc | tggagagact | tggagctggc | 360 |
| gtccaacagg | atgcccatt | ggtttgttgc | tcaaggaatc | caaaaaaaag | gagcgtgtgg | 420 |
| cgatgatgat | gcataactcg | cctctgttca | ttatcacctg | gctggcaatg | ctcaagatca | 480 |
| tggttgtacc | tgcttttatc | aataaccaga | ttgcaggacc | tgttctggtt | cattctctta | 540 |
| aagtggccga | cgccaagttt | ctcttgttcg | attacgagtt | ggcacctgtc | atccaaaagt | 600 |
| cgctcaatga | gatcaaggac | atgggttaca | atctctacac | tgtcacaccc | aaggatcaag | 660 |
| ttctaggtca | actttacgcc | aatctgcccg | aggctgctcg | tcaggtgttg | gatgaggctc | 720 |
| cttcattctt | tggttatgtc | gaatggcaga | acctcagtac | cgaaggtttc | tcgaacgaga | 780 |
| gtcgtcagga | ggtggtgatc | tccgaccccg | cagccttgat | ttacaccagc | gggaccacgg | 840 |
| gattccccaa | ggctgctatc | atggaccatg | gacgttgcaa | cttggcttcg | atctcttatg | 900 |
| gcactctatg | cggcatcaaa | ccagagaaca | aggtttacat | cacattgccg | ctctatcatt | 960 |
| ctgctggagc | catcattggt | ctgggccaga | gcttcaccag | cggatgcacc | attgtgctgg | 1020 |
| cgcgaaagtt | ctccgtgaca | aagttttggc | gtgattgcgt | tgagtacgac | gtaactcatt | 1080 |
| ttcagtacat | tggcgaactc | tgccgctacc | ttctaaatgc | ccccgaaagt | ccactggaca | 1140 |
| aaaggcataa | ggttcggatg | gcgtttggca | acggaatgcg | cccggatgtt | tgggcaaagt | 1200 |
| ttcaggaacg | attcaatatc | cccattattg | ttgagtacta | cgccatgagc | gaaggaacat | 1260 |
| cgtcgctttt | gaatgtggcc | aggaacaagc | gcgaccaagg | tgcggtggga | ttccgtggcc | 1320 |
| ccgtcgtgag | ggccttgacg | cctcccgttc | aactggtcaa | ggtggacttt | gacacggagg | 1380 |
| agctgatccg | cgataagaag | acgggacttt | gcgtcctatg | ccagcctggt | gagattggag | 1440 |
| aactggtcac | gctagccgac | aacaagacga | ctggcgcacg | ctatgctggg | tatttcaatc | 1500 |
| agccagaggt | ttcgaaggca | aggctggtcc | agaacgtggt | agtgaaggac | gacatctact | 1560 |
| tccggacggg | tgacctcttg | tactccaagg | accagtactg | gtactttgct | gatcgcgcag | 1620 |
| gagacacgta | ccgtggaaa | ggagagaacg | tgtcgacagc | cgagattgca | gacactatcg | 1680 |
| gccgtgttga | gggcgtggct | agttgtactg | tttatggcgt | atcggtcccg | ggcatggatg | 1740 |
| gacgcgcggg | catggctgct | ttggtgctca | agaactcgat | tgtgcagatg | gcaggtggaa | 1800 |
| gccaggcaaa | gttccatgtg | gatgaggctg | cgctgaacgc | gttttttgcgt | gacttgagca | 1860 |
| aggatgtggt | caaaaaactg | ccggcgtatg | cgattcctcg | gttcttgcgc | attgcagagc | 1920 |
| aggaactgga | gacgacgggc | acgttcaaga | acaagaggt | ggagctgaag | aaggaagggt | 1980 |
| tcgacctcgg | taaggtcaag | gagcggctgt | actggtggac | acccaagggt | gaatatgccc | 2040 |
| cttttggcgt | ggcggagaac | gagcagatcc | tcgcaggacg | cgctcgtctt | tgagcgatgt | 2100 |
| ttgtcaatga | agtcatcggc | atcatcatca | tcatcaaaaa | aaaaaaaaaa | aaaaa | 2155 |

<210> SEQ ID NO 10
<211> LENGTH: 3041
<212> TYPE: DNA
<213> ORGANISM: Mortierella alpina
<220> FEATURE:
<221> NAME/KEY: modified_base
<222> LOCATION: (118)..(459)
<223> OTHER INFORMATION: n is a, c, g, or t

<400> SEQUENCE: 10

```
atggcaagta ccaaatcact aaggacttgg cgcttgttcg cgttggtctc catgcacgca      60
aaaggtatga acgatgcact tgggggacgc atctgtctca atgtgatttg cttgttcnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnc gtctactttt tttttttttt     480
tttttttgag agagaaaggt cgaatgtggg gaccgaacct atttttttc cgtgcctttt      540
aggtttgttg cttcagcgtt cttttgagct gatatctttt cgccactctt gcataccta      600
gacttgaggc cttggtcgag aatcgggact gcagtcttta caacaggttc gaggaacaat     660
gccagatccg gcctttctct gttgcccttg tttttgagaa cacgtcttac acctggagag     720
acttggagct gggtatgtgc agtaggattt tttggacgcc tgatgctgca ttctgtgata     780
gaggacatac attaaataat tgatatcatt tcgtctgtcg acctgtctgt ctatcgatat     840
acagcgtcca acaggatggt aagttggcaa ctgcatacaa gtacttcgtg ctctttatca     900
tgcgttactc acgcttcatt gcctcaatgt ttcctttgaa ctaggcccat ggtttgttg      960
ctcaaggaat ccaaaaaaaa ggagcgtgtg gcgatgatga tgcataactc gcctctgttc    1020
attatcacct ggctggcaat gctcaagatc atggttgtac ctgcttttat caataaccag    1080
attgcaggac ctgttctggt tcattctctt aaagtggccg acgccaagtt tctcttgttc    1140
gattacgagt tggcacctgt catccaaaag tcgctcaatg agatcaagga catgggttac    1200
aatctctaca ctgtcacacc caaggatcaa gttctaggtc aactttacgc caatctgccc    1260
gaggctgctc gtcaggtgtt ggatgaggct ccttcattct ttggttatgt cgaatggcag    1320
aacctcagta ccgaaggttt ctcgaacgag agtcgtcagg aggtggtgat ctccgacccc    1380
gcagccttga tttacaccag cgggaccacg ggattcccca aggctgctat catggaccat    1440
ggacgttgca actgtaagca atcgcatagg atcgatagcg ctgaatggct ggcgagtgga    1500
tgcaaatggt cgagatgctt accattatcg tggtgtgcct ttttatagtg gcttcgatct    1560
cttatggcac tctatgcggc atcaaaccag agaacaaggt ttacatcaca ttgccgctct    1620
atcattctgc tggaggtacg tgcttccatc tcaccctcaa catctcttac gacggtttga    1680
tcctgttctt acactcatta cttctgggca tgggaacaaa gccatcattg gtctgggcca    1740
gagcttcacc agcggatgca ccattgtgct ggcgcgaaag ttctccgtga caaagttttg    1800
gcgtgattgc gttgagtacg acgtaactca ttttcaggta caagtcctat ccaatggtct    1860
acataccgtc cttgtgtatt ttcaacgcgc accgccacta accgcttttt atatgtatac    1920
ccgcagtaca ttggcgaact ctgccgctac cttctaaatg cccccgaaag tccactggac    1980
aaaaggcata aggttcggat ggcgtttggc aacggaatgc gcccggatgt ttgggcaaag    2040
```

```
tttcaggaac gattcaatat ccccattatt gttgagtact acgccatgag cgaaggaaca    2100
tcgtcgcttt tgaatgtggc caggaacaag cgcgaccaag gtgcggtggg attccgtggc    2160
cccgtcgtga ggtatgcggc atctgggcgc tttagttctt cgtgttcaat ggtttcatta    2220
taacatcttc agctcaactt tgcccgtgc tttttccttt caattttgtt tccactaggg     2280
ccttgacgcc tcccgttcaa ctggtcaagg tggactttga cacggaggag ctgatccgcg    2340
ataagaagac gggactttgc gtcctatgcc agcctggtga gattggagaa ctggtcacgc    2400
tagccgacaa caagacgact ggcgcacgct atgctgggta tttcaatcag ccagaggttt    2460
cgaaggcaag gctggtccag aacgtggtag tgaaggacga catctacttc cggacgggtg    2520
acctcttgta ctccaaggac cagtactggt actttgctga tcgcgcagga gacacgtacc    2580 ggtgaaagg agaaacgtg tcgacagccg agattcaga cactatcggc cgtgttgagg       2640
gcgtggctag ttgtactgtt tatggcgtat cggtcccggg catggatgga cgcgcgggca    2700
tggctgcttt ggtgctcaag aactcgattg tgcagatggc aggtggaagc caggcaaagt    2760
tccatgtgga tgaggctgcg ctgaacgcgt ttttgcgtga cttgagcaag gatgtggtca    2820
aaaaactgcc ggcgtatgcg attcctcggt tcttgcgcat tgcagagcag gaactggaga    2880
cgacgggcac gttcaagaac aagaaggtgg agctgaagaa ggaagggttc gacctcggta    2940
aggtcaagga gcggctgtac tggtggacac ccaagggtga atatgcccct tttggcgtgg    3000
cggagaacga gcagatcctc gcaggacgcg ctcgtctttg a                        3041

<210> SEQ ID NO 11
<211> LENGTH: 1650
<212> TYPE: DNA
<213> ORGANISM: Mortierella alpina

<400> SEQUENCE: 11
atggaaacgg atgctcttac catcgctttg accatcgcca tcgccatcgt gctggctttg      60
gtcaaattca acgaaaaaga gcctgacctg catccgctcc tgctcgggca gcaatcgtct     120
gtcacgccca ttcggaacga gggcgagtcc gttatccata gatccaaaac ggtgccacac     180
gggacactgc tgacgaagcg cccgagcgag aaaatcaaga ctctgcacga tgtctggcag     240
actggagcag ctgtcaaccc agccggccga tcgttgatgt ttatgctgca gaaccagttt     300
gcgtttatcg aggccacgta tgagcaagtc aataggagga ttggcggctt cggaacaggt     360
ttcgtgaagg caacagggct aaagcccaag acggacacac cagtaggaat ctttatgccc     420
tactctcaag aatcgttcgt tgcccagcag gcattctatc gatacagctt tgttgctgtc     480
cccatccatg atctgaggaa caacgacctc ttggtggagg tagtagacca gaccaagctc     540
aaggccatca tagtctcaca aaaggtgctc cgttattgc tgcaatctct gaaggagtgt      600
ccaaccatca agacaatcat catggcagga atctacatct cacaggagca gctggaaatg     660
gcagcacagc atggagtaaa gctgctcaaa ttcgcggcag tggaatatga gggatcctcg     720
actctgatgg agcctgttca gcctgatccg gaggatgttg ccatgatcaa ctataacaca     780
aagtcgtctt cgctctcgaa aggcgtcatg cttacccatg ccaacctgat cgcggcgatg     840
actgccttca cggagtcact tccggcaaaa agcgtttct ccagcaaaga tcgtcttctc      900
tctcattttt ccaatggaga tgtcatctct gtcttcatgt cgagcgccat catcctgatg     960
ggaggttctt tggtctttcc atctggtttg atgaagaacg ttttgcatga ttcccaagct    1020
tctgcaccaa cgatctttgc aagcacaccc atcatcctgg aaaagattca cgaagcactt    1080
```

```
cagttgacgt atggccaagg ctccatgttc aggcgcggct ttgctgccaa attggccata      1140
cttcaagctg gacgaatcac tacaacaagc ctatgggact tgattggact gggcgaggtc      1200
cgcagcaaac ttggtggaaa ggttcgaatg gttgtaacaa cacatcctac caaacctgag      1260
acgctggatt atatcagagc cgcgatgggc atccatgtca ttaccactta cggcaggaca      1320
gagacgtcgg gcattgtgac agcccgcaac atgctggatt atgccaacgc acctcattta      1380
ggaccaccag tgggttgcaa cgaggttaag cttgtggacg atgttgcagc tggctttaca      1440
agtgcagacg agcccaaccc acgaggcgag atccttatcc gaggccccaa tgtgatgaaa      1500
ggttattaca agaagccggg tgccacttca acggctatcg atgaggaagg gtggttccat      1560
tcaggagagc tgggcacatt ccactccaac ggcactttag acgtgttggg caagaagaag      1620
aagacgaagt ctgcagttgg atcaccgtca                                       1650
```

<210> SEQ ID NO 12
<211> LENGTH: 550
<212> TYPE: PRT
<213> ORGANISM: Mortierella alpina

<400> SEQUENCE: 12

```
Met Glu Thr Asp Ala Leu Thr Ile Ala Leu Thr Ile Ala Ile Ala Ile
1               5                   10                  15

Val Leu Ala Leu Val Lys Phe Asn Glu Lys Glu Pro Asp Leu His Pro
            20                  25                  30

Leu Leu Leu Gly Gln Gln Ser Ser Val Thr Pro Ile Arg Asn Glu Gly
        35                  40                  45

Glu Ser Val Ile His Arg Ser Lys Thr Val Pro His Gly Thr Leu Leu
    50                  55                  60

Thr Lys Arg Pro Ser Glu Lys Ile Lys Thr Leu His Asp Val Trp Gln
65                  70                  75                  80

Thr Gly Ala Ala Val Asn Pro Ala Gly Arg Ser Leu Met Phe Met Leu
                85                  90                  95

Gln Asn Gln Phe Ala Phe Ile Glu Ala Thr Tyr Glu Gln Val Asn Arg
            100                 105                 110

Arg Ile Gly Gly Phe Gly Thr Gly Phe Val Lys Ala Thr Gly Leu Lys
        115                 120                 125

Pro Lys Thr Asp Thr Pro Val Gly Ile Phe Met Pro Tyr Ser Gln Glu
    130                 135                 140

Ser Phe Val Ala Gln Gln Ala Phe Tyr Arg Tyr Ser Phe Val Ala Val
145                 150                 155                 160

Pro Ile His Asp Leu Arg Asn Asn Asp Leu Leu Val Glu Val Val Asp
                165                 170                 175

Gln Thr Lys Leu Lys Ala Ile Val Ser Gln Lys Val Leu Pro Leu
            180                 185                 190

Leu Leu Gln Ser Leu Lys Glu Cys Pro Thr Ile Lys Thr Ile Ile Met
        195                 200                 205

Ala Gly Ile Tyr Ile Ser Gln Glu Gln Leu Glu Met Ala Ala Gln His
    210                 215                 220

Gly Val Lys Leu Leu Lys Phe Ala Ala Val Glu Tyr Glu Gly Ser Ser
225                 230                 235                 240

Thr Leu Met Glu Pro Val Gln Pro Asp Pro Glu Asp Val Ala Met Ile
                245                 250                 255

Asn Tyr Asn Thr Lys Ser Ser Ser Leu Ser Lys Gly Val Met Leu Thr
            260                 265                 270
```

```
His Ala Asn Leu Ile Ala Ala Met Thr Ala Phe Thr Glu Ser Leu Pro
                275                 280                 285

Ala Lys Lys Arg Phe Ser Ser Lys Asp Arg Leu Leu Ser His Phe Ser
290                 295                 300

Asn Gly Asp Val Ile Ser Val Phe Met Ser Ser Ala Ile Ile Leu Met
305                 310                 315                 320

Gly Gly Ser Leu Val Phe Pro Ser Gly Leu Met Lys Asn Val Leu His
                325                 330                 335

Asp Ser Gln Ala Ser Ala Pro Thr Ile Phe Ala Ser Thr Pro Ile Ile
                340                 345                 350

Leu Glu Lys Ile His Glu Ala Leu Gln Leu Thr Tyr Gly Gln Gly Ser
                355                 360                 365

Met Phe Arg Arg Gly Phe Ala Ala Lys Leu Ala Ile Leu Gln Ala Gly
                370                 375                 380

Arg Ile Thr Thr Thr Ser Leu Trp Asp Leu Ile Gly Leu Gly Glu Val
385                 390                 395                 400

Arg Ser Lys Leu Gly Gly Lys Val Arg Met Val Val Thr Thr His Pro
                405                 410                 415

Thr Lys Pro Glu Thr Leu Asp Tyr Ile Arg Ala Ala Met Gly Ile His
                420                 425                 430

Val Ile Thr Thr Tyr Gly Arg Thr Glu Thr Ser Gly Ile Val Thr Ala
                435                 440                 445

Arg Asn Met Leu Asp Tyr Ala Asn Ala Pro His Leu Gly Pro Pro Val
                450                 455                 460

Gly Cys Asn Glu Val Lys Leu Val Asp Asp Val Ala Ala Gly Phe Thr
465                 470                 475                 480

Ser Ala Asp Glu Pro Asn Pro Arg Gly Glu Ile Leu Ile Arg Gly Pro
                485                 490                 495

Asn Val Met Lys Gly Tyr Tyr Lys Lys Pro Gly Ala Thr Ser Thr Ala
                500                 505                 510

Ile Asp Glu Glu Gly Trp Phe His Ser Gly Glu Leu Gly Thr Phe His
                515                 520                 525

Ser Asn Gly Thr Leu Asp Val Leu Gly Lys Lys Lys Thr Lys Ser
530                 535                 540

Ala Val Gly Ser Pro Ser
545                 550

<210> SEQ ID NO 13
<211> LENGTH: 1653
<212> TYPE: DNA
<213> ORGANISM: Mortierella alpina

<400> SEQUENCE: 13
atggaaacgg atgctcttac catcgctttg accatcgcca tcgccatcgt gctggctttg      60
gtcaaattca cgaaaaaga gcctgacctg catccgctcc tgctcgggca gcaatcgtct     120
gtcacgccca ttcggaacga gggcgagtcc gttatccata gatccaaaac ggtgccacac     180
gggacactgc tgacgaagcg cccgagcgag aaaatcaaga ctctgcacga tgtctggcag     240
actggagcag ctgtcaaccc agccggccga tcgttgatgt ttatgctgca gaaccagttt     300
gcgtttatcg aggccacgta tgagcaagtc aataggagga ttggcggctt cggaacaggt     360
ttcgtgaagg caacagggct aaagcccaag acggacacac cagtaggaat ctttatgccc     420
tactctcaag aatcgttcgt tgcccagcag gcattctatc gatacagctt tgttgctgtc     480
cccatccatg atctgaggaa caacgacctc ttggtggagg tagtagacca gaccaagctc     540
```

```
aaggccatca tagtctcaca aaaggtgctc ccgttattgc tgcaatctct gaaggagtgt      600
ccaaccatca agacaatcat catggcagga atctacatct cacaggagca gctggaaatg      660
gcagcacagc atggagtaaa gctgctcaaa ttcgcggcag tggaatatga gggatcctcg      720
actctgatgg agcctgttca gcctgatccg gaggatgttg ccatgatcaa ctataacaca      780
aagtcgtctt cgctctcgaa aggcgtcatg cttacccatg ccaacctgat cgcggcgatg      840
actgccttca cggagtcact tccggcaaaa aagcgtttct ccagcaaaga tcgtcttctc      900
tctcattttt ccaatggaga tgtcatctct gtcttcatgt cgagcgccat catcctgatg      960
ggaggttctt tggtctttcc atctggtttg atgaagaacg ttttgcatga ttcccaagct     1020
tctgcaccaa cgatctttgc aagcacaccc atcatcctgg aaaagattca cgaagcactt     1080
cagttgacgt atggccaagg ctccatgttc aggcgcggct ttgctgccaa attggccata     1140
cttcaagctg acgaatcac tacaacaagc ctatgggact tgattggact gggcgaggtc     1200
cgcagcaaac ttggtggaaa ggttcgaatg gttgtaacaa cacatcctac caaacctgag     1260
acgctggatt atatcagagc cgcgatgggc atccatgtca ttaccactta cggcaggaca     1320
gagacgtcgg gcattgtgac agcccgcaac atgctggatt atgccaacgc acctcattta     1380
ggaccaccag tgggttgcaa cgaggttaag cttgtggacg atgttgcagc tggctttaca     1440
agtgcagacg agcccaaccc acgaggcgag atccttatcc gaggcccaa tgtgatgaaa     1500 ggttattaca agaagccggg tgccacttca acggctatcg atgaggaagg gtggttccat     1560
tcaggagagc tgggcacatt ccactccaac ggcactttag acgtgttggg caagaagaag     1620
aagacgaagt ctgcagttgg atcaccgtca tga                                 1653

<210> SEQ ID NO 14
<211> LENGTH: 1773
<212> TYPE: DNA
<213> ORGANISM: Mortierella alpina

<400> SEQUENCE: 14
gcctactttg cgctcgcctc atcgacccaa aggcagcaat ggaaacggat gctcttacca       60
tcgctttgac catcgccatc gccatcgtgc tggctttggt caaattcaac gaaaaagagc      120
ctgacctgca tccgctcctg ctcgggcagc aatcgtctgt cacgcccatt cggaacgagg      180
gcgagtccgt tatccataga tccaaaacgg tgccacacgg acactgctg acgaagcgcc      240 cgagcgagaa aatcaagact ctgcacgatg tctggcagac tggagcagct gtcaacccag      300
ccggccgatc gttgatgttt atgctgcaga accagtttgc gtttatcgag gccacgtatg      360
agcaagtcaa taggaggatt ggcggcttcg gaacaggttt cgtgaaggca acagggctaa      420
agcccaagac ggacacacca gtaggaatct ttatgcccta ctctcaagaa tcgttcgttg      480
cccagcaggc attctatcga tacagctttg ttgctgtccc catccatgat ctgaggaaca      540
acgacctctt ggtggaggta gtagaccaga ccaagctcaa ggccatcata gtctcacaaa      600
aggtgctccc gttattgctg caatctctga aggagtgtcc aaccatcaag acaatcatca      660
tggcaggaat ctacatctca caggagcagc tggaaatggc agcacagcat ggagtaaagc      720
tgctcaaatt cgcggcagtg aatatgagg atcctcgac tctgatggag cctgttcagc      780
ctgatccgga ggatgttgcc atgatcaact ataacacaaa gtcgtcttcg ctctcgaaag      840
gcgtcatgct tacccatgcc aacctgatcg cggcgatgac tgccttcacg gagtcacttc      900
cggcaaaaaa gcgtttctcc agcaaagatc gtcttctctc tcattttttcc aatggagatg      960
```

```
tcatctctgt cttcatgtcg agcgccatca tcctgatggg aggttctttg gtctttccat    1020
ctggtttgat gaagaacgtt ttgcatgatt cccaagcttc tgcaccaacg atctttgcaa    1080
gcacacccat catcctggaa aagattcacg aagcacttca gttgacgtat ggccaaggct    1140
ccatgttcag gcgcggcttt gctgccaaat tggccatact tcaagctgga cgaatcacta    1200
caacaagcct atgggacttg attggactgg gcgaggtccg cagcaaactt ggtggaaagg    1260
ttcgaatggt tgtaacaaca catcctacca aacctgagac gctggattat atcagagccg    1320
cgatgggcat ccatgtcatt accacttacg gcaggacaga gacgtcgggc attgtgacag    1380
cccgcaacat gctggattat gccaacgcac ctcatttagg accaccagtg ggttgcaacg    1440
aggttaagct tgtggacgat gttgcagctg gctttacaag tgcagacgag cccaacccac    1500
gaggcgagat ccttatccga ggccccaatg tgatgaaagg ttattacaag aagccgggtg    1560
ccacttcaac ggctatcgat gaggaagggt ggttccattc aggagagctg gcacattcc     1620 actccaacgg cactttagac gtgttgggca agaagaagaa gacgaagtct gcagttggat    1680
caccgtcatg aaaggagatg ctgcatgtgc tacagaatat aaaaagggag aagatacgtt    1740
cggtaaccac atcaaaaaaa aaaaaaaaa aaa                                  1773
```

<210> SEQ ID NO 15
<211> LENGTH: 2391
<212> TYPE: DNA
<213> ORGANISM: Mortierella alpina

<400> SEQUENCE: 15

```
atggaaacgg atgctcttac catcgctttg accatcgcca tcgccatcgt gctggctttg     60
gtcaaattca cgaaaaaga gcctgacctg catccgctcc tgctcgggca gcaatcgtct    120
gtcacgccca ttcggaacga gggcgagtcc gttatccata gatccaaaac ggtgccacac    180
gggacactgc tgacgaagcg cccgagcgag aaaatcaaga ctctgcacga tgtctggcag    240
actggagcag ctgtcaaccc agccggccga tcgttgatgt ttatgctgca gaaccagttt    300
gcgtttatcg aggtacgatg gacccgctgt agtaaccccg ctgtctcttg agcaatatcg    360
caggagtctc accattagag gattcattct ccttcgcata ggccacgtat ggtaacgtgt    420
gattcggtag cctttctgtc tgttgaagat gcggtgatgt ggatctctaa cagatcttgg    480
ttcaatggtg acacagagca agtcaatagg aggattggcg gcttcggaac aggtttcgtg    540
aaggcaacag ggctaaagcc caagacggac acaccagtag gaatctttat gccctactct    600
caaggtacgc gaacaagcgc gtgagtactg atccagcaac gcatagggac tgacgcgagt    660
gagccacgtg tttgaccttg caccgcgcct ctttactgta gaatcgttcg ttgcccagca    720
ggcattctat cgatacagct tgttgctgt ccccatccat gatctgagga caacgacct     780 cttggtggag gtagtagacc agaccaagct caaggccatc atagtctcac aaaaggtgct    840
cccgttattg ctgcaatctc tgaaggagtg tccaaccatc aagacaatca tcatggcagg    900
aatctacatc tcacaggagc agctggaaat ggcagcacag catggagtaa agctgctcaa    960
attcgcggca gtggaatatg agggatcctc gactctgatg gagcctgttc agcctggtat   1020
gtgaagcaaa agtcaaggaa atgcggttgc ttgatgttcg ctgcgatgtt ttgaccacca   1080
cgacctcttt taatagatcc ggaggatgtt gccatgatca actataacac aaagtcgtct   1140
tcggtatgga tgcttgtttt tcagtggtag ttttgtataa gcgggcatgg agatgattga   1200
gcttacttga agtactttcg cgctgcatca ttgatccgat agctctcgaa aggcgtcatg   1260
cttacccatg ccaacctgat cgcggcgatg actgccttca cggagtcact tccggcaaaa   1320
```

-continued

```
aagcgtttct ccagcaaaga tcgtcttctc tctcattttt ccaatggaga tgtcatctct    1380
gtcttcatgt cgagcgccat catcctgatg ggaggttctt tggtctttcc atctggtttg    1440
atgaagaacg ttttgcatga ttcccaagct tctgcaccaa cgatctttgc aaggtacaag    1500
atgttccagt gtgatctgtg gattgtctcg ttattcatgt gcaagatact tacggcgctg    1560
ttccatttat ttttgacccc tcctagcaca cccatcatcc tggaaaagat tcacgaagca    1620
cttcagttga cgtatggcca aggctccatg ttcaggcgcg ctttgctgc caaattggcc     1680 atacttcaag ctggacgaat cactacaaca agcctatggg acttgattgg actgggcgag    1740
gtccgcagca aacttggtgg aaaggttcga atggttgtaa caacacgtaa gtctcctttt    1800
ttaccatgcg ggcttacgta cttgcagcat gatattcgaa gatactaaca gtcttttcat    1860
gacgctcctg tagatcctac caaacctgag acgctggatt atatcagagc cgcgatgggc    1920
atccatgtca ttaccactta cggcaggaca gagacgtcgg gcattgtgac agcccgcaac    1980
atgctggatt atgccaacgc acctcattta ggaccaccag tggttgcaa cgaggttaag     2040 cttgtggacg atgttgcagc tggctttaca agtgcagacg agcccaaccc acgaggcgag    2100
gtaaggagtg catatctctt gctgcttcat gggcgataaa aaggctcaaa tgccgttgat    2160
tctactctaa cagcgttatt ttattgttca acaatatttt gtgcctagat ccttatccga    2220
ggccccaatg tgatgaaagg ttattacaag aagcccggtg ccacttcaac ggctatcgat    2280
gaggaagggt ggttccattc aggagagctg gcacattcc actccaacgg cactttagac     2340
gtgttgggca agaagaagaa gacgaagtct gcagttggat caccgtcatg a             2391
```

<210> SEQ ID NO 16
<211> LENGTH: 2064
<212> TYPE: DNA
<213> ORGANISM: Mortierella alpina

<400> SEQUENCE: 16

```
atgtccctcg accagaacgc ccagtccgtt gagctcccag gcacccggca accaggccag    60
acaggcatct atcgccgcaa aggcttcgag aatgcccttc tcgccgtccc acccagcaga    120
ccgcacatca agaccatcta cgatgccttc agcacggact gaagcttaa tcccaacgga     180 gctgccctgg gcagccgagt gtacgacccg gtgacggaca cctttggagg ctatgtctgg    240
cagacgtatg cacaggtgaa cgaccgcatc actcgcttcg cagtggatt ggtcaaaatt     300 cataaggacg tccatggtct tgccaccgtg ggcagaagt ggtctctcgg aatctgggcc     360
atcaaccgac ccgagtggac catcgcgtcc gaggcttgct cggcctacaa cctggtctcc    420
gtgggtcttt acgatacttt gggacccgag gctgtgactt atggcattaa tcacgctgag    480
tgctctattg tcgtaacaag tgtggatcat atcgcgacgc tgctgaacga atcttccaag    540
atgcctgggc tcaaaatcat catcagcatg gatgacctcg atactgggag agcaggccca    600
ggactggctc ccaccggcac catcctcagg acttacgctc aggacaaagg ggtactactt    660
tatgattggt ctgaggttga agccgtcggt attcagcatg acgaaagca tacgccacca     720 acctcctccg acgcatatac gatctgctat accagcggga caacaggctt gccaaaaggt    780
gccattttga cccatggaaa cttgatcgcc cttttggcct ccagtgatgt ggccacacca    840
gtgctggctg acgattgcct catcagtttc ttgcccctgc ctcacgtctt tggtcgggtc    900
atggagctct tcgcgatggc cgcaggagga aagattggct acagcacggg agatcctttg    960
cgtctcttgg aggacgtctc gcacctaaag ccctccatct tccccgctgt gcccagactg    1020
```

```
ctgaaccgcg tgtatgccaa ggtgtatgcg gcaactgttg gagcgcctgg actcacaggg      1080
gcactggcgc gacgaggatt ggccaccaag ctcaccaatt tgagagaggg caaaggtttc      1140
caccacccat tgtgggaccg aatcctcttc tcaaaggtca agcaagcgct cggcggcaat      1200
gtgagactga tgttgactgc ctccgctccc atctcggccg agatcttgga attcgtccgt      1260
gtcgctttct gctgcgaggt cgtggaggca tatggacaga ctgagggcgg tggagcggcc      1320
acaaacaccg tgattggcga gaccgaggct ggacacgtcg gtcctcctca agcttgttgc      1380
gagatcaaac tggtggatgt acccgagctg aactactttg cgaccgataa accattccct      1440
cgtggtgaga tttgtgtccg tggacccggt gtcattcctg gttatctcaa ggatgaggcc      1500
aagaccaagg agaccattga tgaggagggc tggctgcact cgggcgatat cgccatcatg      1560
agtggcaaag gcaccgttac catcattgac aggaagaaga acgtgttcaa gctgagccaa      1620
ggagaataca tcgcggcaga gaacattgaa gggcgtttcc tctccaaggt tccattcatc      1680
caacaaattc tggtgcacgg cgactcgacc gagagctgtt tggtggccat cttgatccca      1740
gagcctgagg ccttcatccc ctttgtgaac aaagtgctcg agaacgtcaa tcttcaacct      1800
ggagatcttg cagcctacag gaagatcgtt aacaacccaa agctgcgcca ggctgtcctc      1860
aaagagctga tcaaggctgg caaggatgct ggattgaaag ctttgagat tccaaaggcg       1920
atcctcctcg aatctgaggc attcacggtc gaaaacgaca agatgacccc gactttcaag      1980
atcaaaagac accctgtcgt ccaggcttac cgcgagcaac tgacagccct ctacaacgaa      2040
atccatcaaa aggaatccaa gctg                                             2064
```

<210> SEQ ID NO 17
<211> LENGTH: 688
<212> TYPE: PRT
<213> ORGANISM: Mortierella alpina

<400> SEQUENCE: 17

```
Met Ser Leu Asp Gln Asn Ala Gln Ser Val Glu Leu Pro Gly Thr Arg
1               5                   10                  15

Gln Pro Gly Gln Thr Gly Ile Tyr Arg Arg Lys Gly Phe Glu Asn Ala
            20                  25                  30

Leu Leu Ala Val Pro Pro Ser Arg Pro His Ile Lys Thr Ile Tyr Asp
        35                  40                  45

Ala Phe His Gly Leu Lys Leu Asn Pro Asn Gly Ala Ala Leu Gly
    50                  55                  60

Ser Arg Val Tyr Asp Pro Val Thr Asp Thr Phe Gly Gly Tyr Val Trp
65                  70                  75                  80

Gln Thr Tyr Ala Gln Val Asn Asp Arg Ile Thr Arg Phe Gly Ser Gly
                85                  90                  95

Leu Val Lys Ile His Lys Asp Val His Gly Leu Ala Thr Val Gly Gln
            100                 105                 110

Lys Trp Ser Leu Gly Ile Trp Ala Ile Asn Arg Pro Glu Trp Thr Ile
        115                 120                 125

Ala Ser Glu Ala Cys Ser Ala Tyr Asn Leu Val Ser Val Gly Leu Tyr
    130                 135                 140

Asp Thr Leu Gly Pro Glu Ala Val Thr Tyr Gly Ile Asn His Ala Glu
145                 150                 155                 160

Cys Ser Ile Val Val Thr Ser Val Asp His Ile Ala Thr Leu Leu Asn
                165                 170                 175

Glu Ser Ser Lys Met Pro Gly Leu Lys Ile Ile Ile Ser Met Asp Asp
            180                 185                 190
```

-continued

```
Leu Asp Thr Gly Arg Ala Gly Pro Gly Leu Ala Pro Thr Gly Thr Ile
        195                 200                 205
Leu Arg Thr Tyr Ala Gln Asp Lys Gly Val Leu Leu Tyr Asp Trp Ser
210                 215                 220
Glu Val Glu Ala Val Gly Ile Gln His Gly Arg Lys His Thr Pro Pro
225                 230                 235                 240
Thr Ser Ser Asp Ala Tyr Thr Ile Cys Tyr Thr Ser Gly Thr Thr Gly
                245                 250                 255
Leu Pro Lys Gly Ala Ile Leu Thr His Gly Asn Leu Ile Ala Leu Leu
            260                 265                 270
Ala Ser Ser Asp Val Ala Thr Pro Val Leu Ala Asp Asp Cys Leu Ile
        275                 280                 285
Ser Phe Leu Pro Leu Pro His Val Phe Gly Arg Val Met Glu Leu Phe
290                 295                 300
Ala Met Ala Ala Gly Gly Lys Ile Gly Tyr Ser Thr Gly Asp Pro Leu
305                 310                 315                 320
Arg Leu Leu Glu Asp Val Ser His Leu Lys Pro Ser Ile Phe Pro Ala
                325                 330                 335
Val Pro Arg Leu Leu Asn Arg Val Tyr Ala Lys Val Tyr Ala Ala Thr
            340                 345                 350
Val Gly Ala Pro Gly Leu Thr Gly Ala Leu Ala Arg Arg Gly Leu Ala
        355                 360                 365
Thr Lys Leu Thr Asn Leu Arg Glu Gly Lys Gly Phe His His Pro Leu
370                 375                 380
Trp Asp Arg Ile Leu Phe Ser Lys Val Lys Gln Ala Leu Gly Gly Asn
385                 390                 395                 400
Val Arg Leu Met Leu Thr Ala Ser Ala Pro Ile Ser Ala Glu Ile Leu
                405                 410                 415
Glu Phe Val Arg Val Ala Phe Cys Cys Glu Val Val Glu Ala Tyr Gly
            420                 425                 430
Gln Thr Glu Gly Gly Gly Ala Ala Thr Asn Thr Val Ile Gly Glu Thr
        435                 440                 445
Glu Ala Gly His Val Gly Pro Pro Gln Ala Cys Cys Glu Ile Lys Leu
450                 455                 460
Val Asp Val Pro Glu Leu Asn Tyr Phe Ala Thr Asp Lys Pro Phe Pro
465                 470                 475                 480
Arg Gly Glu Ile Cys Val Arg Gly Pro Gly Val Ile Pro Gly Tyr Leu
                485                 490                 495
Lys Asp Glu Ala Lys Thr Lys Glu Thr Ile Asp Glu Gly Trp Leu
            500                 505                 510
His Ser Gly Asp Ile Ala Ile Met Ser Gly Lys Gly Thr Val Thr Ile
        515                 520                 525
Ile Asp Arg Lys Lys Asn Val Phe Lys Leu Ser Gln Gly Glu Tyr Ile
530                 535                 540
Ala Ala Glu Asn Ile Glu Gly Arg Phe Leu Ser Lys Val Pro Phe Ile
545                 550                 555                 560
Gln Gln Ile Leu Val His Gly Asp Ser Thr Glu Ser Cys Leu Val Ala
                565                 570                 575
Ile Leu Ile Pro Glu Pro Glu Ala Phe Ile Pro Phe Val Asn Lys Val
            580                 585                 590
Leu Glu Asn Val Asn Leu Gln Pro Gly Asp Leu Ala Ala Tyr Arg Lys
        595                 600                 605
```

```
Ile Val Asn Asn Pro Lys Leu Arg Gln Ala Val Lys Glu Leu Ile
        610                 615                 620
Lys Ala Gly Lys Asp Ala Gly Leu Lys Gly Phe Glu Ile Pro Lys Ala
625                 630                 635                 640
Ile Leu Leu Glu Ser Glu Ala Phe Thr Val Glu Asn Asp Lys Met Thr
                645                 650                 655
Pro Thr Phe Lys Ile Lys Arg His Pro Val Val Gln Ala Tyr Arg Glu
                660                 665                 670
Gln Leu Thr Ala Leu Tyr Asn Glu Ile His Gln Lys Glu Ser Lys Leu
                675                 680                 685

<210> SEQ ID NO 18
<211> LENGTH: 2067
<212> TYPE: DNA
<213> ORGANISM: Mortierella alpina

<400> SEQUENCE: 18
atgtccctcg accagaacgc ccagtccgtt gagctcccag gcacccggca accaggccag    60
acaggcatct atcgccgcaa aggcttcgag aatgcccttc tcgccgtccc acccagcaga   120
ccgcacatca agaccatcta cgatgccttc cagcacggac tgaagcttaa tcccaacgga   180
gctgccctgg gcagccgagt gtacgacccg gtgacggaca cctttggagg ctatgtctgg   240
cagacgtatg cacaggtgaa cgaccgcatc actcgcttcg gcagtggatt ggtcaaaatt   300
cataaggacg tccatggtct tgccaccgtg ggccagaagt ggtctctcgg aatctgggcc   360
atcaaccgac ccgagtggac catcgcgtcc gaggcttgct cggcctacaa cctggtctcc   420
gtgggtcttt acgatacttt gggacccgag gctgtgactt atggcattaa tcacgctgag   480
tgctctattg tcgtaacaag tgtggatcat atcgcgacgc tgctgaacga atcttccaag   540
atgcctgggc tcaaaatcat catcagcatg gatgacctcg atactgggag agcaggccca   600
ggactggctc ccaccggcac catcctcagg acttacgctc aggacaaagg ggtactactt   660
tatgattggt ctgaggttga agccgtcggt attcagcatg gacgaaagca tacgccacca   720
acctcctccg acgcatatac gatctgctat accagcggga caacaggctt gccaaaaggt   780
gccatttga cccatggaaa cttgatcgcc cttttggcct ccagtgatgt ggccacacca   840
gtgctggctg acgattgcct catcagtttc ttgcccctgc ctcacgtctt tggtcgggtc   900
atggagctct tcgcgatggc cgcaggagga aagattggct acagcacggg agatcctttg   960
cgtctcttgg aggacgtctc gcacctaaag ccctccatct tccccgctgt gcccagactg  1020
ctgaaccgcg tgtatgccaa ggtgtatgcg caactgttg gagcgcctgg actcacaggg  1080
gcactggcgc gacgaggatt ggccaccaag ctcaccaatt tgagagaggg caaaggtttc  1140
caccacccat tgtgggaccg aatcctcttc tcaaaggtca gcaagcgct cggcggcaat  1200
gtgagactga tgttgactgc ctccgctccc atctcggccg agatcttgga attcgtccgt  1260
gtcgctttct gctgcgaggt cgtggaggca tatggacaga ctgagggcgg tggagcggcc  1320
acaaacaccg tgattggcga gaccgaggct ggacacgtcg gtcctcctca gcttgttgc  1380
gagatcaaac tggtggatgt acccgagctg aactactttg cgaccgataa accattccct  1440
cgtggtgaga tttgtgtccg tggacccggt gtcattcctg gttatctcaa ggatgaggcc  1500
aagaccaagg agaccattga tgaggagggc tggctgcact cgggcgatat cgccatcatg  1560
agtggcaaag gcaccgttac catcattgac aggaagaaga acgtgttcaa gctgagccaa  1620
ggagaataca tcgcggcaga gaacattgaa gggcgttccc tctccaaggt tccattcatc  1680
```

| caacaaattc tggtgcacgg cgactcgacc gagagctgtt tggtggccat cttgatccca | 1740 |
| gagcctgagg ccttcatccc ctttgtgaac aaagtgctcg agaacgtcaa tcttcaacct | 1800 |
| ggagatcttg cagcctacag gaagatcgtt aacaacccaa agctgcgcca ggctgtcctc | 1860 |
| aaagagctga tcaaggctgg caaggatgct ggattgaaag ctttgagat tccaaaggcg | 1920 |
| atcctcctcg aatctgaggc attcacggtc gaaaacgaca agatgacccc gactttcaag | 1980 |
| atcaaaagac accctgtcgt ccaggcttac cgcgagcaac tgacagccct ctacaacgaa | 2040 |
| atccatcaaa aggaatccaa gctgtaa | 2067 |

<210> SEQ ID NO 19
<211> LENGTH: 2337
<212> TYPE: DNA
<213> ORGANISM: Mortierella alpina

<400> SEQUENCE: 19

| cacacgctca cgttcgctct cacccgaccc actccccact ctcgctctca ttctctccct | 60 |
| tgtccttccc ttgtcccttt caaggtctaa cagcatcaac atcagcatca gcatcaagct | 120 |
| tctcattcct ccctcgtcta aatctctgaa agagttcgct ttgcaattca gcaatgtccc | 180 |
| tcgaccagaa cgcccagtcc gttgagctcc caggcacccg gcaaccaggc cagacaggca | 240 |
| tctatcgccg caaaggcttc gagaatgccc ttctcgccgt cccacccagc agaccgcaca | 300 |
| tcaagaccat ctacgatgcc ttccagcacg gactgaagct taatcccaac ggagctgccc | 360 |
| tgggcagccg agtgtacgac ccggtgacgg acacctttgg aggctatgtc tggcagacgt | 420 |
| atgcacaggt gaacgaccgc atcactcgct tcggcagtgg attggtcaaa attcataagg | 480 |
| acgtccatgg tcttgccacc gtgggccaga agtggtctct cggaatctgg gccatcaacc | 540 |
| gacccgagtg gaccatcgcg tccgaggctt gctcggccta caacctggtc tccgtgggtc | 600 |
| tttacgatac tttgggaccc gaggctgtga cttatggcat taatcacgct gagtgctcta | 660 |
| ttgtcgtaac aagtgtggat catatcgcga cgctgctgaa cgaatcttcc aagatgcctg | 720 |
| ggctcaaaat catcatcagc atggatgacc tcgatactgg gagagcaggc ccaggactgg | 780 |
| ctcccaccgg caccatcctc aggacttacg ctcaggacaa aggggtacta ctttatgatt | 840 |
| ggtctgaggt tgaagccgtc ggtattcagc atggacgaaa gcatacgcca ccaacctcct | 900 |
| ccgacgcata tacgatctgc tataccagcg ggacaacagg cttgccaaaa ggtgccattt | 960 |
| tgacccatgg aaacttgatc gcccttttgg cctccagtga tgtgccacca ccagtgctgg | 1020 |
| ctgacgattg cctcatcagt ttcttgcccc tgcctcacgt ctttggtcgg tcatggagc | 1080 |
| tcttcgcgat ggccgcagga ggaaagattg ctacagcac gggagatcct ttgcgtctct | 1140 |
| tggaggacgt ctcgcaccta aagccctcca tcttccccgc tgtgcccaga ctgctgaacc | 1200 |
| gcgtgtatgc caaggtgtat gcggcaactg ttggagcgcc tggactcaca ggggcactgg | 1260 |
| cgcgacgagg attggccacc aagctccacca atttgagaga gggcaaaggt ttccaccacc | 1320 |
| cattgtggga ccgaatcctc ttctcaaagg tcaagcaagc gctcggcggc aatgtgagac | 1380 |
| tgatgttgac tgcctccgct cccatctcgg ccgagatctt ggaattcgtc cgtgtcgctt | 1440 |
| tctgctgcga ggtcgtggag gcatatgac agactgaggg cggtggagcg ccacaaaaca | 1500 |
| ccgtgattgg cgagaccgag gctggacacg tcggtcctcc tcaagcttgt tgcgagatca | 1560 |
| aactggtgga tgtacccgag ctgaactact ttgcgaccga taaaccattc cctcgtggtg | 1620 |
| agatttgtgt ccgtggaccc ggtgtcattc ctggttatct caaggatgag gccaagacca | 1680 |
| aggagaccat tgatgaggag ggctggctgc actcgggcga tatcgccatc atgagtggca | 1740 |

-continued

| | |
|---|---|
| aaggcaccgt taccatcatt gacaggaaga agaacgtgtt caagctgagc caaggagaat | 1800 |
| acatcgcggc agagaacatt gaagggcgtt tcctctccaa ggttccattc atccaacaaa | 1860 |
| ttctggtgca cggcgactcg accgagagct gtttggtggc catcttgatc ccagagcctg | 1920 |
| aggccttcat ccccttttgtg aacaaagtgc tcgagaacgt caatcttcaa cctggagatc | 1980 |
| ttgcagccta caggaagatc gttaacaacc caaagctgcg ccaggctgtc ctcaaagagc | 2040 |
| tgatcaaggc tggcaaggat gctggattga aaggctttga gattccaaag gcgatcctcc | 2100 |
| tcgaatctga ggcattcacg gtcgaaaacg acaagatgac cccgactttc aagatcaaaa | 2160 |
| gacaccctgt cgtccaggct taccgcgagc aactgacagc cctctacaac gaaatccatc | 2220 |
| aaaaggaatc caagctgtaa aaagaaaccc ttagaacctg cggtgctcgc agcaattaaa | 2280 |
| aaaaaaagag agatattact ctcacagcta aaaaaaaaaa aaaaaaaaaa aaaaaaa | 2337 |

<210> SEQ ID NO 20
<211> LENGTH: 2801
<212> TYPE: DNA
<213> ORGANISM: Mortierella alpina

<400> SEQUENCE: 20

| | |
|---|---|
| atgtccctcg accagaacgc ccagtccgtt gagctcccag gcacccggca accaggccag | 60 |
| acaggtaaca caggccagca gtactgcacc cgttttccat taaggttcca accccagtct | 120 |
| tggacatggg gcgagacctg cttgttgtta ctgtggattc acacccgcg cgccccttcc | 180 |
| cttctggtgc cttgacccgt gtgacacccc gcaaactgct cagctcttct cggctgacca | 240 |
| accttcattc acatccacgt aggcatctat cgccgcaaag gcttcgagaa tgcccttctc | 300 |
| gccgtcccac ccagcagacc gcacatcaag accatctacg atgccttcca gcacggactg | 360 |
| aagcttaatc ccaacggagc tgccctgggc agccgagtgt acgacccggt gacggacacc | 420 |
| tttggaggct atgtctggca gacgtatgca caggtgaacg accgcatcac tcgcttcggc | 480 |
| agtggattgg tcaaaattca taaggacgtc catggtcttg ccaccgtggg ccagaagtgg | 540 |
| tctctcggaa tctgggccat caaccgaccg gagtggacca tcgcgtccga ggcttgctcg | 600 |
| gcctacaacc tggtctccgt gggtctttac gatactttgg acccgaggc tgtgacttat | 660 |
| ggcattaatc acgctgagtg ctctattgtc gtaacaagtg gtaaggacat gaagccataa | 720 |
| cgacaacggc taaaaaaaaa catggttctc atgacaagta tcgatagtaa cgttattctt | 780 |
| ggcgcttgta tgtgtttcta gtggatcata tcgcgacgct gctgaacgaa tcttccaaga | 840 |
| tgcctgggct caaaatcatc atcagcatgg atgacctcga tactgggaga gcaggcccag | 900 |
| gactggctcc caccggcacc atcctcagga cttacgctca ggacaaaggg gtactacttt | 960 |
| atgattggtc tgaggttgaa gccgtcggta ttcagcatgg acgaaagcat acgccaccaa | 1020 |
| cctcctccga cgcatatacg atctgctata ccagcgggac aacaggcttg ccagtaatat | 1080 |
| gttgctttta ttcccacgca tacagtgtgc cgatattttc aatgttcaat tgctctcatt | 1140 |
| agatgcatga cacttatcat tacttaagcg actttccttt ggcgttcata gaaaggtgcc | 1200 |
| attttgaccc atggaaactt gatcgcccct ttggcctcca gtgatgtggc cacaccagtg | 1260 |
| ctggctgacg attgcctcat cagtttcttg cccctgcctc acgtctttgg tcgggtcatg | 1320 |
| gagctcttcg cgatggccgc aggaggaaag attggctaca gcacgggaga tcctttgcgt | 1380 |
| ctcttggagg acgtctcgca cctaaagccc tccatcttcc ccgctgtgcc cagactgctg | 1440 |
| aaccgcgtgt atgccaaggt gtatgcggca actgttggag cgcctggact cacaggggca | 1500 |

-continued

```
ctggcgcgac gaggattggc caccaagctc accaatttga gagagggcaa aggtttccac    1560
cacccattgt gggaccgaat cctcttctca aaggtcaagc aagcgctcgg cggcaatgtg    1620
agactgatgt tgactggtaa gtgtgctttt ggaagatgaa atcacgttta tgtaaccccc    1680 ccccccccc cttgtttata acattaatc gttgtactgt cgtcgtctag cctccgctcc     1740
catctcggcc gagatcttgg aattcgtccg tgtcgctttc tgctgcgagg tcgtggaggc    1800
atatggacag actgagggcg gtggagcggc acaaacacc gtgattggcg agaccgaggc     1860
tggacacgtc ggtcctcctc aagcttgttg cgagatcaaa ctggtggatg tacccgagct    1920
gaactacttt gcgaccgata accattccc tcgtggtgag atttgtgtcc gtggacccgg     1980
tgtcattcct ggttatctca aggatgaggc caagaccaag gagaccattg atgaggaggg    2040
ctggctgcac tcgggcgata tcgccatcat gagtggcaaa ggcaccgtta ccatcattga    2100
caggaagaag aacgtgttca aggtaacaaa aacagtgcgc tctccacaga tctgttagcg    2160
cgctttttct gcgcacagta cactgaaacc accctgtttt gctttgttcc tgaactagct    2220
gagccaagga gaatacatcg cggcagagaa cattgaaggg cgtttcctct ccaaggttcc    2280
attcatccaa caaattctgg tgcacggcga ctcgaccgag agctgtttgg tggccatctt    2340
gatcccagag cctgaggcct tcatcccctt tgtgaacaaa gtgctcgaga cgtcaatct     2400 tcaacctgga gatcttgcag cctacaggaa gatcgttaac aacccaaagc tgcgccaggc    2460
tgtcctcaaa gagctgatca aggctggcaa ggatgctgga ttgaaagggt acgtacagaa    2520
ctctctttgc taccgtagcg gaggcccact agagttgagg tgatacagat cgacagaaaa    2580 aaaaaaaaa ctaaacaatc tctcttcaaa aacttggtgt tctcttgtac cacagctttg     2640
agattccaaa ggcgatcctc ctcgaatctg aggcattcac ggtcgaaaac gacaagatga    2700
ccccgacttt caagatcaaa agacaccctg tcgtccaggc ttaccgcgag caactgacag    2760
ccctctacaa cgaaatccat caaaaggaat ccaagctgta a                        2801
```

<210> SEQ ID NO 21
<211> LENGTH: 1977
<212> TYPE: DNA
<213> ORGANISM: Mortierella alpina

<400> SEQUENCE: 21

```
atgaccaccc aattgtactc catcgaagtg gcaggcagcc cagagattcc gggcgagggc     60
aaacctcggc gcagcgttct cagcccagac aaactcgtcc agagctatca gtcttttcaag   120 ggcgacggct ccatcaccac tctatatgag aacttttttgg agggcatcca gcgctcagag   180
ggaggagagt ttctcggaca ccgccccatc gtcgataatg tagctcagcc gtacgaatgg    240
ctaagctaca cgcgcgttca ggaacgtgtc gccaactttg gcgctggtct catccagctg    300
ggcctgaaag tcgactcgaa ctttggcatc ttttccatca acaggcccga atggacaatg    360
agtgagctgg caggctacat gtacaacttt acatctgtgc cgctttacga cactctgggc    420
gtctcggcca tcgaatacat cgttaatcag accgagatga gaccatcat cgcgtcggct    480 gataaagcct cgatcctgtt aaacatgaaa tcaactctgc cgacactcaa gaacattgtc    540
gttatgggct cgctcgaaga cgcgctcgtt gtcgagggta gggaaatgga tatccacatc    600
gttgcgtgga gtgacgtcga acgcgatggc ttcaacaacc ccgcgccagc caaccctcca    660 acaccgacg acgtcgccac catctgctac acgtcaggaa caaccgggac accaaagggc    720
gcaatcctga cccacaaaaa ctttgtggct ggccttgcct cgttccatat gatggcaaag    780
caccaaaagt ttttcatccc ctcgagcgtt gacactcaca tatcttacct gccctggca    840
```

```
catgtgttcg agcgtttgtc tcaggctgtt atgatttctg gcgcagctcg gattgggtat      900
taccaaggag acactttgaa gctactcgat gatgtggcga tcttgcagcc caccatcttt      960
gtgtccgttc cacgactctt aacaggatt tacgacaagg ttctagcagg tgtgaaagcc     1020
aagggcggtc tcgcagcttt cttattcaac cgcgcttttg aaaccaagaa ggctaatttg     1080
aaacgcggta tcctggagca cgccatctgg gatcgactgg tatttggtgc aattcgtgcg     1140
cgactcggtg gcaaagttaa gcatattgtc tcaggatcag ccctatagc cccgacgtc      1200
atggatttcc ttcgcatttg cttcagtgcc gacgtttatg aagggtatgg acagacggag     1260
caggctgctg gtttgtgtat gagctacaga ggtgacttga cctcgggtca gtgggaccc      1320
cctcagctgt gcgtcgaagt gaagctcaga gacgttccgg acatgcacta cacaagccag     1380
gacaagcctc gccctcgcgg ggagatcatg cttcgaggcc attcagtttt caaaggctat     1440
tacaaggctc caaagcaaac agaggagaca ctggacgcac agggatgggc aagcactgga     1500
gacgttggtg aatgggacga gcgtggccgc ttggtggtga tcgaccgtgt caaaaacatt     1560
ttcaagttgg ctcaaggcga atacattgca cctgaaaaga tcgaagccgt cctggccaaa     1620
cactaccttg tcgcccaggt ctttgtctac ggagactcct tccaagcgac attggtggga     1680
gttgtcgtgc ccgatgcgga gacgctaaag ccttgggccg atgaccatgg ccttggaggc     1740
aagagctatg aagaactatg cgctcatccc gctgtcaaag aaactttgct gaaggagctc     1800
aaagagtttg gtcgtgaaaa tgatctgaag ggctttgaga tattgaagaa cattcatgta     1860
acggcggagc aattctcaat tgagaatgat cttttgacac ccacattcaa gctgaagaga     1920
cacaccgcga aagagaagta catcgccgag attgagctga tgtataacgg gatccac       1977
```

<210> SEQ ID NO 22
<211> LENGTH: 659
<212> TYPE: PRT
<213> ORGANISM: Mortierella alpina

<400> SEQUENCE: 22

```
Met Thr Thr Gln Leu Tyr Ser Ile Glu Val Ala Gly Ser Pro Glu Ile
1               5                   10                  15

Pro Gly Glu Gly Lys Pro Arg Arg Ser Val Leu Ser Pro Asp Lys Leu
            20                  25                  30

Val Gln Ser Tyr Gln Ser Phe Lys Gly Asp Gly Ser Ile Thr Thr Leu
        35                  40                  45

Tyr Glu Asn Phe Leu Glu Gly Ile Gln Arg Ser Glu Gly Gly Glu Phe
    50                  55                  60

Leu Gly His Arg Pro Ile Val Asp Asn Val Ala Gln Pro Tyr Glu Trp
65                  70                  75                  80

Leu Ser Tyr Thr Arg Val Gln Glu Arg Val Ala Asn Phe Gly Ala Gly
                85                  90                  95

Leu Ile Gln Leu Gly Leu Lys Val Asp Ser Asn Phe Gly Ile Phe Ser
            100                 105                 110

Ile Asn Arg Pro Glu Trp Thr Met Ser Glu Leu Ala Gly Tyr Met Tyr
        115                 120                 125

Asn Phe Thr Ser Val Pro Leu Tyr Asp Thr Leu Gly Val Ser Ala Ile
    130                 135                 140

Glu Tyr Ile Val Asn Gln Thr Glu Met Glu Thr Ile Ile Ala Ser Ala
145                 150                 155                 160

Asp Lys Ala Ser Ile Leu Leu Asn Met Lys Ser Thr Leu Pro Thr Leu
                165                 170                 175
```

```
Lys Asn Ile Val Val Met Gly Ser Leu Glu Asp Ala Leu Val Val Glu
                180                 185                 190

Gly Arg Glu Met Asp Ile His Ile Val Ala Trp Ser Asp Val Glu Arg
            195                 200                 205

Asp Gly Phe Asn Asn Pro Ala Pro Ala Asn Pro Pro Thr Pro Asp Asp
        210                 215                 220

Val Ala Thr Ile Cys Tyr Thr Ser Gly Thr Thr Gly Thr Pro Lys Gly
225                 230                 235                 240

Ala Ile Leu Thr His Lys Asn Phe Val Ala Gly Leu Ala Ser Phe His
                245                 250                 255

Met Met Ala Lys His Gln Lys Phe Phe Ile Pro Ser Ser Val Asp Thr
            260                 265                 270

His Ile Ser Tyr Leu Pro Leu Ala His Val Phe Glu Arg Leu Ser Gln
        275                 280                 285

Ala Val Met Ile Ser Gly Ala Ala Arg Ile Gly Tyr Tyr Gln Gly Asp
        290                 295                 300

Thr Leu Lys Leu Leu Asp Asp Val Ala Ile Leu Gln Pro Thr Ile Phe
305                 310                 315                 320

Val Ser Val Pro Arg Leu Phe Asn Arg Ile Tyr Asp Lys Val Leu Ala
                325                 330                 335

Gly Val Lys Ala Lys Gly Gly Leu Ala Ala Phe Leu Phe Asn Arg Ala
            340                 345                 350

Phe Glu Thr Lys Lys Ala Asn Leu Lys Arg Gly Ile Leu Glu His Ala
        355                 360                 365

Ile Trp Asp Arg Leu Val Phe Gly Ala Ile Arg Ala Arg Leu Gly Gly
        370                 375                 380

Lys Val Lys His Ile Val Ser Gly Ser Ala Pro Ile Ala Pro Asp Val
385                 390                 395                 400

Met Asp Phe Leu Arg Ile Cys Phe Ser Ala Asp Val Tyr Glu Gly Tyr
                405                 410                 415

Gly Gln Thr Glu Gln Ala Ala Gly Leu Cys Met Ser Tyr Arg Gly Asp
            420                 425                 430

Leu Thr Ser Gly Gln Val Gly Pro Pro Gln Leu Cys Val Glu Val Lys
        435                 440                 445

Leu Arg Asp Val Pro Asp Met His Tyr Thr Ser Gln Asp Lys Pro Arg
450                 455                 460

Pro Arg Gly Glu Ile Met Leu Arg Gly His Ser Val Phe Lys Gly Tyr
465                 470                 475                 480

Tyr Lys Ala Pro Lys Gln Thr Glu Glu Thr Leu Asp Ala Gln Gly Trp
                485                 490                 495

Ala Ser Thr Gly Asp Val Gly Glu Trp Asp Glu Arg Gly Arg Leu Val
            500                 505                 510

Val Ile Asp Arg Val Lys Asn Ile Phe Lys Leu Ala Gln Gly Glu Tyr
        515                 520                 525

Ile Ala Pro Glu Lys Ile Glu Ala Val Leu Ala Lys His Tyr Leu Val
        530                 535                 540

Ala Gln Val Phe Val Tyr Gly Asp Ser Phe Gln Ala Thr Leu Val Gly
545                 550                 555                 560

Val Val Val Pro Asp Ala Glu Thr Leu Lys Pro Trp Ala Asp Asp His
                565                 570                 575

Gly Leu Gly Gly Lys Ser Tyr Glu Glu Leu Cys Ala His Pro Ala Val
            580                 585                 590
```

```
Lys Glu Thr Leu Leu Lys Glu Leu Lys Glu Phe Gly Arg Glu Asn Asp
            595                 600                 605

Leu Lys Gly Phe Glu Ile Leu Lys Asn Ile His Val Thr Ala Glu Gln
    610                 615                 620

Phe Ser Ile Glu Asn Asp Leu Leu Thr Pro Thr Phe Lys Leu Lys Arg
625                 630                 635                 640

His Thr Ala Lys Glu Lys Tyr Ile Ala Glu Ile Glu Leu Met Tyr Asn
                645                 650                 655

Gly Ile His

<210> SEQ ID NO 23
<211> LENGTH: 1980
<212> TYPE: DNA
<213> ORGANISM: Mortierella alpina

<400> SEQUENCE: 23
```

| | | | | | |
|---|---|---|---|---|---|
| atgaccaccc | aattgtactc | catcgaagtg | gcaggcagcc | cagagattcc | gggcgagggc | 60 |
| aaacctcggc | gcagcgttct | cagcccagac | aaactcgtcc | agagctatca | gtctttcaag | 120 |
| ggcgacggct | ccatcaccac | tctatatgag | aactttttgg | agggcatcca | gcgctcagag | 180 |
| ggaggagagt | ttctcggaca | ccgccccatc | gtcgataatg | tagctcagcc | gtacgaatgg | 240 |
| ctaagctaca | cgcgcgttca | ggaacgtgtc | gccaactttg | gcgctggtct | catccagctg | 300 |
| ggcctgaaag | tcgactcgaa | cttggcatc | ttttccatca | caggcccga | atggacaatg | 360 |
| agtgagctgg | caggctacat | gtacaacttt | acatctgtgc | cgctttacga | cactctgggc | 420 |
| gtctcggcca | tcgaatacat | cgttaatcag | accgagatgg | agaccatcat | cgcgtcggct | 480 |
| gataaagcct | cgatcctgtt | aaacatgaaa | tcaactctgc | cgacactcaa | gaacattgtc | 540 |
| gttatgggct | cgctcgaaga | cgcgctcgtt | gtcgagggta | gggaaatgga | tatccacatc | 600 |
| gttgcgtgga | gtgacgtcga | acgcgatggc | ttcaacaacc | ccgcgccagc | caaccctcca | 660 |
| acaccggacg | acgtcgccac | catctgctac | acgtcaggaa | caaccgggac | accaaagggc | 720 |
| gcaatcctga | cccacaaaaa | ctttgtggct | ggccttgcct | cgttccatat | gatggcaaag | 780 |
| caccaaaagt | ttttcatccc | ctcgagcgtt | gacactcaca | tatcttacct | gcccctggca | 840 |
| catgtgttcg | agcgtttgtc | tcaggctgtt | atgatttctg | gcgcagctcg | gattgggtat | 900 |
| taccaaggag | acactttgaa | gctactcgat | gatgtggcga | tcttgcagcc | caccatcttt | 960 |
| gtgtccgttc | cacgactctt | taacaggatt | tacgacaagg | ttctagcagg | tgtgaaagcc | 1020 |
| aagggcggtc | tcgcagcttt | cttattcaac | gcgcttttg | aaaccaagaa | ggctaatttg | 1080 |
| aaacgcggta | tcctggagca | cgccatctgg | gatcgactgg | tatttggtgc | aattcgtgcg | 1140 |
| cgactcggtg | gcaaagttaa | gcatattgtc | tcaggatcag | ccctatagc | cccggacgtc | 1200 |
| atggatttcc | ttcgcatttg | cttcagtgcc | gacgtttatg | aagggtatgg | acagacggag | 1260 |
| caggctgctg | gtttgtgtat | gagctacaga | ggtgacttga | cctcgggtca | agtgggaccc | 1320 |
| cctcagctgt | gcgtcgaagt | gaagctcaga | gacgttccgg | acatgcacta | cacaagccag | 1380 |
| gacaagcctc | gccctcgcgg | ggagatcatg | cttcgaggcc | attcagtttt | caaggctat | 1440 |
| tacaaggctc | caaagcaaac | agaggagaca | ctggacgcac | agggatgggc | aagcactgga | 1500 |
| gacgttggtg | aatgggacga | gcgtggccgc | ttggtggtga | tcgaccgtgt | caaaaacatt | 1560 |
| ttcaagttgg | ctcaaggcga | atacattgca | cctgaaaaga | tcgaagccgt | cctggccaaa | 1620 |
| cactaccttg | tcgcccaggt | cttttgtctac | ggagactcct | tccaagcgac | attggtggga | 1680 |
| gttgtcgtgc | ccgatgcgga | gacgctaaag | ccttgggccg | atgaccatgg | ccttggaggc | 1740 |

```
aagagctatg aagaactatg cgctcatccc gctgtcaaag aaactttgct gaaggagctc    1800
aaagagtttg gtcgtgaaaa tgatctgaag ggctttgaga tattgaagaa cattcatgta    1860
acggcggagc aattctcaat tgagaatgat cttttgacac ccacattcaa gctgaagaga    1920
cacaccgcga agagaagta catcgccgag attgagctga tgtataacgg gatccactga    1980
```

<210> SEQ ID NO 24
<211> LENGTH: 2216
<212> TYPE: DNA
<213> ORGANISM: Mortierella alpina

<400> SEQUENCE: 24

```
tttttttttt tttcttttct ctccaaccct ttcaccccca cgcctcggct cgtactcaag      60
cctcacgtcc acactctcgt cctctagcct gctgcattca cgattcacat tcctcctcga     120
ctccagcatc gctactccct cgtgctactt tcaccatgac cacccaattg tactccatcg     180
aagtggcagg cagcccagag attccgggcg agggcaaacc tcggcgcagc gttctcagcc     240
cagacaaact cgtccagagc tatcagtctt tcaagggcga cggctccatc accactctat     300
atgagaactt tttggagggc atccagcgct cagagggagg agagtttctc ggacaccgcc     360
ccatcgtcga taatgtagct cagccgtacg aatggctaag ctacacgcgc gttcaggaac     420
gtgtcgccaa ctttggcgct ggtctcatcc agctgggcct gaaagtcgac tcgaactttg     480
gcatcttttc catcaacagg cccgaatgga caatgagtga gctggcaggc tacatgtaca     540
actttacatc tgtgccgctt tacgacactc tgggcgtctc ggccatcgaa tacatcgtta     600
atcagaccga gatggagacc atcatcgcgt cggctgataa agcctcgatc ctgttaaaca     660
tgaaatcaac tctgccgaca ctcaagaaca ttgtcgttat gggctcgctc gaagacgcgc     720
tcgttgtcga gggtagggaa atggatatcc acatcgttgc gtggagtgac gtcgaacgcg     780
atggcttcaa caaccccgcg ccagccaacc ctccaacacc ggacgacgtc gccaccatct     840
gctacacgtc aggaacaacc gggacaccaa agggcgcaat cctgacccac aaaaactttg     900
tggctggcct tgcctcgttc catatgatgg caaagcacca aaagttttc atcccctcga     960 gcgttgacac tcacatatct tacctgcccc tggcacatgt gttcgagcgt ttgtctcagg    1020
ctgttatgat ttctggcgca gctcggattg ggtattacca aggagacact ttgaagctac    1080
tcgatgatgt ggcgatcttg cagcccacca tctttgtgtc cgttccacga ctctttaaca    1140
ggatttacga caaggttcta gcaggtgtga agccaaggg cggtctcgca gctttcttat    1200
tcaaccgcgc ttttgaaacc aagaaggcta atttgaaacg cggtatcctg gagcacgcca    1260
tctgggatcg actggtattt ggtgcaattc gtgcgcgact cggtggcaaa gttaagcata    1320
ttgtctcagg atcagcccct atagcccgg acgtcatgga tttccttcgc atttgcttca    1380
gtgccgacgt ttatgaaggg tatggacaga cggagcaggc tgctggtttg tgtatgagct    1440
acagaggtga cttgacctcg ggtcaagtgg accccctca gctgtgcgtc gaagtgaagc    1500
tcagagacgt tccggacatg cactacacaa gccaggacaa gcctcgccct cgcggggaga    1560
tcatgcttcg aggccattca gttttcaaag gctattacaa ggctccaaag caaacagagg    1620
agacactgga cgcacaggga tgggcaagca ctggagacgt tggtgaatgg acgagcgtg    1680 gccgcttggt ggtgatcgac cgtgtcaaaa acattttcaa gttggctcaa ggcgaataca    1740
ttgcacctga aaagatcgaa gccgtcctgg ccaaacacta ccttgtcgcc caggtctttg    1800
tctacggaga ctccttccaa gcgacattgg tgggagttgt cgtgcccgat gcggagacgc    1860
```

```
taaagccttg ggccgatgac catggccttg gaggcaagag ctatgaagaa ctatgcgctc    1920
atcccgctgt caaagaaact ttgctgaagg agctcaaaga gtttggtcgt gaaaatgatc    1980
tgaagggctt tgagatattg aagaacattc atgtaacggc ggagcaattc tcaattgaga    2040
atgatctttt gacacccaca ttcaagctga agagacacac cgcgaaagag aagtacatcg    2100
ccgagattga gctgatgtat aacgggatcc actgaaagag tctagccaaa gcagatcttt    2160
ttattactgt cgttaaaaaa actactcgta accatcaaaa aaaaaaaaaa aaaaaa        2216
```

<210> SEQ ID NO 25
<211> LENGTH: 2586
<212> TYPE: DNA
<213> ORGANISM: Mortierella alpina

<400> SEQUENCE: 25

```
atgaccaccc aattgtactc catcgaagtg gcaggcagcc cagagattcc gggcgagggc      60
aaacctcggc gcagcgttct cagcccagac aaactcgtcc agagctatca gtctttcaag     120
ggcgacggct ccatcaccac tctatatgag aacttttgg agggcatcca cgctcaggt      180 actgacaccc cacatggtca gcgagacttc tccacatgac accagcgttt ctctattaac     240
gttatccctt ggcgcctttg gctttgttgt ggttaacgat gtgcctaatc atagagggag     300
gagagtttct cggacaccgc cccatcgtcg ataatgtagc tcagccgtac gaatggctaa     360
gctacacgcg cgttcaggaa cgtgtcgcca actttggcgc tggtctcatc cagctgggcc     420
tgaaagtcga ctcgaacttt ggcatctttt ccatcaacag gcccgaatgg gtgagtgcag     480
tgggaggatc ctttttcttt tatgaaatgg gcccgtgcga gtctagattc gatgatggct     540
gcggttggac ccggcctcgg cccccaacca aacacgtgtg ggaaacccca accgactcta     600
atagaactcc gttcctctga tttggcgacg aacatactat tacctgtaga caatgagtga     660
gctggcaggc tacatgtaca actttacatc tgtgccgctt tacgacactc tgggcgtctc     720
ggccatcgaa tacatcgtta atcagaccga gatggagacc atcatcgcgt cggctgataa     780
agcctcgatc ctgttaaaca tgaaatcaac tctgccgaca ctcaagaaca ttgtcgttat     840
gggctcgctc gaagacgcgc tcgttgtcga gggtagggaa atggatatcc acatcgttgc     900
gtggagtgac gtcgaacgcg atggcttcaa caaccccgcg ccagccaacc ctccaacacc     960
ggacgacgtc gccaccatct gctacacgtc aggaacaacc gggacaccaa gtaacgttaa    1020
agatgtcgat atgagaatat ctctaaaatg tggcatgcag cttgaatgag aattcactcc    1080
ttcatagaca cttgttgtcc tttctcaagt cactcacctc tcttcattta tcctacgtgt    1140
atgtgtatgt agggggcgcaa tcctgaccca caaaaacttt gtggctggcc ttgcctcgtt    1200
ccatatgatg gcaaagcacc aaaagttttt catcccctcg agcgttgaca ctcacatatc    1260
ttacctgccc ctggcacatg tgttcgagcg tttgtctcag gctgttatga tttctggcgc    1320
agctcggatt gggtattacc aaggagacac tttgaagcta ctcgatgatg tggcgatctt    1380
gcagcccacc atctttgtgt ccgttccacg actctttaac aggatttacg acaaggttct    1440
agcaggtgtg aaagccaagg gcggtctcgc agctttctta ttcaaccgcg cttttgaaac    1500
caagaaggct aatttgaaac gcggtatcct ggagcacgcc atctgggatc gactggtatt    1560
tggtgcaatt cgtgcgcgac tcggtggcaa agttaagcat attgtctcag gatcagcccc    1620
tatagccccg gacgtcatgg atttccttcg catttgcttc agtgccgacg tttatgaagg    1680
gtatggacag acggagcagg ctgctggttt tgtgtatgagc tacagaggtg acttgacctc    1740
gggtcaagtg ggaccccctc agctgtgcgt cgaagtgaag ctcagagacg ttccggacat    1800
```

-continued

```
gcactacaca agccaggaca agcctcgccc tcgcggggag atcatgcttc gaggccattc    1860
agttttcaaa ggctattaca aggctccaaa gcaaacagag gagacactgg acgcacaggg    1920
atgggcaagg tatggttttg tgcaaccaac tattttgtca attacgctta acactggttg    1980
tcatcagccc gcatctgact aaggtcacat tgtacgcgac atagcactgg agacgttggt    2040
gaatgggacg agcgtggccg cttggtggtg atcgaccgtg tcaaaaacat tttcaagttg    2100
gctcaaggcg aatacattgc acctgaaaag atcgaagccg tcctggccaa acactacctt    2160
gtcgcccagg tctttgtcta cggagactcc ttccaagcga cattggtggg agttgtcgtg    2220
cccgatgcgg agacgctaaa gccttgggcc gatgaccatg gccttggagg caagagctat    2280
gaagaactat gcgctcatcc cgctgtcaaa gaaaccttgc tgaaggagct caaagagttt    2340
ggtcgtgaaa atgatctgaa gggctttgag atattgaaga acattcatgt aacggcggag    2400
caattctcaa ttgagaatga tcttttggtg agtcgatcgg acttgcgcac cgaacagttt    2460
gagagtcaag gatcgtatat taactaagcc ttgctttggt agacacccac attcaagctg    2520
aagagacaca ccgcgaaaga gaagtacatc gccgagattg agctgatgta taacgggatc    2580
cactga                                                              2586
```

<210> SEQ ID NO 26
<211> LENGTH: 1977
<212> TYPE: DNA
<213> ORGANISM: Mortierella alpina

<400> SEQUENCE: 26

```
atggctactc aaatgtactc ggtggtcgtc cccaacagcc ccgacattcc cggcgaaggc      60
aagccccgcc gtagtgtgct ttgtccagac aagctcctgg agaactaccc ctcagtgaaa     120
gcaggctcaa cgatcacgac cctgtacgag aacttccaag aaggtgttct ccgttcaggc     180
ggcgcccatt ttttgggcca tcgtcccatt gtgaatggcc agcctcaggc ttacaagtgg     240
cagtcgtatg tcgatgtcag caagcgtgtt acgcacttcg gcgctggcct ggctcatctc     300
ggcttgtctc caaagcaaaa cttttggaatt ttctctatca accggcctga gtggaccatg     360
agtgagcttg ctggctatat gcacaactac accagcgtcc cctctatga tacattggga     420 gtcgccgcga tcgagtatat cgttaaccag actgagatgc agatcatcat tgcttcgtcc     480
gacaaagctt ctatcatcct ccacatgaaa tcagcacttc caaccgttca gacgattgtc     540
gtcatggggg aatttactga cgctctcgtc gcagagggta aggagctcaa catcaacatt     600
gtatcctgga ccgatgtcga aaagagcggt cttgagcggc tgtcgaagc cgtgcacccc     660 acagccgagg atatcgctac catctgttac acatctggaa ccactggaac gccaaaaggt     720
gctatcttga cccacaagaa ctttgttgcc actatcgctt cattccacat gatggcaaag     780
catggcaggt tcttcattcc ctcgcctgcc gacacacatg tatcctacct gccccttgcc     840
cacgtctttg agcgcctttg ccaggctgtt atgatctcgg gcgctgcgcg tattggttac     900
taccaaggag atacgctgaa gctgctggac gatgttgccg tcctgcatcc caccattttt     960
gcctccgtcc ctcgtctctt taaccgtatc tacgacaagg tgcttgctgg cgtcaaggcc    1020
aagggtggta tcgccgcctt cttgtttaac cgcgcatata attccaagaa ggccaacttg    1080
cgaaagggcg tacttgagca tccgctctgg gacaagctgg tctttggagc gattcgcgcg    1140
cgcttgggtg gcaaggttaa gcacatcgtg tcaggatctg cccccatctc tcctgatgtg    1200
atggatttcc tccgcatctg cttcagcgct gatgtgtatg agggatatgg ccagacggaa    1260
```

-continued

```
caggcagccg gattaagtat gagctatcgc ggtgatttga ctccaggaca ggttggccca      1320
cctcaactgt gcacagaggt caagttgaag gacatcccta gtatgaacta tagcagcgcg      1380
gacaagcctt tccccgtgg agaaatcatg cttcgcggaa actctgtgtt caagggctat       1440
tacaaagcac caaagcagac tgaagaaaca ttggatgctg acggttggtc cagtaccgga      1500
gacgttggac agtgggatgc ccaaggccgt ctggtggtca ttgatcgcgt caagaacatc      1560
ttcaagttgg cgcaaggaga atatattgcg cctgaaaaga tcgaggctgt cctcgccaag      1620
cacttcctcg ttgcccagat ttttgtctat gggcactcgc tccaggccac cattgtcgcg      1680
gtggttgtcc ctgatgctga gacgctcaag ttgtgggcta agaaaacaa gctgggtgac       1740 aagtcttacg aggagctgtg cgctctccct cagcttcgca caaccctcca aaaggagttg      1800
gctacttttg gcaaagaatc ggatctgaag ggctttgaga ttcctaagaa cattcatgtt      1860
atctccgagc agtttttcaat tgagaacgat cttttgaccc ccaccttcaa gctgaagaga      1920
catgctgcca agagaagta taacgccgaa atcgaccgca tgtatgcaga aatcgct         1977
```

<210> SEQ ID NO 27
<211> LENGTH: 659
<212> TYPE: PRT
<213> ORGANISM: Mortierella alpina

<400> SEQUENCE: 27

```
Met Ala Thr Gln Met Tyr Ser Val Val Pro Asn Ser Pro Asp Ile
 1               5                  10                  15

Pro Gly Glu Gly Lys Pro Arg Arg Ser Val Leu Cys Pro Asp Lys Leu
                20                  25                  30

Leu Glu Asn Tyr Pro Ser Val Lys Ala Gly Ser Thr Ile Thr Thr Leu
            35                  40                  45

Tyr Glu Asn Phe Gln Glu Gly Val Leu Arg Ser Gly Ala His Phe
        50                  55                  60

Leu Gly His Arg Pro Ile Val Asn Gly Gln Pro Gln Ala Tyr Lys Trp
65                  70                  75                  80

Gln Ser Tyr Val Asp Val Ser Lys Arg Val Thr His Phe Gly Ala Gly
                85                  90                  95

Leu Ala His Leu Gly Leu Ser Pro Lys Gln Asn Phe Gly Ile Phe Ser
            100                 105                 110

Ile Asn Arg Pro Glu Trp Thr Met Ser Glu Leu Ala Gly Tyr Met His
        115                 120                 125

Asn Tyr Thr Ser Val Pro Leu Tyr Asp Thr Leu Gly Val Ala Ala Ile
    130                 135                 140

Glu Tyr Ile Val Asn Gln Thr Glu Met Gln Ile Ile Ala Ser Ser
145                 150                 155                 160

Asp Lys Ala Ser Ile Ile Leu His Met Lys Ser Ala Leu Pro Thr Val
                165                 170                 175

Gln Thr Ile Val Val Met Gly Glu Phe Thr Asp Ala Leu Val Ala Glu
            180                 185                 190

Gly Lys Glu Leu Asn Ile Asn Ile Val Ser Trp Thr Asp Val Glu Lys
        195                 200                 205

Ser Gly Leu Glu Arg Pro Val Glu Ala Val His Pro Thr Ala Glu Asp
    210                 215                 220

Ile Ala Thr Ile Cys Tyr Thr Ser Gly Thr Thr Gly Thr Pro Lys Gly
225                 230                 235                 240

Ala Ile Leu Thr His Lys Asn Phe Val Ala Thr Ile Ala Ser Phe His
                245                 250                 255
```

```
Met Met Ala Lys His Gly Arg Phe Phe Ile Pro Ser Pro Ala Asp Thr
            260                 265                 270

His Val Ser Tyr Leu Pro Leu Ala His Val Phe Glu Arg Leu Cys Gln
            275                 280                 285

Ala Val Met Ile Ser Gly Ala Ala Arg Ile Gly Tyr Tyr Gln Gly Asp
            290                 295                 300

Thr Leu Lys Leu Leu Asp Asp Val Ala Val Leu His Pro Thr Ile Phe
305                 310                 315                 320

Ala Ser Val Pro Arg Leu Phe Asn Arg Ile Tyr Asp Lys Val Leu Ala
                325                 330                 335

Gly Val Lys Ala Lys Gly Gly Ile Ala Ala Phe Leu Phe Asn Arg Ala
            340                 345                 350

Tyr Asn Ser Lys Lys Ala Asn Leu Arg Lys Gly Val Leu Glu His Pro
            355                 360                 365

Leu Trp Asp Lys Leu Val Phe Gly Ala Ile Arg Ala Arg Leu Gly Gly
            370                 375                 380

Lys Val Lys His Ile Val Ser Gly Ser Ala Pro Ile Ser Pro Asp Val
385                 390                 395                 400

Met Asp Phe Leu Arg Ile Cys Phe Ser Ala Asp Val Tyr Glu Gly Tyr
                405                 410                 415

Gly Gln Thr Glu Gln Ala Ala Gly Leu Ser Met Ser Tyr Arg Gly Asp
            420                 425                 430

Leu Thr Pro Gly Gln Val Gly Pro Pro Gln Leu Cys Thr Glu Val Lys
            435                 440                 445

Leu Lys Asp Ile Pro Ser Met Asn Tyr Ser Ser Ala Asp Lys Pro Phe
            450                 455                 460

Pro Arg Gly Glu Ile Met Leu Arg Gly Asn Ser Val Phe Lys Gly Tyr
465                 470                 475                 480

Tyr Lys Ala Pro Lys Gln Thr Glu Glu Thr Leu Asp Ala Asp Gly Trp
            485                 490                 495

Ser Ser Thr Gly Asp Val Gly Gln Trp Asp Ala Gln Gly Arg Leu Val
            500                 505                 510

Val Ile Asp Arg Val Lys Asn Ile Phe Lys Leu Ala Gln Gly Glu Tyr
            515                 520                 525

Ile Ala Pro Glu Lys Ile Glu Ala Val Leu Ala Lys His Phe Leu Val
            530                 535                 540

Ala Gln Ile Phe Val Tyr Gly His Ser Leu Gln Ala Thr Ile Val Ala
545                 550                 555                 560

Val Val Val Pro Asp Ala Glu Thr Leu Lys Leu Trp Ala Lys Glu Asn
                565                 570                 575

Lys Leu Gly Asp Lys Ser Tyr Glu Glu Leu Cys Ala Leu Pro Gln Leu
            580                 585                 590

Arg Thr Thr Leu Gln Lys Glu Leu Ala Thr Phe Gly Lys Glu Ser Asp
            595                 600                 605

Leu Lys Gly Phe Glu Ile Pro Lys Asn Ile His Val Ile Ser Glu Gln
            610                 615                 620

Phe Ser Ile Glu Asn Asp Leu Leu Thr Pro Thr Phe Lys Leu Lys Arg
625                 630                 635                 640

His Ala Ala Lys Glu Lys Tyr Asn Ala Glu Ile Asp Arg Met Tyr Ala
                645                 650                 655

Glu Ile Ala
```

<210> SEQ ID NO 28
<211> LENGTH: 1980
<212> TYPE: DNA
<213> ORGANISM: Mortierella alpina

<400> SEQUENCE: 28

```
atggctactc aaatgtactc ggtggtcgtc cccaacagcc ccgacattcc cggcgaaggc     60
aagccccgcc gtagtgtgct ttgtccagac aagctcctgg agaactaccc ctcagtgaaa    120
gcaggctcaa cgatcacgac cctgtacgag aacttccaag aaggtgttct ccgttcaggc    180
ggcgcccatt ttttgggcca tcgtcccatt gtgaatggcc agcctcaggc ttacaagtgg    240
cagtcgtatg tcgatgtcag caagcgtgtt acgcacttcg cgctggcct ggctcatctc     300
ggcttgtctc caaagcaaaa ctttggaatt ttctctatca accggcctga gtggaccatg    360
agtgagcttg ctggctatat gcacaactac accagcgtcc ccctctatga tacattggga    420
gtcgccgcga tcgagtatat cgttaaccag actgagatgc agatcatcat tgcttcgtcc    480
gacaaagctt ctatcatcct ccacatgaaa tcagcacttc caaccgttca gacgattgtc    540
gtcatggggg aatttactga cgctctcgtc gcagagggta aggagctcaa catcaacatt    600
gtatcctgga ccgatgtcga aaagagcggg cttgagcggc ctgtcgaagc cgtgcacccc    660
acagccgagg atatcgctac catctgttac acatctggaa ccactggaac gccaaaaggt    720
gctatcttga cccacaagaa ctttgttgcc actatcgctt cattccacat gatggcaaag    780
catggcaggt tcttcattcc ctcgcctgcc gacacacatg tatcctacct gcccttgcc     840
cacgtctttg agcgcctttg ccaggctgtt atgatctcgg cgctgcgcg tattggttac     900
taccaaggag atacgctgaa gctgctggac gatgttgccg tcctgcatcc caccattttt    960
gcctccgtcc ctcgtctctt taaccgtatc tacgacaagg tgcttgctgg cgtcaaggcc   1020
aagggtggta tcgccgcctt cttgtttaac cgcgcatata attccaagaa ggccaacttg   1080
cgaaagggcg tacttgagca tccgctctgg gacaagctgg tctttggagc gattcgcgcg   1140
cgcttgggtg gcaaggttaa gcacatcgtg tcaggatctg cccccatctc tcctgatgtg   1200
atggatttcc tccgcatctg cttcagcgct gatgtgtatg agggatatgg ccagacggaa   1260
caggcagccg gattaagtat gagctatcgc ggtgatttga ctccaggaca ggttggccca   1320
cctcaactgt gcacagaggt caagttgaag gacatcccta gtatgaacta tagcagcgcg   1380
gacaagcctt tcccccgtgg agaaatcatg cttcgcggaa actctgtgtt caagggctat   1440
tacaaagcac caaagcagac tgaagaaaca ttggatgctg acggttggtc cagtaccgga   1500
gacgttggac agtgggatgc ccaaggccgt ctggtggtca ttgatcgcgt caagaacatc   1560
ttcaagttgg cgcaaggaga atatattgcg cctgaaaaga tcgaggctgt cctcgccaag   1620
cacttcctcg ttgcccagat ttttgtctat gggcactcgc tccaggccac cattgtcgcg   1680
gtggttgtcc ctgatgctga gacgctcaag ttgtgggcta agaaaacaa gctgggtgac    1740
aagtcttacg aggagctgtg cgctctccct cagcttcgca caaccctcca aaaggagttg   1800
gctactttg gcaaagaatc ggatctgaag gctttgaga ttcctaagaa cattcatgtt      1860
atctccgagc agttttcaat tgagaacgat cttttgaccc ccaccttcaa gctgaagaga   1920
catgctgcca agagaagta taacgccgaa atcgaccgca tgtatgcaga aatcgcttaa    1980
```

<210> SEQ ID NO 29
<211> LENGTH: 2123
<212> TYPE: DNA
<213> ORGANISM: Mortierella alpina

<400> SEQUENCE: 29

```
tttcctcacc ttccctccgc tgccctctgc tgcacactcc tctggcttat accatccacc    60
cctctagccc cgccacttcg ccgccaacct catccgactc acaccgcaat ggctactcaa   120
atgtactcgg tggtcgtccc caacagcccc gacattcccg cgcgaaggcaa gccccgccgt   180
agtgtgcttt gtccagacaa gctcctggag aactacccct cagtgaaagc aggctcaacg   240
atcacgaccc tgtacgagaa cttccaagaa ggtgttctcc gttcaggcgg cgcccatttt   300
ttgggccatc gtcccattgt gaatggccag cctcaggctt acaagtggca gtcgtatgtc   360
gatgtcagca agcgtgttac gcacttcggc gctggcctgg ctcatctcgg cttgtctcca   420
aagcaaaact ttggaatttt ctctatcaac cggcctgagt ggaccatgag tgagcttgct   480
ggctatatgc acaactacac cagcgtcccc ctctatgata cattgggagt cgccgcgatc   540
gagtatatcg ttaaccagac tgagatgcag atcatcattg cttcgtccga caaagcttct   600
atcatcctcc acatgaaatc agcacttcca accgttcaga cgattgtcgt catgggggaa   660
tttactgacg ctctcgtcgc agagggtaag gagctcaaca tcaacattgt atcctggacc   720
gatgtcgaaa agagcggtct tgagcggcct gtcgaagccg tgcaccccac agccgaggat   780
atcgctacca tctgttacac atctggaacc actggaacgc caaaaggtgc tatcttgacc   840
cacaagaact tgttgccac tatcgcttca ttccacatga tggcaaagca tggcaggttc   900
ttcattccct cgcctgccga cacacatgta tcctacctgc cccttgccca cgtctttgag   960
cgcctttgcc aggctgttat gatctcgggc gctgcgcgta ttggttacta ccaaggagat  1020
acgctgaagc tgctggacga tgttgccgtc ctgcatccca ccatttttgc ctccgtccct  1080
cgtctcttta accgtatcta cgacaaggtg cttgctggcg tcaaggccaa gggtggtatc  1140
gccgccttct tgtttaaccg cgcatataat tccaagaagg ccaacttgcg aaagggcgta  1200
cttgagcatc cgctctggga caagctggtc tttggagcga ttcgcgcgcg cttgggtggc  1260
aaggttaagc acatcgtgtc aggatctgcc cccatctctc ctgatgtgat ggatttcctc  1320
cgcatctgct tcagcgctga tgtgtatgag ggatatggcc agacggaaca ggcagccgga  1380
ttaagtatga gctatcgcgg tgatttgact ccaggacagg ttggcccacc tcaactgtgc  1440
acagaggtca agttgaagga catccctagt atgaactata gcagcgcgga caagcctttc  1500
ccccgtggag aaatcatgct tcgcggaaac tctgtgttca agggctatta caaagcacca  1560
aagcagactg aagaaacatt ggatgctgac ggttggtcca gtaccggaga cgttggacag  1620
tgggatgccc aaggccgtct ggtggtcatt gatcgcgtca agaacatctt caagttggcg  1680
caaggagaat atattgcgcc tgaaaagatc gaggctgtcc tcgccaagca cttcctcgtt  1740
gcccagattt ttgtctatgg gcactcgctc caggccacca ttgtcgcggt ggttgtccct  1800
gatgctgaga cgctcaagtt gtgggctaaa gaaaacaagc tgggtgacaa gtcttacgag  1860
gagctgtgcg ctctccctca gcttcgcaca accctccaaa aggagttggc tactttggc  1920
aaagaatcgg atctgaaggg ctttgagatt cctaagaaca ttcatgttat ctccgagcag  1980
ttttcaattg agaacgatct tttgacccc accttcaagc tgaagagaca tgctgccaaa  2040
gagaagtata acgccgaaat cgaccgcatg tatgcagaaa tcgcttaata taaataatgg  2100
ttgtactcaa tataaaaaaa aaa                                         2123
```

<210> SEQ ID NO 30
<211> LENGTH: 2581
<212> TYPE: DNA
<213> ORGANISM: Mortierella alpina

```
<220> FEATURE:
<221> NAME/KEY: modified_base
<222> LOCATION: (1538)..(1937)
<223> OTHER INFORMATION: n is a, c, g, or t

<400> SEQUENCE: 30
atggctactc aaatgtactc ggtggtcgtc cccaacagcc ccgacattcc cggcgaaggc       60
aagccccgcc gtagtgtgct ttgtccagac aagctcctgg agaactaccc ctcagtgaaa      120
gcaggctcaa cgatcacgac cctgtacgag aacttccaag aaggtgttct ccgttcaggt      180
aacaacgctt accacgtcga cgttcgcctc gcaatggcac ctttcccttc ggtcaaactt      240
cttaaatgtt tcctttacaa tcgtaggcgg cgcccatttt ttgggccatc gtcccattgt      300
gaatggccag cctcaggctt acaagtggca gtcgtatgtc gatgtcagca agcgtgttac      360
gcacttcggc gctggcctgg ctcatctcgg cttgtctcca aagcaaaact ttggaatttt      420
ctctatcaac cggcctgagt gggtaggtga tgccttgctt tcttttgccc actcgtcgtc      480
aaggtaacgc agggcctgcg ccgattttta acagtacatt ctatgcactg tcgttacata      540
gaccatgagt gagcttgctg gctatatgca caactacacc agcgtccccc tctatgatac      600
attgggagtc gccgcgatcg agtatatcgt taaccagact gagatgcaga tcatcattgc      660
ttcgtccgac aaagcttcta tcatcctcca catgaaatca gcacttccaa ccgttcagac      720
gattgtcgtc atgggggaat ttactgacgc tctcgtcgca gagggtaagg agctcaacat      780
caacattgta tcctggaccg atgtcgaaaa gagcggtctt gagcggcctg tcgaagccgt      840
gcacccaca gccgaggata tcgctaccat ctgttacaca tctggaacca ctggaacgcc      900
aaagtaagtc aagatcatta catggtgagc ctccattgct tggactgaac agtctactca      960
cgcaggttct tcgtttactt tgacatgcgc agaggtgcta tcttgaccca caagaacttt     1020
gttgccacta tcgcttcatt ccacatgatg gcaaagcatg gcaggttctt cattccctcg     1080
cctgccgaca cacatgtatc ctacctgccc cttgccacg tctttgagcg cctttgccag      1140
gctgttatga tctcgggcgc tgcgcgtatt ggttactacc aaggagatac gctgaagctg     1200
ctggacgatg ttgccgtcct gcatcccacc atttttgcct ccgtccctcg tctctttaac     1260
cgtatctacg acaaggtgct tgctggcgtc aaggccaagg tggtatcgc cgccttcttg     1320
tttaaccgcg catataattc caagaaggcc aacttgcgaa agggcgtact tgagcatccg     1380
ctctgggaca agctggtctt tggagcgatt cgcgcgcgct tgggtggcaa ggttaagcac     1440
atcgtgtcag gatctgcccc catctctcct gatgtgatgg atttcctccg catctgcttc     1500
agcgctgatg tgtatgaggg atatggccag acggaacnnn nnnnnnnnn nnnnnnnnnn     1560
nnnnnnnnnn nnnnnnnnnn nnnnnnnnnn nnnnnnnnnn nnnnnnnnnn nnnnnnnnnn     1620
nnnnnnnnnn nnnnnnnnnn nnnnnnnnnn nnnnnnnnnn nnnnnnnnnn nnnnnnnnnn     1680
nnnnnnnnnn nnnnnnnnnn nnnnnnnnnn nnnnnnnnnn nnnnnnnnnn nnnnnnnnnn     1740
nnnnnnnnnn nnnnnnnnnn nnnnnnnnnn nnnnnnnnnn nnnnnnnnnn nnnnnnnnnn     1800
nnnnnnnnnn nnnnnnnnnn nnnnnnnnnn nnnnnnnnnn nnnnnnnnnn nnnnnnnnnn     1860
nnnnnnnnnn nnnnnnnnnn nnnnnnnnnn nnnnnnnnnn nnnnnnnnnn nnnnnnnnnn     1920
nnnnnnnnnn nnnnnnntta ccccacgact ttcttttgtc tcggcctgtt ccgcaatcat     1980
agtaccggag acgttggaca gtgggatgcc caaggccgtc tggtggtcat tgatcgcgtc     2040
aagaacatct tcaagttggc gcaaggagaa tatattgcgc tgaaaagat cgaggctgtc      2100
ctcgccaagc acttcctcgt tgcccagatt tttgtctatg ggcactcgct ccaggccacc     2160
```

```
attgtcgcgg tggttgtccc tgatgctgag acgctcaagt tgtgggctaa agaaaacaag    2220
ctgggtgaca agtcttacga ggagctgtgc gctctccctc agcttcgcac aaccctccaa    2280
aaggagttgg ctacttttgg caaagaatcg gatctgaagg gctttgagat tcctaagaac    2340
attcatgtta tctccgagca gttttcaatt gagaacgatc ttttggtgag tgtgcttccg    2400
agtatgaacc actgtgtcgt atgtacgttc gcattctgaa agctaactct ccgtacccct    2460
ctacttcaat tgtgaattct cctcttgtcg catacagacc cccaccttca agctgaagag    2520
acatgctgcc aaagagaagt ataacgccga aatcgaccgc atgtatgcag aaatcgctta    2580
a                                                                    2581

<210> SEQ ID NO 31
<211> LENGTH: 1824
<212> TYPE: DNA
<213> ORGANISM: Mortierella alpina

<400> SEQUENCE: 31
atgcacattc tgaatgccac aagaccattc tccaggctgt ctccaaccgt aaggagacct     60
tggctaggac tcggccagac gcgcccttat gctatcgcgc agaccgaggc cagtcctagg    120
ctgtcatatg tccgaggcac caccgtcggc acccagctat gcgaggatcc catcggtgcg    180
tactgggaca gggtcgtcaa tcgtcacggt gaccgcctcg gacttgtcgt caagcacgag    240
caggacctgc actggacctt ccgtcagttt ggcgggcagg ttgatagcct ctgccgtggg    300
ctctatgagt ctggcttgcg aaagggtgat cgactcgctg tctggatgcc gaacaacagc    360
gcgtgggcca cgctccagta tgctactgcc aagtctggca tcattctggt aactctcaac    420
cctgcgtacc ggaggcaaga gctactgcag acattgtctt tggtcgagtg caagtcattg    480
gtctatgtgc caagtctaaa gacttcgaat atagcgaga tgttgctcga cctcctacca    540
gaactccagt accagtcgcc aaatcagctc ttgaccgaga agctacccct acttcgtcaa    600
gtcatcgtgt ttgacaatgg ctcgcaagtc ccagagacag caaaattgaa gggattgaca    660
aagtatcagg atttgttgat caagaatccc tcgaccgctg tcgacggagc tcttgaaaag    720
gaacggctcg ctatcgacaa cagggatatc atcaatctcc agtttactag cggaactaca    780
ggccttccca agggcgtctc gctgtcgcat cgaaacatct tgaataacgg cattcatatt    840
ggagataaca tgcgactgac ggaaaaggat ttgctttgct gcccggtccc gctctttcac    900
tgctttggac tggtgctggc aagcttggct gcaatgaccc atggcgcagg aattatttac    960
ccttcgcagt cctttgatgc tgaggccaca ctgagggctg tttctgagga gggtgctaca   1020
gcgctgcatg gcgtgccgac tatgctgttg aaagagatga accaccccaa ctttgcaaag   1080 tacaacctttc cgacacttcg gacaggaatt gcagctggat cccctgtgcc cattgaggtc   1140
atgaagaacg tgcagacaaa gatgaacctg aaggagctga ctatctgtta cggcatgacc   1200
gagacctcgc ccgtgtcctt catgacactc acaacggatg aattacggga tcgatgtgag   1260
actgttggac gaattatgcc acatctcgag gccaaagtcg tcaaccctga cgggagag    1320 actttgccag tgaattcatc aggagagttg tgcacgcgcg ggtatgctgt gatggagggt   1380
ggttactggc gatcccagga gcagacagat gcagtggtgg acaaggatgg ctggatgcac   1440
actggcgaca ctgccgtgct cgatgaccgt ggcttttgca ggatcgacgg acgcatcaag   1500
gacatggtga tccgaggagg cgaaaaaatc catcctgtag aggtcgagaa ctgtctcttt   1560
gagatggacg cgtcaagaa cgtgtctgtg attggcgttc ccgacaagcg gtatggcgag   1620
caggtgtgtg cgtggatctc gaccaaggac gggaagacgg tcagtctgga ggcagtgcaa   1680
```

```
aagttctgtg agggcaagat tgcgcactac aaggtgccgc ggtatgtggt tgtggtggag    1740
tccaatgagt tcccgactac cccctcgggc aagatccaaa agaatgtgat gcgcgagctg    1800
accaaggcga agctgcagct gcct                                            1824
```

<210> SEQ ID NO 32
<211> LENGTH: 608
<212> TYPE: PRT
<213> ORGANISM: Mortierella alpina

<400> SEQUENCE: 32

```
Met His Ile Leu Asn Ala Thr Arg Pro Phe Ser Arg Leu Ser Pro Thr
1               5                   10                  15

Val Arg Arg Pro Trp Leu Gly Leu Gly Gln Thr Arg Pro Tyr Ala Ile
            20                  25                  30

Ala Gln Thr Glu Ala Ser Pro Arg Leu Ser Tyr Val Arg Gly Thr Thr
        35                  40                  45

Val Gly Thr Gln Leu Cys Glu Asp Pro Ile Gly Ala Tyr Trp Asp Arg
    50                  55                  60

Val Val Asn Arg His Gly Asp Arg Leu Gly Leu Val Val Lys His Glu
65                  70                  75                  80

Gln Asp Leu His Trp Thr Phe Arg Gln Phe Gly Gly Gln Val Asp Ser
                85                  90                  95

Leu Cys Arg Gly Leu Tyr Glu Ser Gly Leu Arg Lys Gly Asp Arg Leu
            100                 105                 110

Ala Val Trp Met Pro Asn Asn Ser Ala Trp Ala Thr Leu Gln Tyr Ala
        115                 120                 125

Thr Ala Lys Ser Gly Ile Ile Leu Val Thr Leu Asn Pro Ala Tyr Arg
    130                 135                 140

Arg Gln Glu Leu Leu Gln Thr Leu Ser Leu Val Glu Cys Lys Ser Leu
145                 150                 155                 160

Val Tyr Val Pro Ser Leu Lys Thr Ser Asn Tyr Ser Glu Met Leu Leu
                165                 170                 175

Asp Leu Leu Pro Glu Leu Gln Tyr Gln Ser Pro Asn Gln Leu Leu Thr
            180                 185                 190

Glu Lys Leu Pro Ser Leu Arg Gln Val Ile Val Phe Asp Asn Gly Ser
        195                 200                 205

Gln Val Pro Glu Thr Ala Lys Leu Lys Gly Leu Thr Lys Tyr Gln Asp
    210                 215                 220

Leu Leu Ile Lys Asn Pro Ser Thr Ala Val Asp Gly Ala Leu Glu Lys
225                 230                 235                 240

Glu Arg Leu Ala Ile Asp Asn Arg Asp Ile Ile Asn Leu Gln Phe Thr
                245                 250                 255

Ser Gly Thr Thr Gly Leu Pro Lys Gly Val Ser Leu Ser His Arg Asn
            260                 265                 270

Ile Leu Asn Asn Gly Ile His Ile Gly Asp Asn Met Arg Leu Thr Glu
        275                 280                 285

Lys Asp Leu Leu Cys Cys Pro Val Pro Leu Phe His Cys Phe Gly Leu
    290                 295                 300

Val Leu Ala Ser Leu Ala Met Thr His Gly Ala Gly Ile Ile Tyr
305                 310                 315                 320

Pro Ser Gln Ser Phe Asp Ala Glu Ala Thr Leu Arg Ala Val Ser Glu
                325                 330                 335

Glu Gly Ala Thr Ala Leu His Gly Val Pro Thr Met Leu Leu Glu Glu
```

```
                340             345             350
Met Asn His Pro Asn Phe Ala Lys Tyr Asn Leu Ser Thr Leu Arg Thr
            355                 360                 365

Gly Ile Ala Ala Gly Ser Pro Val Pro Ile Glu Val Met Lys Asn Val
            370                 375                 380

Gln Thr Lys Met Asn Leu Lys Glu Leu Thr Ile Cys Tyr Gly Met Thr
385                 390                 395                 400

Glu Thr Ser Pro Val Ser Phe Met Thr Leu Thr Thr Asp Glu Leu Arg
                405                 410                 415

Asp Arg Cys Glu Thr Val Gly Arg Ile Met Pro His Leu Glu Ala Lys
            420                 425                 430

Val Val Asn Pro Glu Thr Gly Glu Thr Leu Pro Val Asn Ser Ser Gly
            435                 440                 445

Glu Leu Cys Thr Arg Gly Tyr Ala Val Met Glu Gly Tyr Trp Arg
            450                 455                 460

Ser Gln Glu Gln Thr Asp Ala Val Val Asp Lys Asp Gly Trp Met His
465                 470                 475                 480

Thr Gly Asp Thr Ala Val Leu Asp Asp Arg Gly Phe Cys Arg Ile Asp
                485                 490                 495

Gly Arg Ile Lys Asp Met Val Ile Arg Gly Gly Glu Lys Ile His Pro
            500                 505                 510

Val Glu Val Glu Asn Cys Leu Phe Glu Met Asp Gly Val Lys Asn Val
            515                 520                 525

Ser Val Ile Gly Val Pro Asp Lys Arg Tyr Gly Glu Gln Val Cys Ala
            530                 535                 540

Trp Ile Ser Thr Lys Asp Gly Lys Thr Val Ser Leu Glu Ala Val Gln
545                 550                 555                 560

Lys Phe Cys Glu Gly Lys Ile Ala His Tyr Lys Val Pro Arg Tyr Val
                565                 570                 575

Val Val Val Glu Ser Asn Glu Phe Pro Thr Thr Pro Ser Gly Lys Ile
            580                 585                 590

Gln Lys Asn Val Met Arg Glu Leu Thr Lys Ala Lys Leu Gln Leu Pro
            595                 600                 605

<210> SEQ ID NO 33
<211> LENGTH: 1827
<212> TYPE: DNA
<213> ORGANISM: Mortierella alpina

<400> SEQUENCE: 33
atgcacattc tgaatgccac aagaccattc tccaggctgt ctccaaccgt aaggagacct    60
tggctaggac tcggccagac gcgcccttat gctatcgcgc agaccgaggc cagtcctagg   120
ctgtcatatg tccgaggcac caccgtcggc acccagctat gcgaggatcc catcggtgcg   180
tactgggaca gggtcgtcaa tcgtcacggt gaccgcctcg acttgtcgt caagcacgag   240 caggacctgc actggacctt ccgtcagttt ggcgggcagg ttgatagcct ctgccgtggg   300
ctctatgagt ctggcttgcg aaagggtgat cgactcgctg tctggatgcc gaacaacagc   360
gcgtgggcca cgctccagta tgctactgcc aagtctggca tcattctggt aactctcaac   420
cctgcgtacc ggaggcaaga gctactgcag acattgtctt tggtcgagtg caagtcattg   480
gtctatgtgc aagtctaaa gacttcgaat tatagcgaga tgttgctcga cctcctacca   540
gaactccagt accagtcgcc aaatcagctc ttgaccgaga gctaccctc acttcgtcaa   600 gtcatcgtgt ttgacaatgg ctcgcaagtc ccagagacag caaaattgaa gggattgaca   660
```

```
aagtatcagg atttgttgat caagaatccc tcgaccgctg tcgacggagc tcttgaaaag        720
gaacggctcg ctatcgacaa cagggatatc atcaatctcc agtttactag cggaactaca        780
ggccttccca agggcgtctc gctgtcgcat cgaaacatct tgaataacgg cattcatatt        840
ggagataaca tgcgactgac ggaaaaggat ttgctttgct gcccggtccc gctctttcac        900
tgctttggac tggtgctggc aagcttggct gcaatgaccc atggcgcagg aattatttac        960
ccttcgcagt cctttgatgc tgaggccaca ctgagggctg tttctgagga gggtgctaca       1020
gcgctgcatg gcgtgccgac tatgctgttg aagagatga accaccccaa ctttgcaaag        1080
tacaaccttt cgacacttcg gacaggaatt gcagctggat cccctgtgcc cattgaggtc       1140
atgaagaacg tgcagacaaa gatgaacctg aaggagctga ctatctgtta cggcatgacc       1200
gagacctcgc ccgtgtcctt catgacactc acaacggatg aattacggga tcgatgtgag       1260
actgttggac gaattatgcc acatctcgag gccaaagtcg tcaaccctga cgggagag        1320 actttgccag tgaattcatc aggagagttg tgcacgcgcg ggtatgctgt gatgagggt       1380 ggttactggc gatcccagga gcagacagat gcagtggtgg acaaggatgg ctggatgcac       1440
actggcgaca ctgccgtgct cgatgaccgt ggcttttgca ggatcgacgg acgcatcaag       1500
gacatggtga tccgaggagg cgaaaaaatc catcctgtag aggtcgagaa ctgtctcttt       1560
gagatggacg gcgtcaagaa cgtgtctgtg attggcgttc ccgacaagcg gtatggcgag       1620
caggtgtgtg cgtggatctc gaccaaggac gggaagacgg tcagtctgga ggcagtgcaa       1680
aagttctgtg agggcaagat tgcgcactac aaggtgccgc ggtatgtggt tgtggtggag       1740
tccaatgagt tcccgactac cccctcgggc aagatccaaa agaatgtgat gcgcgagctg       1800
accaaggcga agctgcagct gccttga                                          1827

<210> SEQ ID NO 34
<211> LENGTH: 2085
<212> TYPE: DNA
<213> ORGANISM: Mortierella alpina

<400> SEQUENCE: 34
ggcacgaggc tctactctcc attgcccact cactcattgc ccctctgtcc atcaccggca         60
ttgctcgttc gcgccttccg ccactccact ctttctttca ttccttcttt acaacggcca        120 tctcccctc gctctgcgct ctcccatcc acgctaacaa tgcacattct gaatgccaca        180
agaccattct ccaggctgtc tccaaccgta aggagacctt ggctaggact cggccagacg        240
cgcccttatg ctatcgcgca gaccgaggcc agtcctaggc tgtcatatgt ccgaggcacc        300
accgtcggca cccagctatg cgaggatccc atcggtgcgt actgggacag gtcgtcaat        360 cgtcacggtg accgctcgg acttgtcgtc aagcacgagc aggacctgca ctggaccttc        420
cgtcagtttg gcgggcaggt tgatagcctc tgccgtgggc tctatgagtc tggcttgcga        480
aagggtgatc gactcgctgt ctggatgccg aacaacagcg cgtgggccac gctccagtat       540
gctactgcca agtctggcat cattctggta actctcaacc ctgcgtaccg gaggcaagag       600
ctactgcaga cattgtcttt ggtcgagtgc aagtcattgg tctatgtgcc aagtctaaag       660
acttcgaatt atagcgagat gttgctcgac ctcctaccag aactccagta ccagtcgcca       720
aatcagctct tgaccgagaa gctaccctca cttcgtcaag tcatcgtgtt tgacaatggc       780
tcgcaagtcc cagagacagc aaaattgaag ggattgacaa agtatcagga tttgttgatc       840
aagaatccct cgaccgctgt cgacggagct cttgaaaagg aacggctcgc tatcgacaac       900
```

-continued

| | |
|---|---|
| agggatatca tcaatctcca gtttactagc ggaactacag gccttcccaa gggcgtctcg | 960 |
| ctgtcgcatc gaaacatctt gaataacggc attcatattg gagataacat gcgactgacg | 1020 |
| gaaaaggatt tgctttgctg cccggtcccg ctctttcact gctttggact ggtgctggca | 1080 |
| agcttggctg caatgaccca tggcgcagga attatttacc cttcgcagtc ctttgatgct | 1140 |
| gaggccacac tgagggctgt ttctgaggag ggtgctacag cgctgcatgg cgtgccgact | 1200 |
| atgctgttgg aagagatgaa ccaccccaac tttgcaaagt acaacctttc gacacttcgg | 1260 |
| acaggaattg cagctggatc ccctgtgccc attgaggtca tgaagaacgt gcagacaaag | 1320 |
| atgaacctga aggagctgac tatctgttac ggcatgaccg agacctcgcc cgtgtccttc | 1380 |
| atgacactca caacggatga attacgggat cgatgtgaga ctgttggacg aattatgcca | 1440 |
| catctcgagg ccaaagtcgt caaccctgag acgggagaga ctttgccagt gaattcatca | 1500 |
| ggagagttgt gcacgcgcgg gtatgctgtg atggagggtg gttactggcg atcccaggag | 1560 |
| cagacagatg cagtggtgga caaggatggc tggatgcaca ctggcgacac tgccgtgctc | 1620 |
| gatgaccgtg gcttttgcag gatcgacgga cgcatcaagg acatggtgat ccgaggaggc | 1680 |
| gaaaaaatcc atcctgtaga ggtcgagaac tgtctctttg agatggacgg cgtcaagaac | 1740 |
| gtgtctgtga ttggcgttcc cgacaagcgg tatggcgagc aggtgtgtgc gtggatctcg | 1800 |
| accaaggacg ggaagacggt cagtctggag gcagtgcaaa agttctgtga gggcaagatt | 1860 |
| gcgcactaca aggtgccgcg gtatgtggtt gtggtggagt ccaatgagtt cccgactacc | 1920 |
| ccctcgggca agatccaaaa gaatgtgatg cgcgagctga ccaaggcgaa gctgcagctg | 1980 |
| ccttgatggt actaggatat ggagccgacg aaagtaataa aggcgtatgc tggcatggcg | 2040 |
| caagatctga gccctgcggt gaggtgcatt cagtgacgcc attag | 2085 |

<210> SEQ ID NO 35
<211> LENGTH: 2242
<212> TYPE: DNA
<213> ORGANISM: Mortierella alpina

<400> SEQUENCE: 35

| | |
|---|---|
| atgcacattc tgaatgccac aagaccattc tccaggctgt ctccaaccgt aaggagacct | 60 |
| tggctaggac tcggccagac gcgcccttat gctatcgcgc agaccgaggc cagtcctagg | 120 |
| ctgtcatatg tccgaggcac caccgtcggc acccagctat gcgaggatcc catcggtgcg | 180 |
| tactgggaca gggtcgtcaa tcgtcacggt gaccgcctcg gacttgtcgt caagcacgag | 240 |
| caggacctgc actggacctt ccgtcagttt ggcgggcagg ttgatagcct ctgccgtggg | 300 |
| ctctatgagt ctggcttgcg aaagggtgat cgactcgcgt atgtacactc tcgtcgtgcc | 360 |
| tgaagcgctt gaagggaaaa actgtattga accccgcccc gctgcattag cgtcgtttca | 420 |
| acatttggct aattttttct ttccctcgtc ctttgccgat gcaaacagtg tctggatgcc | 480 |
| gaacaacagc gcgtgggcca cgctccagta tgctactgcc aagtctggca tcattctggt | 540 |
| aactctcaac cctgcgtatg tactgcatgt cataatcata ctcgcgtcgc ctcaaaaata | 600 |
| tgcttttttg acgtgtttac ttatcctgcg cgttctcata acaggtaccg gaggcaagag | 660 |
| ctactgcaga cattgtcttt ggtcgagtgc aagtcattgg tctatgtgcc aagtctaaag | 720 |
| acttcgaatt atagcgagat gttgctcgac ctcctaccag aactccagta ccagtcgcca | 780 |
| aatcagctct tgaccgagaa gctacccctca cttcgtcaag tcatcgtgtt tgacaatggc | 840 |
| tcgcaagtcc cagagacagc aaaattgaag ggattgacaa agtatcagga tttgttgatc | 900 |
| aagaatccct cgaccgctgt cgacggagct cttgaaaagg aacggctcgc tatcgacaac | 960 |

```
aggggatatca tcaatctcca gtttactagc ggaactacag gccttcccaa gtatgtgtca    1020
gaaattgaac ttgacacgcg atgcataatc gacgttcaac cacccttgtc ctgacaccgt    1080
cttgcatcta caatactatg gtccaaattt taggggcgtc tcgctgtcgc atcgaaacat    1140
cttgaataac ggcattcata ttggagataa catgcgactg acggaaaagg atttgctttg    1200
ctgcccggtc ccgctctttc actgctttgg actggtgctg gcaagcttgg ctgcaatgac    1260
ccatggcgca ggaattattt acccttcgca gtcctttgat gctgaggcca cactgagggc    1320
tgtttctgag gagggtgcta cagcgctgca tggcgtgccg actatgctgt ggaagagat     1380 gaaccacccc aactttgcaa agtacaacct ttcgacactt cggacaggaa ttgcagctgg    1440
atcccctgtg cccattgagg tcatgaagaa cgtgcagaca agatgaaacc tgaaggagct    1500
gactatctgt tacggcatga ccgagacctc gcccgtgtcc ttcatgacac tcacaacgga    1560
tgaattacgg gatcgatgtg agactgttgg acgaattatg ccacatctcg aggccaaagg    1620
taaaacggct gtcagcctgg tgttcataat tttgtcttga atctcggtgg tctgttgcta    1680
attttgggta cattgcttgc acaatacggt agtcgtcaac cctgagacgg gagagacttt    1740
gccagtgaat tcatcaggag agttgtgcac gcgcgggtat gctgtgatgg aggtggtta    1800 ctggcgatcc caggagcaga cagatgcagt ggtggacaag gatggctgga tgcacactgg    1860
cgacactgcc gtgctcgatg accgtggctt ttgcaggatc gacggacgca tcaaggacat    1920
ggtgatccga ggaggcgaaa aaatccatcc tgtagaggtc gagaactgtc tctttgagat    1980
ggacggcgtc aagaacgtgt ctgtgattgg cgttcccgac aagcggtatg cgagcaggt    2040 gtgtgcgtgg atctcgacca aggacgggaa gacggtcagt ctggaggcag tgcaaaagtt    2100
ctgtgagggc aagattgcgc actacaaggt gccgcggtat gtggttgtgg tggagtccaa    2160
tgagttcccg actacccct cgggcaagat ccaaaagaat gtgatgcgcg agctgaccaa    2220
ggcgaagctg cagctgcctt ga                                             2242
```

<210> SEQ ID NO 36
<211> LENGTH: 2076
<212> TYPE: DNA
<213> ORGANISM: Mortierella alpina

<400> SEQUENCE: 36

```
atgccttcct tcaaaaagta caacctcgac aagcagagtg ttgaggtccc tggcactcgg     60
aagcctggcg cttcaggcca ctacagacat gccgcctacg gcgatgctct tgtcaccaac    120
atccgtgagg cccctcatat cgaaactctt tacgacatgt ggcagaactc tgtgacaaag    180
tatggcggca atgactttt gggtcaccgt cccttcaaca ctgttgccca gacctatggt    240
ggctacagtt gggagacgta ccgccagatt aaccagcgcg ttaatgcgtt cggcagcggt    300
atcatgcacc tgaacgaggt gatcctcggc aaccgccagc ttaaccgctg ggcgttgggc    360
atctggtccc acggtcgccc tgagtggttc attacggaga tgagctgcaa ctgctacaac    420
ctcatttctg ttgcattgta cgacacccct tggacctgatg cagtcgagta cattgtcaac    480
cacgccgaga ttgagattgt tgtctcaagt gccaaccata tcgcctcttt gctcgagaac    540
gccgagaagc tccccaagct caaggccatt gtcagcatga tgctcttca cgataccgtc    600 ccgtccccg cgccacctc tgccgcacag gttcttcgtg cctggggtgc acaaagggc     660 atcaaggtct atgactttaa cgagattgag tccctcggtg ccgagttccc tcgcaagcac    720
ctgcctccca ccgctgatga ggtcgcctcc atctgctaca cttccggcac caccggtcag    780
```

```
cctaaaggag ccatgctcac ccacagaaac tttgttgcta ctgttggtac caaccgcgag    840
ggcatgcttc tcaccgagga cgacgttttg atcagtttct tgcccttggc tcacattatg    900
ggacgcgtca ttgacacttg ctcgatgtac agcggtggca agattggtta cttccgtgga    960
gatattcttt tgcttctcga ggacgttgct gagctccgtc ccacattctt cccagctgtg   1020
cctcgcctct tgaaccgcat ttatgccaag ctcgttgcct ctaccattga ggcccccggt   1080
ttggtcggtg ccttggcccg tcgcggtgtc gccgccaaga tggccaacct tgctgccgga   1140
aagggtgtca accacgctct ctgggacaga ctgctgttca caaggtcaa gatggccctg    1200
ggtggtcgcg ttcaggtcat cctgactgga tctgcgccca ttgccaagga ggttctcagc   1260
ttcttgagaa ttgctttcgg atgcgtggtt ttggagggat acggctccac tgagggcatg   1320
gctaccgcca ccatcacaat ggctgatgag tacattcctg gtcacattgg ctgccctcgt   1380
gctggatgcg agctcaagct ggtggatgtg cccgcgatga actacctctc taccgaccag   1440
ccctaccccc gtggagagat ctggatccgt ggtgacactg ttttcaaagg atacttcaag   1500
gacgagaaga acactagtga gactatcgac tctgaaggct ggctcgctac cggtgatatt   1560
ggatttgtgg ataagcgtgg atgctttacg atcattgacc gcaagaagaa catcttcaag   1620
ttggcacaag gtgaatacat tgctcctgaa aagattgaga cgtcttggg cgcacgctgc    1680
aatcttgtcc agcagatcta tgttcatggt gattcgcttg agtccacctt ggtcgcagtt   1740
cttattcccg agcccgagac cttcctgccc ttcgcgaatg ccattgctgg tgcctccgtc   1800
actgctggag atgttgaggg tttgaacaag ctgtgccaag atcccaaggt caagatcgcg   1860
gttctgaagg agttggagaa ggccggaaag gccggtgcga tgcgcggatt cgagttcgtg   1920
aagcgtgtcc acttgaccac ggatgcattc tcggtcgaca acggcatgat gacacctacc   1980
ttcaaggtcc gtcgcccaca gtagccgagc atttcagggg agcaaatcac ggccatgtat   2040
aaggagatca atgcctcgac ccctgttgcc aagctg                             2076
```

<210> SEQ ID NO 37
<211> LENGTH: 692
<212> TYPE: PRT
<213> ORGANISM: Mortierella alpina

<400> SEQUENCE: 37

```
Met Pro Ser Phe Lys Lys Tyr Asn Leu Asp Lys Gln Ser Val Glu Val
1               5                   10                  15

Pro Gly Thr Arg Lys Pro Gly Ala Ser Gly His Tyr Arg His Ala Ala
            20                  25                  30

Tyr Gly Asp Ala Leu Val Thr Asn Ile Arg Glu Ala Pro His Ile Glu
        35                  40                  45

Thr Leu Tyr Asp Met Trp Gln Asn Ser Val Thr Lys Tyr Gly Gly Asn
    50                  55                  60

Asp Phe Leu Gly His Arg Pro Phe Asn Thr Val Ala Gln Thr Tyr Gly
65                  70                  75                  80

Gly Tyr Ser Trp Glu Thr Tyr Arg Gln Ile Asn Gln Arg Val Asn Ala
                85                  90                  95

Phe Gly Ser Gly Ile Met His Leu Asn Glu Val Ile Leu Gly Asn Arg
            100                 105                 110

Gln Leu Asn Arg Trp Ala Leu Gly Ile Trp Ser His Gly Arg Pro Glu
        115                 120                 125

Trp Phe Ile Thr Glu Met Ser Cys Asn Cys Tyr Asn Leu Ile Ser Val
    130                 135                 140
```

```
Ala Leu Tyr Asp Thr Leu Gly Pro Asp Ala Val Glu Tyr Ile Val Asn
145                 150                 155                 160

His Ala Glu Ile Glu Ile Val Val Ser Ser Ala Asn His Ile Ala Ser
            165                 170                 175

Leu Leu Glu Asn Ala Glu Lys Leu Pro Lys Leu Lys Ala Ile Val Ser
            180                 185                 190

Met Asp Ala Leu His Asp Thr Val Pro Val Pro Gly Ala Thr Ser Ala
            195                 200                 205

Ala Gln Val Leu Arg Ala Trp Gly Ala Gln Lys Gly Ile Lys Val Tyr
        210                 215                 220

Asp Phe Asn Glu Ile Glu Ser Leu Gly Ala Glu Phe Pro Arg Lys His
225                 230                 235                 240

Leu Pro Pro Thr Ala Asp Glu Val Ala Ser Ile Cys Tyr Thr Ser Gly
                245                 250                 255

Thr Thr Gly Gln Pro Lys Gly Ala Met Leu Thr His Arg Asn Phe Val
            260                 265                 270

Ala Thr Val Gly Thr Asn Arg Glu Gly Met Leu Leu Thr Glu Asp Asp
            275                 280                 285

Val Leu Ile Ser Phe Leu Pro Leu Ala His Ile Met Gly Arg Val Ile
        290                 295                 300

Asp Thr Cys Ser Met Tyr Ser Gly Gly Lys Ile Gly Tyr Phe Arg Gly
305                 310                 315                 320

Asp Ile Leu Leu Leu Leu Glu Asp Val Ala Glu Leu Arg Pro Thr Phe
                325                 330                 335

Phe Pro Ala Val Pro Arg Leu Leu Asn Arg Ile Tyr Ala Lys Leu Val
            340                 345                 350

Ala Ser Thr Ile Glu Ala Pro Gly Leu Val Gly Ala Leu Ala Arg Arg
        355                 360                 365

Gly Val Ala Ala Lys Met Ala Asn Leu Ala Ala Gly Lys Gly Val Asn
    370                 375                 380

His Ala Leu Trp Asp Arg Leu Leu Phe Asn Lys Val Lys Met Ala Leu
385                 390                 395                 400

Gly Gly Arg Val Gln Val Ile Leu Thr Gly Ser Ala Pro Ile Ala Lys
                405                 410                 415

Glu Val Leu Ser Phe Leu Arg Ile Ala Phe Gly Cys Val Val Leu Glu
            420                 425                 430

Gly Tyr Gly Ser Thr Glu Gly Met Ala Thr Ala Thr Ile Thr Met Ala
        435                 440                 445

Asp Glu Tyr Ile Pro Gly His Ile Gly Cys Pro Arg Ala Gly Cys Glu
450                 455                 460

Leu Lys Leu Val Asp Val Pro Ala Met Asn Tyr Leu Ser Thr Asp Gln
465                 470                 475                 480

Pro Tyr Pro Arg Gly Glu Ile Trp Ile Arg Gly Asp Thr Val Phe Lys
                485                 490                 495

Gly Tyr Phe Lys Asp Glu Lys Asn Thr Ser Glu Thr Ile Asp Ser Glu
            500                 505                 510

Gly Trp Leu Ala Thr Gly Asp Ile Gly Phe Val Asp Lys Arg Gly Cys
        515                 520                 525

Phe Thr Ile Ile Asp Arg Lys Lys Asn Ile Phe Lys Leu Ala Gln Gly
            530                 535                 540

Glu Tyr Ile Ala Pro Glu Lys Ile Glu Asn Val Leu Gly Ala Arg Cys
545                 550                 555                 560

Asn Leu Val Gln Gln Ile Tyr Val His Gly Asp Ser Leu Glu Ser Thr
```

```
                  565                 570                 575
Leu Val Ala Val Leu Ile Pro Glu Pro Glu Thr Phe Leu Pro Phe Ala
            580                 585                 590

Asn Ala Ile Ala Gly Ala Ser Val Thr Ala Gly Asp Val Glu Gly Leu
            595                 600                 605

Asn Lys Leu Cys Gln Asp Pro Lys Val Lys Ile Ala Val Leu Lys Glu
610                 615                 620

Leu Glu Lys Ala Gly Lys Ala Gly Ala Met Arg Gly Phe Glu Phe Val
625                 630                 635                 640

Lys Arg Val His Leu Thr Thr Asp Ala Phe Ser Val Asp Asn Gly Met
                645                 650                 655

Met Thr Pro Thr Phe Lys Val Arg Arg Pro Gln Val Ala Glu His Phe
            660                 665                 670

Arg Glu Gln Ile Thr Ala Met Tyr Lys Glu Ile Asn Ala Ser Thr Pro
            675                 680                 685

Val Ala Lys Leu
    690

<210> SEQ ID NO 38
<211> LENGTH: 2079
<212> TYPE: DNA
<213> ORGANISM: Mortierella alpina

<400> SEQUENCE: 38
atgccttcct tcaaaaagta caacctcgac aagcagagtg ttgaggtccc tggcactcgg      60
aagcctggcg cttcaggcca ctacagacat gccgcctacg gcgatgctct tgtcaccaac     120
atccgtgagg cccctcatat cgaaactctt tacgacatgt ggcagaactc tgtgacaaag     180
tatggcggca atgactttt  gggtcaccgt cccttcaaca ctgttgccca gacctatggt     240
ggctacagtt gggagacgta ccgccagatt aaccagcgcg ttaatgcgtt cggcagcggt     300
atcatgcacc tgaacgaggt gatcctcggc aaccgccagc ttaaccgctg gcgttgggc      360
atctggtccc acggtcgccc tgagtggttc attacggaga tgagctgcaa ctgctacaac     420
ctcatttctg ttgcattgta cgacaccctt ggacctgatg cagtcgagta cattgtcaac     480
cacgccgaga ttgagattgt tgtctcaagt gccaaccata tcgcctcttt gctcgagaac     540
gccgagaagc tccccaagct caaggccatt gtcagcatgg atgctcttca cgataccgtc     600
cccgtccccg gcgccacctc tgccgcacag gttcttcgtg cctggggtgc acaaaagggc     660
atcaaggtct atgactttaa cgagattgag tccctcggtg ccgagttccc tgcaagcac      720
ctgcctccca ccgctgatga ggtcgcctcc atctgctaca cttccggcac caccggtcag     780
cctaaaggag ccatgctcac ccacagaaac tttgttgcta ctgttggtac caaccgcgag     840
ggcatgcttc tcaccgagga cgacgttttg atcagtttct tgcccttggc tcacattatg     900
ggacgcgtca ttgacacttg ctcgatgtac agcggtggca agattggtta cttccgtgga     960
gatattcttt tgcttctcga ggacgttgct gagctccgtc ccacattctt ccagctgtg    1020
cctcgcctct tgaaccgcat ttatgccaag ctcgttgcct ctaccattga ggccccggt    1080
ttggtcggtg ccttggcccg tcgcggtgtc gccgccaaga tggccaacct tgctgccgga    1140
aagggtgtca accacgctct ctgggacaga ctgctgttca acaaggtcaa gatggccctg    1200
ggtggtcgcg ttcaggtcat cctgactgga tctgcgccca ttgccaagga ggttctcagc    1260
ttcttgagaa ttgctttcgg atgcgtggtt ttggagggat acggctccac tgagggcatg    1320
gctaccgcca ccatcacaat ggctgatgag tacattcctg gtcacattgg ctgccctcgt    1380
```

-continued

```
gctggatgcg agctcaagct ggtggatgtg cccgcgatga actacctctc taccgaccag    1440
ccctaccccc gtggagagat ctggatccgt ggtgacactg ttttcaaagg atacttcaag    1500
gacgagaaga acactagtga gactatcgac tctgaaggct ggctcgctac cggtgatatt    1560
ggatttgtgg ataagcgtgg atgctttacg atcattgacc gcaagaagaa catcttcaag    1620
ttggcacaag gtgaatacat tgctcctgaa aagattgaga acgtcttggg cgcacgctgc    1680
aatcttgtcc agcagatcta tgttcatggt gattcgcttg agtccacctt ggtcgcagtt    1740
cttattcccg agcccgagac cttcctgccc ttcgcgaatg ccattgctgg tgcctccgtc    1800
actgctggag atgttgaggg tttgaacaag ctgtgccaag atcccaaggt caagatcgcg    1860
gttctgaagg agttggagaa ggccggaaag gccggtgcga tgcgcggatt cgagttcgtg    1920
aagcgtgtcc acttgaccac ggatgcattc tcggtcgaca acggcatgat gacacctacc    1980
ttcaaggtcc gtcgcccaca gtagccgagc atttcaggg agcaaatcac ggccatgtat    2040
aaggagatca atgcctcgac ccctgttgcc aagctgtag                           2079
```

<210> SEQ ID NO 39
<211> LENGTH: 2306
<212> TYPE: DNA
<213> ORGANISM: Mortierella alpina

<400> SEQUENCE: 39

```
tgctttctc ttcttcgtca ccctccttct tcccattcct ccggtcctcc tccgttccta      60
atcagtttct cagaccctgt ccattcctct ggcctccaca cacacccac tctcccttga    120 acaaatacct tatccagatc aaagacatgc cttccttcaa aaagtacaac ctcgacaagc    180
agagtgttga ggtccctggc actcggaagc ctggcgcttc aggccactac agacatgccg    240
cctacggcga tgctcttgtc accaacatcc gtgaggcccc tcatatcgaa actctttacg    300
acatgtggca gaactctgtg acaaagtatg cggcaatga ctttttgggt caccgtccct    360
tcaacactgt tgcccagacc tatggtggct acagttggga gacgtaccgc cagattaacc    420
agcgcgttaa tgcgttcggc agcggtatca tgcacctgaa cgaggtgatc ctcggcaacc    480
gccagcttaa ccgctgggcg ttgggcatct ggtcccacgg tcgccctgag tggttcatta    540
cggagatgag ctgcaactgc tacaacctca tttctgttgc attgtacgac acccttggac    600
ctgatgcagt cgagtacatt gtcaaccacg ccgagattga gattgttgtc tcaagtgcca    660
accatatcgc ctctttgctc gagaacgccg agaagctccc caagctcaag gccattgtca    720
gcatggatgc tcttcacgat accgtccccg tccccggcgc cacctctgcc gcacaggttc    780
ttcgtgcctg gggtgcacaa aagggcatca aggtctatga ctttaacgag attgagtccc    840
tcggtgccga gttccctcgc aagcacctgc ctccccaccgc tgatgaggtc gcctccatct    900
gctacacttc cggcaccacc ggtcagccta aggagccat gctcacccac agaaactttg    960
ttgctactgt tggtaccaac cgcgagggca tgcttctcac cgaggacgac gttttgatca   1020
gtttcttgcc cttggctcac attatgggac gcgtcattga cacttgctcg atgtacagcg   1080
gtggcaagat tggttacttc cgtggagata ttcttttgct tctcgaggac gttgctgagc   1140
tccgtcccac attcttccca gctgtgcctc gcctcttgaa ccgcatttat gccaagctcg   1200
ttgcctctac cattgaggcc cccggttgg tcggtgcctt ggcccgtcgc ggtgtcgccg   1260
ccaagatggc caaccttgct gccggaaagg gtgtcaacca cgctctctgg gacagactgc   1320
tgttcaacaa ggtcaagatg gccctgggtg gtcgcgttca ggtcatcctg actggatctg   1380
```

| | |
|---|---|
| cgcccattgc caaggaggtt ctcagcttct tgagaattgc tttcggatgc gtggttttgg | 1440 |
| agggatacgg ctccactgag ggcatggcta ccgccaccat cacaatggct gatgagtaca | 1500 |
| ttcctggtca cattggctgc cctcgtgctg gatgcgagct caagctggtg gatgtgcccg | 1560 |
| cgatgaacta cctctctacc gaccagccct accccgtgg agagatctgg atccgtggtg | 1620 |
| acactgtttt caaaggatac ttcaaggacg agaagaacac tagtgagact atcgactctg | 1680 |
| aaggctggct cgctaccggt gatattgat tgtggataa gcgtggatgc tttacgatca | 1740 |
| ttgaccgcaa gaagaacatc ttcaagttgg cacaaggtga atacattgct cctgaaaaga | 1800 |
| ttgaaacgt cttgggcgca cgctgcaatc ttgtccagca gatctatgtt catggtgatt | 1860 |
| cgcttgagtc caccttggtc gcagttctta ttcccgagcc cgagaccttc ctgcccttcg | 1920 |
| cgaatgccat tgctggtgcc tccgtcactg ctggagatgt tgagggtttg aacaagctgt | 1980 |
| gccaagatcc caaggtcaag atcgcggttc tgaaggagtt ggagaaggcc ggaaaggccg | 2040 |
| gtgcgatgcg cggattcgag ttcgtgaagc gtgtccactt gaccacggat gcattctcgg | 2100 |
| tcgacaacgg catgatgaca cctaccttca aggtccgtcg cccacaagta gccgagcatt | 2160 |
| tcagggagca aatcacggcc atgtataagg agatcaatgc ctcgacccct gttgccaagc | 2220 |
| tgtagataga aaactctttg ccccttatta cccctttgaat agaaggtgac acgttgtttg | 2280 |
| attcacacaa aaaaaaaaaa aaaaaa | 2306 |

<210> SEQ ID NO 40
<211> LENGTH: 2816
<212> TYPE: DNA
<213> ORGANISM: Mortierella alpina

<400> SEQUENCE: 40

| | |
|---|---|
| atgccttcct tcaaaaagta caacctcgac aagcagagtg ttgaggtccc tggcactcgg | 60 |
| aagcctggcg cttcaggcaa gttggatagt ggctcatgag atccaactgt tgggccacgc | 120 |
| taccatgaaa ctagtcgcta atgcagattc tctattgcct ttcaccttct cacaggccac | 180 |
| tacagacatg ccgcctacgg cgatgctctt gtcaccaaca tccgtgaggc ccctcatatc | 240 |
| gaaactcttt acgacatgtg gcagaactgt aagttgattc ccgaggacct gggaaatctt | 300 |
| tactcggatc tgtctcacaa gaagactcac actctgctct ccacaattac cttgtaacct | 360 |
| tcagctgtga caaagtatgg cggcaatgac ttttgggtc accgtccctt caacactgtt | 420 |
| gcccagacct atggtggcta cagttgggag acgtaccgcc agattaacca gcgcgttaat | 480 |
| gcgttcggca gcggtatcat gcacctgaac gaggtgatcc tcggcaaccg ccagcttaac | 540 |
| cgctgggcgt tgggcatctg gtcccacggt cgccctgagt ggttcattac ggagatgagc | 600 |
| tgcaactgct acaacctcat ttctgttgca ttgtacgaca cccttggacc tgatgcagtc | 660 |
| gagtacattg tcaaccacgc cgagattgag attgttgtct caagtggtaa gtcgcttttt | 720 |
| tttttttgct attggcgcct gcttgcttgc ctgcacgtga aaactataat ggtttctgat | 780 |
| ctcccttttg tgtacctcct cctttcgatc aacttctttg taattttatt cccgggcatt | 840 |
| gactctatat gcagccaacc atatcgcctc tttgctcgag aacgccgaga agctccccaa | 900 |
| gctcaaggcc attgtcagca tggatgctct tcacgatacc gtccccgtcc ccggcgccac | 960 |
| ctctgccgca caggttcttc gtgcctgggg tgcacaaaag ggcatcaagg tctatgactt | 1020 |
| taacagagat tgagtccctcg gtgccgagtt ccctcgcaag cacctgcctc ccaccgctga | 1080 |
| tgaggtcgcc tccatctgct acacttccgg caccaccggt cagcctgtaa gtgtgttttc | 1140 |
| ccttcactga cgatgtcggc tgaggatgca ttttgctgat tgaaacttcc catctaacat | 1200 |

-continued

```
cgcttgatct atagaaagga gccatgctca cccacagaaa ctttgttgct actgttggta        1260
ccaaccgcga gggcatgctt ctcaccgagg acgacgtttt gatcaggtat aactcatctt        1320
gaagctgatc aatgacacgc gatgtacaac gcgacgatgg agcgagatct acaatgcgga        1380
atggctcacc tccggtttac aattaccaca cttctagttt cttgcccttg gctcacatta        1440
tgggacgcgt cattgacact tgctcgatgt acagcggtgg caagattggt tacttccgtg        1500
gagatattct tttgcttctc gaggacgttg ctgagctccg tcccacattc ttcccagctg        1560
tgcctcgcct cttgaaccgc atttatgcca agctcgttgc ctctaccatt gaggcccccg        1620
gtttggtcgg tgccttggcc cgtcgcggtg tcgccgccaa gatggccaac cttgctgccg        1680
gaaagggtgt caaccacgct ctctgggaca gactgctgtt caacaaggtc aagatggccc        1740
tgggtggtcg cgttcaggtc atcctgactg gatctgcgcc cattgccaag gaggttctca        1800
gcttcttgag aattgctttc ggatgcgtgg ttttgaggg atacggctcc actgagggca        1860
tggctaccgc caccatcaca atggctgagt acgtgaacct agttatttta ttgaaatgtc        1920
gtggagcctg tcgactgtag catttcaatc taaccattag taatctttc aaaaatagtg         1980 agtacattcc tggtcacatt ggctgccctc gtgctggatg cgagctcaag ctggtggatg        2040
tgcccgcgat gaactacctc tctaccgacc agccctaccc ccgtggagag atctggatcc        2100 gtggtgcac tgttttcaaa ggatacttca aggacgagaa gaacactagt gagactatcg         2160
actctgaagg ctggctcgct accggtgata ttggatttgt ggataagcgt ggatgcttta        2220
cgatcattga ccgcaagaag aacatcttca aggtatgagc aaaaagtggg attgatctga        2280
tcgtttctct tctcgttttc ccgttaagga attccgctca tactaacgtt ctcgtcaatg        2340
gtttgcatgt attatagttg gcacaaggtg aatacattgc tcctgaaaag attgagaacg        2400
tcttgggcgc acgctgcaat cttgtccagc agatctatgt tcatggtgat tcgcttgagt        2460
ccaccttggt cgcagttctt attcccgagc ccgagacctt cctgcccttc gcgaatgcca        2520 tgctggtgc ctccgtcact gctggagatg ttgagggttt gaacaagctg tgccaagatc         2580
ccaaggtcaa gatcgcggtt ctgaaggagt tggagaaggc cggaaaggcc ggtgcgatgc        2640
gcggattcga gttcgtgaag cgtgtccact tgaccacgga tgcattctcg gtcgacaacg        2700
gcatgatgac acctaccttc aaggtccgtc gcccacaagt agccgagcat ttcagggagc        2760
aaatcacggc catgtataag gagatcaatg cctcgacccc tgttgccaag ctgtag            2816
```

<210> SEQ ID NO 41
<211> LENGTH: 1848
<212> TYPE: DNA
<213> ORGANISM: Mortierella alpina

<400> SEQUENCE: 41

```
atggttgctc tcccactcgt cgcagcagct gtcccagctg ccatgtatgt gagctcaaag         60
ctggcacttc ctcgggatat gaagttgatt aagagcttga tcgagccaa gatgcctac         120 agtgccatgg aaaagaacga cgccctcaac ctgacactcc gcttcgacga gtgctaccgc        180
aagtatcctg accgtgaagc cctggtcttt gagggcaaat cctattcatt ccgtgatatt        240
cagcttgcct ccaacaggtg cggcaactgg ttgctggcca aagggatcaa gcgaggagat        300
atcgtctcgc ttttcatgtt gaacaggcca gagttcatct tctgctggct gggtctcaac        360
aagattggag ccactggtgc cttcatcaat accaacctta cgggcaaacc cctgacacat        420
tccctccgga cagccacgtc gtcaatgttg atcatggaca cggagttgac agacgcgatc        480
```

-continued

```
gccaactcccc tggatgagat tcaggagatg ggctattcaa tttactctta cggacccgaa    540
gccgtggact tgctacccc gatggatatc tcgcaggtcc cagacaccga tacacccgaa      600
cacctgcgcc ggaacacgac cgcggatgac attgcgatgc tcatctacac ctctggaact    660
actggtcttc ccaaggccgg tcgtgtctct catgcgcgtg cctctatggg acctcagttt    720
tggaaccgat tctatcactt cagtgagagc gacagggtct atctgtcctt gcccttgtac    780
cacagtgctg gcgccatctt gggagtgatt gcttgttgga cctcgggagc aaccttgatc    840
ctggcccgca agttctccgc gacacatttc tgggaggatt gccgcgtgaa caacgcaact    900
gtgattcaat acattggaga aatttgcaga tatctgctca acacgccaga atcacccctg    960
gacaaggcac actcgatacg actggcacat ggtaatggaa tgcgacccga tgtctggact   1020
cgcttcagag atcggttcgg catcccgttg attggcgagt ggtatgcatc gactgaggga   1080
actggagcct tgtcgaatta taacacaggc ccaggcggcg ctggagcgat tggataccgc   1140
ggtacccttg ccagagcatt ggataaagga ctcaggattg cgagatttga tgtccagaca   1200
gaggagttgg ttcgggacaa aaacggttat tgcattgagt gcaaacctgg cgagcccgga   1260
gaattgctga cgcttgttga tgctaaagag ccgaacaaag acttcaaagg ataccatcaa   1320
aaccaggcag cgaccaacaa aaagattgtc aaagatgttt tcaaagccgg cgacatgtac   1380
ttccgtaccg gagatatcct tcggcgcgat agcgatgggt acttttactt tggcgaccgt   1440
gtgggcgata cattccggtg gaagtccgag aatgtgtcta cggccgaggt gtctgaagtc   1500
ctctcgcagt atccggactg tatcgaagtc aatgtgtatg gagttcagat cccagggcag   1560
gacggacgcg ccggtatggc agcgattgtg tccaagagca cgatggattg ggagaaattt   1620
gcggcgtatg cactcaagaa cctgccgcgg tattctgttc cgatctttat ccgcaagatg   1680
cccgagatgg agatcacagg gacgttcaag cagcgcaaag tcgagttggt gaatgaggga   1740
atcgaccccca agacgattgc caacgagatg ctgtggttgg acggacacca ctataagccg   1800
ttcaaggcgg ccgagcacca gcgcgtcatc agcggcaagg ccaagcta              1848
```

<210> SEQ ID NO 42
<211> LENGTH: 616
<212> TYPE: PRT
<213> ORGANISM: Mortierella alpina

<400> SEQUENCE: 42

```
Met Val Ala Leu Pro Leu Val Ala Ala Val Pro Ala Ala Met Tyr
1               5                   10                  15

Val Ser Ser Lys Leu Ala Leu Pro Arg Asp Met Lys Leu Ile Lys Ser
            20                  25                  30

Leu Ile Gly Ala Lys Met Ala Tyr Ser Ala Met Glu Lys Asn Asp Ala
        35                  40                  45

Leu Asn Leu Thr Leu Arg Phe Asp Glu Cys Tyr Arg Lys Tyr Pro Asp
    50                  55                  60

Arg Glu Ala Leu Val Phe Glu Gly Lys Ser Tyr Ser Phe Arg Asp Ile
65                  70                  75                  80

Gln Leu Ala Ser Asn Arg Cys Gly Asn Trp Leu Leu Ala Lys Gly Ile
                85                  90                  95

Lys Arg Gly Asp Ile Val Ser Leu Phe Met Leu Asn Arg Pro Glu Phe
            100                 105                 110

Ile Phe Cys Trp Leu Gly Leu Asn Lys Ile Gly Ala Thr Gly Ala Phe
        115                 120                 125

Ile Asn Thr Asn Leu Thr Gly Lys Pro Leu Thr His Ser Leu Arg Thr
```

```
                    130                 135                 140
        Ala Thr Ser Ser Met Leu Ile Met Asp Thr Glu Leu Thr Asp Ala Ile
        145                 150                 155                 160

Ala Asn Ser Leu Asp Glu Ile Gln Glu Met Gly Tyr Ser Ile Tyr Ser
                            165                 170                 175

Tyr Gly Pro Glu Ala Val Asp Phe Ala Thr Pro Met Asp Ile Ser Gln
                        180                 185                 190

Val Pro Asp Thr Asp Thr Pro Glu His Leu Arg Arg Asn Thr Thr Ala
                    195                 200                 205

Asp Asp Ile Ala Met Leu Ile Tyr Thr Ser Gly Thr Thr Gly Leu Pro
                210                 215                 220

Lys Ala Gly Arg Val Ser His Ala Arg Ala Ser Met Gly Pro Gln Phe
        225                 230                 235                 240

Trp Asn Arg Phe Tyr His Phe Ser Glu Ser Asp Arg Val Tyr Leu Ser
                            245                 250                 255

Leu Pro Leu Tyr His Ser Ala Gly Ala Ile Leu Gly Val Ile Ala Cys
                        260                 265                 270

Trp Thr Ser Gly Ala Thr Leu Ile Leu Ala Arg Lys Phe Ser Ala Thr
                    275                 280                 285

His Phe Trp Glu Asp Cys Arg Val Asn Asn Ala Thr Val Ile Gln Tyr
                290                 295                 300

Ile Gly Glu Ile Cys Arg Tyr Leu Leu Asn Thr Pro Glu Ser Pro Leu
        305                 310                 315                 320

Asp Lys Ala His Ser Ile Arg Leu Ala His Gly Asn Gly Met Arg Pro
                            325                 330                 335

Asp Val Trp Thr Arg Phe Arg Asp Arg Phe Gly Ile Pro Leu Ile Gly
                        340                 345                 350

Glu Trp Tyr Ala Ser Thr Glu Gly Thr Gly Ala Leu Ser Asn Tyr Asn
                    355                 360                 365

Thr Gly Pro Gly Ala Gly Ala Ile Gly Tyr Arg Gly Thr Leu Ala
                370                 375                 380

Arg Ala Leu Asp Lys Gly Leu Arg Ile Ala Arg Phe Asp Val Gln Thr
        385                 390                 395                 400

Glu Glu Leu Val Arg Asp Lys Asn Gly Tyr Cys Ile Glu Cys Lys Pro
                            405                 410                 415

Gly Glu Pro Gly Glu Leu Leu Thr Leu Val Asp Ala Lys Glu Pro Asn
                        420                 425                 430

Lys Asp Phe Lys Gly Tyr His Gln Asn Gln Ala Ala Thr Asn Lys Lys
                    435                 440                 445

Ile Val Lys Asp Val Phe Lys Ala Gly Asp Met Tyr Phe Arg Thr Gly
        450                 455                 460

Asp Ile Leu Arg Arg Asp Ser Asp Gly Tyr Tyr Phe Gly Asp Arg
        465                 470                 475                 480

Val Gly Asp Thr Phe Arg Trp Lys Ser Glu Asn Val Ser Thr Ala Glu
                        485                 490                 495

Val Ser Glu Val Leu Ser Gln Tyr Pro Asp Cys Ile Glu Val Asn Val
                    500                 505                 510

Tyr Gly Val Gln Ile Pro Gly Gln Asp Gly Arg Ala Gly Met Ala Ala
                515                 520                 525

Ile Val Ser Lys Ser Thr Met Asp Trp Glu Lys Phe Ala Ala Tyr Ala
        530                 535                 540

Leu Lys Asn Leu Pro Arg Tyr Ser Val Pro Ile Phe Ile Arg Lys Met
        545                 550                 555                 560
```

```
Pro Glu Met Glu Ile Thr Gly Thr Phe Lys Gln Arg Lys Val Glu Leu
            565                 570                 575

Val Asn Glu Gly Ile Asp Pro Lys Thr Ile Ala Asn Glu Met Leu Trp
        580                 585                 590

Leu Asp Gly His His Tyr Lys Pro Phe Lys Ala Ala Glu His Gln Arg
    595                 600                 605

Val Ile Ser Gly Lys Ala Lys Leu
    610                 615

<210> SEQ ID NO 43
<211> LENGTH: 1851
<212> TYPE: DNA
<213> ORGANISM: Mortierella alpina

<400> SEQUENCE: 43
```

| | | | | | |
|---|---|---|---|---|---|
| atggttgctc | tcccactcgt | cgcagcagct | gtcccagctg | ccatgtatgt | gagctcaaag | 60 |
| ctggcacttc | ctcgggatat | gaagttgatt | aagagcttga | tcggagccaa | gatggcctac | 120 |
| agtgccatgg | aaaagaacga | cgccctcaac | ctgacactcc | gcttcgacga | gtgctaccgc | 180 |
| aagtatcctg | accgtgaagc | cctggtcttt | gagggcaaat | cctattcatt | ccgtgatatt | 240 |
| cagcttgcct | ccaacaggtg | cggcaactgg | ttgctggcca | aagggatcaa | gcgaggagat | 300 |
| atcgtctcgc | ttttcatgtt | gaacaggcca | gagttcatct | tctgctggct | gggtctcaac | 360 |
| aagattggag | ccactggtgc | cttcatcaat | accaacctta | cgggcaaacc | cctgacacat | 420 |
| tccctccgga | cagccacgtc | gtcaatgttg | atcatggaca | cggagttgac | agacgcgatc | 480 |
| gccaactccc | tggatgagat | tcaggagatg | ggctattcaa | tttactctta | cggacccgaa | 540 |
| gccgtggact | tgctaccccc | gatggatatc | tcgcaggtcc | agacaccgaa | tacacccgaa | 600 |
| cacctgcgcc | ggaacacgac | cgcggatgac | attgcgatgc | tcatctacac | ctctggaact | 660 |
| actggtcttc | ccaaggccgg | tgtgtctct | catgcgcgtg | cctctatggg | acctcagttt | 720 |
| tggaaccgat | tctatcactt | cagtgagagc | gacagggtct | atctgtcctt | gcccttgtac | 780 |
| cacagtgctg | cgccatcatt | gggagtgatt | gcttgttgga | cctcgggagc | aaccttgatc | 840 |
| ctggcccgca | agttctccgc | gacacatttc | tgggaggatt | gccgcgtgaa | caacgcaact | 900 |
| gtgattcaat | acattggaga | aatttgcaga | tatctgctca | acacgccaga | atcccctg | 960 |
| gacaaggcac | actcgatacg | actggcacat | ggtaatgaa | tgcgacccga | tgtctggact | 1020 |
| cgcttcagag | atcggttcgg | catcccgttg | attggcgagt | ggtatgcatc | gactgaggga | 1080 |
| actggagcct | tgtcgaatta | taacacaggc | ccaggcggcg | ctggagcgat | ggataccgc | 1140 |
| ggtacccttg | ccagagcatt | ggataaagga | ctcaggattg | cgagatttga | tgtccagaca | 1200 |
| gaggagttgg | ttcgggacaa | aaacggttat | tgcattgagt | gcaaacctgg | cgagcccgga | 1260 |
| gaattgctga | cgcttgttga | tgctaaagag | ccgaacaaag | acttcaaagg | ataccatcaa | 1320 |
| aaccaggcag | cgaccaacaa | aaagattgtc | aaagatgttt | tcaaagccgg | cgacatgtac | 1380 |
| ttccgtaccg | gagatatcct | tcggcgcgat | agcgatgggt | actttactt | tggcgaccgt | 1440 |
| gtgggcgata | cattccggtg | gaagtccgag | aatgtgtcta | cggccgaggt | gtctgaagtc | 1500 |
| ctctcgcagt | atccggactg | tatcgaagtc | aatgtgtatg | agttcagat | cccagggcag | 1560 |
| gacggacgcg | ccggtatggc | agcgattgtg | tccaagagca | cgatggattg | ggagaaattt | 1620 |
| gcggcgtatg | cactcaagaa | cctgccgcgg | tattctgttc | cgatctttat | ccgcaagatg | 1680 |
| cccgagatgg | agatcacagg | gacgttcaag | cagcgcaaag | tcgagttggt | gaatgaggga | 1740 |

-continued

| | |
|---|---:|
| atcgacccca agacgattgc caacgagatg ctgtggttgg acggacacca ctataagccg | 1800 |
| ttcaaggcgg ccgagcacca gcgcgtcatc agcggcaagg ccaagctata g | 1851 |

<210> SEQ ID NO 44
<211> LENGTH: 2042
<212> TYPE: DNA
<213> ORGANISM: Mortierella alpina

<400> SEQUENCE: 44

| | |
|---|---:|
| tcgctatcta tcacccctca ctccccactc cgcactctgc tcttcctttt tcctttctct | 60 |
| ctctcaccgt cgccactgtc tctactttct ttaccaccca cgcatcagtc acagcatggt | 120 |
| tgctctccca ctcgtcgcag cagctgtccc agctgccatg tatgtgagct caaagctggc | 180 |
| acttcctcgg gatatgaagt tgattaagag cttgatcgga gccaagatgg cctacagtgc | 240 |
| catggaaaag aacgacgccc tcaacctgac actccgcttc gacgagtgct accgcaagta | 300 |
| tcctgaccgt gaagccctgg tctttgaggg caaatcctat tcattccgtg atattcagct | 360 |
| tgcctccaac aggtgcggca actggttgct ggccaaaggg atcaagcgag agatatcgt | 420 |
| ctcgcttttc atgttgaaca ggccagagtt catcttctgc tggctgggtc tcaacaagat | 480 |
| tggagccact ggtgccttca tcaataccaa ccttacgggg aaaccctga cacattccct | 540 |
| ccggacagcc acgtcgtcaa tgttgatcat ggacacggag ttgacagacg cgatcgccaa | 600 |
| ctccctggat gagattcagg agatgggcta ttcaatttac tcttacggac ccgaagccgt | 660 |
| ggactttgct accccgatgg atatctcgca ggtcccagac accgatacac ccgaacacct | 720 |
| gcgccggaac acgaccgcgg atgacattgc gatgctcatc tacacctctg gaactactgg | 780 |
| tcttcccaag gccggtcgtg tctctcatgc gcgtgcctct atgggacctc agttttggaa | 840 |
| ccgattctat cacttcagtg agagcgacag ggtctatctg tccttgccct tgtaccacag | 900 |
| tgctggcgcc atcttgggag tgattgcttg ttggacctcg ggagcaacct tgatcctggc | 960 |
| ccgcaagttc tccgcgacac atttctggga ggattgccgc gtgaacaacg caactgtgat | 1020 |
| tcaatacatt ggagaaattt gcagatatct gctcaacacg ccagaatcac ccctggacaa | 1080 |
| ggcacactcg atacgactgg cacatggtaa tggaatgcga cccgatgtct ggactcgctt | 1140 |
| cagagatcgg ttcggcatcc cgttgattgg cgagtggtat gcatcgactg agggaactgg | 1200 |
| agccttgtcg aattataaca caggcccagg cggcgctgga gcgattggat accgcggtac | 1260 |
| ccttgccaga gcattggata aaggactcag gattgcgaga tttgatgtcc agacagagga | 1320 |
| gttggttcgg gacaaaaacg gttattgcat tgagtgcaaa cctggcgagc cggagaatt | 1380 |
| gctgacgctt gttgatgcta agagccgaa caaagacttc aaaggatacc atcaaaacca | 1440 |
| ggcagcgacc aacaaaaaga ttgtcaaaga tgttttcaaa gccggcgaca tgtacttccg | 1500 |
| taccggagat atccttcggc gcgatagcga tgggtacttt actttggcg accgtgtggg | 1560 |
| cgatacattc cggtggaagt ccgagaatgt gtctacggcc gaggtgtctg aagtcctctc | 1620 |
| gcagtatccg gactgtatcg aagtcaatgt gtatggagtt cagatcccag gcaggacgg | 1680 |
| acgcgccggt atggcagcga ttgtgtccaa gagcacgatg gattgggaga atttgcggc | 1740 |
| gtatgcactc aagaacctgc cgcggtattc tgttccgatc tttatccgca agatgccga | 1800 |
| gatggagatc acagggacgt tcaagcagcg caaagtcgag ttggtgaatg agggaatcga | 1860 |
| ccccaagacg attgccaacg agatgctgtg gttggacgga caccactata gccgttcaa | 1920 |
| ggcggccgag caccagcgcg tcatcagcgg caaggccaag ctatagtagg gcgcgtgcgc | 1980 |
| caatgcagta gcaatactat tccccgcttt gtccattaaa aaaaaaaaaa aaaaaaaaa | 2040 |

|  |  |
|---|---|
| aa | 2042 |

<210> SEQ ID NO 45
<211> LENGTH: 2345
<212> TYPE: DNA
<213> ORGANISM: Mortierella alpina

<400> SEQUENCE: 45

|  |  |
|---|---|
| atggttggtg agtaaacagc gatcgccctg ggtccaatcg actcatctgc taatctgatc | 60 |
| tcacacgtcc cttatcaatt cacaaaagaa aaaaagaga caagagagag aattactaac | 120 |
| attgctctct ccctcgtgtc gatgcagctc tcccactcgt cgcagcagct gtcccagctg | 180 |
| ccatgtatgt gagctcaaag ctggcacttc ctcgggatat gaagttgatt aagagcttga | 240 |
| tcggagccaa gatggcctac agtgccatgg aaaagaacga cgccctcaac ctgacactcc | 300 |
| gcttcgacga gtgctaccgc aagtatcctg accgtgaagc cctggtcttt gagggcaaat | 360 |
| cctattcatt ccgtgatatt cagcttggta agccattgtt acacggcact caccccacgc | 420 |
| ttcctgcttt cagagctcac gactgctcga accttcaatt ttttgtatcg atcgatcacc | 480 |
| gatcgatcat gcgcccacat tgcctagagc tatggcacac gcgctaatgc atgccttctt | 540 |
| gttatgaagc ctccaacagg tgcggcaact ggttgctggc caagggatc aagcgaggag | 600 |
| atatcgtctc gcttttcatg ttgaacaggc cagagttcat cttctgctgg ctgggtctca | 660 |
| acaagattgg agccactggt gccttcatca ataccaacct tacgggcaaa cccctgacac | 720 |
| attccctccg gacagccacg tcgtcaatgt tgatcatgga cacggagttg acagacgcga | 780 |
| tcgccaactc cctggatgag attcaggaga tgggctattc aatttactct tacggacccg | 840 |
| aagccgtgga ctttgctacc ccgatggata tctcgcaggt cccagacacc gatacacccg | 900 |
| aacacctgcg ccggaacacg accgcggatg acattgcgat gctcatctac acctctggaa | 960 |
| ctactggtct tcccaaggcc ggtcgtgtct ctcatgcgcg tgcctctagt aagttgagag | 1020 |
| tcttcagcct ttgacatacg tatttttttga gcgtgctact aacagttctc gttgccgtta | 1080 |
| tctgcatatt tttagtggga cctcagtttt ggaaccgatt ctatcacttc agtgagagcg | 1140 |
| acagggtcta tctgtccttg cccttgtacc acagtgctgg cgccatcttg ggagtgattg | 1200 |
| cttgttggac ctcgggagca accttgatcc tggcccgcaa gttctccgcg acacatttct | 1260 |
| gggaggattg ccgcgtgaac aacgcaactg tgattcaata cattggagaa atttgcagat | 1320 |
| atctgctcaa cacgccagaa tcaccccctgg acaaggcaca ctcgatacga ctggcacatg | 1380 |
| gtaatggaat gcgacccgat gtctggactc gcttcagaga tcggttcggc atcccgttga | 1440 |
| ttggcgagtg gtatgcatcg actgagggaa ctggagcctt gtcgaattat aacacaggcc | 1500 |
| caggcggcgc tggagcgatt ggataccgcg gtacccttgc cagagcattg gataaaggac | 1560 |
| tcaggattgc gagatttgat gtccagacag aggagttggt tcgggacaaa acggttatt | 1620 |
| gcattgaggt aaaacataag gcgcattgtt gaagtctaaa tcacttcaga tgctttgttc | 1680 |
| ggcatgctta ccaaacgcac cgaccatctt ttcactggtg cggcatataa tagtgcaaac | 1740 |
| ctggcgagcc cggagaattg ctgacgcttg ttgatgctaa agagccgaac aaagacttca | 1800 |
| aaggatacca tcaaaaccag gcagcgacca acaaaaagat tgtcaaagat gtttttcaaag | 1860 |
| ccggcgacat gtacttccgt accggagata tccttcggcg cgatagcgat gggtactttt | 1920 |
| actttgcgca ccgtgtgggc gatacattcc ggtggaagtc cgagaatgtg tctacggccg | 1980 |
| aggtgtctga agtcctctcg cagtatccgg actgtatcga agtcaatgtg tatggagttc | 2040 |

| | |
|---|---:|
| agatcccagg gcaggacgga cgcgccggta tggcagcgat tgtgtccaag agcacgatgg | 2100 |
| attgggagaa atttgcggcg tatgcactca agaacctgcc gcggtattct gttccgatct | 2160 |
| ttatccgcaa gatgcccgag atggagatca cagggacgtt caagcagcgc aaagtcgagt | 2220 |
| tggtgaatga gggaatcgac cccaagacga ttgccaacga gatgctgtgg ttggacggac | 2280 |
| accactataa gccgttcaag gcggccgagc accagcgcgt catcagcggc aaggccaagc | 2340 |
| tatag | 2345 |

```
<210> SEQ ID NO 46
<211> LENGTH: 2073
<212> TYPE: DNA
<213> ORGANISM: Mortierella alpina

<400> SEQUENCE: 46
```

| | |
|---|---:|
| atggaaacct tggttaacgg aaagtatgcg gtcgagtacg acgaggtcga tcacatctat | 60 |
| cgcaacgtca tggctacagg cgggctcctc gacaggccta tgcctccata ctacgacatc | 120 |
| aaggagcgca ccatggccca cctctttgag tatatgccaa acacctacga agacaaagac | 180 |
| gccatgggct ggcgagacat tatcaaggtc cacaaggtcg agaagcaggc tgccaatcct | 240 |
| ggcgagaagc caaagacctg gatcacttat gagctctcgg actacaactg gatgtcgtac | 300 |
| cgccaagcca gaactatgc agatcgagtt ggcttgggca tcacacgcct tggagttgag | 360 |
| aagggagact ttgtcatgat ctttgctagc acatgtcccg aatggttcct gacagcgcat | 420 |
| ggatgcttct cgcagtcagt gactatcgtg acagcctacg actcgatgga cgagaagtcg | 480 |
| atccagttta ttgttgacca gtcccagccc aaggccatct tgctgatgc cacacgctc | 540 |
| cctgtggtgt ccaaactcat gcagaagggc aacagtggtg tcaaggcagt catttacaca | 600 |
| ggccaagagt gggaagtgac cgatgcaatc aagaagatgg agcaagtaga aaaccgctca | 660 |
| tttgagctgg ttcatatcga cgaactcaag aagaccaagt cagcatctaa cggcgaacag | 720 |
| tctgccggaa aggggaagca gagatcatct gaggatgccg aaggcgctca ggacgagatc | 780 |
| gaggtcatat accctaaggc ggatgatctg gcctgtatta tgtataccct cgggtcgacg | 840 |
| ggtcagccca gggcgcgca attgacacat ggcaacttga tggcggccat ggaagtgct | 900 |
| gcggccatgg agggcgacca gctggacaag gaaacagaca ttgttatttc atatctgcca | 960 |
| ttggcccatg tcctcgagtt tgtcatttcc cactttgtgg tatccatggg ctgccgtctt | 1020 |
| ggattcggac gagcacgcac tctgatggat gatgcagtcg ctcccaccgc aggaagtggc | 1080 |
| aggtccaagg ccttggtga tctgaaggcg ctccagccaa cattgatggc tggtgtgcca | 1140 |
| acgatctggg agcgtatccg caagggcatc ctggccgagg tcaacaagca atccttccct | 1200 |
| atccgtacac tcttctttgc tgcactcaac accaagtggg ctatcgtcca ggctaccgga | 1260 |
| tctgagaact tgtcaccaa gactattgac tcgttggtct ttagtaaggc taaggagctc | 1320 |
| gttggaggca agctgcgcct taccttgact ggaggggccg gaatcagtga tgagacgcac | 1380 |
| cggttcttga gcatggtaat gtgctacgtt atctcgggat atggtctcac tgaagtctgt | 1440 |
| ggtgttgccg ctgtcacccct gccacgtatg ggtcaccgtc tcaggaccgt tggaccaccc | 1500 |
| gcgcccagtc ttgagctgaa gttggtgaat gtgcccgaca ccgagtacac aggagacaat | 1560 |
| ggatcgggcg aaatctggtt ccgtggacct gcagtgatga agggatactt caaactcgag | 1620 |
| gaagagacca agaaggtgat gaccggggat ggttggttca agacaggcga cattggcacg | 1680 |
| atgaacccag acggcacact gtcaatcaag gacaggtca gaatctggt caagctgtct | 1740 |
| catggagaat atgtcgccct ggagaaatgt gaagccgttt atcgcgattc caaggagatc | 1800 |

```
aagagcattt gcatcgttgc ggacaatggg tgccctgtgt tgctggccgt tgtggaaccg    1860
agccacgcag gggcgtctga caaggagatt ttggatatcc tgaagagcca agccaaggcg    1920
gcgggcctct ccaagtccga gactgtgcaa ggcgttatca ttgatgattc ggactggatg    1980
acgaatgggt tcatgacctc gagcagcaag gtcaagagac gcgaggtccg caaggcacac    2040
aacaaggata ttgaggagat gtggaagaag ttc                                 2073

<210> SEQ ID NO 47
<211> LENGTH: 691
<212> TYPE: PRT
<213> ORGANISM: Mortierella alpina

<400> SEQUENCE: 47

Met Glu Thr Leu Val Asn Gly Lys Tyr Ala Val Glu Tyr Asp Glu Val
1               5                   10                  15

Asp His Ile Tyr Arg Asn Val Met Ala Thr Gly Gly Leu Leu Asp Arg
            20                  25                  30

Pro Met Pro Pro Tyr Tyr Asp Ile Lys Glu Arg Thr Met Ala His Leu
        35                  40                  45

Phe Glu Tyr Met Ala Asn Thr Tyr Glu Asp Lys Asp Ala Met Gly Trp
    50                  55                  60

Arg Asp Ile Ile Lys Val His Lys Val Glu Lys Gln Ala Ala Asn Pro
65                  70                  75                  80

Gly Glu Lys Pro Lys Thr Trp Ile Thr Tyr Glu Leu Ser Asp Tyr Asn
                85                  90                  95

Trp Met Ser Tyr Arg Gln Ala Lys Asn Tyr Ala Asp Arg Val Gly Leu
            100                 105                 110

Gly Ile Thr Arg Leu Gly Val Glu Lys Gly Asp Phe Val Met Ile Phe
        115                 120                 125

Ala Ser Thr Cys Pro Glu Trp Phe Leu Thr Ala His Gly Cys Phe Ser
    130                 135                 140

Gln Ser Val Thr Ile Val Thr Ala Tyr Asp Ser Met Asp Glu Lys Ser
145                 150                 155                 160

Ile Gln Phe Ile Val Asp Gln Ser Gln Pro Lys Ala Ile Phe Ala Asp
                165                 170                 175

Ala His Thr Leu Pro Val Val Ser Lys Leu Met Gln Lys Gly Asn Ser
            180                 185                 190

Gly Val Lys Ala Val Ile Tyr Thr Gly Gln Glu Trp Glu Val Thr Asp
        195                 200                 205

Ala Ile Lys Lys Met Glu Gln Val Glu Asn Arg Ser Phe Glu Leu Val
    210                 215                 220

His Ile Asp Glu Leu Lys Lys Thr Lys Ser Ala Ser Asn Gly Glu Gln
225                 230                 235                 240

Ser Ala Gly Lys Gly Lys Gln Arg Ser Ser Glu Asp Ala Glu Gly Ala
                245                 250                 255

Gln Asp Glu Ile Glu Val Ile Tyr Pro Lys Ala Asp Asp Leu Ala Cys
            260                 265                 270

Ile Met Tyr Thr Ser Gly Ser Thr Gly Gln Pro Lys Gly Ala Gln Leu
        275                 280                 285

Thr His Gly Asn Leu Met Ala Ala Ile Gly Ser Ala Ala Ala Met Glu
    290                 295                 300

Gly Asp Gln Leu Asp Lys Glu Thr Asp Ile Val Ile Ser Tyr Leu Pro
305                 310                 315                 320
```

-continued

| | | | | | | | | | | |
|---|---|---|---|---|---|---|---|---|---|---|
|Leu|Ala|His|Val|Leu|Glu|Phe|Val|Ile|Ser|His|Phe|Val|Ser|Met|
| | | |325| | | |330| | | |335|

Gly Cys Arg Leu Gly Phe Gly Arg Ala Arg Thr Leu Met Asp Asp Ala
          340                 345                 350

Val Ala Pro Thr Ala Gly Ser Gly Arg Ser Lys Gly Leu Gly Asp Leu
          355                 360                 365

Lys Ala Leu Gln Pro Thr Leu Met Ala Gly Val Pro Thr Ile Trp Glu
          370                 375                 380

Arg Ile Arg Lys Gly Ile Leu Ala Glu Val Asn Lys Gln Ser Phe Pro
385                 390                 395                 400

Ile Arg Thr Leu Phe Phe Ala Ala Leu Asn Thr Lys Trp Ala Ile Val
              405                 410                 415

Gln Ala Thr Gly Ser Glu Asn Phe Val Thr Lys Thr Ile Asp Ser Leu
              420                 425                 430

Val Phe Ser Lys Ala Lys Glu Leu Val Gly Lys Leu Arg Leu Thr
              435                 440                 445

Leu Thr Gly Gly Ala Gly Ile Ser Asp Glu Thr His Arg Phe Leu Ser
     450                 455                 460

Met Val Met Cys Tyr Val Ile Ser Gly Tyr Gly Leu Thr Glu Val Cys
465                 470                 475                 480

Gly Val Ala Ala Val Thr Leu Pro Arg Met Gly His Arg Leu Arg Thr
              485                 490                 495

Val Gly Pro Pro Ala Pro Ser Leu Glu Leu Lys Leu Val Asn Val Pro
              500                 505                 510

Asp Thr Glu Tyr Thr Gly Asp Asn Gly Ser Gly Glu Ile Trp Phe Arg
              515                 520                 525

Gly Pro Ala Val Met Lys Gly Tyr Phe Lys Leu Glu Glu Thr Lys
              530                 535                 540

Lys Val Met Thr Gly Asp Gly Trp Phe Lys Thr Gly Asp Ile Gly Thr
545                 550                 555                 560

Met Asn Pro Asp Gly Thr Leu Ser Ile Lys Asp Arg Val Lys Asn Leu
              565                 570                 575

Val Lys Leu Ser His Gly Glu Tyr Val Ala Leu Glu Lys Cys Glu Ala
              580                 585                 590

Val Tyr Arg Asp Ser Lys Glu Ile Lys Ser Ile Cys Ile Val Ala Asp
              595                 600                 605

Asn Gly Cys Pro Val Leu Leu Ala Val Val Glu Pro Ser His Ala Gly
              610                 615                 620

Ala Ser Asp Lys Glu Ile Leu Asp Ile Leu Lys Ser Gln Ala Lys Ala
625                 630                 635                 640

Ala Gly Leu Ser Lys Ser Glu Thr Val Gln Gly Val Ile Ile Asp Asp
              645                 650                 655

Ser Asp Trp Met Thr Asn Gly Phe Met Thr Ser Ser Lys Val Lys
              660                 665                 670

Arg Arg Glu Val Arg Lys Ala His Asn Lys Asp Ile Glu Glu Met Trp
              675                 680                 685

Lys Lys Phe
     690

<210> SEQ ID NO 48
<211> LENGTH: 2076
<212> TYPE: DNA
<213> ORGANISM: Mortierella alpina

<400> SEQUENCE: 48

```
atggaaacct tggttaacgg aaagtatgcg gtcgagtacg acgaggtcga tcacatctat    60
cgcaacgtca tggctacagg cgggctcctc gacaggccta tgcctccata ctacgacatc   120
aaggagcgca ccatggccca cctctttgag tatatggcca acacctacga agacaaagac   180
gccatgggct ggcgagacat tatcaaggtc cacaaggtcg agaagcaggc tgccaatcct   240
ggcgagaagc caaagacctg gatcacttat gagctctcgg actacaactg gatgtcgtac   300
cgccaagcca agaactatgc agatcgagtt ggcttgggca tcacacgcct tggagttgag   360
aagggagact ttgtcatgat ctttgctagc acatgtcccg aatggttcct gacagcgcat   420
ggatgcttct cgcagtcagt gactatcgtg acagcctacg actcgatgga cgagaagtcg   480
atccagttta ttgttgacca gtcccagccc aaggccatct tgctgatgc gcacacgctc   540
cctgtggtgt ccaaactcat gcagaagggc aacagtggtg tcaaggcagt catttacaca   600
ggccaagagt gggaagtgac cgatgcaatc aagaagatgg agcaagtaga aaaccgctca   660
tttgagctgg ttcatatcga cgaactcaag aagaccaagt cagcatctaa cggcgaacag   720
tctgccggaa aggggaagca gagatcatct gaggatgccg aaggcgctca ggacgagatc   780
gaggtcatat accctaaggc ggatgatctg gcctgtatta tgtataccct ctgggtcgacg  840
ggtcagccca agggcgcgca attgacacat ggcaacttga tggcggccat tggaagtgct   900
gcggccatgg agggcgacca gctggacaag gaaacagaca ttgttatttc atatctgcca   960
ttggcccatg tcctcgagtt tgtcatttcc cactttgtgg tatccatggg ctgccgtctt  1020
ggattcggac gagcacgcac tctgatggat gatgcagtcg ctcccaccgc aggaagtggc  1080
aggtccaagg gccttggtga tctgaaggcg ctccagccaa cattgatggc tggtgtgcca  1140
acgatctggg agcgtatccg caagggcatc ctggccgagg tcaacaagca atccttccct  1200
atccgtacac tcttctttgc tgcactcaac accaagtggg ctatcgtcca ggctaccgga  1260
tctgagaact ttgtcaccaa gactattgac tcgttggtct ttagtaaggc taaggagctc  1320
gttggaggca agctgcgcct taccttgact ggaggggccg gaatcagtga tgagacgcac  1380
cggttcttga gcatggtaat gtgctacgtt atctcgggat atggtctcac tgaagtctgt  1440
ggtgttgccg ctgtcaccct gccacgtatg ggtcaccgtc tcaggaccgt tggaccaccc  1500
gcgcccagtc ttgagctgaa gttggtgaat gtgcccgaca ccgagtacac aggagacaat  1560
ggatcgggcg aaatctggtt ccgtggacct gcagtgatga agggatactt caaactcgag  1620
gaagagacca agaaggtgat gaccggggat ggttggttca agacaggcga cattggcacg  1680
atgaacccag acggcacact gtcaatcaag gacagggtca agaatctggt caagctgtct  1740
catggagaat atgtcgccct ggagaaatgt gaagccgttt atcgcgattc caaggagatc  1800
aagagcattt gcatcgttgc ggacaatggg tgccctgtgt tgctggccgt tgtggaaccg  1860
agccacgcag gggcgtctga caaggagatt ttggatatcc tgaagagcca agccaaggcg  1920
gcgggcctct ccaagtccga gactgtgcaa ggcgttatca ttgatgattc ggactggatg  1980
acgaatgggt tcatgaccct cgagcagcaa gtcaagagac gcgaggtccg caaggcacac  2040
aacaaggata ttgaggagat gtggaagaag ttctag                             2076
```

<210> SEQ ID NO 49
<211> LENGTH: 2076
<212> TYPE: DNA
<213> ORGANISM: Mortierella alpina

<400> SEQUENCE: 49

```
atggaaacct tggttaacgg aaagtatgcg gtcgagtacg acgaggtcga tcacatctat      60
cgcaacgtca tggctacagg cgggctcctc gacaggccta tgcctccata ctacgacatc     120
aaggagcgca ccatggccca cctctttgag tatatggcca cacctacga agacaaagac     180 gccatgggct ggcgagacat tatcaaggtc cacaaggtcg agaagcaggc tgccaatcct     240
ggcgagaagc caaagacctg gatcacttat gagctctcgg actacaactg gatgtcgtac     300
cgccaagcca gaactatgc agatcgagtt ggcttgggca tcacacgcct tggagttgag     360
aagggagact tgtcatgat ctttgctagc acatgtcccg aatggttcct gacagcgcat     420
ggatgcttct cgcagtcagt gactatcgtg acagcctacg actcgatgga cgagaagtcg     480
atccagttta ttgttgacca gtcccagccc aaggccatct ttgctgatgc gcacacgctc     540
cctgtggtgt ccaaactcat gcagaagggc aacagtggtg tcaaggcagt catttacaca     600
ggccaagagt gggaagtgac cgatgcaatc aagaagatgg agcaagtaga aaaccgctca     660
tttgagctgg ttcatatcga cgaactcaag aagaccaagt cagcatctaa cggcgaacag     720
tctgccggaa aggggaagca gagatcatct gaggatgccg aaggcgctca ggacgagatc     780
gaggtcatat accctaaggc ggatgatctg gcctgtatta tgtataccte tgggtcgacg     840 ggtcagccca agggcgcgca attgacacat ggcaacttga tggcggccat tggaagtgct     900
gcggccatgg agggcgacca gctgacaag gaaacagaca ttgttatttc atatctgcca     960
ttggcccatg tcctcgagtt tgtcatttcc cactttgtgg tatccatggg ctgccgtctt    1020
ggattcggac gagcacgcac tctgatggat gatgcagtcg ctcccaccgc aggaagtggc    1080
aggtccaagg gccttggtga tctgaaggcg ctccagccaa cattgatggc tggtgtgcca    1140
acgatctggg agcgtatccg caagggcatc ctggccgagg tcaacaagca atccttccct    1200
atccgtacac tcttctttgc tgcactcaac accaagtggg ctatcgtcca ggctaccgga    1260
tctgagaact ttgtcaccaa gactattgac tcgttggtct ttagtaaggc taaggagctc    1320
gttggaggca agctgcgcct taccttgact ggaggggccg gaatcagtga tgagacgcac    1380
cggttcttga gcatggtaat gtgctacgtt atctcgggat atggtctcac tgaagtctgt    1440
ggtgttgccg ctgtcaccct gccacgtatg ggtcaccgtc tcaggaccgt tggaccaccc    1500
gcgcccagtc ttgagctgaa gttggtgaat gtgcccgaca ccgagtacac aggagacaat    1560
ggatcgggcg aaatctggtt ccgtggacct gcagtgatga agggatactt caaactcgag    1620
gaagagacca agaaggtgat gaccggggat ggttggttca agacaggcga cattggcacg    1680
atgaacccag acggcacact gtcaatcaag gacagggtca agaatctggt caagctgtct    1740
catggagaat atgtcgccct ggagaaatgt gaagccgttt atcgcgattc caaggagatc    1800
aagagcattt gcatcgttgc ggacaatggg tgccctgtgt tgctggccgt tgtggaaccg    1860
agccacgcag gggcgtctga caaggagatt ttggatatcc tgaagagcca agccaaggcg    1920
gcgggcctct ccaagtccga gactgtgcaa ggcgttatca ttgatgattc ggactggatg    1980
acgaatgggt tcatgacctc gagcagcaag gtcaagagac gcgaggtccg caaggcacac    2040
aacaaggata ttgaggagat gtggaagaag ttctag                              2076
```

<210> SEQ ID NO 50
<211> LENGTH: 3236
<212> TYPE: DNA
<213> ORGANISM: Mortierella alpina

<400> SEQUENCE: 50

```
atggaaacct tggttaacgg aaagtatgcg gtcgagtacg acgaggtcga tcacatctat      60
```

```
cgcaacgtca tggctacagg cgggctcctc gacaggccta tgcctccata ctacgacatc    120
aaggagcgca ccatggccca cctctttgag tatatggcca cacctacga agacaaagac    180 gccatgggct ggcgagacat tatcaaggta ttgactgccc cggcctatca cttttttaccc   240 cacacgatcc tccctttttt ttctctccca ttcttctatc ctgaccgtat cgctatcgaa    300
cgagtcaacg agatcagttc ccacgcttac tttactccct cgtctgattc tgattatttt    360
ctctctctgc ctcttcgtga tttgttcgca ggtccacaag gtcgagaagc aggctgccaa    420
tcctggcgag aagccaaaga cctggatcac ttatgagctc tcggactaca actggatgtc    480
gtaccgccaa gccaagaact atgcagatcg agttggcttg gcatcacac gccttggagt     540 tgagaaggga gactttgtca tgatctttgc tagcacatgg tataacctca tgcagacaac    600
tttcgcatcc atgacagcat cgcaagaaaa aaaaaagaga aggaaattat gataattcgg    660
gccaagcgac taaaacaccg ctatcgcacg cttttttttt tttttcgct atcttgcatt     720 tcttatcgtt caaatagtcc cgaatggttc ctgacagcgc atggtaagct ttttcttttt    780
gcggatgatg atttcttctt atgacagcat gatgagattc aaccgggatt aggtgacggc    840
tgttgattgt gcaaaagggg ggccggacaa tttgaagaga cttggggagg tgtttgtgat    900
gacgacaaat ccaagattca acagaagact ggtgccaggg aagagtagag agggtgcctc    960
gttctttggc atatgaaagt ggattacgat atggctgagt taggagtcta attcatcgcg   1020
gaaaaagagt cgcgactgaa gtcccaagtc ggggactgta gaaagtattc cactcgtgtc   1080
tggtgaaatg aggaggactg ggttgggtt tggagtgccg acgagaaatc atggaatacg    1140
cttctcggtc ttcagtccac tgatcactca tggcgcaatt gactctacaa taataggatg   1200
cttctcgcag tcagtgacta tcgtgacagc ctacgactcg atggacgaga agtcgatcca   1260
gtttattgtt gaccagtccc agcccaaggc catctttgct gatgcgcaca cgctccctgt   1320
ggtgtccaaa ctcatgcaga agggcaacag tggtgtcaag gcagtcattt acacaggcca   1380
agagtgggaa gtgaccgatg caatcaagaa gatggagcaa gtagaaaacc gctcatttga   1440
gctggttcat atcgacgaac tcaagaagac caagtcagca tctaacggcg aacagtctgc   1500
cggaaagggg aagcagagat catctgagga tgccgaaggc gctcaggacg agatcgaggt   1560 catatacct aaggcggatg atctggcctg tattatgtat acctctgggt cgacgggtca    1620
gcccaagggc gcgcaattga cacatggcaa cttgatggcg ccattggaa gtgctgcggc    1680 catggagggc gaccagctgg acaaggaaac agacattgtt atttcatatc tgccattggc   1740
ccatgtcctc gagtttgtca tttcccactt tgtggtatcc atggtaagtc gaacatccct   1800
ttacatctgc atcccaaaat gcggctaaag tcaagttgtt gacctgaacg tttatattca   1860
tcttagggct gccgtcttgg attcggacga gcacgcactc tgatggatga tgcagtcgct   1920
cccaccgcag gaagtggcag gtccaagggc cttggtgatc tgaaggcgct ccagccaaca   1980
ttgatgggta tgattggcat gaagccagag actaatatga cgtagagtgg acaaaaacct   2040
tattttgacg tattgcatat tgtgtcgatt ttcaaaaacg atagctggtg tgccaacgat   2100
ctgggagcgt atccgcaagg gcatcctggc cgaggtcaac aagcaatcct tccctatccg   2160
tacactcttc tttgctgcac tcaacaccaa gtgggctatc gtccaggcta ccggatctga   2220
gaactttgtc accaagacta ttgactcgtt ggtctttagt aaggctaagg agctcgttgg   2280
aggcaagctg cgccttacct tgactggagg ggccggaatc agtgatgaga cgcaccggtt   2340
cttgagcatg gtaatgtgct acgttatctc gggatatggt ctcactgaag tctgtggtgt   2400
```

| | |
|---|---|
| tgccgctgtc acccctgccac gtatgggtca ccgtctcagg accgttggac cacccgtaag | 2460 |
| tccgctcgca tatcttctcg cgatctgaat atgcgagctg ttttttttg tctttcaaaa | 2520 |
| gctaacactt tgcttttcg cgacaacagg cgcccagtct tgagctgaag ttggtgaatg | 2580 |
| tgcccgacac cgagtacaca ggagacaatg gatcgggcga aatctggttc cgtggacctg | 2640 |
| cagtgatgaa gggatacttc aaactcgagg aagagaccaa gaaggtgatg accggggatg | 2700 |
| gttggttcaa gacaggcgac attggcacga tgaacccaga cggcacactg tcaatcaagg | 2760 |
| acagggtcaa gaatctggtc aagctgtctc atggagaata tgtcgccctg gagaaatgtg | 2820 |
| aagccgttta tcgcgattcc aaggagatca agagcatttg catcgttgcg gacaatgggt | 2880 |
| gccctgtgtt gctggccgtt gtggaaccga gccacgcagg ggtgagtgag acgcttttgg | 2940 |
| cctgacaagg tctcgttctt atgggaatgt ggatcattac tctatcacta acgagagagg | 3000 |
| ctgtattatt ctacttgcgt aacgtggcat aggcgtctga caaggagatt ttggatatcc | 3060 |
| tgaagagcca agccaaggcg gcgggcctct ccaagtccga gactgtgcaa ggcgttatca | 3120 |
| ttgatgattc ggactggatg acgaatgggt tcatgacctc gagcagcaag gtcaagagac | 3180 |
| gcgaggtccg caaggcacac aacaaggata ttgaggagat gtggaagaag ttctag | 3236 |

<210> SEQ ID NO 51
<211> LENGTH: 2040
<212> TYPE: DNA
<213> ORGANISM: Mortierella alpina

<400> SEQUENCE: 51

| | |
|---|---|
| atgccaaagt gctttaccgt caacgtcggc cccgaggacg tcaagggcga gactcgcatc | 60 |
| cgtcgctcca tccaggccgt cgacaaactc atggactcac cctcaagcga catcaagacc | 120 |
| ttgtacgatg tcatccagta ctctgccaag gtccgcccca acctcaacgc catcggctac | 180 |
| cgcaagattg tcaagatgat cgaagaggaa aaggagatca ccaagatggt cagcggcgag | 240 |
| cctgtcaagg agaaaaagac gtggaaatac ttcaagctct ccggctacca ctatctgacc | 300 |
| tacaaggaca ccaaggccgt catcgacagc attggaagtg gcctgcgcaa gtggggtgtt | 360 |
| gagcccaagg agaggatcac cgtctttggt tccacaagtg ccaactggct gctggtcgct | 420 |
| catggtgcct tcacgcagtc catgaccatc gtcaccgtgt atgacacttt gggcgaggaa | 480 |
| ggattgctgc actcgatgaa cgaggccgag gtgggaacgg cctacacgaa cgctgatttg | 540 |
| atcaagacaa tgaccaacgt ttcaggacgc tgccccaccc tcaagaggat cgtctatgac | 600 |
| ggcgaagcca acgcagcaga cgtgatcgcc cttcagacgg cccatcctca ccttcagctt | 660 |
| atcactctgg aggagctgaa gcagctcggt gtggatcacc ctgtggagcc cactcctccc | 720 |
| accgccgagg attgctcctg catcatgtac acttctggat cgaccggaaa ccctaaggga | 780 |
| gtcatcctca ctcacggaaa cctcattgcc gccattggcg gagttaacaa gatgctggaa | 840 |
| aagtacattc gcgaaggcga tgtccttgct gcctaccttc ccttggctca cgttctggaa | 900 |
| ttcatggttg agaacctctg tctcttctgg ggtgtaaccc ttggatatgg tactgtccgc | 960 |
| acgctgacgg atgcctctgt gcgtgagtgc cagggtgata tcaaggaatt gcggcctacg | 1020 |
| cttatgaccg gcgttccagc agtgtgggag accatccgca aggtgttct cgcccaagta | 1080 |
| aaccagggtt cacctctggt tcaatccgtc ttcaacgcgg ctctgaacgc caaggcctgg | 1140 |
| tgcatggacc gcaaactagg cgctttgact ggaattttcg acactgtggt gttcaacaag | 1200 |
| gtccgtcagc aaactggagg tcgtcttcgc tacgcgctct cgggcggcgc gcctatctcc | 1260 |
| caggagaccc agcgcttctt gaccacagca ctgtgcccta tccttcaagc ctatggcatg | 1320 |

```
actgagtcgt gcggcatgtg ctcgatcatg actccagagg cgttcaacta caaccgcgtc   1380
ggttcccctg ttccctgcac agaggtcaag ctcgtggatg tgcccgatgc aggatacttt   1440
tcgactgatt cgccccgccc tcgtggtgag atttggattc gcggaccctc catcacctct   1500
ggatacttca agaacgctga ggagacctcg gcagccatca cagaggaccg ctggctcaag   1560
actggagata ttggagagtg gcatgctgat ggcacactct cggtcattga tcgcaagaag   1620
aacttggtca agttgtcgca tggcgagtac attgctctag agaaacttga gtcggtgtac   1680
aagagcacgg cttactgcaa caacatctgc gtttatgccg attccatgca aaacaagcct   1740
gtggcgctga ttgttgcgag tgaaccccgc atcctcgagc tggccaaggc caagggcctg   1800
gagagccgcg actttgcagt gctctgccac gataaggtga tcatcaaggc tgtcctcgac   1860
gcctgtctcg cgactgccaa aaaggctggc ctcaagcccg ccgagttgct gcagggtgtg   1920
tacctggagt ctgaggagtg gaccgctcaa ggcggtttgt tgactgctgc tcagaaattg   1980
aagcgcaagg aaatcaacca ggcttatgct gaccagatca agcagatcta tggctccaag   2040
```

<210> SEQ ID NO 52
<211> LENGTH: 680
<212> TYPE: PRT
<213> ORGANISM: Mortierella alpina

<400> SEQUENCE: 52

```
Met Pro Lys Cys Phe Thr Val Asn Val Gly Pro Glu Asp Val Lys Gly
1               5                   10                  15

Glu Thr Arg Ile Arg Arg Ser Ile Gln Ala Val Asp Lys Leu Met Asp
            20                  25                  30

Ser Pro Ser Ser Asp Ile Lys Thr Leu Tyr Asp Val Ile Gln Tyr Ser
        35                  40                  45

Ala Lys Val Arg Pro Asn Leu Asn Ala Ile Gly Tyr Arg Lys Ile Val
    50                  55                  60

Lys Met Ile Glu Glu Lys Glu Ile Thr Lys Met Val Ser Gly Glu
65                  70                  75                  80

Pro Val Lys Glu Lys Lys Thr Trp Lys Tyr Phe Lys Leu Ser Gly Tyr
                85                  90                  95

His Tyr Leu Thr Tyr Lys Asp Thr Lys Ala Val Ile Asp Ser Ile Gly
            100                 105                 110

Ser Gly Leu Arg Lys Trp Gly Val Glu Pro Lys Glu Arg Ile Thr Val
        115                 120                 125

Phe Gly Ser Thr Ser Ala Asn Trp Leu Leu Val Ala His Gly Ala Phe
    130                 135                 140

Thr Gln Ser Met Thr Ile Val Thr Val Tyr Asp Thr Leu Gly Glu Glu
145                 150                 155                 160

Gly Leu Leu His Ser Met Asn Glu Ala Glu Val Gly Thr Ala Tyr Thr
                165                 170                 175

Asn Ala Asp Leu Ile Lys Thr Met Thr Asn Val Ser Gly Arg Cys Pro
            180                 185                 190

Thr Leu Lys Arg Ile Val Tyr Asp Gly Glu Ala Asn Ala Ala Asp Val
        195                 200                 205

Ile Ala Leu Gln Thr Ala His Pro His Leu Gln Leu Ile Thr Leu Glu
    210                 215                 220

Glu Leu Lys Gln Leu Gly Val Asp His Pro Val Glu Pro Thr Pro Pro
225                 230                 235                 240

Thr Ala Glu Asp Cys Ser Cys Ile Met Tyr Thr Ser Gly Ser Thr Gly
```

```
                    245                 250                 255
Asn Pro Lys Gly Val Ile Leu Thr His Gly Asn Leu Ile Ala Ala Ile
            260                 265                 270

Gly Gly Val Asn Lys Met Leu Glu Lys Tyr Ile Arg Glu Gly Asp Val
            275                 280                 285

Leu Leu Ala Tyr Leu Pro Leu Ala His Val Leu Glu Phe Met Val Glu
            290                 295                 300

Asn Leu Cys Leu Phe Trp Gly Val Thr Leu Gly Tyr Gly Thr Val Arg
305                 310                 315                 320

Thr Leu Thr Asp Ala Ser Val Arg Glu Cys Gln Gly Asp Ile Lys Glu
                325                 330                 335

Leu Arg Pro Thr Leu Met Thr Gly Val Pro Ala Val Trp Glu Thr Ile
            340                 345                 350

Arg Lys Gly Val Leu Ala Gln Val Asn Gln Gly Ser Pro Leu Val Gln
            355                 360                 365

Ser Val Phe Asn Ala Ala Leu Asn Ala Lys Ala Trp Cys Met Asp Arg
        370                 375                 380

Lys Leu Gly Ala Leu Thr Gly Ile Phe Asp Thr Val Val Phe Asn Lys
385                 390                 395                 400

Val Arg Gln Gln Thr Gly Gly Arg Leu Arg Tyr Ala Leu Ser Gly Gly
                405                 410                 415

Ala Pro Ile Ser Gln Glu Thr Gln Arg Phe Leu Thr Thr Ala Leu Cys
            420                 425                 430

Pro Ile Leu Gln Ala Tyr Gly Met Thr Glu Ser Cys Gly Met Cys Ser
        435                 440                 445

Ile Met Thr Pro Glu Ala Phe Asn Tyr Asn Arg Val Gly Ser Pro Val
    450                 455                 460

Pro Cys Thr Glu Val Lys Leu Val Asp Val Pro Asp Ala Gly Tyr Phe
465                 470                 475                 480

Ser Thr Asp Ser Pro Arg Pro Arg Gly Glu Ile Trp Ile Arg Gly Pro
                485                 490                 495

Ser Ile Thr Ser Gly Tyr Phe Lys Asn Ala Glu Glu Thr Ser Ala Ala
            500                 505                 510

Ile Thr Glu Asp Arg Trp Leu Lys Thr Gly Asp Ile Gly Glu Trp His
        515                 520                 525

Ala Asp Gly Thr Leu Ser Val Ile Asp Arg Lys Lys Asn Leu Val Lys
    530                 535                 540

Leu Ser His Gly Glu Tyr Ile Ala Leu Glu Lys Leu Glu Ser Val Tyr
545                 550                 555                 560

Lys Ser Thr Ala Tyr Cys Asn Asn Ile Cys Val Tyr Ala Asp Ser Met
                565                 570                 575

Gln Asn Lys Pro Val Ala Leu Ile Val Ala Ser Glu Pro Arg Ile Leu
            580                 585                 590

Glu Leu Ala Lys Ala Lys Gly Leu Glu Ser Arg Asp Phe Ala Val Leu
        595                 600                 605

Cys His Asp Lys Val Ile Ile Lys Ala Val Leu Asp Ala Cys Leu Ala
    610                 615                 620

Thr Ala Lys Lys Ala Gly Leu Lys Pro Ala Glu Leu Leu Gln Gly Val
625                 630                 635                 640

Tyr Leu Glu Ser Glu Glu Trp Thr Ala Gln Gly Gly Leu Leu Thr Ala
                645                 650                 655

Ala Gln Lys Leu Lys Arg Lys Glu Ile Asn Gln Ala Tyr Ala Asp Gln
            660                 665                 670
```

```
Ile Lys Gln Ile Tyr Gly Ser Lys
    675                 680

<210> SEQ ID NO 53
<211> LENGTH: 2043
<212> TYPE: DNA
<213> ORGANISM: Mortierella alpina

<400> SEQUENCE: 53
atgccaaagt gctttaccgt caacgtcggc cccgaggacg tcaagggcga gactcgcatc      60
cgtcgctcca tccaggccgt cgacaaactc atggactcac cctcaagcga catcaagacc     120
ttgtacgatg tcatccagta ctctgccaag gtccgcccca acctcaacgc catcggctac     180
cgcaagattg tcaagatgat cgaagaggaa aaggagatca ccaagatggt cagcggcgag     240
cctgtcaagg agaaaaagac gtggaaatac ttcaagctct ccggctacca ctatctgacc     300
tacaaggaca ccaaggccgt catcgacagc attggaagtg cctgcgcaa gtggggtgtt      360 gagcccaagg agaggatcac cgtctttggt tccacaagtg ccaactggct gctggtcgct     420
catggtgcct tcacgcagtc catgaccatc gtcaccgtgt atgacacttt gggcgaggaa     480
ggattgctgc actcgatgaa cgaggccgag gtgggaacgg cctacacgaa cgctgatttg     540
atcaagacaa tgaccaacgt ttcaggacgc tgccccaccc tcaagaggat cgtctatgac     600
ggcgaagcca acgcagcaga cgtgatcgcc cttcagacgg cccatcctca ccttcagctt     660
atcactctgg aggagctgaa gcagctcggt gtggatcacc ctgtggagcc cactcctccc     720
accgccgagg attgctcctg catcatgtac acttctggat cgaccggaaa ccctaaggga     780
gtcatcctca ctcacggaaa cctcattgcc gccattggcg agttaacaa gatgctggaa      840 aagtacattc gcgaaggcga tgtcttgctt gcctaccttc ccttggctca cgttctggaa     900
ttcatggttg agaacctctg tctcttctgg ggtgtaaccc ttggatatgg tactgtccgc     960
acgctgacga tgcctctgt gcgtgagtgc cagggtgata tcaaggaatt gcggcctacg    1020
cttatgaccg gcgttccagc agtgtgggag accatccgca aggtgttct cgcccaagta     1080 aaccagggtt cacctctggt tcaatccgtc ttcaacgcgg ctctgaacgc caaggcctgg    1140
tgcatggacc gcaaactagg cgctttgact ggaattttcg acactgtggt gttcaacaag    1200
gtccgtcagc aaactggagg tcgtcttcgc tacgcgctct cgggcggcgc gcctatctcc    1260
caggagaccc agcgcttctt gaccacagca ctgtgcccta tccttcaagc ctatggcatg    1320
actgagtcgt gcggcatgtg ctcgatcatg actccagagg cgttcaacta caaccgcgtc    1380
ggttcccctg ttccctgcac agaggtcaag ctcgtggatg tgcccgatgc aggatacttt    1440
tcgactgatt cgcccccgcc tcgtggtgag atttggattc gcggaccctc catcaccctct   1500 ggatacttca agaacgctga ggagacctcg gcagccatca cagaggaccg ctggctcaag    1560
actggagata ttggagagtg gcatgctgat ggcacactct cggtcattga tcgcaagaag    1620
aacttggtca agttgtcgca tggcgagtac attgctctag agaaacttga gtcggtgtac    1680
aagagcacgg cttactgcaa caacatctgc gtttatgccg attccatgca aaacaagcct    1740
gtggcgctga ttgttgcgag tgaaccccgc atcctcgagc tggccaaggc caagggcctg    1800
gagagccgcg actttgcagt gctctgccac gataaggtga tcatcaaggc gtcctcgac     1860 gcctgtctcg cgactgccaa aaaggctggc ctcaagcccg ccgagttgct gcagggtgtg    1920
tacctggagt ctgaggagtg gaccgctcaa ggcggtttgt tgactgctgc tcagaaattg    1980
aagcgcaagg aaatcaacca ggcttatgct gaccagatca agcagatcta tggctccaag    2040
``` taa 2043

<210> SEQ ID NO 54
<211> LENGTH: 2052
<212> TYPE: DNA
<213> ORGANISM: Mortierella alpina

<400> SEQUENCE: 54

```
catgccaaag tgctttaccg tcaacgtcgg ccccgaggac gtcaagggcg agactcgcat      60
ccgtcgctcc atccaggccg tcgacaaact catggactca ccctcaagcg acatcaagac     120
cttgtacgat gtcatccagt actctgccaa ggtccgcccc aacctcaacg ccatcggcta     180
ccgcaagatt gtcaagatga tcgaagagga aaaggagatc accaagatgg tcagcggcga     240
gcctgtcaag gagaaaaaga cgtggaaata cttcaagctc tccggctacc actatctgac     300
ctacaaggac accaaggccg tcatcgacag cattggaagt ggcctgcgca agtggggtgt     360
tgagcccaag gagaggatca ccgtctttgg ttccacaagt gccaactggc tgctggtcgc     420
tcatggtgcc ttcacgcagt ccatgaccat cgtcaccgtg tatgacactt gggcgagga      480
aggattgctg cactcgatga acgaggccga ggtgggaacg gcctacacga acgctgattt     540
gatcaagaca atgaccaacg tttcaggacg ctgccccacc ctcaagagga tcgtctatga     600
cggcgaagcc aacgcagcag acgtgatcgc ccttcagacg gcccatcctc accttcagct     660
tatcactctg gaggagctga agcagctcgg tgtggatcac cctgtggagc ccactcctcc     720
caccgccgag gattgctcct gcatcatgta cacttctgga tcgaccggaa accctaaggg     780
agtcatcctc actcacggaa acctcattgc cgccattggc ggagttaaca agatgctgga     840
aaagtacatt cgcgaaggcg atgtcttgct tgcctacctt cccttggctc acgttctgga     900
attcatggtt gagaacctct gtctcttctg gggtgtaacc cttggatatg gtactgtccg     960
cacgctgacg gatgcctctg tgcgtgagtg ccagggtgat atcaaggaat gcgcgcctac    1020
gcttatgacc ggcgttccag cagtgtggga gaccatccgc aaaggtgttc tcgcccaagt    1080
aaaccagggt tcacctctgg ttcaatccgt cttcaacgcg gctctgaacg ccaaggcctg    1140
gtgcatggac cgcaaactag cgcctttgac tggaattttc gacactgtgg tgttcaacaa    1200
ggtccgtcag caaactggag gtcgtcttcg ctacgcgctc tcgggcggcg cgcctatctc    1260
ccaggagacc cagcgcttct tgaccacagc actgtgccct atccttcaag cctatggcat    1320
gactgagtcg tgcggcatgt gctcgatcat gactccagag gcgttcaact caaccgcgt    1380
cggttcccct gttccctgca cagaggtcaa gctcgtggat gtgcccgatg caggatactt    1440
ttcgactgat tcgccccgcc ctcgtggtga gatttggatt cgcggaccct ccatcacctc    1500
tggatacttc aagaacgctg aggagacctc ggcagccatc acagaggacc gctggctcaa    1560
gactggagat attggagagt ggcatgctga tggcacactc tcggtcattg atcgcaagaa    1620
gaacttggtc aagttgtcgc atggcgagta cattgctcta gagaaacttg agtcggtgta    1680
caagagcacg gcttactgca caacatctg cgtttatgcc gattccatgc aaaacaagcc    1740
tgtggcgctg attgttgcga gtgaaccccg catcctcgag ctggccaagg ccaagggcct    1800
ggagagccgc gactttgcag tgctctgcca cgataaggtg atcatcaagg ctgtcctcga    1860
cgcctgtctc gcgactgcca aaaaggctgg cctcaagccc gccgagttgc tgcagggtgt    1920
gtacctggag tctgaggagt ggaccgctca aggcggtttg ttgactgctg ctcagaaatt    1980
gaagcgcaag gaaatcaacc aggcttatgc tgaccagatc aagcagatct atggctccaa    2040
```
gtaaaaatga ac    2052

<210> SEQ ID NO 55
<211> LENGTH: 2569
<212> TYPE: DNA
<213> ORGANISM: Mortierella alpina
<220> FEATURE:
<221> NAME/KEY: modified_base
<222> LOCATION: (557)..(767)
<223> OTHER INFORMATION: n is a, c, g, or t

<400> SEQUENCE: 55

| | | | | | |
|---|---|---|---|---|---|
| atgccaaagt | gctttaccgt | caacgtcggc | cccgaggacg | tcaagggcga | gactcgcatc | 60 |
| cgtcgctcca | tccaggccgt | cgacaaactc | atggactcac | cctcaagcga | catcaagacc | 120 |
| ttgtacgatg | tcatccagta | ctctgccaag | gtccgcccca | acctcaacgc | catcggctac | 180 |
| cgcaagattg | tcaagatgat | cgaagaggaa | aaggagatca | ccaagatggt | cagcggcgag | 240 |
| cctgtcaagg | agaaaaagac | gtggaaatac | ttcaagctct | ccggctacca | ctatctgacc | 300 |
| tacaaggaca | ccaaggccgt | catcgacagc | attggaagtg | gcctgcgcaa | gtggggtgtt | 360 |
| gagcccaagg | agaggatcac | cgtctttggt | tccacaaggt | aatgtgtagc | gccacgaaaa | 420 |
| tacgatcatt | gcagcgtgaa | gggtgggaag | aattaggggg | gaaatgacat | cgataacagg | 480 |
| aacgaaaaaa | aaaaaaaaca | agacgaagtc | ggagatcctc | gctattggcg | tttaagcacc | 540 |
| gccagcgttc | ttttttnnnn | nnnnnnnnnn | nnnnnnnnnn | nnnnnnnnnn | nnnnnnnnnn | 600 |
| nnnnnnnnnn | nnnnnnnnnn | nnnnnnnnnn | nnnnnnnnnn | nnnnnnnnnn | nnnnnnnnnn | 660 |
| nnnnnnnnnn | nnnnnnnnnn | nnnnnnnnnn | nnnnnnnnnn | nnnnnnnnnn | nnnnnnnnnn | 720 |
| nnnnnnnnnn | nnnnnnnnnn | nnnnnnnnnn | nnnnnnnnnn | nnnnnnctt | gttaaccaaa | 780 |
| ggctgacccg | tacctcgttt | gcttgacttg | acacgtatag | tgccaactgg | ctgctggtcg | 840 |
| ctcatggtgc | cttcacgcag | tccatgacca | tcgtcaccgt | gtatgacact | ttgggcgagg | 900 |
| aaggattgct | gcactcgatg | aacgaggccg | aggtgggaac | ggcctacacg | aacgctgatt | 960 |
| tgatcaagac | aatgaccaac | gtttcaggac | gctgccccac | cctcaagagg | atcgtctatg | 1020 |
| acggcgaagc | caacgcagca | gacgtgatcg | cccttcagac | ggcccatcct | caccttcagc | 1080 |
| ttatcactct | ggaggagctg | aagcagctcg | gtgtggatca | ccctgtggag | cccactcctc | 1140 |
| ccaccgccga | ggattgctcc | tgcatcatgt | acacttctgg | atcgaccgga | aaccctaagg | 1200 |
| gagtcatcct | cactcacgga | aacctcattg | ccgccagtag | gtgtttctct | cactctcttt | 1260 |
| aaccctctct | ctttcacttg | caaatatgct | gggaatctct | acttacctga | atgttactgt | 1320 |
| tcttcgggtt | atcaacctag | ttggcggagt | taacaagatg | ctggaaaagt | acattcgcga | 1380 |
| aggcgatgtc | ttgcttgcct | accttcccctt | ggctcacgtt | ctggaattca | tggttgagaa | 1440 |
| cctctgtctc | ttctggggtg | taaccctcgg | atatggtact | gtccgcacgc | tgacggatgc | 1500 |
| ctctgtgcgt | gagtgccagg | gtgatatcaa | ggaattgcgg | cctacgctta | tgaccggcgt | 1560 |
| tccagcagtg | tgggagacca | tccgcaaagg | tgttctcgcc | caagtaaacc | agggttcacc | 1620 |
| tctggttcaa | tccgtcttca | acgcggctct | gaacgccaag | gcctggtgca | tggaccgcaa | 1680 |
| actaggcgct | ttgactggaa | ttttcgacac | tgtggtgttc | aacaaggtcc | gtcagcaaac | 1740 |
| tggaggtcgt | cttcgctacg | cgctctcggg | cggcgcgcct | atctcccagg | agacccagcg | 1800 |
| cttcttgacc | acagcactgt | gccctatcct | tcaagcctat | ggcatgactg | agtcgtgcgg | 1860 |
| catgtgctcg | atcatgactc | cagaggcgtt | caactacaac | cgcgtcggtt | ccctgttcc | 1920 |
| ctgcacagag | gtcaagctcg | tggatgtgcc | cgatgcagga | tacttttcga | ctgattcgcc | 1980 |

-continued

| | |
|---|---|
| ccgccctcgt ggtgagattt ggattcgcgg accctccatc acctctggat acttcaagaa | 2040 |
| cgctgaggag acctcggcag ccatcacaga ggaccgctgg ctcaagactg agatatttgg | 2100 |
| agagtggcat gctgatggca cactctcggt cattgatcgc aagaagaact tggtcaagtt | 2160 |
| gtcgcatggc gagtacattg ctctagagaa acttgagtcg gtgtacaaga gcacggctta | 2220 |
| ctgcaacaac atctgcgttt atgccgattc catgcaaaac aagcctgtgg cgctgattgt | 2280 |
| tgcgagtgaa ccccgcatcc tcgagctggc caaggccaag ggcctggaga ccgcgacttt | 2340 |
| tgcagtgctc tgccacgata aggtgatcat caaggctgtc ctcgacgcct gtctcgcgac | 2400 |
| tgccaaaaag gctggcctca gcccgccga gttgctgcag ggtgtgtacc tggagtctga | 2460 |
| ggagtggacc gctcaaggcg gtttgttgac tgctgctcag aaattgaagc gcaaggaaat | 2520 |
| caaccaggct tatgctgacc agatcaagca gatctatggc tccaagtaa | 2569 |

<210> SEQ ID NO 56
<211> LENGTH: 2040
<212> TYPE: DNA
<213> ORGANISM: Mortierella alpina

<400> SEQUENCE: 56

| | |
|---|---|
| atgacaaagt gcctcaccgt cgaagtcgga cccgccgacg tccagggcga gacccgcatc | 60 |
| cgccgctccg tcctctctgc aaagcgcctc atgtcctcgc cctcggatga catcaagacc | 120 |
| ctctacgacg tcttcaacca ctccgtcacc gtccgcccca acctcaacgc gatcggatac | 180 |
| cgcaaggtcg tcaagattgt cgaggaagaa aaggaggtcg tcaaggttgt caacggcgag | 240 |
| gaagtcaagg aaaagaagac ctggaagttc ttcaagatgt ccggctacca ctggctcacc | 300 |
| tacaaggatg cgaagcaggt cgtcgacagc atcggatgcg gtcttcgcaa gtttggcgtc | 360 |
| gagcccaagg acaagctgac cgttttcggt gccacaagtg ccaactggct cctgcttgcc | 420 |
| cacggtgctt tcacccagtc catcaccatt gttaccgcct acgacaccct gggcgaggac | 480 |
| ggtcttttgc actctatgaa cgaggccgag gtggccaccg cttacacaaa cgccgacttg | 540 |
| ctcaacacta tcaagaacgt tgccggcaaa tgccccaccc tgaagaagat catctacgac | 600 |
| ggcgatgcca agcccgcaga tgtcattgcc ctccaggagg cccatcctca cctccagctc | 660 |
| atcaccctcg aggagctgaa gcagctcgga gtgacaacc ctgtcgcccc aaccctcct | 720 |
| gctgccaagg actactgctg catcatgtac acttcgggat cgactggcaa ccccaaggga | 780 |
| gtgttgctga cccatggaaa cctcgttgct gccatcggag gtgtgaacaa gatgctgaca | 840 |
| aagtacgttc acgagggaga cgtcttgctc gcgtacttgc ctcttgctca cgttctcgag | 900 |
| ttcctggtcg aaaacgtctg tctcttctgg ggtgtgactc ttggctacgg taccgtccgc | 960 |
| acattgactg atgcctcagt ccgtgagtgc agggtgata tcaaggagtt cgcccctaca | 1020 |
| ttgatgaccg tgttcctgc tgtgtgggag acgattcgta agggagtgtt ggctcaggtt | 1080 |
| tcccagggct cacctcttgt tcaaaagatc ttccatgctg cttttgaacgc caaggcctgg | 1140 |
| tgcctggacc gcaagttggg tgcgttgact ggaatcttcg atactgtcgt cttcaacaag | 1200 |
| gtcaagcagc agacaggagg acgtcttcgc ttcgcccttt cgggaggtgc acccatctct | 1260 |
| caggagaccc agcgcttctt gacgacagct ttgtgcccta tcctccaggg ctacggtatg | 1320 |
| acagagtctt gcggcatgtg cgccatttg accccgatg tcttcaacta cagccgtgtc | 1380 |
| ggatccccag ttccttgcac ggaggtcaag ttggtcgatg tgcccgatgc aggataccac | 1440 |
| tcaacggact tgcctctccc ccgtggtgag gtctgcattc gtggaccctc catcactgct | 1500 |

```
ggatacttca agaaccccga ggagacctcc gccacattga ctgctgatcg ctggctcaag    1560
actggagata tcggagagtg caccccgac ggcactatct cgatcattga ccgcaagaag    1620
aacttggtca agctgtcaca cggagagtac attgctttgg agaagcttga gtctgtctac    1680
aagagcacag cctactgcaa caacatttgc gtgtatgccg actcgatgca gaacaagccc    1740
gttgccatta ttgttgccag cgaaccccgc atcctcgagt tggccaaggc caagggcatt    1800
gagagccgcg actttgctgc tctctgccac gacaaggtta tcatcaaggc tgtccacgat    1860
gcctgcctcg ccactgccaa gcgtgctgga ctcaagcccg ctgagatgct tcagggagtg    1920
tacttggagt cagaagaatg gacggcccag gctggcatgt tgactgccgc tcagaagctc    1980
aagcgcaagg agatcaacca ggcctatgtc tcacagatca gcagcttta tggaacggcc    2040
```

<210> SEQ ID NO 57
<211> LENGTH: 680
<212> TYPE: PRT
<213> ORGANISM: Mortierella alpina

<400> SEQUENCE: 57

```
Met Thr Lys Cys Leu Thr Val Glu Val Gly Pro Ala Asp Val Gln Gly
 1               5                  10                  15

Glu Thr Arg Ile Arg Arg Ser Val Leu Ser Ala Lys Arg Leu Met Ser
             20                  25                  30

Ser Pro Ser Asp Asp Ile Lys Thr Leu Tyr Asp Val Phe Asn His Ser
         35                  40                  45

Val Thr Val Arg Pro Asn Leu Asn Ala Ile Gly Tyr Arg Lys Val Val
     50                  55                  60

Lys Ile Val Glu Glu Lys Glu Val Lys Val Val Asn Gly Glu
 65                  70                  75                  80

Glu Val Lys Glu Lys Lys Thr Trp Lys Phe Phe Lys Met Ser Gly Tyr
                 85                  90                  95

His Trp Leu Thr Tyr Lys Asp Ala Lys Gln Val Val Asp Ser Ile Gly
            100                 105                 110

Cys Gly Leu Arg Lys Phe Gly Val Glu Pro Lys Asp Lys Leu Thr Val
        115                 120                 125

Phe Gly Ala Thr Ser Ala Asn Trp Leu Leu Leu Ala His Gly Ala Phe
    130                 135                 140

Thr Gln Ser Ile Thr Ile Val Thr Ala Tyr Asp Thr Leu Gly Glu Asp
145                 150                 155                 160

Gly Leu Leu His Ser Met Asn Glu Ala Glu Val Ala Thr Ala Tyr Thr
                165                 170                 175

Asn Ala Asp Leu Leu Asn Thr Ile Lys Asn Val Ala Gly Lys Cys Pro
            180                 185                 190

Thr Leu Lys Lys Ile Ile Tyr Asp Gly Asp Ala Lys Pro Ala Asp Val
        195                 200                 205

Ile Ala Leu Gln Glu Ala His Pro His Leu Gln Leu Ile Thr Leu Glu
    210                 215                 220

Glu Leu Lys Gln Leu Gly Val Asp Asn Pro Val Ala Pro Thr Pro Pro
225                 230                 235                 240

Ala Ala Lys Asp Tyr Cys Cys Ile Met Tyr Thr Ser Gly Ser Thr Gly
                245                 250                 255

Asn Pro Lys Gly Val Leu Leu Thr His Gly Asn Leu Val Ala Ala Ile
            260                 265                 270

Gly Gly Val Asn Lys Met Leu Thr Lys Tyr Val His Glu Gly Asp Val
        275                 280                 285
```

```
Leu Leu Ala Tyr Leu Pro Leu Ala His Val Leu Glu Phe Leu Val Glu
        290                 295                 300
Asn Val Cys Leu Phe Trp Gly Val Thr Leu Gly Tyr Gly Thr Val Arg
305                 310                 315                 320
Thr Leu Thr Asp Ala Ser Val Arg Glu Cys Gln Gly Asp Ile Lys Glu
                325                 330                 335
Leu Arg Pro Thr Leu Met Thr Gly Val Pro Ala Val Trp Glu Thr Ile
            340                 345                 350
Arg Lys Gly Val Leu Ala Gln Val Ser Gln Gly Ser Pro Leu Val Gln
        355                 360                 365
Lys Ile Phe His Ala Ala Leu Asn Ala Lys Ala Trp Cys Leu Asp Arg
    370                 375                 380
Lys Leu Gly Ala Leu Thr Gly Ile Phe Asp Thr Val Val Phe Asn Lys
385                 390                 395                 400
Val Lys Gln Gln Thr Gly Gly Arg Leu Arg Phe Ala Leu Ser Gly Gly
                405                 410                 415
Ala Pro Ile Ser Gln Glu Thr Gln Arg Phe Leu Thr Thr Ala Leu Cys
            420                 425                 430
Pro Ile Leu Gln Gly Tyr Gly Met Thr Glu Ser Cys Gly Met Cys Ala
        435                 440                 445
Ile Leu Thr Pro Asp Val Phe Asn Tyr Ser Arg Val Gly Ser Pro Val
    450                 455                 460
Pro Cys Thr Glu Val Lys Leu Val Asp Val Pro Asp Ala Gly Tyr His
465                 470                 475                 480
Ser Thr Asp Leu Pro Leu Pro Arg Gly Glu Val Cys Ile Arg Gly Pro
                485                 490                 495
Ser Ile Thr Ala Gly Tyr Phe Lys Asn Pro Glu Glu Thr Ser Ala Thr
            500                 505                 510
Leu Thr Ala Asp Arg Trp Leu Lys Thr Gly Asp Ile Gly Glu Trp His
        515                 520                 525
Pro Asp Gly Thr Ile Ser Ile Ile Asp Arg Lys Lys Asn Leu Val Lys
    530                 535                 540
Leu Ser His Gly Glu Tyr Ile Ala Leu Glu Lys Leu Glu Ser Val Tyr
545                 550                 555                 560
Lys Ser Thr Ala Tyr Cys Asn Asn Ile Cys Val Tyr Ala Asp Ser Met
                565                 570                 575
Gln Asn Lys Pro Val Ala Ile Ile Val Ala Ser Glu Pro Arg Ile Leu
            580                 585                 590
Glu Leu Ala Lys Ala Lys Gly Ile Glu Ser Arg Asp Phe Ala Ala Leu
        595                 600                 605
Cys His Asp Lys Val Ile Ile Lys Ala Val His Asp Ala Cys Leu Ala
    610                 615                 620
Thr Ala Lys Arg Ala Gly Leu Lys Pro Ala Glu Met Leu Gln Gly Val
625                 630                 635                 640
Tyr Leu Glu Ser Glu Glu Trp Thr Ala Gln Ala Gly Met Leu Thr Ala
                645                 650                 655
Ala Gln Lys Leu Lys Arg Lys Glu Ile Asn Gln Ala Tyr Val Ser Gln
            660                 665                 670
Ile Lys Gln Leu Tyr Gly Thr Ala
        675                 680

<210> SEQ ID NO 58
<211> LENGTH: 2043
```

<212> TYPE: DNA
<213> ORGANISM: Mortierella alpina

<400> SEQUENCE: 58

```
atgacaaagt gcctcaccgt cgaagtcgga cccgccgacg tccagggcga gacccgcatc     60
cgccgctccg tcctctctgc aaagcgcctc atgtcctcgc cctcggatga catcaagacc    120
ctctacgacg tcttcaacca ctccgtcacc gtccgcccca acctcaacgc gatcggatac    180
cgcaaggtcg tcaagattgt cgaggaagaa aaggaggtcg tcaaggttgt caacggcgag    240
gaagtcaagg aaaagaagac ctggaagttc ttcaagatgt ccggctacca ctggctcacc    300
tacaaggatg cgaagcaggt cgtcgacagc atcggatgcg gtcttcgcaa gtttggcgtc    360
gagcccaagg acaagctgac cgttttcggt gccacaagtg ccaactggct cctgcttgcc    420
cacggtgctt tcacccagtc catcaccatt gttaccgcct acgacaccct gggcgaggac    480
ggtcttttgc actctatgaa cgaggccgag gtggccaccg cttacacaaa cgccgacttg    540
ctcaacacta tcaagaacgt tgccggcaaa tgccccaccc tgaagaagat catctacgac    600
ggcgatgcca agcccgcaga tgtcattgcc ctccaggagg cccatcctca cctccagctc    660
atcaccctcg aggagctgaa gcagctcgga gtggacaacc ctgtcgcccc aacccctcct    720
gctgccaagg actactgctg catcatgtac acttcgggat cgactggcaa ccccaaggga    780
gtgttgctga cccatggaaa cctcgttgct gccatcggag gtgtgaacaa gatgctgaca    840
aagtacgttc acgagggaga cgtcttgctc gcgtacttgc ctcttgctca cgttctcgag    900
ttcctggtcg aaaacgtctg tctcttctgg ggtgtgactc ttggctacgg taccgtccgc    960
acattgactg atgcctcagt ccgtgagtgc caggtgata tcaaggagtt gcgccctaca   1020
ttgatgaccg tgttcctgc tgtgtgggag acgattcgta agggagtgtt ggctcaggtt   1080
tcccagggct cacctcttgt tcaaaagatc ttccatgctg ctttgaacgc caaggcctgg   1140
tgcctggacc gcaagttggg tgcgttgact ggaatcttcg atactgtcgt cttcaacaag   1200
gtcaagcagc agacaggagg acgtcttcgc ttcgcccttt cgggaggtgc acccatctct   1260
caggagaccc agcgcttctt gacgacagct ttgtgcccta tcctccaggg ctacggtatg   1320
acagagtctt gcggcatgtg cgccatttg acccccgatg tcttcaacta cagccgtgtc   1380
ggatccccag ttccttgcac ggaggtcaag ttggtcgatg tgcccgatgc aggataccac   1440
tcaacggact gcctctcccc cgtggtgag gtctgcattc gtggacccctc catcactgct   1500
ggatacttca agaaccccga ggagacctcc gccacattga ctgctgatcg ctggctcaag   1560
actggagata tcggagagtg gcaccccgac ggcactatct cgatcattga ccgcaagaag   1620
aacttggtca gctgtcaca cggagagtac attgctttgg agaagcttga gtctgtctac   1680
aagagcacag cctactgcaa caacatttgc gtgtatgccg actcgatgca gaacaagccc   1740
gttgccatta tgttgccag cgaaccccgc atcctcgagt tggccaaggc caagggcatt   1800
gagagccgcg actttgctgc tctctgccac gacaaggtta tcatcaaggc tgtccacgat   1860
gcctgcctcg ccactgccaa gcgtgctgga ctcaagcccg ctgagatgct tcagggagtg   1920
tacttggagt cagaagaatg gacggcccag gctggcatgt tgactgccgc tcagaagctc   1980
aagcgcaagg agatcaacca ggcctatgtc tcacagatca agcagcttta tggaacggcc   2040
taa                                                                 2043
```

<210> SEQ ID NO 59
<211> LENGTH: 2414
<212> TYPE: DNA

<213> ORGANISM: Mortierella alpina

<400> SEQUENCE: 59

```
cctttatccc cgcaccgcca tctctcgccg ccaccatctc gcattccttt caatccacac      60
tcccacctgt gccccctgct tttcacgtcc cgctctcatc ccgccttctc ctttcatcac     120
cccaattcaa catgacaaag tgcctcaccg tcgaagtcgg acccgccgac gtccagggcg     180
agacccgcat ccgccgctcc gtcctctctg caaagcgcct catgtcctcg ccctcggatg     240
acatcaagac cctctacgac gtcttcaacc actccgtcac cgtccgcccc aacctcaacg     300
cgatcggata ccgcaaggtc gtcaagattg tcgaggaaga aaaggaggtc gtcaaggttg     360
tcaacggcga ggaagtcaag gaaaagaaga cctggaagtt cttcaagatg tccggctacc     420
actggctcac ctacaaggat gcgaagcagg tcgtcgacag catcggatgc ggtcttcgca     480
agtttggcgt cgagcccaag gacaagctga ccgttttcgg tgccacaagt gccaactggc     540
tcctgcttgc ccacggtgct ttcacccagt ccatcaccat tgttaccgcc tacgacaccc     600
tgggcgagga cggtcttttg cactctatga acgaggccga ggtggccacc gcttacacaa     660
acgccgactt gctcaacact atcaagaacg ttgccggcaa atgccccacc ctgaagaaga     720
tcatctacga cggcgatgcc aagcccgcag atgtcattgc cctccaggag gcccatcctc     780
acctccagct catcaccctc gaggagctga agcagctcgg agtggacaac cctgtcgccc     840
caaccccctcc tgctgccaag gactactgct gcatcatgta cacttcggga tcgactggca     900
accccaaggg agtgttgctg acccatggaa acctcgttgc tgccatcgga ggtgtgaaca     960
agatgctgac aaagtacgtt cacgaggag acgtcttgct cgcgtacttg cctcttgctc    1020
acgttctcga gttcctggtc gaaaacgtct gtctcttctg gggtgtgact cttggctacg    1080
gtaccgtccg cacattgact gatgcctcag tccgtgagtg ccagggtgat atcaaggagt    1140
tgcgccctac attgatgacc ggtgttcctg ctgtgtggga gacgattcgt aagggagtgt    1200
tggctcaggt ttcccagggc tcacctcttg ttcaaaagat cttccatgct gctttgaacg    1260
ccaaggcctg gtgcctggac cgcaagttgg gtgcgttgac tggaatcttc gatactgtcg    1320
tcttcaacaa ggtcaagcag cagacaggag gacgtcttcg cttcgccctt cgggaggtg    1380
cacccatctc tcaggagacc cagcgcttct tgacgacagc tttgtgccct atcctccagg    1440
gctacggtat gacagagtct tgcggcatgt gcgccatttt gacccccgat gtcttcaact    1500
acagccgtgt cggatcccca gttccttgca cggaggtcaa gttggtcgat gtgcccgatg    1560
caggatacca ctcaacggac ttgcctctcc cccgtggtga ggtctgcatt cgtgaccct     1620
ccatcactgc tggatacttc aagaaccccg aggagacctc cgccacattg actgctgatc    1680
gctggctcaa gactggagat atcggagagt ggcaccccga cggcactatc tcgatcattg    1740
accgcaagaa gaacttggtc aagctgtcac acggagagta cattgctttg gagaagcttg    1800
agtctgtcta caagagcaca gcctactgca acaacatttg cgtgtatgcc gactcgatgc    1860
agaacaagcc cgttgccatt attgttgcca gcgaaccccg catcctcgag ttggccaagg    1920
ccaagggcat tgagagccgc gactttgctg ctctctgcca cgacaaggtt atcatcaagg    1980
ctgtccacga tgcctgcctc gccactgcca agcgtgctgg actcaagccc gctgagatgc    2040
ttcagggagt gtacttggag tcagaagaat ggacggccca ggctggcatg ttgactgccg    2100
ctcagaaagct caagcgcaag gagatcaacc aggcctatgt ctcacagatc aagcagcttt    2160
atggaacggc ctaagtcgct gaaaggtgtg cctttgtccg tctcttcaac cccacaagtc    2220
ctatgtataa tgacccgcgc ggccctcctt taatcctata cccacccttt tttacacgtt    2280
```

```
aaagaagcca catttttggt tcttttttt ctctcgcaca cactacacac tccccatcca    2340
ttccctccaa acaggatggt tgtctgcaaa taaattgacg aattttctct tgaaaaaaaa    2400
aaaaaaaaaa aaaa                                                     2414

<210> SEQ ID NO 60
<211> LENGTH: 2537
<212> TYPE: DNA
<213> ORGANISM: Mortierella alpina

<400> SEQUENCE: 60
atgacaaagt gcctcaccgt cgaagtcgga cccgccgacg tccagggcga gacccgcatc      60
cgccgctccg tcctctctgc aaagcgcctc atgtcctcgc cctcggatga catcaagacc     120
ctctacgacg tcttcaacca ctccgtcacc gtccgcccca acctcaacgc gatcggatac     180
cgcaaggtcg tcaagattgt cgaggaagaa aaggaggtcg tcaaggttgt caacggcgag     240
gaagtcaagg aaaagaagac ctggaagttc ttcaagatgt ccggctacca ctggctcacc     300
tacaaggatg cgaagcaggt cgtcgacagc atcggatgcg gtcttcgcaa gtttggcgtc     360
gagcccaagg acaagctgac cgttttcggt gccacaaggt aagaaagagg cataacaaga     420
aaatgcaaga gaggcaaaaa aaatggcttg acgtgagagc ataagggaac caacagacag     480
gtgtttgtgt gggttgcgga tagtgggtga gcatgcttcg ttatcgaatg tgggagaaga     540
gagcggacgc gaatatggct ctcgtctctg gcgggatgcg agtggccaag tgtgggatac     600
atatcctcgc ggtggggtgt ccgggtcggc ccttgaatct tgttgaagca tgataatgtg     660
aatgtggacc gcaatcacgc tcagattatg cgtagcaagc gtgttgctag tctacatcat     720
gctcacacgt attcacattt attcattttc actctatctc gctcttagtg ccaactggct     780
cctgcttgcc cacggtgctt tcacccagtc catcaccatt gttaccgcct acgacaccct     840
gggcgaggac ggtcttttgc actctatgaa cgaggccgag gtggccaccg cttacacaaa     900
cgccgacttg ctcaacacta tcaagaacgt tgccggcaaa tgccccaccc tgaagaagat     960
catctacgac ggcgatgcca agcccgcaga tgtcattgcc ctccaggagg cccatcctca    1020
cctccagctc atcaccctcg aggagctgaa gcagctcgga gtggacaacc ctgtcgcccc    1080 aaccccctcct gctgccaagg actactgctg catcatgtac acttcgggat cgactggcaa    1140 cccccaaggga gtgttgctga cccatggaaa cctcgttgct gccagtacgt atctttctcg    1200
tcatgatcgt cctcccgcat ttccactgcg cttgttacca tttgatggga aatgtattta    1260
acccgaacca cacatttttt cttttttctca cacttgccac gtcactagtc ggaggtgtga    1320
acaagatgct gacaaagtac gttcacgagg agacgtcttt gctcgcgtac ttgcctcttg    1380
ctcacgttct cgagttcctg gtcgaaaacg tctgtctctt ctggggtgtg actcttggct    1440
acggtaccgt ccgcacattg actgatgcct cagtccgtga gtgccagggt gatatcaagg    1500
agttgcgccc tacattgatg accggtgttc tgctctgtgt ggagacgatt cgtaagggag    1560
tgttggctca ggtttcccag ggctcacctc ttgttcaaaa gatcttccat gctgctttga    1620
acgccaaggc ctggtgcctg gaccgcaagt tgggtgcgtt gactggaatc ttcgatactg    1680
tcgtcttcaa caaggtcaag cagcagacag gaggacgtct tcgcttcgcc ctttcgggag    1740
gtgcacccat ctctcaggag acccagcgct tcttgacgac agctttgtgc cctatcctcc    1800
agggctacgg tatgacagag tcttgcggca tgtgcgccat tttgacccccg atgtcttca    1860 actacagccg tgtcggatcc ccagttcctt gcacggaggt caagttggtc gatgtgcccg    1920
```

```
atgcaggata ccactcaacg gacttgcctc tccccgtgg tgaggtctgc attcgtggac    1980
cctccatcac tgctggatac ttcaagaacc ccgaggagac ctccgccaca ttgactgctg    2040
atcgctggct caagactgga gatatcggag agtggcaccc cgacggcact atctcgatca    2100
ttgaccgcaa gaagaacttg gtcaagctgt cacacggaga gtacattgct ttggagaagc    2160
ttgagtctgt ctacaagagc acagcctact gcaacaacat ttgcgtgtat gccgactcga    2220
tgcagaacaa gcccgttgcc attattgttg ccagcgaacc ccgcatcctc gagttggcca    2280
aggccaaggg cattgagagc cgcgactttg ctgctctctg ccacgacaag gttatcatca    2340
aggctgtcca cgatgcctgc ctcgccactg ccaagcgtgc tggactcaag cccgctgaga    2400
tgcttcaggg agtgtacttg gagtcagaag aatggacggc ccaggctggc atgttgactg    2460
ccgctcagaa gctcaagcgc aaggagatca accaggccta tgtctcacag atcaagcagc    2520
tttatggaac ggcctaa                                                  2537
```

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtcggctcca agcttgcaat cc                                              22

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggacagctcc agcactgtgg taaag                                           25

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaccacggga ttccccaagg ctgc                                            24

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cttggtcgcg cttgttcctg gccac                                           25

<210> SEQ ID NO 65
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 65
tacagctttg ttgctgtccc catc                                          24

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gatgatgggt gtgcttgcaa agatc                                         25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aacccaaagc tgcgccaggc tgtcc                                         25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttacagcttg gattcctttt gatgg                                         25

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtcgtgcccg atgcggagac gc                                            22

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcagtggatc ccgttataca tcag                                          24

<210> SEQ ID NO 71
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 71
gcgtccccct ctatgataca ttg                                           23

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgggatgca ggacggcaac atcg                                          24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggatgccgaa caacagcgcg tgg                                           23

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcaccctcct cagaaacagc cctc                                          24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cagtcgagta cattgtcaac cacg                                          24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcggttcaag aggcgaggca cagc                                          24

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
gttcatcttc tgctggctgg gtctc                                              25

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gttgcgttgt tcacgcggca atcc                                               24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atggaaacct tggttaacgg aaag                                               24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tcagcaaaga tggccttggg ctgg                                               24

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gtcaagggcg agactcgcat cc                                                 22

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cggtgacgat ggtcatggac tgc                                                23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcgagacccg catccgccgc tcc                                          23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaccgtcctc gcccagggtg tcg                                          23

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggatccatgc cttccttcaa aaagtacaac c                                 31

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cccgggcaaa gagttttcta tctacagctt                                   30

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gaattcatgg ttgctctccc actcg                                        25

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggatccctac tatagcttgg ccttgcc                                      27

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 89
ggatccatgt atgtcggctc caagcttgc                                      29

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gtcgactcaa agcctggctt tgccgctgac g                                   31

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggatccatgg aaaccttggt taacggaaag                                     30

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggtacctaga acttcttcca catctcctc                                      29

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gagctcatgc aaagtgctt taccgtcaac g                                    31

<210> SEQ ID NO 94
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggatccttac ttggagccat agatctgctt g                                   31

<210> SEQ ID NO 95
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
```
tctagaatgg cacctcccaa cactattg                                          28

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aagcttttac ttcttgaaaa agaccacgtc                                        30

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tctagaatgg ctgctgctcc cagtgtgag                                         29

<210> SEQ ID NO 98
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aagcttttac tgtgccttgc ccatcttgg                                         29

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tctagaatgg agtcgattgc gcaattcc                                          28

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gagctcttac tgcaacttcc ttgccttctc                                        30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tctagaatgg gtgcggacac aggaaaaacc                                30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aagcttttac tcttccttgg gacgaagacc                                30

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaattcatga caaagtgcct caccgtcg                                  28

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cccgggactt aggccgttcc ataaagctg                                 29

<210> SEQ ID NO 105
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aattcataag aatgcggccg ctaaactatt ctagactagg tcgacggcgc gcca      54

<210> SEQ ID NO 106
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
agcttggcgc gccgtcgacc tagtctagaa tagtttagcg gccgcattct tatg      54

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
agcggccgca tagggagat cgaacc                                     26

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
agaattcggc gcgccatgca cgggtccttc tca                                33

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gtcgaccatg acaagtttgc                                               20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gtcgactgga agacgagcac g                                             21

<210> SEQ ID NO 111
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggcaaacttg tcatgaagcg aaagagagat tatgaaaaca agc                     43

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cactcccttt tcttaattgt tgagagagtg ttgggtgaga gt                      42

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
taagaaaagg gagtgaatcg cataggg                                       27

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
catgacaagt tgccaagat gcg                                            23

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
attgttgaga gagtgttggg tgagagtg                                      28

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
cactctctca acaatatgga aaccttggtt aacggaaagt                         40

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
cactcccttt tcttactaga acttcttcca catctcctca atatc                   45

<210> SEQ ID NO 118
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
cactcccttt tcttattact tggagccata gatctgcttg a                       41

<210> SEQ ID NO 119
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
cactctctca acaatatgcc aaagtgcttt accgtcaac                          39

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gtcccgaatg gttcct                                                    16

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
agcggttttc tacttgc                                                   17

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
aactacaacc gcgtcg                                                    16

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
cggcataaac gcagat                                                    16

<210> SEQ ID NO 124
<211> LENGTH: 700
<212> TYPE: PRT
<213> ORGANISM: Saccharomyces cerevisiae

<400> SEQUENCE: 124

Met Val Ala Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
            20                  25                  30

Arg Pro Pro Asn Thr Lys Cys Ser Thr Val Tyr Glu Phe Val Leu Glu
        35                  40                  45

Cys Phe Gln Lys Asn Lys Asn Ser Asn Ala Met Gly Trp Arg Asp Val
    50                  55                  60

Lys Glu Ile His Glu Ser Lys Ser Val Met Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
            100                 105                 110

```
Gly Arg Gly Leu Val Lys Ile Gly Leu Lys Pro Asn Asp Asp Lys
            115                 120                 125

Leu His Leu Tyr Ala Ala Thr Ser His Lys Trp Met Lys Met Phe Leu
130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
            180                 185                 190

Ala Ala Gln Asp Val Lys Tyr Ile Ile His Phe Asp Ser Ile Ser Ser
        195                 200                 205

Glu Asp Arg Arg Gln Ser Gly Lys Ile Tyr Gln Ser Ala His Asp Ala
    210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
            260                 265                 270

Ser Thr Gly Glu Pro Lys Gly Val Val Leu Lys His Ser Asn Val Val
        275                 280                 285

Ala Gly Val Gly Gly Ala Ser Leu Asn Val Leu Lys Phe Val Gly Asn
    290                 295                 300

Thr Asp Arg Val Ile Cys Phe Leu Pro Leu Ala His Ile Phe Glu Leu
305                 310                 315                 320

Val Phe Glu Leu Leu Ser Phe Tyr Trp Gly Ala Cys Ile Gly Tyr Ala
                325                 330                 335

Thr Val Lys Thr Leu Thr Ser Ser Val Arg Asn Cys Gln Gly Asp
            340                 345                 350

Leu Gln Glu Phe Lys Pro Thr Ile Met Val Gly Val Ala Ala Val Trp
        355                 360                 365

Glu Thr Val Arg Lys Gly Ile Leu Asn Gln Ile Asp Asn Leu Pro Phe
    370                 375                 380

Leu Thr Lys Lys Ile Phe Trp Thr Ala Tyr Asn Thr Lys Leu Asn Met
385                 390                 395                 400

Gln Arg Leu His Ile Pro Gly Gly Gly Ala Leu Gly Asn Leu Val Phe
                405                 410                 415

Lys Lys Ile Arg Thr Ala Thr Gly Gly Gln Leu Arg Tyr Leu Leu Asn
            420                 425                 430

Gly Gly Ser Pro Ile Ser Arg Asp Ala Gln Glu Phe Ile Thr Asn Leu
        435                 440                 445

Ile Cys Pro Met Leu Ile Gly Tyr Gly Leu Thr Glu Thr Cys Ala Ser
    450                 455                 460

Thr Thr Ile Leu Asp Pro Ala Asn Phe Glu Leu Gly Val Ala Gly Asp
465                 470                 475                 480

Leu Thr Gly Cys Val Thr Val Lys Leu Val Asp Val Glu Glu Leu Gly
                485                 490                 495

Tyr Phe Ala Lys Asn Asn Gln Gly Glu Val Trp Ile Thr Gly Ala Asn
            500                 505                 510

Val Thr Pro Glu Tyr Tyr Lys Asn Glu Glu Thr Ser Gln Ala Leu
        515                 520                 525
```

```
Thr Ser Asp Gly Trp Phe Lys Thr Gly Asp Ile Gly Glu Trp Glu Ala
530                 535                 540

Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
                565                 570                 575

Ser Asn Glu Tyr Val Ala Asn Ile Cys Val Tyr Ala Asp Gln Ser Lys
                580                 585                 590

Thr Lys Pro Val Gly Ile Ile Val Pro Asn His Ala Pro Leu Thr Lys
                595                 600                 605

Leu Ala Lys Lys Leu Gly Ile Met Glu Gln Lys Asp Ser Ser Ile Asn
610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
                645                 650                 655

Leu Ala Gly Ile Val Phe Phe Asp Gly Glu Trp Thr Pro Gln Asn Gly
                660                 665                 670

Phe Val Thr Ser Ala Gln Lys Leu Lys Arg Lys Asp Ile Leu Asn Ala
                675                 680                 685

Val Lys Asp Lys Val Asp Ala Val Tyr Ser Ser Ser
690                 695                 700

<210> SEQ ID NO 125
<211> LENGTH: 744
<212> TYPE: PRT
<213> ORGANISM: Saccharomyces cerevisiae

<400> SEQUENCE: 125

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
                20                  25                  30

Asp Glu Tyr Ile Glu Glu Leu Tyr Ser Gln Leu Pro Leu Thr Ser Tyr
            35                  40                  45

Pro Arg Tyr Lys Thr Phe Leu Lys Lys Gln Ala Val Ala Ile Ser Asn
50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
                100                 105                 110

Gly Ser Arg Pro Ile Asp Lys Ala Thr Gly Thr Trp Glu Glu Thr Phe
            115                 120                 125

Arg Phe Glu Ser Tyr Ser Thr Val Ser Lys Arg Cys His Asn Ile Gly
            130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
            195                 200                 205
```

-continued

Thr Glu Ala Pro Ile Leu Ile Phe Ala Lys Ser Asn Met Tyr His Val
    210             215                 220

Leu Lys Met Val Pro Asp Met Lys Phe Val Asn Thr Leu Val Cys Met
225             230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
                260                 265                 270

Glu Gln Val Glu Gln Val Gly Cys Phe Asn Lys Ile Pro Ala Ile Pro
            275                 280                 285

Pro Thr Pro Asp Ser Leu Tyr Thr Ile Ser Phe Thr Ser Gly Thr Thr
    290                 295                 300

Gly Leu Pro Lys Gly Val Glu Met Ser His Arg Asn Ile Ala Ser Gly
305             310                 315                 320

Ile Ala Phe Ala Phe Ser Thr Phe Arg Ile Pro Pro Asp Lys Arg Asn
                325                 330                 335

Gln Gln Leu Tyr Asp Met Cys Phe Leu Pro Leu Ala His Ile Phe Glu
                340                 345                 350

Arg Met Val Ile Ala Tyr Asp Leu Ala Ile Gly Phe Gly Ile Gly Phe
                355                 360                 365

Leu His Lys Pro Asp Pro Thr Val Leu Val Glu Asp Leu Lys Ile Leu
    370                 375                 380

Lys Pro Tyr Ala Val Ala Leu Val Pro Arg Ile Leu Thr Arg Phe Glu
385             390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
                420                 425                 430

Gly Pro Asp Lys Ser Ile Met Asn Phe Leu Val Tyr His Arg Val Leu
                435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465             470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
                500                 505                 510

Cys Gly Ala Ile Gly Ile Ser Ala Glu Cys Arg Leu Lys Ser Val Pro
                515                 520                 525

Glu Met Gly Tyr His Ala Asp Lys Asp Leu Lys Gly Glu Leu Gln Ile
    530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
                580                 585                 590

Phe Phe Lys Leu Ala His Gly Glu Tyr Ile Ala Pro Glu Lys Ile Glu
            595                 600                 605

Asn Ile Tyr Leu Ser Ser Cys Pro Tyr Ile Thr Gln Ile Phe Val Phe
    610                 615                 620

```
Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
            645                 650                 655

Trp Thr Lys Glu Val Leu Val Glu Asn Leu Asn Arg Asn Lys Lys Leu
        660                 665                 670

Arg Lys Glu Phe Leu Asn Lys Ile Asn Lys Cys Thr Asp Gly Leu Gln
    675                 680                 685

Gly Phe Glu Lys Leu His Asn Ile Lys Val Gly Leu Glu Pro Leu Thr
690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
            725                 730                 735

Ser Leu Val Lys Thr Glu Lys Leu
            740
```

```
<210> SEQ ID NO 126
<211> LENGTH: 694
<212> TYPE: PRT
<213> ORGANISM: Saccharomyces cerevisiae

<400> SEQUENCE: 126

Met Ser Glu Gln His Ser Val Ala Val Gly Lys Ala Ala Asn Glu His
1               5                   10                  15

Glu Thr Ala Pro Arg Arg Asn Val Arg Val Lys Lys Arg Pro Leu Ile
            20                  25                  30

Arg Pro Leu Asn Ser Ser Ala Ser Thr Leu Tyr Glu Phe Ala Leu Glu
        35                  40                  45

Cys Phe Asn Lys Gly Gly Lys Arg Asp Gly Met Ala Trp Arg Asp Val
    50                  55                  60

Ile Glu Ile His Glu Thr Lys Lys Thr Ile Val Arg Lys Val Asp Gly
65                  70                  75                  80

Lys Asp Lys Ser Ile Glu Lys Thr Trp Leu Tyr Tyr Glu Met Ser Pro
                85                  90                  95

Tyr Lys Met Met Thr Tyr Gln Glu Leu Ile Trp Val Met His Asp Met
            100                 105                 110

Gly Arg Gly Leu Ala Lys Ile Gly Ile Lys Pro Asn Gly Glu His Lys
        115                 120                 125

Phe His Ile Phe Ala Ser Thr Ser His Lys Trp Met Lys Ile Phe Leu
    130                 135                 140

Gly Cys Ile Ser Gln Gly Ile Pro Val Val Thr Ala Tyr Asp Thr Leu
145                 150                 155                 160

Gly Glu Ser Gly Leu Ile His Ser Met Val Thr Glu Ser Ala Ala
                165                 170                 175

Ile Phe Thr Asp Asn Gln Leu Leu Ala Lys Met Ile Val Pro Leu Gln
            180                 185                 190

Ser Ala Lys Asp Ile Lys Phe Leu Ile His Asn Glu Pro Ile Asp Pro
        195                 200                 205

Asn Asp Arg Arg Gln Asn Gly Lys Leu Tyr Lys Ala Ala Lys Asp Ala
    210                 215                 220

Ile Asn Lys Ile Arg Glu Val Arg Pro Asp Ile Lys Ile Tyr Ser Phe
225                 230                 235                 240

Glu Glu Val Val Lys Ile Gly Lys Lys Ser Lys Asp Glu Val Lys Leu
                245                 250                 255
```

```
His Pro Pro Glu Pro Lys Asp Leu Ala Cys Ile Met Tyr Thr Ser Gly
            260                 265                 270

Ser Ile Ser Ala Pro Lys Gly Val Val Leu Thr His Tyr Asn Ile Val
            275                 280                 285

Ser Gly Ile Ala Gly Val Gly His Asn Val Phe Gly Trp Ile Gly Ser
            290                 295                 300

Thr Asp Arg Val Leu Ser Phe Leu Pro Leu Ala His Ile Phe Glu Leu
305                 310                 315                 320

Val Phe Glu Phe Glu Ala Phe Tyr Trp Asn Gly Ile Leu Gly Tyr Gly
                325                 330                 335

Ser Val Lys Thr Leu Thr Asn Thr Ser Thr Arg Asn Cys Lys Gly Asp
            340                 345                 350

Leu Val Glu Phe Lys Pro Thr Ile Met Ile Gly Val Ala Ala Val Trp
            355                 360                 365

Glu Thr Val Arg Lys Ala Ile Leu Glu Lys Ile Ser Asp Leu Thr Pro
            370                 375                 380

Val Leu Gln Lys Ile Phe Trp Ser Ala Tyr Ser Met Lys Glu Lys Ser
385                 390                 395                 400

Val Pro Cys Thr Gly Phe Leu Ser Arg Met Val Phe Lys Val Arg
            405                 410                 415

Gln Ala Thr Gly Gly His Leu Lys Tyr Ile Met Asn Gly Ser Ala
            420                 425                 430

Ile Ser Ile Asp Ala Gln Lys Phe Phe Ser Ile Val Leu Cys Pro Met
            435                 440                 445

Ile Ile Gly Tyr Gly Leu Thr Glu Thr Val Ala Asn Ala Cys Val Leu
            450                 455                 460

Glu Pro Asp His Phe Glu Tyr Gly Ile Val Gly Asp Leu Val Gly Ser
465                 470                 475                 480

Val Thr Ala Lys Leu Val Asp Val Lys Asp Leu Gly Tyr Tyr Ala Lys
                485                 490                 495

Asn Asn Gln Gly Glu Leu Leu Leu Lys Gly Ala Pro Val Cys Ser Glu
            500                 505                 510

Tyr Tyr Lys Asn Pro Ile Glu Thr Ala Val Ser Phe Thr Tyr Asp Gly
            515                 520                 525

Trp Phe Arg Thr Gly Asp Ile Val Glu Trp Thr Pro Lys Gly Gln Leu
            530                 535                 540

Lys Ile Ile Asp Arg Arg Lys Asn Leu Val Lys Thr Leu Asn Gly Glu
545                 550                 555                 560

Tyr Ile Ala Leu Glu Lys Leu Glu Ser Val Tyr Arg Ser Asn Ser Tyr
                565                 570                 575

Val Lys Asn Ile Cys Val Tyr Ala Asp Glu Ser Arg Val Lys Pro Val
            580                 585                 590

Gly Ile Val Val Pro Asn Pro Gly Pro Leu Ser Lys Phe Ala Val Lys
            595                 600                 605

Leu Arg Ile Met Lys Lys Gly Glu Asp Ile Glu Asn Tyr Ile His Asp
            610                 615                 620

Lys Ala Leu Arg Asn Ala Val Phe Lys Glu Met Ile Ala Thr Ala Lys
625                 630                 635                 640

Ser Gln Gly Leu Val Gly Ile Glu Leu Leu Cys Gly Ile Val Phe Phe
                645                 650                 655

Asp Glu Glu Trp Thr Pro Glu Asn Gly Phe Val Thr Ser Ala Gln Lys
            660                 665                 670
```

Leu Lys Arg Arg Glu Ile Leu Ala Ala Val Lys Ser Glu Val Glu Arg
            675                 680                 685

Val Tyr Lys Glu Asn Ser
            690

<210> SEQ ID NO 127
<211> LENGTH: 694
<212> TYPE: PRT
<213> ORGANISM: Saccharomyces cerevisiae

<400> SEQUENCE: 127

Met Thr Glu Gln Tyr Ser Val Ala Val Gly Glu Ala Ala Asn Glu His
1               5                   10                  15

Glu Thr Ala Pro Arg Arg Asn Ile Arg Val Lys Asp Gln Pro Leu Ile
            20                  25                  30

Arg Pro Ile Asn Ser Ser Ala Ser Thr Leu Tyr Glu Phe Ala Leu Glu
        35                  40                  45

Cys Phe Thr Lys Gly Gly Lys Arg Asp Gly Met Ala Trp Arg Asp Ile
    50                  55                  60

Ile Asp Ile His Glu Thr Lys Lys Thr Ile Val Lys Arg Val Asp Gly
65                  70                  75                  80

Lys Asp Lys Pro Ile Glu Lys Thr Trp Leu Tyr Tyr Glu Leu Thr Pro
                85                  90                  95

Tyr Ile Thr Met Thr Tyr Glu Glu Met Ile Cys Val Met His Asp Ile
            100                 105                 110

Gly Arg Gly Leu Ile Lys Ile Gly Val Lys Pro Asn Gly Glu Asn Lys
        115                 120                 125

Phe His Ile Phe Ala Ser Thr Ser His Lys Trp Met Lys Thr Phe Leu
    130                 135                 140

Gly Cys Met Ser Gln Gly Ile Pro Val Val Thr Ala Tyr Asp Thr Leu
145                 150                 155                 160

Gly Glu Ser Gly Leu Ile His Ser Met Val Glu Thr Asp Ser Val Ala
                165                 170                 175

Ile Phe Thr Asp Asn Gln Leu Leu Ser Lys Leu Ala Val Pro Leu Lys
            180                 185                 190

Thr Ala Lys Asn Val Lys Phe Val Ile His Asn Glu Pro Ile Asp Pro
        195                 200                 205

Ser Asp Lys Arg Gln Asn Gly Lys Leu Tyr Lys Ala Ala Lys Asp Ala
    210                 215                 220

Val Asp Lys Ile Lys Glu Val Arg Pro Asp Ile Lys Ile Tyr Ser Phe
225                 230                 235                 240

Asp Glu Ile Ile Glu Ile Gly Lys Lys Ala Lys Asp Glu Val Glu Leu
                245                 250                 255

His Phe Pro Lys Pro Glu Asp Pro Ala Cys Ile Met Tyr Thr Ser Gly
            260                 265                 270

Ser Thr Gly Thr Pro Lys Gly Val Val Leu Thr His Tyr Asn Ile Val
        275                 280                 285

Ala Gly Ile Gly Gly Val Gly His Asn Val Ile Gly Trp Ile Gly Pro
    290                 295                 300

Thr Asp Arg Ile Ile Ala Phe Leu Pro Leu Ala His Ile Phe Glu Leu
305                 310                 315                 320

Thr Phe Glu Phe Glu Ala Phe Tyr Trp Asn Gly Ile Leu Gly Tyr Ala
                325                 330                 335

Asn Val Lys Thr Leu Thr Pro Ser Thr Arg Asn Cys Gln Gly Asp
            340                 345                 350

```
Leu Met Glu Phe Lys Pro Thr Val Met Val Gly Val Ala Ala Val Trp
        355                 360                 365

Glu Thr Val Arg Lys Gly Ile Leu Ala Lys Ile Asn Glu Leu Pro Gly
    370                 375                 380

Trp Ser Gln Thr Leu Phe Trp Thr Val Tyr Ala Leu Lys Glu Arg Asn
385                 390                 395                 400

Ile Pro Cys Ser Gly Leu Leu Ser Gly Leu Ile Phe Lys Arg Ile Arg
                405                 410                 415

Glu Ala Thr Gly Gly Asn Leu Arg Phe Ile Leu Asn Gly Gly Ser Ala
            420                 425                 430

Ile Ser Ile Asp Ala Gln Lys Phe Leu Ser Asn Leu Leu Cys Pro Met
        435                 440                 445

Leu Ile Gly Tyr Gly Leu Thr Glu Gly Val Ala Asn Ala Cys Val Leu
    450                 455                 460

Glu Pro Glu His Phe Asp Tyr Gly Ile Ala Gly Asp Leu Val Gly Thr
465                 470                 475                 480

Ile Thr Ala Lys Leu Val Asp Val Glu Asp Leu Gly Tyr Phe Ala Lys
                485                 490                 495

Asn Asn Gln Gly Glu Leu Leu Phe Lys Gly Ala Pro Ile Cys Ser Glu
            500                 505                 510

Tyr Tyr Lys Asn Pro Glu Glu Thr Ala Ala Ala Phe Thr Asp Asp Gly
        515                 520                 525

Trp Phe Arg Thr Gly Asp Ile Ala Glu Trp Thr Pro Lys Gly Gln Val
    530                 535                 540

Lys Ile Ile Asp Arg Lys Lys Asn Leu Val Lys Thr Leu Asn Gly Glu
545                 550                 555                 560

Tyr Ile Ala Leu Glu Lys Leu Glu Ser Ile Tyr Arg Ser Asn Pro Tyr
                565                 570                 575

Val Gln Asn Ile Cys Val Tyr Ala Asp Glu Asn Lys Val Lys Pro Val
            580                 585                 590

Gly Ile Val Val Pro Asn Leu Gly His Leu Ser Lys Leu Ala Ile Glu
        595                 600                 605

Leu Gly Ile Met Val Pro Gly Glu Asp Val Glu Ser Tyr Ile His Glu
    610                 615                 620

Lys Lys Leu Gln Asp Ala Val Cys Lys Asp Met Leu Ser Thr Ala Lys
625                 630                 635                 640

Ser Gln Gly Leu Asn Gly Ile Glu Leu Leu Cys Gly Ile Val Phe Phe
                645                 650                 655

Glu Glu Glu Trp Thr Pro Glu Asn Gly Leu Val Thr Ser Ala Gln Lys
            660                 665                 670

Leu Lys Arg Arg Asp Ile Leu Ala Ala Val Lys Pro Asp Val Glu Arg
        675                 680                 685

Val Tyr Lys Glu Asn Thr
    690

<210> SEQ ID NO 128
<211> LENGTH: 669
<212> TYPE: PRT
<213> ORGANISM: Saccharomyces cerevisiae

<400> SEQUENCE: 128

Met Ser Pro Ile Gln Val Val Phe Ala Leu Ser Arg Ile Phe Leu
1               5                   10                  15

Leu Leu Phe Arg Leu Ile Lys Leu Ile Ile Thr Pro Ile Gln Lys Ser
```

```
                 20                  25                  30
Leu Gly Tyr Leu Phe Gly Asn Tyr Phe Asp Glu Leu Asp Arg Lys Tyr
             35                  40                  45
Arg Tyr Lys Glu Asp Trp Tyr Ile Pro Tyr Phe Leu Lys Ser Val
         50                  55                  60
Phe Cys Tyr Ile Ile Asp Val Arg Arg His Arg Phe Gln Asn Trp Tyr
 65                  70                  75                  80
Leu Phe Ile Lys Gln Val Gln Gln Asn Gly Asp His Leu Ala Ile Ser
                 85                  90                  95
Tyr Thr Arg Pro Met Ala Glu Lys Gly Glu Phe Gln Leu Glu Thr Phe
             100                 105                 110
Thr Tyr Ile Glu Thr Tyr Asn Ile Val Leu Arg Leu Ser His Ile Leu
             115                 120                 125
His Phe Asp Tyr Asn Val Gln Ala Gly Asp Tyr Val Ala Ile Asp Cys
             130                 135                 140
Thr Asn Lys Pro Leu Phe Val Phe Leu Trp Leu Ser Leu Trp Asn Ile
145                 150                 155                 160
Gly Ala Ile Pro Ala Phe Leu Asn Tyr Asn Thr Lys Gly Thr Pro Leu
                 165                 170                 175
Val His Ser Leu Lys Ile Ser Asn Ile Thr Gln Val Phe Ile Asp Pro
             180                 185                 190
Asp Ala Ser Asn Pro Ile Arg Glu Ser Glu Glu Ile Lys Asn Ala
             195                 200                 205
Leu Pro Asp Val Lys Leu Asn Tyr Leu Glu Glu Gln Asp Leu Met His
         210                 215                 220
Glu Leu Leu Asn Ser Gln Ser Pro Glu Phe Leu Gln Gln Asp Asn Val
225                 230                 235                 240
Arg Thr Pro Leu Gly Leu Thr Asp Phe Lys Pro Ser Met Leu Ile Tyr
                 245                 250                 255
Thr Ser Gly Thr Thr Gly Leu Pro Lys Ser Ala Ile Met Ser Trp Arg
             260                 265                 270
Lys Ser Ser Val Gly Cys Gln Val Phe Gly His Val Leu His Met Thr
         275                 280                 285
Asn Glu Ser Thr Val Phe Thr Ala Met Pro Leu Phe His Ser Thr Ala
         290                 295                 300
Ala Leu Leu Gly Ala Cys Ala Ile Leu Ser His Gly Gly Cys Leu Ala
305                 310                 315                 320
Leu Ser His Lys Phe Ser Ala Ser Thr Phe Trp Lys Gln Val Tyr Leu
             325                 330                 335
Thr Gly Ala Thr His Ile Gln Tyr Val Gly Glu Val Cys Arg Tyr Leu
             340                 345                 350
Leu His Thr Pro Ile Ser Lys Tyr Glu Lys Met His Lys Val Lys Val
         355                 360                 365
Ala Tyr Gly Asn Gly Leu Arg Pro Asp Ile Trp Gln Asp Phe Arg Lys
         370                 375                 380
Arg Phe Asn Ile Glu Val Ile Gly Glu Phe Tyr Ala Ala Thr Glu Ala
385                 390                 395                 400
Pro Phe Ala Thr Thr Thr Phe Gln Lys Gly Asp Phe Gly Ile Gly Ala
             405                 410                 415
Cys Arg Asn Tyr Gly Thr Ile Ile Gln Trp Phe Leu Ser Phe Gln Gln
         420                 425                 430
Thr Leu Val Arg Met Asp Pro Asn Asp Ser Val Ile Tyr Arg Asn
         435                 440                 445
```

```
Ser Lys Gly Phe Cys Glu Val Ala Pro Val Gly Pro Gly Glu Met
450                 455                 460

Leu Met Arg Ile Phe Phe Pro Lys Lys Pro Glu Thr Ser Phe Gln Gly
465                 470                 475                 480

Tyr Leu Gly Asn Ala Lys Glu Thr Lys Ser Lys Val Val Arg Asp Val
                485                 490                 495

Phe Arg Arg Gly Asp Ala Trp Tyr Arg Cys Gly Asp Leu Leu Lys Ala
                500                 505                 510

Asp Glu Tyr Gly Leu Trp Tyr Phe Leu Asp Arg Met Gly Asp Thr Phe
                515                 520                 525

Arg Trp Lys Ser Glu Asn Val Ser Thr Thr Glu Val Glu Asp Gln Leu
530                 535                 540

Thr Ala Ser Asn Lys Glu Gln Tyr Ala Gln Val Leu Val Gly Ile
545                 550                 555                 560

Lys Val Pro Lys Tyr Glu Gly Arg Ala Gly Phe Ala Val Ile Lys Leu
                565                 570                 575

Thr Asp Asn Ser Leu Asp Ile Thr Ala Lys Thr Lys Leu Leu Asn Asp
                580                 585                 590

Ser Leu Ser Arg Leu Asn Leu Pro Ser Tyr Ala Met Pro Leu Phe Val
            595                 600                 605

Lys Phe Val Asp Glu Ile Lys Met Thr Asp Asn His Lys Ile Leu Lys
            610                 615                 620

Lys Val Tyr Arg Glu Gln Lys Leu Pro Lys Gly Leu Asp Gly Asn Asp
625                 630                 635                 640

Thr Ile Phe Trp Leu Lys Asn Tyr Lys Arg Tyr Glu Val Leu Thr Ala
                645                 650                 655

Ala Asp Trp Glu Ala Ile Asp Ala Gln Thr Ile Lys Leu
                660                 665

<210> SEQ ID NO 129
<211> LENGTH: 543
<212> TYPE: PRT
<213> ORGANISM: Saccharomyces cerevisiae

<400> SEQUENCE: 129

Met Thr Ser Ala Ala Thr Val Thr Ala Ser Phe Asn Asp Thr Phe Ser
1               5                   10                  15

Val Ser Asp Asn Val Ala Val Ile Val Pro Glu Thr Asp Thr Gln Val
                20                  25                  30

Thr Tyr Arg Asp Leu Ser His Met Val Gly His Phe Gln Thr Met Phe
            35                  40                  45

Thr Asn Pro Asn Ser Pro Leu Tyr Gly Ala Val Phe Arg Gln Asp Thr
        50                  55                  60

Val Ala Ile Ser Met Arg Asn Gly Leu Glu Phe Ile Val Ala Phe Leu
65                  70                  75                  80

Gly Ala Thr Met Asp Ala Lys Ile Gly Ala Pro Leu Asn Pro Asn Tyr
                85                  90                  95

Lys Glu Lys Glu Phe Asn Phe Tyr Leu Asn Asp Leu Lys Ser Lys Ala
                100                 105                 110

Ile Cys Val Pro Lys Gly Thr Thr Lys Leu Gln Ser Ser Glu Ile Leu
            115                 120                 125

Lys Ser Ala Ser Thr Phe Gly Cys Phe Ile Val Glu Leu Ala Phe Asp
130                 135                 140

Ala Thr Arg Phe Arg Val Glu Tyr Asp Ile Tyr Ser Pro Glu Asp Asn
```

```
            145                 150                 155                 160
Tyr Lys Arg Val Ile Tyr Arg Ser Leu Asn Asn Ala Lys Phe Val Asn
                165                 170                 175

Thr Asn Pro Val Lys Phe Pro Gly Phe Ala Arg Ser Ser Asp Val Ala
                180                 185                 190

Leu Ile Leu His Thr Ser Gly Thr Ser Thr Pro Lys Thr Val Pro
            195                 200                 205

Leu Leu His Leu Asn Ile Val Arg Ser Thr Leu Asn Ile Ala Asn Thr
            210                 215                 220

Tyr Lys Leu Thr Pro Leu Asp Arg Ser Tyr Val Val Met Pro Leu Phe
225                 230                 235                 240

His Val His Gly Leu Ile Gly Val Leu Leu Ser Thr Phe Arg Thr Gln
                245                 250                 255

Gly Ser Val Val Val Pro Asp Gly Phe His Pro Lys Leu Phe Trp Asp
                260                 265                 270

Gln Phe Val Lys Tyr Asn Cys Asn Trp Phe Ser Cys Val Pro Thr Ile
                275                 280                 285

Ser Met Ile Met Leu Asn Met Pro Lys Pro Asn Pro Phe Pro His Ile
            290                 295                 300

Arg Phe Ile Arg Ser Cys Ser Ser Ala Leu Ala Pro Ala Thr Phe His
305                 310                 315                 320

Lys Leu Glu Lys Glu Phe Asn Ala Pro Val Leu Glu Ala Tyr Ala Met
                325                 330                 335

Thr Glu Ala Ser His Gln Met Thr Ser Asn Asn Leu Pro Pro Gly Lys
            340                 345                 350

Arg Lys Pro Gly Thr Val Gly Gln Pro Gln Gly Val Thr Val Val Ile
            355                 360                 365

Leu Asp Asp Asn Asp Asn Val Leu Pro Pro Gly Lys Val Gly Glu Val
            370                 375                 380

Ser Ile Arg Gly Glu Asn Val Thr Leu Gly Tyr Ala Asn Asn Pro Lys
385                 390                 395                 400

Ala Asn Lys Glu Asn Phe Thr Lys Arg Glu Asn Tyr Phe Arg Thr Gly
                405                 410                 415

Asp Gln Gly Tyr Phe Asp Pro Glu Gly Phe Leu Val Leu Thr Gly Arg
                420                 425                 430

Ile Lys Glu Leu Ile Asn Arg Gly Gly Glu Lys Ile Ser Pro Ile Glu
                435                 440                 445

Leu Asp Gly Ile Met Leu Ser His Pro Lys Ile Asp Glu Ala Val Ala
            450                 455                 460

Phe Gly Val Pro Asp Asp Met Tyr Gly Gln Val Val Gln Ala Ala Ile
465                 470                 475                 480

Val Leu Lys Lys Gly Glu Lys Met Thr Tyr Glu Glu Leu Val Asn Phe
                485                 490                 495

Leu Lys Lys His Leu Ala Ser Phe Lys Ile Pro Thr Lys Val Tyr Phe
                500                 505                 510

Val Asp Lys Leu Pro Lys Thr Ala Thr Gly Lys Ile Gln Arg Arg Val
                515                 520                 525

Ile Ala Glu Thr Phe Ala Lys Ser Ser Arg Asn Lys Ser Lys Leu
            530                 535                 540

<210> SEQ ID NO 130
<211> LENGTH: 30
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 130
tttttttttt tttttttttt tttttttttt                                       30

<210> SEQ ID NO 131
<211> LENGTH: 2066
<212> TYPE: DNA
<213> ORGANISM: Mortierella alpina

<400> SEQUENCE: 131 gctcttttt  gttctgttct  ttgccacccc  actctgctgt  gcctctccac  tccccctgcc     60
cgtcgaacgt  tcttctgtca  ctttgcacag  cagtatctcc  tctgatctcg  cttgrttata    120
ttccctctaa  tctcgtttgg  ttatattccc  tctgatctcg  ctcggttata  ttcttcagat    180
atggatgctg  tccctgcagt  tgctgctgcg  gccatccccg  cagccatgta  tgtcggctcc    240
aagcttgcaa  tcccccgtga  tgtcaagtta  gctaaaggcc  tagtcagtgc  caagctaggt    300
tacaggtcct  acgagaagaa  cgactcgatc  aatatctctt  atcgttttga  agagacctgt    360
aagaagcacc  ctcatcgcga  agctttggtg  tttgaaggca  aatcgtacac  cttccaggac    420
atccagcgag  aatcgaatag  ggtgggacac  tggctgttgt  ccaaaggcgt  caagcgagga    480
gagatcgtgt  cgctcttcat  gcaaaataag  ccagagtttc  tcttcttctg  gcttggactc    540
aacaagatcg  gcgctacggg  agcattcatc  aacacgaacc  tctcgggcaa  acctctgacg    600
cactcattgc  gtaccgcgac  agcatccatt  ctgattatgg  atgcggaact  gccgacgccc    660
atttatagtg  tcctcgatga  agtccttgag  atgggatatc  agatatattc  ctacggagga    720
tcccagcaac  acgcctttgc  tacacaagtt  gaactttctc  aaatctcgga  tgcggccttg    780
cccaagagtc  tgcgaaggaa  aaccactgca  aatgatattg  ccatgttgat  ttacacctcc    840
ggaacgacgg  gtttgcccaa  agctggacgg  ttctcccatg  ctcgagccaa  cgttgccgca    900
cttttctgga  cgtctttcta  ccacttcagc  gaaaagacc   gcctgtacat  cgccttgcct    960
ctttaccaca  gtgctggagc  tgtccttgga  atatgtgtgg  cctgggtcac  cggtgctacg   1020
gtggtcctgg  cgcgcaagtt  ttcaactact  tccttctggg  acgaatgcag  ggccaacaag   1080
gtcaccgtga  tccagtatat  tggagaaatc  tgccgatact  tactgaatgc  tcctccttct   1140
cccttggaca  agacacacac  gatccgaatg  gcgcatggca  acggcatgcg  tccggatgta   1200
tggaacagat  tcagagatcg  tttcggcatc  cctttgatcg  gagaatggta  tgcaagcact   1260
gagggcaccg  gaatcttgac  aaactataac  acaggaccca  atggcgctgg  tgcgatagga   1320
tacagaggct  ccttggccag  aactgtcgat  aagggtctga  agattgcgaa  gttcgacatc   1380
caaaccgagg  aacttattcg  tgacaaaaat  ggtcgatgca  ttgagtgtgt  cgcagatgag   1440
cccggcgagc  tcttgacaat  gattgattca  agtgatccca  ctcgcgcttt  ccaagggtac   1500
cataaaaatg  caggtgcaaa  ctccaagaaa  gtcgtccagg  atgcattcag  tgttggcgac   1560
caatactttc  gtactggtga  catccttcgt  cgcgacgctg  atggctattt  ctattttggc   1620
gatcgtgttg  gagatacttt  ccgctggaaa  tctgaaaacg  tgtcaactgc  ggaggtttct   1680
gaggtgctct  cagcataccc  ggactgcatc  gaggtcaacg  tttatggcgt  tcaagtccct   1740
ggacacgacg  gccgcgcagg  catggctgcc  attgtctcca  aggacaccat  gaactgggat   1800
agtttcgcca  agtttgcact  caaaaatctg  ccgaagtact  ctgtgccgat  tttcatccgc   1860
aaggtcccag  agatggagat  tacgggaacg  ttcaagcaac  gaaaggttga  actggtgaac   1920

| | |
|---|---|
| gagggcatgg acccgagcaa gatcaaagac gaaatgctgt ggttggatgg gcactcctac | 1980 |
| cggcccttca aagaggcgga gcatactaga gtcgtcagcg gcaaagccag gctttgacga | 2040 |
| ataaaattat ttcgttttgt ccgttg | 2066 |

<210> SEQ ID NO 132
<211> LENGTH: 2135
<212> TYPE: DNA
<213> ORGANISM: Mortierella alpina

<400> SEQUENCE: 132

| | |
|---|---|
| atccgcccat ccgctctctt gccactgatc tcaaagcgtg atccaaaggt cattcttagg | 60 |
| cagcactcac gcagctactt agaactctac ccacatatcc cttattgata caatggctcc | 120 |
| cgtcgctgca ctcgccgccg ctctggcggc aggatactat ctcaatggca agtaccaaat | 180 |
| cactaaggac ttggcgcttg ttcgcgttgg tctccatgca cgcaaaagac ttgaggcctt | 240 |
| ggtcgagaat cgggactgca gtcttttacaa caggttcgag gaacaatgcc agatccggcc | 300 |
| tttctctgtt gcccttgttt ttgagaacac gtcttacacc tggagagact ggagctggc | 360 |
| gtccaacagg atggcccatt ggtttgttgc tcaaggaatc caaaaaaaag gagcgtgtgg | 420 |
| cgatgatgat gcataactcg cctctgttca ttatcacctg gctggcaatg ctcaagatca | 480 |
| tggttgtacc tgcttttatc aataaccaga ttgcaggacc tgttctggtt cattctctta | 540 |
| aagtggccga cgccaagttt ctcttgttcg attacgagtt ggcacctgtc atccaaaagt | 600 |
| cgctcaatga gatcaaggac atgggttaca atctctacac tgtcacaccc aaggatcaag | 660 |
| ttctaggtca actttacgcc aatctgcccg aggctgctcg tcaggtgttg gatgaggctc | 720 |
| cttcattctt tggttatgtc gaatggcaga acctcagtac cgaaggtttc tcgaacgaga | 780 |
| gtcgtcagga ggtggtgatc tccgaccccg cagccttgat ttacaccagc gggaccacgg | 840 |
| gattccccaa ggctgctatc atggaccatg gacgttgcaa cttggcttcg atctcttatg | 900 |
| gcactctatg cggcatcaaa ccagagaaca aggtttacat cacattgccg ctctatcatt | 960 |
| ctgctggagc catcattggt ctgggccaga gcttcaccag cggatgcacc attgtgctgg | 1020 |
| cgcgaaagtt ctccgtgaca aagttttggc gtgattgcgt tgagtacgac gtaactcatt | 1080 |
| ttcagtacat tggcgaactc tgccgctacc ttctaaatgc ccccgaaagt ccactggaca | 1140 |
| aaaggcataa ggttcggatg gcgtttggca acggaatgcg cccggatgtt tgggcaaagt | 1200 |
| ttcaggaacg attcaatatc cccattattg ttgagtacta cgccatgagc gaaggaacat | 1260 |
| cgtcgctttt gaatgtggcc aggaacaagc gcgaccaagg tgcggtggga ttccgtggcc | 1320 |
| ccgtcgtgag ggccttgacg cctcccgttc aactggtcaa ggtggacttt gacacggagg | 1380 |
| agctgatccg cgataagaag acgggacttt gcgtcctatg ccagcctggt gagattggag | 1440 |
| aactggtcac gctagccgac aacaagacga ctggcgcacg ctatgctggg tatttcaatc | 1500 |
| agccagaggt ttcgaaggca aggctggtcc agaacgtggt agtgaaggac gacatctact | 1560 |
| tccggacggg tgacctcttg tactccaagg accagtactg gtactttgct gatcgcgcag | 1620 |
| gagacacgta ccggtggaaa ggagagaacg tgtcgacagc cgagattgca gacactatcg | 1680 |
| gccgtgttga gggcgtggct agttgtactg tttatggcgt atcggtcccg ggcatggatg | 1740 |
| dacgcgcggg catggctgct ttggtgctca agaactcgat tgtgcagatg gcaggtggaa | 1800 |
| gccaggcaaa gttccatgtg gatgaggctg cgctgaacgc gttttgcgt gacttgagca | 1860 |
| aggatgtggt caaaaaactg ccggcgtatg cgattcctcg gttcttgcgc attgcagagc | 1920 |

| | |
|---|---|
| aggaactgga gacgacgggc acgttcaaga acaagaaggt ggagctgaag aaggaagggt | 1980 |
| tcgacctcgg taaggtcaag gagcggctgt actggtggac acccaagggt gaatatgccc | 2040 |
| cttttggcgt ggcggagaac gagcagatcc tcgcaggacg cgctcgtctt tgagcgatgt | 2100 |
| ttgtcaatga agtcatcggc atcatcatca tcatc | 2135 |

<210> SEQ ID NO 133
<211> LENGTH: 1753
<212> TYPE: DNA
<213> ORGANISM: Mortierella alpina

<400> SEQUENCE: 133

| | |
|---|---|
| gcctactttg cgctcgcctc atcgacccaa aggcagcaat ggaaacggat gctcttacca | 60 |
| tcgctttgac catcgccatc gccatcgtgc tggctttggt caaattcaac gaaaaagagc | 120 |
| ctgacctgca tccgctcctg ctcgggcagc aatcgtctgt cacgcccatt cggaacgagg | 180 |
| gcgagtccgt tatccataga tccaaaacgt gccacacgg dactgctg acgaagcgcc | 240 |
| cgagcgagaa aatcaagact ctgcacgatg tctggcagac tggagcagct gtcaacccag | 300 |
| ccggccgatc gttgatgttt atgctgcaga accagtttgc gtttatcgag gccacgtatg | 360 |
| agcaagtcaa taggaggatt ggcggcttcg aacaggttt cgtgaaggca acagggctaa | 420 |
| agcccaagac ggacacacca gtaggaatct ttatgcccta ctctcaagaa tcgttcgttg | 480 |
| cccagcaggc attctatcga tacagctttg ttgctgtccc catccatgat ctgaggaaca | 540 |
| acgacctctt ggtggaggta gtagaccaga ccaagctcaa ggccatcata gtctcacaaa | 600 |
| aggtgctccc gttattgctg caatctctga aggagtgtcc aaccatcaag acaatcatca | 660 |
| tggcaggaat ctacatctca caggagcagc tggaaatggc agcacagcat ggagtaaagc | 720 |
| tgctcaaatt cgcggcagtg gaatatgagg gatcctcgac tctgatggag cctgttcagc | 780 |
| ctgatccgga ggatgttgcc atgatcaact ataacacaaa gtcgtcttcg ctctcgaaag | 840 |
| gcgtcatgct tacccatgcc aacctgatcg cggcgatgac tgccttcacg gagtcacttc | 900 |
| cggcaaaaaa gcgtttctcc agcaaagatc gtcttctctc tcattttcc aatggagatg | 960 |
| tcatctctgt cttcatgtcg agcgccatca tcctgatggg aggttctttg gtcttttcat | 1020 |
| ctggtttgat gaagaacgtt ttgcatgatt cccaagcttc tgcaccaacg atctttgcaa | 1080 |
| gcacacccat catcctggaa aagattcacg aagcacttca gttgacgtat ggccaaggct | 1140 |
| ccatgttcag gcgcggcttt gctgccaaat tggccatact tcaagctgga cgaatcacta | 1200 |
| caacaagcct atgggacttg attggactgg gcgaggtccg cagcaaactt ggtggaaagg | 1260 |
| ttcgaatggt tgtaacaaca catcctacca aacctgagac gctggattat atcagagccg | 1320 |
| cgatgggcat ccatgtcatt accacttacg gcaggacaga gacgtcgggc attgtgacag | 1380 |
| cccgcaacat gctggattat gccaacgcac ctcatttagg accaccagtg ggttgcaacg | 1440 |
| aggttaagct tgtggacgat gttgcagctg gctttacaag tgcagacgag cccaacccac | 1500 |
| gaggcgagat cctatccga ggccccaatg tgatgaaagg ttattacaag aagccgggtg | 1560 |
| ccacttcaac ggctatcgat gaggaagggt ggttccattc aggagagctg ggcacattcc | 1620 |
| actccaacgg cactttagac gtgttgggca agaagaagaa gacgcagtct gcagttggat | 1680 |
| caccgtcatg aaaggagatg ctgcatgtgc tacagaatat aaaaagggag aagatacgtt | 1740 |
| cggtaaccac atc | 1753 |

<210> SEQ ID NO 134
<211> LENGTH: 2309

<212> TYPE: DNA
<213> ORGANISM: Mortierella alpina

<400> SEQUENCE: 134

```
cacacgctca cgttcgctct cacccgaccc actccccact ctcgctctca ttctctccct      60
tgtccttccc ttgtcccttt caaggtctaa cagcatcaac atcagcatca gcatcaagct     120
tctcattcct ccctcgtcta aatctctgaa agagttcgct ttgcaattca gcaatgtccc     180
tcgaccagaa cgcccagtcc gttgagctcc caggcacccg gcaaccaggc cagacaggca     240
tctatcgccg caaaggcttc gagaatgccc ttctcgccgt cccacccagc agaccgcaca     300
tcaagaccat ctacgatgcc ttccagcacg gactgaagct taatcccaac ggagctgccc     360
tgggcagccg agtgtacgac ccggtgacgg acacctttgg aggctatgtc tggcagacgt     420
atgcacaggt gaacgaccgc atcactcgct tcggcagtgg attggtcaaa attcataagg     480
acgtccatgg tcttgccacc gtgggccaga agtggtctct cggaatctgg gccatcaacc     540
gacccgagtg gaccatcgcg tccgaggctt gctcggccta caacctggtc tccgtgggtc     600
tttacgatac tttgggaccc gaggctgtga cttatggcat taatcacgct gagtgctcta     660
ttgtcgtaac aagtgtggat catatcgcga cgctgctgaa cgaatcttcc aagatgcctg     720
ggctcaaaat catcatcagc atggatgacc tcgatactgg gagagcaggc ccaggactgg     780
ctcccaccgg caccatcctc aggacttacg ctcaggacaa aggggtacta ctttatgatt     840
ggtctgaggt tgaagccgtc ggtattcagc atggacgaaa gcatacgcca ccaacctcct     900
ccgacgcata tacgatctgc tataccagcg ggacaacagg cttgccaaaa ggtgccattt     960
tgacccatgg aaacttgatc gcccttttgg cctccagtga tgtggccaca ccagtgctgg    1020
ctgacgattg cctcatcagt ttcttgcccc tgcctcacgt ctttggtcgg gtcatggagc    1080
tcttcgcgat ggccgcagga ggaaagattg gctacagcac gggagatcct ttgcgtctct    1140
tggaggacgt ctcgcaccta aagccctcca tcttccccgc tgtgcccaga ctgctgaacc    1200
gcgtgtatgc caaggtgtat gcggcaactg ttggagcgcc tggactcaca ggggcactgg    1260
cgcgacgagg attggccacc aagctcacca atttgagaga gggcaaaggt ttccaccacc    1320
cattgtggga ccgaatcctc ttctcaaagg tcaagcaagc gctcggcggc aatgtgagac    1380
tgatgttgac tgcctccgct cccatctcgg ccgagatctt ggaattcgtc cgtgtcgctt    1440
tctgctgcga ggtcgtggag gcatatggac agactgaggg cggtggagcg gccacaaaca    1500
ccgtgattgg cgagaccgag gctggacacg tcggtcctcc tcaagcttgt tgcgagatca    1560
aactggtgga tgtacccgag ctgaactact ttgcgaccga taaaccattc cctcgtggtg    1620
agatttgtgt ccgtggaccc ggtgtcattc ctggttatct caaggatgag gccaagacca    1680
aggagaccat tgatgaggag ggctggctgc actcgggcga tatcgccatc atgagtggca    1740
aaggcaccgt taccatcatt gacaggaaga gaacgtgtt caagctgagc caaggagaat    1800
acatcgcggc agagaacatt gaagggcgtt tcctctccaa ggttccattc atccaacaaa    1860
ttctggtgca cggcgactcg accgagagct gtttggtggc catcttgatc ccagagcctg    1920
aggccttcat cccctttgtg aacaaagtgc tcgagaacgt caatcttcaa cctggagatc    1980
ttgcagccta caggaagatc gttaacaacc caaagctgcg ccaggctgtc ctcaaagagc    2040
tgatcaaggc tggcaaggat gctggattga aaggctttga gattccaaag gcgatcctcc    2100
tcgaatctga ggcattcacg gtcgaaaacg acaagatgac cccgactttc aagatcaaaa    2160
gacaccctgt cgtccaggct taccgcgagc aactgacagc cctctacaac gaaatccatc    2220
```

```
aaaaggaatc caagctgtaa aaagaaaccc ttagaacctg cggtgctcgc agcaattaaa    2280
aaaaaaagag agatattact ctcacagct                                      2309

<210> SEQ ID NO 135
<211> LENGTH: 2196
<212> TYPE: DNA
<213> ORGANISM: Mortierella alpina

<400> SEQUENCE: 135
tttttttttt tttcttttct ctccaaccct ttcaccccca cgcctcggct cgtactcaag      60
cctcacgtcc acactctcgt cctctagcct gctgcattca cgattcacat tcctcctcga     120
ctccagcatc gctactccct cgtgctactt tcaccatgac cacccaattg tactccatcg     180
aagtggcagg cagcccagag attccgggcg agggcaaacc tcggcgcagc gttctcagcc     240
cagacaaact cgtccagagc tatcagtctt tcaagggcga cggctccatc accactctat     300
atgagaactt tttggagggc atccagcgct cagaggagg agagtttctc ggacaccgcc      360
ccatcgtcga taatgtagct cagccgtacg aatggctaag ctacacgcgc gttcaggaac     420
gtgtcgccaa ctttggcgct ggtctcatcc agctgggcct gaaagtcgac tcgaactttg     480
gcatcttttc catcaacagg cccgaatgga caatgagtga gctggcaggc tacatgtaca     540
actttacatc tgtgccgctt tacgacactc tgggcgtctc ggccatcgaa tacatcgtta     600
atcagaccga gatggagacc atcatcgcgt cggctgataa agcctcgatc ctgttaaaca     660
tgaaatcaac tctgccgaca ctcaagaaca ttgtcgttat gggctcgctc gaagacgcgc     720
tcgttgtcga gggtagggaa atggatatcc acatcgttgc gtggagtgac gtcgaacgcg     780
atggcttcaa caaccccgcg ccagccaacc ctccaacacc ggacgacgtc gccaccatct     840
gctacacgtc aggaacaacc gggacaccaa agggcgcaat cctgacccac aaaaactttg     900
tggctggcct tgcctcgttc catatgatgg caaagcacca aaagttttc atcccctcga      960 gcgttgacac tcacatatct tacctgcccc tggcacatgt gttcgagcgt ttgtctcagg    1020
ctgttatgat ttctggcgca gctcggattg gtattacca aggagacact ttgaagctac     1080
tcgatgatgt ggcgatcttg cagcccacca tctttgtgtc cgttccacga ctctttaaca    1140
ggatttacga caaggttcta gcaggtgtga agccaaggg cggtctcgca gctttcttat     1200
tcaaccgcgc ttttgaaacc aagaaggcta atttgaaacg cggtatcctg gagcacgcca    1260
tctgggatcg actggtattt ggtgcaattc gtgcgcgact cggtggcaaa gttaagcata    1320
ttgtctcagg atcagcccct atagcccgg acgtcatgga tttccttcgc atttgcttca     1380
gtgccgacgt ttatgaaggg tatggacaga cggagcaggc tgctggtttg tgtatgagct    1440
acagaggtga cttgacctcg ggtcaagtgg accccctca gctgtgcgtc gaagtgaagc     1500
tcagagacgt tccggacatg cactacacaa gccaggacaa gcctcgccct cgcggggaga    1560
tcatgcttcg aggccattca gttttcaaag gctattacaa ggctccaaag caaacagagg    1620
agacactgga cgcacaggga tgggcaagca ctggagacgt tggtgaatgg gacgagcgtg    1680
gccgcttggt ggtgatcgac cgtgtcaaaa acatttttcaa gttggctcaa ggcgaataca    1740
ttgcacctga aaagatcgaa gccgtcctgg ccaaacacta ccttgtcgcc caggtctttg    1800
tctacggaga ctccttccaa gcgacattgg tgggagttgt cgtgcccgat gcggagacgc    1860
taaagccttg ggccgatgac catggccttg gaggcaagag ctatgaagaa ctatgcgctc    1920
atcccgctgt caaagaaact ttgctgaagg agctcaaaga gtttggtcgt gaaaatgatc    1980
tgaagggctt tgagatattg aagaacattc atgtaacggc ggagcaattc tcaattgaga    2040
```

| | | |
|---|---|---|
| atgatctttt | gacacccaca ttcaagctga agagacacac cgcgaaagag aagtacatcg | 2100 |
| ccgagattga | gctgatgtat aacgggatcc actgaaagag tctagccaaa gcagatcttt | 2160 |
| ttattactgt | cgttaaaaaa actactcgta accatc | 2196 |

<210> SEQ ID NO 136
<211> LENGTH: 2113
<212> TYPE: DNA
<213> ORGANISM: Mortierella alpina

<400> SEQUENCE: 136

| | | |
|---|---|---|
| tttcctcacc | ttccctccgc tgccctctgc tgcacactcc tctggcttat accatccacc | 60 |
| cctctagccc | cgccacttcg ccgccaacct catccgactc acaccgcaat ggctactcaa | 120 |
| atgtactcgg | tggtcgtccc caacagcccc gacattcccg cgcaaggcaa gccccgccgt | 180 |
| agtgtgcttt | gtccagacaa gctcctggag aactacccct cagtgaaagc aggctcaacg | 240 |
| atcacgaccc | tgtacgagaa cttccaagaa ggtgttctcc gttcaggcgg cgcccatttt | 300 |
| ttgggccatc | gtcccattgt gaatggccag cctcaggctt acaagtggca gtcgtatgtc | 360 |
| gatgtcagca | agcgtgttac gcacttcggc gctggcctgg ctcatctcgg cttgtctcca | 420 |
| aagcaaaact | ttggaatttt ctctatcaac cggcctgagt ggaccatgag tgagcttgct | 480 |
| ggctatatgc | acaactacac cagcgtcccc ctctatgata cattgggagt cgccgcgatc | 540 |
| gagtatatcg | ttaaccagac tgagatgcag atcatcattg cttcgtccga caaagcttct | 600 |
| atcatcctcc | acatgaaatc agcacttcca accgttcaga cgattgtcgt catgggggaa | 660 |
| tttactgacg | ctctcgtcgc agagggtaag gagctcaaca tcaacattgt atcctggacc | 720 |
| gatgtcgaaa | agagcggtct tgagcggcct gtcgaagccg tgcacccac agccgaggat | 780 |
| atcgctacca | tctgttacac atctggaacc actggaacgc aaaaggtgc tatcttgacc | 840 |
| cacaagaact | tgttgccac tatcgcttca ttccacatga tggcaaagca tggcaggttc | 900 |
| ttcattccct | cgcctgccga cacacatgta tcctacctgc ccttgccca cgtctttgag | 960 |
| cgcctttgcc | aggctgttat gatctcgggc gctgcgcgta ttggttacta ccaaggagat | 1020 |
| acgctgaagc | tgctggacga tgttgccgtc ctgcatccca ccattttgc ctccgtccct | 1080 |
| cgtctcttta | accgtatcta cgacaaggtg cttgctggcg tcaaggccaa gggtggtatc | 1140 |
| gccgccttct | tgtttaaccg cgcatataat tccaagaagg ccaacttgcg aaagggcgta | 1200 |
| cttgagcatc | cgctctggga caagctggtc tttggagcga ttcgcgcgcg cttgggtggc | 1260 |
| aaggttaagc | acatcgtgtc aggatctgcc cccatctctc ctgatgtgat ggatttcctc | 1320 |
| cgcatctgct | tcagcgctga tgtgtatgag ggatatggcc agacggaaca ggcagccgga | 1380 |
| ttaagtatga | gctatcgcgg tgatttgact ccaggacagg ttgcccacc tcaactgtgc | 1440 |
| acagaggtca | agttgaagga catccctagt atgaactata gcagcgcgga caagcctttc | 1500 |
| ccccgtggag | aaatcatgct tcgcggaaac tctgtgttca gggctatta caaagcacca | 1560 |
| aagcagactg | aagaaacatt ggatgctgac ggttggtcca gtaccggaga cgttggacag | 1620 |
| tgggatgccc | aaggccgtct ggtggtcatt gatcgcgtca agaacatctt caagttggcg | 1680 |
| caaggagaat | atattgcgcc tgaaaagatc gaggctgtcc tcgccaagca cttcctcgtt | 1740 |
| gcccagattt | tgtctatgg gcactcgctc caggccacca ttgtcgcggt ggttgtccct | 1800 |
| gatgctgaga | cgctcaagtt gtgggctaaa gaaaacaagc tgggtgacaa gtcttacgag | 1860 |
| gagctgtgcg | ctctccctca gcttcgcaca accctccaaa aggagttggc tacttttggc | 1920 |

```
aaagaatcgg atctgaaggg cttttgagatt cctaagaaca ttcatgttat ctccgagcag    1980 tttttcaattg agaacgatct tttgacccccc accttcaagc tgaagagaca tgctgccaaa    2040
gagaagtata acgccgaaat cgaccgcatg tatgcagaaa tcgcttaata taaataatgg    2100
ttgtactcaa tat                                                         2113

<210> SEQ ID NO 137
<211> LENGTH: 2087
<212> TYPE: DNA
<213> ORGANISM: Mortierella alpina

<400> SEQUENCE: 137
ggcacgaggc tctactctcc attgcccact cactcattgc ccctctgtcc atcaccggca      60
ttgctcgttc gcgccttccg ccactccact cttttctttca ttccttcttt acaacggcca    120
tctccccctc gctctgcgct tctcccatcc acgctaacaa tgcacattct gaatgccaca    180
agaccattct ccaggctgtc tccaaccgta aggagacctt ggctaggact cggccagacg    240
cgcccttatg ctatcgcgca gaccgaggcc agtcctaggc tgtcatatgt ccgaggcacc    300
accgtcggca cccagctatg cgaggatccc atcggtgcgt actgggacag ggtcgtcaat    360
cgtcacggtg accgctcgg acttgtcgtc aagcacgagc aggacctgca ctggaccttc    420
cgtcagtttg cgggcaggt tgatagcctc tgccgtgggc tctatgagtc tggcttgcga    480
aagggtgatc gactcgctgt ctggatgccg aacaacagcg cgtgggccac gctccagtat    540
gctactgcca agtctggcat cattctggta actctcaacc ctgcgtaccg gaggcaagag    600
ctactgcaga cattgtcttt ggtcgagtgc aagtcattgg tctatgtgcc aagtctaaag    660
acttcgaatt atagcgagat gttgctcgac ctcctaccag aactccagta ccagtcgcca    720
aatcagctct tgaccgagaa gctaccctca cttcgtcaag tcatcgtgtt tgacaatggc    780
tcgcaagtcc cagagacagc aaaattgaag ggattgacaa agtatcagga tttgttgatc    840
aagaatccct cgaccgctgt cgacggagct cttgaaaagg aacggctcgc tatcgacaac    900
agggatatca tcaatctcca gtttactagc ggaactacag gccttcccaa gggcgtctcg    960
ctgtcgcatc gaaacatctt gaataacggc attcatattg gagataacat gcgactgacg   1020
gaaaaggatt tgctttgctg cccggtcccg ctctttcact gctttggact ggtgctggca   1080
agcttggctg caatgaccca tggcgcagga attatttacc cttcgcagtc ctttgatgct   1140
gaggccacac tgagggctgt ttctgaggag ggtgctacag cgctgcatgg cgtgccgact   1200
atgctgttgg aagagatgaa ccaccccaac tttgcaaagt acaacctttc gacacttcgg   1260
acaggaattg cagctggatc ccctgtgccc attgaggtca tgaagaacgt gcagacaaag   1320
atgaacctga aggagctgac tatctgttac ggcatgaccg agacctcgcc cgtgtccttc   1380
atgacactca acggatga attacgggat cgatgtgaga ctgttggacg aattatgcca   1440
catctcgagg ccaaagtcgt caaccctgag acgggagaga ctttgccagt gaattcatca   1500
ggagagttgt gcacgcgcgg gtatgctgtg atggagggtg gttactggcg atcccaggag   1560
cagacagatg cagtggtgga caaggatggc tggatgcaca ctggcgacac tgccgtgctc   1620
gatgaccgtg gcttttgcag gatcgacgga cgcatcaagg acatggtgat ccgaggaggc   1680
gaaaaaatcc atcctgtaga ggtcgagaac tgtctctttg agatggacgg cgtcaagaac   1740
gtgtctgtga ttggcgttcc cgacaagcgg tatggcgagc aggtgtgtgc gtggatctcg   1800
accaaggacg ggaagacggt cagtctggag gcagtgcaaa agttctgtga gggcaagatt   1860
gcgcactaca aggtgccgcg gtatgtggtt gtggtggagt ccaatgagtt cccgactacc   1920
```

```
ccctcgggca agatccaaaa gaatgtgatg cgcgagctga ccaaggcgaa gctgcagctg    1980
ccttgatggt actaggatat ggagccgacg aaagtaataa aggcgtatgc tggcatggcg    2040
caagatctga gccctgcggt gaggtgcatt cagtgacgcc attagaa                  2087

<210> SEQ ID NO 138
<211> LENGTH: 2288
<212> TYPE: DNA
<213> ORGANISM: Mortierella alpina

<400> SEQUENCE: 138 tgctttctc ttcttcgtca ccctccttct tcccattcct ccggtcctcc tccgttccta      60
atcagtttct cagaccctgt ccattcctct ggcctccaca cacacccccac tctcccttga    120 acaaatacct tatccagatc aaagacatgc cttccttcaa aaagtacaac ctcgacaagc    180
agagtgttga ggtccctggc actcggaagc ctggcgcttc aggccactac agacatgccg    240
cctacggcga tgctcttgtc accaacatcc gtgaggcccc tcatatcgaa actctttacg    300
acatgtggca gaactctgtg acaaagtatg gcggcaatga ctttttgggt caccgtccct    360
tcaacactgt tgcccagacc tatggtggct acagttggga gacgtaccgc cagattaacc    420
agcgcgttaa tgcgttcggc agcggtatca tgcacctgaa cgaggtgatc ctcggcaacc    480
gccagcttaa ccgctgggcg ttgggcatct ggtcccacgg tcgccctgag tggttcatta    540
cggagatgag ctgcaactgc tacaacctca tttctgttgc attgtacgac accttggac    600 ctgatgcagt cgagtacatt gtcaaccacg ccgagattga gattgttgtc tcaagtgcca    660
accatatcgc ctctttgctc gagaacgccg agaagctccc caagctcaag gccattgtca    720
gcatggatgc tcttcacgat accgtccccg tccccggcgc cacctctgcc gcacaggttc    780
ttcgtgcctg gggtgcacaa aagggcatca aggtctatga ctttaacgag attgagtccc    840
tcggtgccga gttccctcgc aagcacctgc ctcccaccgc tgatgaggtc gcctccatct    900
gctacacttc cggcaccacc ggtcagccta aggagccat gctcacccac agaaactttg    960
ttgctactgt tggtaccaac cgcgagggca tgcttctcac cgaggacgac gttttgatca    1020 gttttcttgcc cttggctcac attatgggac gcgtcattga cacttgctcg atgtacagcg    1080
gtggcaagat tggttacttc cgtgagata ttcttttgct tctcgaggac gttgctgagc    1140
tccgtcccac attcttccca gctgtgcctc gcctcttgaa ccgcatttat gccaagctcg    1200
ttgcctctac cattgaggcc cccggtttgg tcggtgcctt ggcccgtcgc ggtgtcgccg    1260
ccaagatggc caaccttgct gccggaaagg gtgtcaacca cgctctctgg gacagactgc    1320
tgttcaacaa ggtcaagatg gccctgggtg gtcgcgttca ggtcatcctg actggatctg    1380
cgcccattgc caaggaggtt ctcagcttct tgagaattgc tttcggatgc gtggttttgg    1440
agggatacgg ctccactgag gcatggctac ccgccaccat cacaatggct gatgagtaca    1500
ttcctggtca cattggctgc cctcgtgctg atgcgagct caagctggtg gatgtgcccg    1560
cgatgaacta cctctctacc gaccagccct acccccgtgg agagatctgg atccgtggtg    1620
acactgtttt caaaggatac ttcaaggacg agaagaacac tagtgagact atcgactctg    1680
aaggctggct cgctaccggt gatattgat ttgtggataa gcgtggatgc tttacgatca    1740
ttgaccgcaa gaagaacatc ttcaagttgg cacaaggtga atacattgct cctgaaaaga    1800
ttgagaacgt cttgggcgca cgctgcaatc ttgtccagca gatctatgtt catggtgatt    1860
cgcttgagtc caccttggtc gcagttctta ttcccgagcc cgagaccttc ctgccctcg    1920
```

| | |
|---|---|
| cgaatgccat tgctggtgcc tccgtcactg ctggagatgt tgagggtttg aacaagctgt | 1980 |
| gccaagatcc caaggtcaag atcgcggttc tgaaggagtt ggagaaggcc ggaaaggccg | 2040 |
| gtgcgatgcg cggattcgag ttcgtgaagc gtgtccactt gaccacggat gcattctcgg | 2100 |
| tcgacaacgg catgatgaca cctaccttca aggtccgtcg cccacaagta gccgagcatt | 2160 |
| tcagggagca aatcacggcc atgtataagg agatcaatgc ctcgacccct gttgccaagc | 2220 |
| tgtagataga aaactctttg ccccttatta cccttttgaat agaaggtgac acgttgtttg | 2280 |
| attcacac | 2288 |

<210> SEQ ID NO 139
<211> LENGTH: 2017
<212> TYPE: DNA
<213> ORGANISM: Mortierella alpina

<400> SEQUENCE: 139

| | |
|---|---|
| tcgctatcta tcacccctca ctccccactc cgcactctgc tcttcctttt tcctttctct | 60 |
| ctctcaccgt cgccactgtc tctactttct ttaccaccca cgcatcagtc acagcatggt | 120 |
| tgctctccca ctcgtcgcag cagctgtccc agctgccatg tatgtgagct caaagctggc | 180 |
| acttcctcgg gatatgaagt tgattaagag cttgatcgga gccaagatgg cctacagtgc | 240 |
| catggaaaag aacgacgccc tcaacctgac actccgcttc gacgagtgct accgcaagta | 300 |
| tcctgaccgt gaagccctgg tctttgaggg caaatcctat tcattccgtg atattcagct | 360 |
| tgcctccaac aggtgcggca actggttgct ggccaaaggg atcaagcgag gagatatcgt | 420 |
| ctcgcttttc atgttgaaca ggccagagtt catcttctgc tggctgggtc tcaacaagat | 480 |
| tggagccact ggtgccttca tcaataccaa ccttacgggc aaaccctga cacattccct | 540 |
| ccggacagcc acgtcgtcaa tgttgatcat ggacacggag ttgacagacg cgatcgccaa | 600 |
| ctccctggat gagattcagg agatgggcta ttcaatttac tcttacggac ccgaagccgt | 660 |
| ggactttgct accccgatgg atatctcgca ggtcccagac accgatacac ccgaacacct | 720 |
| gcgccggaac acgaccgcgg atgacattgc gatgctcatc tacacctctg gaactactgg | 780 |
| tcttcccaag gccggtcgtg tctctcatgc gcgtgcctct atgggacctc agttttggaa | 840 |
| ccgattctat cacttcagtg agagcgacag ggtctatctg tccttgccct tgtaccacag | 900 |
| tgctggcgcc atcttgggag tgattgcttg ttggacctcg ggagcaacct tgatcctggc | 960 |
| ccgcaagttc tccgcgacac atttctggga ggattgccgc gtgaacaacg caactgtgat | 1020 |
| tcaatacatt ggagaaattt gcagatatct gctcaacacg ccagaatcac ccctggacaa | 1080 |
| ggcacactcg atacgactgg cacatggtaa tggaatgcga cccgatgtct ggactcgctt | 1140 |
| cagagatcgt ttcggcatcc cgttgattgg cgagtggtat gcatcgactg agggaactgg | 1200 |
| agccttgtcg aattataaca caggcccagg cggcgctgga gcgattggat accgcggtac | 1260 |
| ccttgccaga gcattggata aaggactcag gattgcgaga tttgatgtcc agacagagga | 1320 |
| gttggttcgg gacaaaaacg gttattgcat tgagtgcaaa cctggcgagc ccggagaatt | 1380 |
| gctgacgctt gttgatgcta agagccgaa caaagacttc aaaggatacc atcaaaacca | 1440 |
| ggcagcgacc aacaaaaaga ttgtcaaaga tgttttcaaa gccggcgaca tgtacttccg | 1500 |
| taccggagat atccttcggc gcgatagcga tgggtacttt actttggcg accgtgtggg | 1560 |
| cgatacattc cggtggaagt ccgagaatgt gtctacggcc gaggtgtctg aagtcctctc | 1620 |
| gcagtatccg gactgtatcg aagtcaatgt gtatggagtt cagatcccag gcaggacgg | 1680 |
| acgcgccggt atggcagcga ttgtgtccaa gagcacgatg gattgggaga aatttgcggc | 1740 |

```
gtatgcactc aagaacctgc cgcggtattc tgttccgatc tttatccgca agatgcccga   1800
gatggagatc acagggacgt tcaagcagcg caaagtcgag ttggtgaatg agggaatcga   1860
ccccaagacg attgccaacg agatgctgtg gttggacgga caccactata agccgttcaa   1920
ggcggccgag caccagcgcg tcatcagcgg caaggccaag ctatagtagg gcgcgtgcgc   1980
caatgcagta gcaatactat tccccgcttt gtccatt                            2017

<210> SEQ ID NO 140
<211> LENGTH: 2170
<212> TYPE: DNA
<213> ORGANISM: Mortierella alpina

<400> SEQUENCE: 140
ttcacgcact accttctttt ttcacccatc cagcagtaaa gacaacatgg aaaccttggt     60
taacggaaag tatgcggtcg agtacgacga ggtcgatcac atctatcgca acgtcatggc    120
tacaggcggg ctcctcgaca ggcctatgcc tccatactac gacatcaagg agcgcaccat    180
ggcccacctc tttgagtata tggccaacac ctacgaagac aaagacgcca tgggctggcg    240
agacattatc aaggtccaca aggtcgaaga gcaggctgcc aatcctggcg agaagccaaa    300
gacctggatc acttatgagc tctcggacta caactggatg tcgtaccgcc aagccaagaa    360
ctatgcagat cgagttggct tgggcatcac acgccttgga gttgagaagg gagactttgt    420
catgatcttt gctagcacat gtcccgaatg gttcctgaca gcgcatggat gcttctcgca    480
gtcagtgact atcgtgacag cctacgactc gatggacgag aagtcgatcc agtttattgt    540
tgaccagtcc cagcccaagg ccatctttgc tgatgcgcac acgctccctg tggtgtccaa    600
actcatgcag aagggcaaca gtggtgtcaa ggcagtcatt tacacaggcc aagagtggga    660
agtgaccgat gcaatcaaga gatggagca agtagaaaac cgctcatttg agctggttca    720
tatcgacgaa ctcaagaaga ccaagtcagc atctaacggc gaacagtctg ccggaaaggg    780
gaagcagaga tcatctgagg atgccgaagg cgctcaggac gagatcgagg tcatataccc    840
taaggcggat gatctggcct gtattatgta tacctctggg tcgacgggtc agcccaaggg    900
cgcgcaattg acacatggca acttgatggc ggccattgga agtgctgcgg ccatggaggg    960
cgaccagctg acaaggaaa cagacattgt tatttcatat ctgccattgg cccatgtcct   1020
cgagtttgtc atttcccact ttgtggtatc catgggctgc cgtcttggat cggacgagc   1080 acgcactctg atggatgatg cagtcgctcc caccgcagga agtggcaggt ccaagggcct   1140
tggtgatctg aaggcgctcc agccaacatt gatggctggt gtgccaacga tctgggagcg   1200
tatccgcaag ggcatcctgg ccgaggtcaa caagcaatcc ttccctatcc gtacactctt   1260
ctttgctgca ctcaacacca gtgggctat cgtccaggct accggatctg agaactttgt   1320
caccaagact attgactcgt tggtctttag taaggctaag gagctcgttg gaggcaagct   1380
gcgccttacc ttgactggag gggccggaat cagtgatgag acgcaccggt tcttgagcat   1440
ggtaatgtgc tacgttatct cgggatatgg tctcactgaa gtctgtggtg ttgccgctgt   1500
caccctgcca cgtatgggtc accgtctcag gaccgttgga ccaccgcgc ccagtcttga   1560 gctgaagttg gtgaatgtgc ccgacaccga gtacacagga acaatggat cgggcgaaat   1620 ctggttccgt ggacctgcag tgatgaaggg atacttcaaa ctcgaggaag agaccaagaa   1680
ggtgatgacc ggggatggtt ggttcaagac aggcgacatt ggcacgatga acccagacgg   1740
cacactgtca atcaaggaca gggtcaagaa tctggtcaag ctgtctcatg gagaatatgt   1800
```

```
cgccctggag aaatgtgaag ccgtttatcg cgattccaag gagatcaaga gcatttgcat    1860
cgttgcggac aatgggtgcc ctgtgttgct ggccgttgtg gaaccgagcc acgcaggggc    1920
gtctgacaag gagattttgg atatcctgaa gagccaagcc aaggcggcgg gcctctccaa    1980
gtccgagact gtgcaaggcg ttatcattga tgattcggac tggatgacga atgggttcat    2040
gacctcgagc agcaaggtca agagacgcga ggtccgcaag gcacacaaca aggatattga    2100
ggagatgtgg aagaagttct agagaagcgt gggaagggca tgaaataaac atacgcaatg    2160
gatttattgg                                                            2170
```

<210> SEQ ID NO 141
<211> LENGTH: 2392
<212> TYPE: DNA
<213> ORGANISM: Mortierella alpina

<400> SEQUENCE: 141

```
cctttatccc cgcaccgcca tctctcgccg ccaccatctc gcattccttt caatccacac      60
tcccacctgt gcccctgct tttcacgtcc cgctctcatc ccgccttctc ctttcatcac     120
cccaattcaa catgacaaag tgcctcaccg tcgaagtcgg accgccgac gtccagggcg     180
agaccccgcat ccgccgctcc gtcctctctg caaagcgcct catgtcctcg ccctcggatg    240
acatcaagac cctctacgac gtcttcaacc actccgtcac cgtccgcccc aacctcaacg    300
cgatcggata ccgcaaggtc gtcaagattg tcgaggaaga aaaggaggtc gtcaaggttg    360
tcaacggcga ggaagtcaag gaaaagaaga cctggaagtt cttcaagatg tccggctacc    420
actggctcac ctacaaggat gcgaagcagg tcgtcgacag catcggatgc ggtcttcgca    480
agtttggcgt cgagcccaag gacaagctga ccgttttcgg tgccacaagt gccaactggc    540
tcctgcttgc ccacggtgct ttcacccagt ccatcaccat tgttaccgcc tacgacaccc    600
tgggcgagga cggtcttttg cactctatga cgaggccga ggtggccacc gcttacacaa    660
acgccgactt gctcaacact atcaagaacg ttgccggcaa atgccccacc ctgaagaaga    720
tcatctacga cggcgatgcc aagcccgcag atgtcattgc cctccaggag gcccatcctc    780
acctccagct catcaccctc gaggagctga agcagctcgg agtggacaac cctgtcgccc    840
caacccctcc tgctgccaag gactactgct gcatcatgta cacttcggga tcgactggca    900
accccaaggg agtgttgctg acccatggaa acctcgttgc tgccatcgga ggtgtgaaca    960
agatgctgac aaagtacgtt cacgagggag acgtcttgct cgcgtacttg cctcttgctc   1020
acgttctcga gttcctggtc gaaaacgtct gtctcttctg gggtgtgact cttggctacg   1080
gtaccgtccg cacattgact gatgcctcag tccgtgagtg ccagggtgat atcaaggagt   1140
tgcgccctac attgatgacc ggtgttcctg ctgtgtggga cgattcgt aagggagtgt   1200
tggctcaggt ttcccagggc tcacctcttg ttcaaaagat cttccatgct gctttgaacg   1260
ccaaggcctg gtgcctggac cgcaagttgg gtgcgttgac tggaatcttc gatactgtcg   1320
tcttcaacaa ggtcaagcag cagacaggag gacgtcttcg cttcgccctt tcgggaggtg   1380
cacccatctc tcaggagacc cagcgcttct tgacgacagc tttgtgccct atcctccagg   1440
gctacggtat gacagagtct tgcggcatgt gcgccatttt gaccccgat gtcttcaact   1500
acagccgtgt cggatcccca gttccttgca cggaggtcaa gttggtcgat gtgcccgatg   1560
caggatacca ctcaacggac ttgcctctcc ccgtggtga ggtctgcatt cgtggaccct   1620
ccatcactgc tggatacttc aagaaccccg aggagcctc cgccacattg actgctgatc   1680
gctggctcaa gactggagat atcggagagt ggcaccccga cggcactatc tcgatcattg   1740
```

-continued

```
accgcaagaa gaacttggtc aagctgtcac acggagagta cattgctttg gagaagcttg    1800
agtctgtcta caagagcaca gcctactgca acaacatttg cgtgtatgcc gactcgatgc    1860
agaacaagcc cgttgccatt attgttgcca gcgaacccg catcctcgag ttggccaagg     1920
ccaagggcat tgagagccgc gactttgctg ctctctgcca cgacaaggtt atcatcaagg    1980
ctgtccacga tgcctgcctc gccactgcca agcgtgctgg actcaagccc gctgagatgc    2040
ttcagggagt gtacttggag tcagaagaat ggacggccca ggctggcatg ttgactgccg    2100
ctcagaagct caagcgcaag gagatcaacc aggcctatgt ctcacagatc aagcagcttt    2160
atggaacggc ctaagtcgct gaaaggtgtg cctttgtccg tctcttcaac cccacaagtc    2220
ctatgtataa tgacccgcgc ggccctcctt taatcctata cccacccttt tttacacgtt    2280
aaagaagcca catttttggt tcttttttt ctctcgcaca cactacacac tccccatcca    2340
ttccctccaa acaggatggt tgtctgcaaa taaattgacg aatttctct tg             2392
```

<210> SEQ ID NO 142
<211> LENGTH: 627
<212> TYPE: PRT
<213> ORGANISM: Mortierella alpina

<400> SEQUENCE: 142

| | | | | | | | | | | | | | | | |
|---|---|---|---|---|---|---|---|---|---|---|---|---|---|---|---|
| Met | Asp | Ala | Val | Pro | Ala | Val | Ala | Ala | Ala | Ile | Pro | Ala | Ala | Met | |
| 1 | | | | 5 | | | | | 10 | | | | | 15 | |
| Tyr | Val | Gly | Ser | Lys | Leu | Ala | Ile | Pro | Arg | Asp | Val | Lys | Leu | Ala | Lys |
| | | | 20 | | | | | 25 | | | | | 30 | | |
| Gly | Leu | Val | Ser | Ala | Lys | Leu | Gly | Tyr | Arg | Ser | Tyr | Glu | Lys | Asn | Asp |
| | | 35 | | | | | 40 | | | | | 45 | | | |
| Ser | Ile | Asn | Ile | Ser | Tyr | Arg | Phe | Glu | Glu | Thr | Cys | Lys | Lys | His | Pro |
| | 50 | | | | | 55 | | | | | 60 | | | | |
| His | Arg | Glu | Ala | Leu | Val | Phe | Glu | Gly | Lys | Ser | Tyr | Thr | Phe | Gln | Asp |
| 65 | | | | | 70 | | | | | 75 | | | | | 80 |
| Ile | Gln | Arg | Glu | Ser | Asn | Arg | Val | Gly | His | Trp | Leu | Leu | Ser | Lys | Gly |
| | | | | 85 | | | | | 90 | | | | | 95 | |
| Val | Lys | Arg | Gly | Glu | Ile | Val | Ser | Leu | Phe | Met | Gln | Asn | Lys | Pro | Glu |
| | | | 100 | | | | | 105 | | | | | 110 | | |
| Phe | Leu | Phe | Phe | Trp | Leu | Gly | Leu | Asn | Lys | Ile | Gly | Ala | Thr | Gly | Ala |
| | | | 115 | | | | | 120 | | | | | 125 | | |
| Phe | Ile | Asn | Thr | Asn | Leu | Ser | Gly | Lys | Pro | Leu | Thr | His | Ser | Leu | Arg |
| | 130 | | | | | 135 | | | | | 140 | | | | |
| Thr | Ala | Thr | Ala | Ser | Ile | Leu | Ile | Met | Asp | Ala | Glu | Leu | Pro | Thr | Pro |
| 145 | | | | | 150 | | | | | 155 | | | | | 160 |
| Ile | Tyr | Ser | Val | Leu | Asp | Glu | Val | Leu | Glu | Met | Gly | Tyr | Gln | Ile | Tyr |
| | | | | 165 | | | | | 170 | | | | | 175 | |
| Ser | Tyr | Gly | Gly | Ser | Gln | Gln | His | Ala | Phe | Ala | Thr | Gln | Val | Glu | Leu |
| | | | 180 | | | | | 185 | | | | | 190 | | |
| Ser | Gln | Ile | Ser | Asp | Ala | Ala | Leu | Pro | Lys | Ser | Leu | Arg | Arg | Lys | Thr |
| | | | 195 | | | | | 200 | | | | | 205 | | |
| Thr | Ala | Asn | Asp | Ile | Ala | Met | Leu | Ile | Tyr | Thr | Ser | Gly | Thr | Thr | Gly |
| | 210 | | | | | 215 | | | | | 220 | | | | |
| Leu | Pro | Lys | Ala | Gly | Arg | Phe | Ser | His | Ala | Arg | Ala | Asn | Val | Ala | Ala |
| 225 | | | | | 230 | | | | | 235 | | | | | 240 |
| Leu | Phe | Trp | Thr | Ser | Phe | Tyr | His | Phe | Ser | Glu | Lys | Asp | Arg | Leu | Tyr |
| | | | | 245 | | | | | 250 | | | | | 255 | |

```
Ile Ala Leu Pro Leu Tyr His Ser Ala Gly Ala Val Leu Gly Ile Cys
            260                 265                 270

Val Ala Trp Val Thr Gly Ala Thr Val Val Leu Ala Arg Lys Phe Ser
        275                 280                 285

Thr Thr Ser Phe Trp Asp Glu Cys Arg Ala Asn Lys Val Thr Val Ile
290                 295                 300

Gln Tyr Ile Gly Glu Ile Cys Arg Tyr Leu Leu Asn Ala Pro Pro Ser
305                 310                 315                 320

Pro Leu Asp Lys Thr His Thr Ile Arg Met Ala His Gly Asn Gly Met
                325                 330                 335

Arg Pro Asp Val Trp Asn Arg Phe Arg Asp Arg Phe Gly Ile Pro Leu
            340                 345                 350

Ile Gly Glu Trp Tyr Ala Ser Thr Glu Gly Thr Gly Ile Leu Thr Asn
        355                 360                 365

Tyr Asn Thr Gly Pro Asn Gly Ala Gly Ala Ile Gly Tyr Arg Gly Ser
    370                 375                 380

Leu Ala Arg Thr Val Asp Lys Gly Leu Lys Ile Ala Lys Phe Asp Ile
385                 390                 395                 400

Gln Thr Glu Glu Leu Ile Arg Asp Lys Asn Gly Arg Cys Ile Glu Cys
                405                 410                 415

Val Ala Asp Glu Pro Gly Glu Leu Leu Thr Met Ile Asp Ser Ser Asp
            420                 425                 430

Pro Thr Arg Ala Phe Gln Gly Tyr His Lys Asn Ala Gly Ala Asn Ser
        435                 440                 445

Lys Lys Val Val Gln Asp Ala Phe Ser Val Gly Asp Gln Tyr Phe Arg
    450                 455                 460

Thr Gly Asp Ile Leu Arg Arg Asp Ala Asp Gly Tyr Phe Tyr Phe Gly
465                 470                 475                 480

Asp Arg Val Gly Asp Thr Phe Arg Trp Lys Ser Glu Asn Val Ser Thr
                485                 490                 495

Ala Glu Val Ser Glu Val Leu Ser Ala Tyr Pro Asp Cys Ile Glu Val
            500                 505                 510

Asn Val Tyr Gly Val Gln Val Pro Gly His Asp Gly Arg Ala Gly Met
        515                 520                 525

Ala Ala Ile Val Ser Lys Asp Thr Met Asn Trp Asp Ser Phe Ala Lys
    530                 535                 540

Phe Ala Leu Lys Asn Leu Pro Lys Tyr Ser Val Pro Ile Phe Ile Arg
545                 550                 555                 560

Lys Val Pro Glu Met Glu Ile Thr Gly Thr Phe Lys Gln Arg Lys Val
                565                 570                 575

Glu Leu Val Asn Glu Gly Met Asp Pro Ser Lys Ile Lys Asp Glu Met
            580                 585                 590

Leu Trp Leu Asp Gly His Ser Tyr Arg Pro Phe Lys Glu Ala Glu His
        595                 600                 605

Thr Arg Val Val Ser Gly Lys Ala Arg Leu Arg Ile Lys Leu Phe Arg
    610                 615                 620

Phe Val Arg
625
```